(12) United States Patent
Luehr et al.

(10) Patent No.: US 11,768,319 B2
(45) Date of Patent: Sep. 26, 2023

(54) GLYCYRRHETINIC ACID DERIVATIVES FOR TREATING HYPERKALEMIA

(71) Applicant: Ardelyx, Inc., Fremont, CA (US)

(72) Inventors: Gary Luehr, Fremont, CA (US); Dean Dragoli, Fremont, CA (US); Michael Leadbetter, Fremont, CA (US); Tao Chen, Fremont, CA (US); Jason Lewis, Fremont, CA (US)

(73) Assignee: Ardelyx, Inc., Fremont, CA (US)

( * ) Notice: Subject to any disclaimer, the term of this patent is extended or adjusted under 35 U.S.C. 154(b) by 325 days.

(21) Appl. No.: 16/636,596

(22) PCT Filed: Aug. 6, 2018

(86) PCT No.: PCT/US2018/045421
§ 371 (c)(1),
(2) Date: Feb. 4, 2020

(87) PCT Pub. No.: WO2019/060051
PCT Pub. Date: Mar. 28, 2019

(65) Prior Publication Data
US 2021/0163524 A1    Jun. 3, 2021

Related U.S. Application Data
(60) Provisional application No. 62/541,095, filed on Aug. 4, 2017.

(51) Int. Cl.
| | |
|---|---|
| *C07J 63/00* | (2006.01) |
| *A61P 5/44* | (2006.01) |
| *G02B 5/02* | (2006.01) |
| *G02B 5/20* | (2006.01) |
| *G02B 3/00* | (2006.01) |
| *G02F 1/1335* | (2006.01) |
| *G02B 27/00* | (2006.01) |

(52) U.S. Cl.
CPC .............. *G02B 5/0294* (2013.01); *A61P 5/44* (2018.01); *C07J 63/008* (2013.01); *G02B 3/0056* (2013.01); *G02B 5/0215* (2013.01); *G02B 5/201* (2013.01); *G02B 27/0018* (2013.01); *G02F 1/133502* (2013.01); *G02B 5/021* (2013.01); *G02B 2207/123* (2013.01); *G02F 1/133526* (2013.01)

(58) Field of Classification Search
CPC .................................................. C07J 63/008
See application file for complete search history.

(56) References Cited

U.S. PATENT DOCUMENTS

| | | | | |
|---|---|---|---|---|
| 5,624,909 | A | * | 4/1997 | Rao .................. C07H 15/24 435/7.1 |
| 2004/0143124 | A1 | | 7/2004 | Vicker et al. |
| 2010/0087413 | A1 | * | 4/2010 | Wilckens ................ A61P 29/00 514/254.02 |
| 2015/0218206 | A1 | | 8/2015 | Yoon |

FOREIGN PATENT DOCUMENTS

| | | |
|---|---|---|
| WO | 2005027882 A1 | 3/2005 |
| WO | 2007105015 A2 | 9/2007 |
| WO | 2010103046 A1 | 9/2010 |

OTHER PUBLICATIONS

Stanetty et al. (Bioorganic & Medicinal Chemistry, 2010, vol. 18, pp. 7522-7541).*
Yoshida et al. (Biotechnology Letters, 2001, 23(19), pp. 1619-1624).*
Database CA, "Triterpenoids. XXV. PMR spectra of glycyrrhetic acid derivatives", Accession No. 1971:420694 Abstract, 1 page (1971).
Gaware, R, et al., "Synthesis of new glycyrrhetinic acid derived ring A azepanone, 29-urea and 29-hydroxamic acid derivatives as selective 11 beta-hydroxysteroid dehydrogenase 2 inhibitors", Bioorganic Med Chem 19, 1866-1880 (2011).
Kratschmar, D, et al., "Characterization of activity and binding mode of glycyrrhetinic acid derivatives inhibiting 11 beta-hydroxysteroid dehydrogenase type 2", Journal of Steroid Biochemistry & Molecular Biology 125, 129-142 (2011).
Patent Cooperation Treaty, International Searching Authority, Search Report and Written Opinion for PCT/US2018/045421, 24 pages (dated Jan. 10, 2019).

(Continued)

*Primary Examiner* — Susanna Moore
(74) *Attorney, Agent, or Firm* — Viksnins Harris Padys Malen LLP

(57) ABSTRACT

The present invention provides a compound of formula (I) or a salt thereof: (I) wherein X, L, V, $R_1$, $R_2$, $R_3$ and $R_4$, are as defined herein. These compounds are inhibitors of 11-hydroxysteroid dehydrogenase type 2 (11-HSD-2) and are used to treat hyperkalemia.

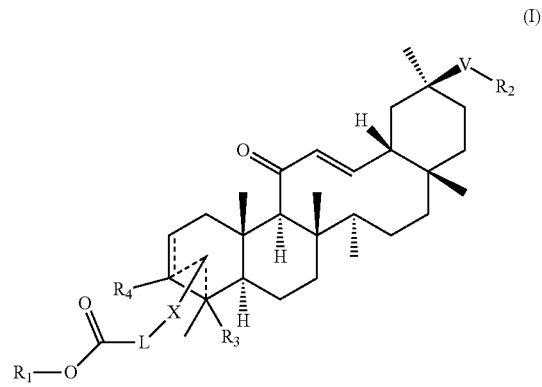

(I)

18 Claims, 3 Drawing Sheets

(56) References Cited

OTHER PUBLICATIONS

Schuster, D., et al., "The Discovery of New 11β-Hydroxysteroid Dehydrogenase Type 1 Inhibitors by Common Feature Pharmacophore Modeling and Virtual Screening", J Med Chem 49, 3454-3466 (2006).
Yoon, Y., et al., "Discovery of ursolic acid prodrug (NX-201): Pharmacokinetics and in vivo antitumor effects in PANC-1 pancreatic cancer", Bioorganic Medicinal Chemistry Letters 26, 5524-5527 (2016).
CAPLUS, Registry No. 32285-33-9, 2 pages (Nov. 16, 1984).

\* cited by examiner

GLYCYRRHETINIC ACID DERIVATIVES FOR TREATING HYPERKALEMIA

CROSS-REFERENCE TO RELATED APPLICATIONS

This application claims the benefit of priority under 35 U.S.C. 119(e) to U.S. provisional application 62/541,095 filed on 4 Aug. 2017, the entire contents of which is hereby incorporated by reference.

FIELD OF THE INVENTION

The present invention relates to compounds that inhibit 11β-HSD2 and methods of using these compounds to remove potassium from the gastrointestinal tract, including methods of treating hyperkalemia.

BACKGROUND OF THE INVENTION

Potassium is the most abundant cation in the intracellular fluid and plays an important role in normal human physiology, especially with regard to the firing of action potential in nerve and muscle cells. Total body potassium content is about 50 mmol/kg of body weight, which translates to approximately 3500 mmols of potassium in a 70 kg adult. The bulk of total body potassium is intracellular (~98%), with only approximately 70 mmol (~2%) in the extracellular space. This large differential between intracellular potassium (~120-140 mmol/L) and extracellular potassium (4 mmol/L) largely determines the resting membrane potential of cells.

As a consequence, very small absolute changes in the extracellular potassium concentration will have a major effect on this ratio and consequently on the function of excitable tissues (muscle and nerve). Extracellular potassium levels are therefore tightly regulated.

Two separate and cooperative systems participate in potassium homeostasis, one regulating external potassium balance (the body parity of potassium intake vs. potassium elimination) while the other regulates internal potassium balance (distribution between intracellular and extracellular fluid compartments. Intracellular/extracellular balance provides short-term management of changes in serum potassium, and is primarily driven physiologically by the action of $Na^+$, $K^+$-ATPase "pumps," which use the energy of ATP hydrolysis to pump $Na^+$ and $K^+$ against their concentration gradients. Almost all cells possess a $Na^+$, $K^+$-ATPase. Body parity is managed by elimination mechanisms via the kidney and gastrointestinal tract: in healthy kidneys, 90-95% of the daily potassium load is excreted through the kidneys with the balance eliminated in the feces.

Due to the fact that intracellular/extracellular potassium ratio ($K_i:K_e$ ratio) is the major determinant of the resting membrane potential of cells, small changes in $K_e$ (i.e., serum [K]) have profound effects on the function of electrically active tissues, such as muscle and nerve. Potassium and sodium ions drive action potentials in nerve and muscle cells by actively crossing the cell membrane and shifting the membrane potential, which is the difference in electrical potential between the exterior and interior of the cell. In addition to active transport, $K^+$ can also move passively between the extracellular and intracellular compartments. An overload of passive $K^+$ transport, caused by higher levels of blood potassium, depolarizes the membrane in the absence of a stimulus. Excess serum potassium, known as hyperkalemia, can disrupt the membrane potential in cardiac cells that regulate ventricular conduction and contraction. Clinically, the effects of hyperkalemia on cardiac electrophysiology are of greatest concern because they can cause arrhythmias and death. Since the bulk of body parity is maintained by renal excretion, it is therefore to be expected that as kidney function declines, the ability to manage total body potassium becomes impaired.

Hyperkalemia is defined as a serum potassium level above the normal range, typically >5.0 mmol/L. Moderate hyperkalemia (serum potassium above 6.0 mEq/L) has been reported to have a 1-day mortality rate up to 30 times higher than that of patients with serum potassium less than 5.5 mEq/L. Severe hyperkalemia (serum K+ of at least 6.5 mmol/L) is a potentially life-threatening electrolyte disorder that has been reported to occur in 1% to 10% of all hospitalized patients and constitutes a medical emergency requiring immediate treatment. Hyperkalemia is caused by deficiencies in potassium excretion, and since the kidney is the primary mechanism of potassium removal, hyperkalemia commonly affects patients with kidney diseases such as chronic kidney disease (CKD) or end-stage renal disease (ESRD). However, episodes of hyperkalemia can occur in patients with normal kidney function, where it is still a life-threatening condition. For example, in hospitalized patients, hyperkalemia has been associated with increased mortality in patients both with and without CKD. While CKD is the most common predisposing condition for hyperkalemia, the mechanisms driving hyperkalemia typically involve a combination of factors, such as increased dietary potassium intake, disordered distribution of potassium between intracellular and extracellular compartments and abnormalities in potassium excretion. These mechanisms can be modulated by a variety of factors with causality outside of CKD. These include the presence of other comorbidities, such as type 2 diabetes mellitus (T2DM), cardiovascular disease (CVD) or the use of co-medications that can disrupt potassium homeostasis as side effects, such as blockade of the renin-angiotensin-aldosterone system (RAAS), for example, with angiotensin-converting-enzyme (ACE) inhibitors and angiotensin-receptor blockers (ARBs).

Serum potassium can be lowered by two general mechanisms: the first is by shifting potassium intracellularly using agents such as insulin, albuterol or sodium bicarbonate. The second is by excreting it from the body using 1 of 4 routes: the stool with K binding resins such as sodium polystyrene sulfonate (Na PSS), the urine with diuretics, the blood with hemodialysis or the peritoneal fluid with peritoneal dialysis. Other than Na PSS, the medications that treat hyperkalemia, such as insulin, diuretics, beta agonists and sodium bicarbonate, simply cause hypokalemia as a side effect and are not suitable as chronic treatments. Definitive therapy necessitates the removal of potassium from the body. Studies have confirmed that reducing serum potassium levels in hyperkalemia patients actually reduces the mortality risk, further solidifying the role of excess potassium in the risk of death. While Na PSS is the current standard of care treatment for potassium reduction in the U.S., the calcium salt of PSS (Ca PSS) is also commonly used in other parts of the world, including Europe (e.g., Resonium) and Japan. Kayexalate/Na PSS is poorly tolerated causing a high incidence of GI side effects including nausea, vomiting, constipation and diarrhea. In addition, Kayexalate is a milled product and consists of irregularly shaped particles ranging in size from about 1-150 μm in size, and has sand-like properties in the human mouth: on ingestion, it gives a strong sensation of foreign matter on the palate and this sensation contributes negatively to patient compliance. In total, the physical properties and associated side-effects of Kayexalate lead to poor compliance and render the drug suboptimal for chronic use. Due to these properties, there has been a long felt need to provide an optimal drug for chronic use.

The mineralocorticoid receptor (or MR, MLR, MCR), also known as the aldosterone receptor or nuclear receptor subfamily 3, group C, member 2, (NR3C2) is a protein that in humans is encoded by the NR3C2 gene that is located on chromosome 4q31.1-31.2. MR is a receptor with equal affinity for mineralocorticoids and glucocorticoids including cortisol. It belongs to the nuclear receptor family where the ligand diffuses into cells, interacts with the receptor and results in a signal transduction affecting specific gene expression in the nucleus. MR is expressed in many tissues, such as the kidney, colon, heart, central nervous system (hippocampus), brown adipose tissue and sweat glands. Activation of the mineralocorticoid receptor by ligands aldosterone and cortisol in epithelial tissues promotes excretion of potassium. In intact animals, the MR is "protected" from the greater concentration of cortisol (100-1000 fold) by co-localization of an enzyme, 11β-hydroxysteroid dehydrogenase 2; (referred to herein as HSD2), that oxidizes cortisol to the inactive metabolite cortisone. HSD2, thus prevents MR activation and therefore inhibits excretion of potassium.

Accordingly, inhibition of HSD2 to prevent inactivation of cortisol activation of the MR is a promising mechanism for promoting potassium excretion, for example, in the treatment of hyperkalemia.

SUMMARY OF THE INVENTION

In one aspect of the present invention there is provided a compound of formula I or a salt thereof:

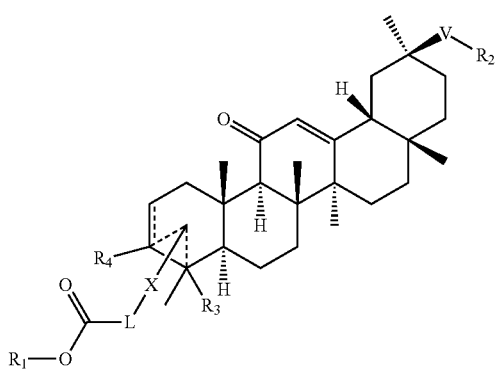

I wherein,
X is a bond, —O—, —C(O)—, —N($R_x$)—, —C(O)N ($R_x$)—, —N($R_x$)—C(O)—, —S(O)$_n$—N($R_x$)— or —N($R_x$)—S(O)$_n$—;
V is —C(O)O—, —C(O)N($R_5$)—, —C(O)N($R_5$)O—, —NH—C(O)—N($R_5$)— or NH—S(O)$_n$—;
L is a bond, alkylene wherein one or more non-adjacent methylene groups of said alkylene are replaced with —O—; divalent aryl or divalent heteroaryl; or L is alkylene-Y-alkylene wherein Y is O, N$R_x$, S, SO, SO$_2$ or a divalent heterocycle; wherein said alkylene groups are optionally substituted with OH, —C(O)O—$R_1$, alkyl or alkyl substituted with OH or —C(O)O—$R_1$; and wherein a carbon of said alkylene groups and $R_x$ optionally together form a heterocycle; provided that when X is other than a bond, then L is other than a bond;

$R_1$ is alkyl optionally substituted with halogen, OH, amino, oxo, carboxy, acyloxy, alkoxycarbonyl, alkoxyacyloxy, alkoxycarbonyloxy, aminocarbonyl, a carbocycle optionally substituted with alkyl, haloalkyl, oxo, amino and halogen and a heterocycle optionally substituted with alkyl, oxo, amino and halogen; and a carbocycle or heterocycle optionally substituted with alkyl, haloalkyl, oxo, amino and halogen; wherein one or more non-adjacent methylene groups in any of the foregoing alkyl groups is replaced with O;
$R_2$ is H or $R_1$;
$R_3$ is absent, Me; provided that when —X-L-C(O)O—$R_1$ depends from the carbon to which $R_3$ depends then $R_3$ is absent; or $R_3$ is —Z-L-C(O)O—$R_1$ wherein Z is a bond, —O—, —N($R_x$)—, —C(O)N($R_x$)—, —N($R_x$)—C(O)—, —S(O)$_n$—N($R_x$)— or —N($R_x$)—S(O)$_n$—; and
$R_4$ is absent, H or OH; provided that when —X-L-C(O) O—$R_1$ depends from the carbon to which $R_4$ depends then $R_4$ is H or absent;
$R_5$ is H or alkyl;
$R_x$ is H, —C(O)O—$R_1$, or alkyl optionally substituted with —C(O)O—$R_1$; and
n is 1 or 2.

In another aspect of the invention, there are provided compositions comprising compounds of Formula I and a carrier, diluent or excipient.

In another aspect of the invention, there is provided a method of inhibiting conversion of cortisol to cortisone by HSD2 comprising contacting HSD2 with a compound of Formula I.

In another aspect of the invention, there is provided a method for promoting activation MR in a mammal, comprising administering to said mammal an effective amount of a compound of Formula I.

In another aspect of the invention, there is provided a method of reducing potassium levels in plasma of a mammal, comprising administering to said mammal an effective amount of a compound of Formula I.

In another aspect of the invention, there is provided a method for promoting potassium ion secretion into the colonic lumen of a mammal, comprising administering to said mammal an effective amount of a compound of Formula I.

In another aspect of the invention, there is provided a method for treating hyperkalemia in a mammal, comprising administering to said mammal an effective amount of a compound of Formula I.

In another aspect of the invention, there is provided a method for treating or preventing hyperkalemia in a mammal comprising coadministering a compound of Formula I with an inhibitor of the renin-angiotensin-aldosterone system (RAAS).

DETAILED DESCRIPTION OF THE INVENTION

Figure 1:
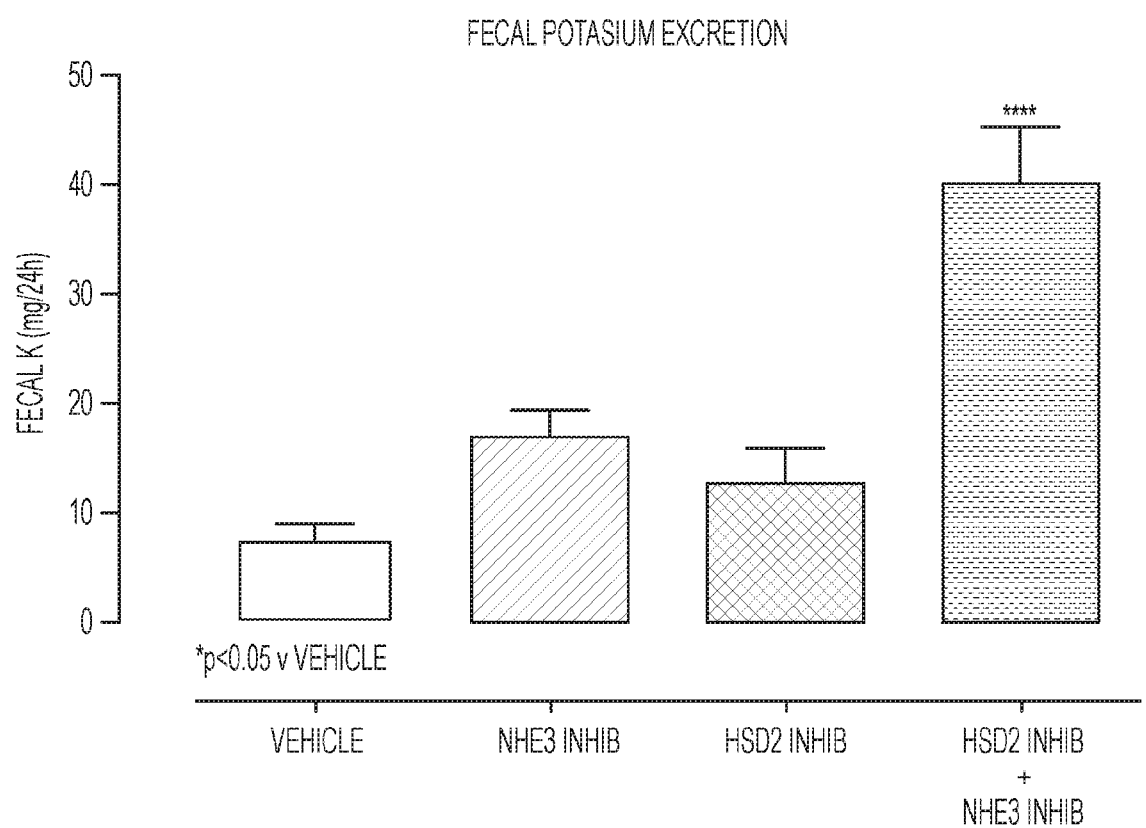
FIG. 1 illustrates the synergistic effect on potassium excretion in feces upon administration of an HSD2 inhibitor in combination with an NHE3 inhibitor.
Figure 2:
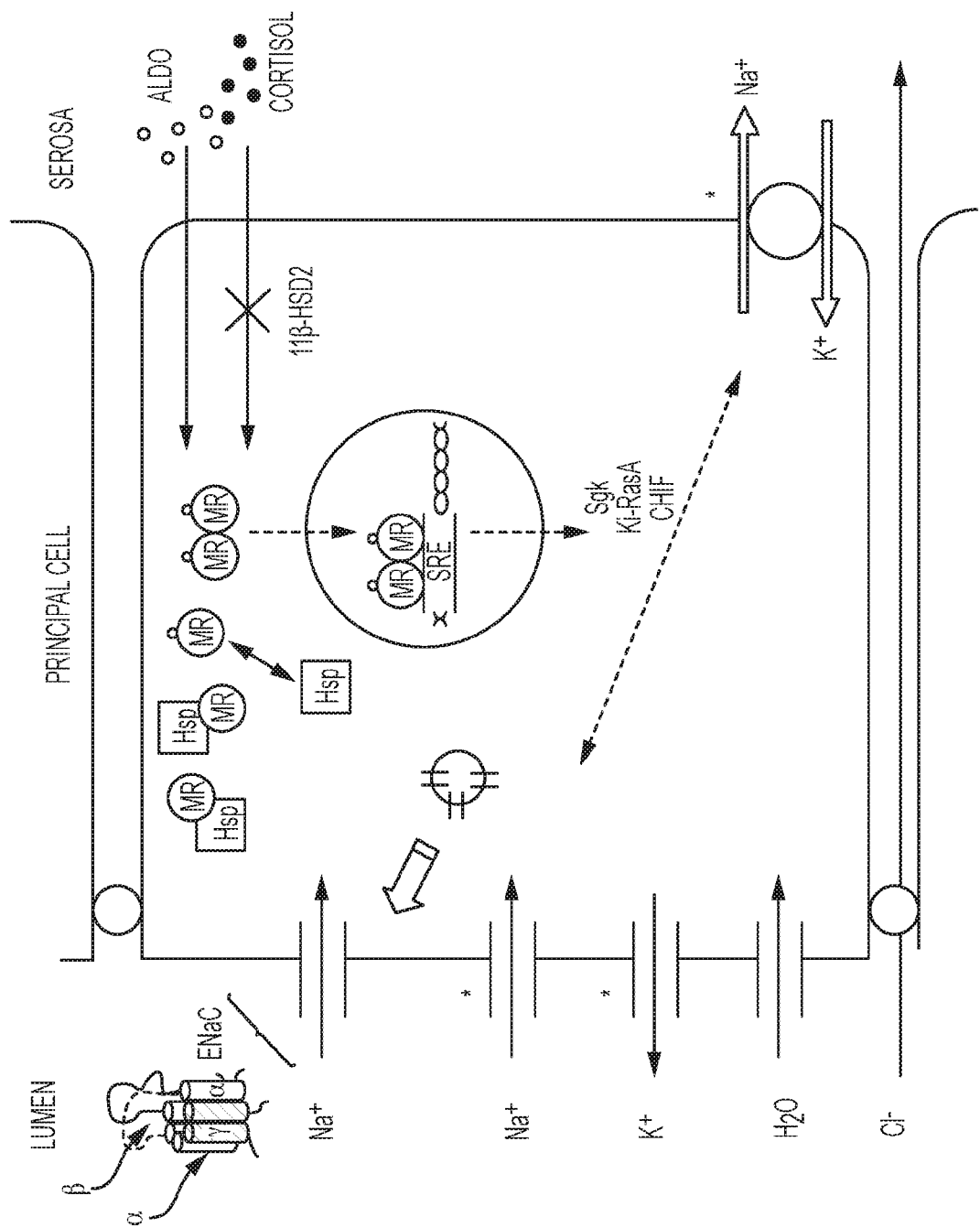
FIG. 2 is an illustration of 11-β-hydroxysteroid dehydrogenase 2 (HSD2) inhibition in an epithelial cell allowing cortisol to activate the mineralocorticoid receptor (MR) which facilitates excretion of potassium into the lumen.
Figure 3:
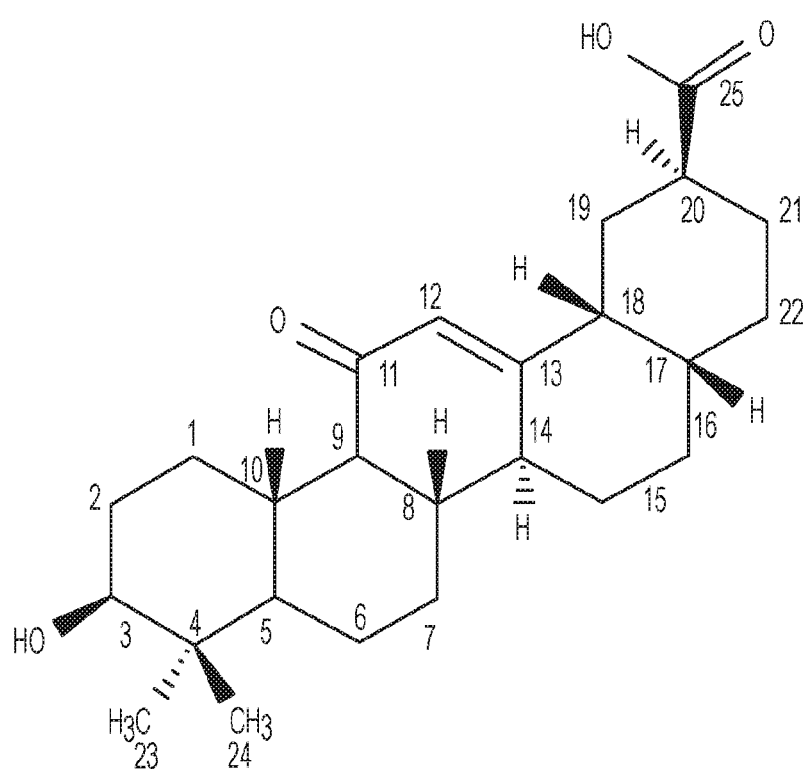
FIG. 3 depicts the structure of glycyrrhetinic acid with the numbering of the carbon atoms.

Glycyrrhizin (or glycyrrhizie acid or glycyrrtzinic acid) is extract of the plant called *Glycyrrhiza* which is derived from the ancient Greek term 'glykos', meaning sweet, and 'rhiza', meaning root. *Glycyrrhiza* was indulged upon by many prophets and pharaohs. Licorice extract has been utilized in the battlefields and the desert where soldiers and travelers drank it to suppress their thirst sensation on long marches. Glycyrrhetic acid, the active metabolite in licorice, inhibits HSD2 with a resultant cortisol-induced mineralocorticoid effect and the tendency towards the reduction of potassium levels. While glycyrrhetic acid lowers potassium levels, it is associated with abnormal heart rhythms, hypertension, edema, lethargy, congestive heart failure, hypokalemia and rhabdomyolysis. Accordingly, it would be desirable to provide a compound that promotes potassium excretion in patients suffering from hyperkalemia like glycyrrhetinic acid without the undesirable side effects.

The present invention provides a compound of formula I or a salt thereof:

wherein,

X is a bond, —O—, —C(O)—, —N($R_x$)—, —C(O)N($R_x$)—, —N($R_x$)—C(O)—, —S(O)$_n$—N($R_x$)— or —N($R_x$)—S(O)$_n$—;

V is —C(O)O—, —C(O)N($R_5$)—, —C(O)N($R_5$)O—, —NH—C(O)—N($R_5$)— or NH—S(O)$_n$—;

L is a bond, alkylene wherein one or more non-adjacent methylene groups of said alkylene are replaced with —O—; divalent aryl or divalent heteroaryl; or L is alkylene-Y-alkylene wherein Y is O, N$R_x$, S, SO, SO$_2$ or a divalent heterocycle; wherein said alkylene groups are optionally substituted with OH, —C(O)O—$R_1$, alkyl or alkyl substituted with OH or —C(O)O—$R_1$; and wherein a carbon of said alkylene groups and $R_x$ optionally together form a heterocycle; provided that when X is other than a bond, then L is other than a bond;

$R_1$ is alkyl optionally substituted with halogen, OH, amino, oxo, carboxy, acyloxy, alkoxycarbonyl, alkoxyacyloxy, alkoxycarbonyloxy, aminocarbonyl, a carbocycle optionally substituted with alkyl, haloalkyl, oxo, amino and halogen and a heterocycle optionally substituted with alkyl, oxo, amino and halogen; and a carbocycle or heterocycle optionally substituted with alkyl, haloalkyl, oxo, amino and halogen; wherein one or more non-adjacent methylene groups in any of the foregoing alkyl groups is replaced with O;

$R_2$ is H or $R_1$;

$R_3$ is absent, Me; provided that when —X-L-C(O)O—$R_1$ depends from the carbon to which $R_3$ depends then $R_3$ is absent; or $R_3$ is —Z-L-C(O)O—$R_1$ wherein Z is a bond, —O—, —N($R_x$)—, —C(O)N($R_x$)—, —N($R_x$)—C(O)—, —S(O)$_n$—N($R_x$)— or —N($R_x$)—S(O)$_n$—; and $R_4$ is absent, H or OH; provided that when —X-L-C(O)O—$R_1$ depends from the carbon to which $R_4$ depends then $R_4$ is H or absent;

$R_5$ is H or alkyl;

$R_x$ is H, —C(O)O—$R_1$, or alkyl optionally substituted with —C(O)O—$R_1$; and n is 1 or 2.

In a particular embodiment, compounds of the invention contain an ester moiety pending from the 3-, 23- and/or 24-position of the fused ring system. In an embodiment, following administration to a subject of a compound of the invention, the ester moiety is metabolized in plasma or liver to a less active acid form. In another embodiment, the compound of the invention has equal or greater HSD2 inhibitory activity than glycyrrhetinic acid. In another embodiment, the compound of the invention has greater HSD2 inhibitory activity than glycyrrhetinic acid.

"Acyl" means a carbonyl containing substituent represented by the formula —C(O)—R in which R is H, alkyl, a carbocycle, a heterocycle, carbocycle-substituted alkyl or heterocycle-substituted alkyl, wherein the alkyl, alkoxy, carbocycle and heterocycle are as defined herein. Acyl groups include alkanoyl (e.g., acetyl), aroyl (e.g., benzoyl), and heteroaroyl.

"Alkyl" means a branched or unbranched, saturated or unsaturated (i.e. alkenyl, alkynyl) aliphatic hydrocarbon group, having up to 12 carbon atoms unless otherwise specified. When used as part of another term, for example, "alkylamino", "cycloalkyl", "alkylene" etc., the alkyl portion may be a saturated hydrocarbon chain, however also includes unsaturated hydrocarbon carbon chains such as "alkenylamino" and "alkynylamino. Examples of particular alkyl groups are methyl, ethyl, n-propyl, isopropyl, n-butyl, iso-butyl, sec-butyl, tert-butyl, n-pentyl, 2-methylbutyl, 2,2-dimethylpropyl, n-hexyl, 2-methylpentyl, 2,2-dimethylbutyl, n-heptyl, 3-heptyl, 2-methylhexyl, and the like. The terms "lower alkyl" "$C_1$-$C_4$ alkyl" and "alkyl of 1 to 4 carbon atoms" are synonymous and used interchangeably to mean methyl, ethyl, 1-propyl, isopropyl, cyclopropyl, 1-butyl, sec-butyl or t-butyl. Unless specified, substituted, alkyl groups may contain, for example, one, two, three or four substituents, which may be the same or different. Examples of substituents are, unless otherwise defined, halogen, amino, hydroxyl, protected hydroxyl, mercapto, carboxy, alkoxy, nitro, cyano, amidino, guanidino, urea, sulfonyl, sulfinyl, aminosulfonyl, alkylsulfonylamino, arylsulfonylamino, aminocarbonyl, acylamino, alkoxy, acyl, acyloxy, a carbocycle, and a heterocycle. Examples of the above substituted alkyl groups include, but are not limited to; cyanomethyl, nitromethyl, hydroxymethyl, trityloxymethyl, propionyloxymethyl, aminomethyl, carboxymethyl, carboxyethyl, carboxypropyl, alkyloxycarbonylmethyl, allyloxycarbonylaminomethyl, carbamoyloxymethyl, methoxymethyl, ethoxymethyl, t-butoxymethyl, acetoxymethyl, chloromethyl, bromomethyl, iodomethyl, trifluoromethyl, 6-hydroxyhexyl, 2,4-dichloro(n-butyl), 2-amino(isopropyl), 2-carbamoyloxyethyl and the like. The alkyl group may also be substituted with a carbocycle group. Examples include cyclopropylmethyl, cyclobutylmethyl, cyclopentylmethyl, and cyclohexylmethyl groups, as well as the corresponding -ethyl, -propyl, -butyl, -pentyl, -hexyl groups, etc. Substituted alkyls include substituted methyls, e.g., a methyl group substituted by the same substituents as the "substituted $C_n$-$C_m$ alkyl" group. Examples of the substituted methyl group include groups such as hydroxymethyl, protected hydroxymethyl (e.g., tetrahydropyranyloxymethyl), acetoxymethyl, carbamoyloxymethyl, trifluoromethyl, chloromethyl, carboxymethyl, bromomethyl and iodomethyl. In an embodiment, alkyl is saturated. In an embodiment, alkyl is unsaturated. In an embodiment, alkyl is partially unsaturated.

"Amidine" means the group —C(NH)—NHR in which R is H, alkyl, a carbocycle, a heterocycle, carbocycle-substituted alkyl or heterocycle-substituted alkyl wherein the alkyl, alkoxy, carbocycle and heterocycle are as defined herein. A particular amidine is the group —NH—C(NH)—NH$_2$.

"Amino" means primary (i.e. —NH$_2$), secondary (i.e. —NRH) and tertiary (i.e. —NRR) amines in which R is H, alkyl, a carbocycle, a heterocycle, carbocycle-substituted alkyl or heterocycle-substituted alkyl wherein the alkyl, alkoxy, carbocycle and heterocycle are as defined herein. Particular secondary and tertiary amines are alkylamine, dialkylamine, arylamine, diarylamine, aralkylamine and diaralkylamine, wherein the alkyl is as herein defined and optionally substituted. Particular secondary and tertiary amines are methylamine, ethylamine, propylamine, isopropylamine, phenylamine, benzylamine dimethylamine, diethylamine, dipropylamine and diisopropylamine.

"Amino-protecting group" as used herein refers to a derivative of the groups commonly employed to block or protect an amino group while reactions are carried out on other functional groups on the compound. Examples of such protecting groups include carbamates, amides, alkyl and aryl groups, imines, as well as many N-heteroatom derivatives which can be removed to regenerate the desired amine group. Suitable amino-protecting groups (NH-Pg) include acetyl, trifluoroacetyl, t-butyloxycarbonyl ("Boc"), benzyloxycarbonyl ("CBz") and 9-fluorenylmethyleneoxycarbonyl ("Fmoc"). Further examples of these groups are found in Wuts. *Greene's Protective Groups in Organic Synthesis*. 5th ed. New York: John Wiley & Sons, Inc., 2014. The term "protected amino" refers to an amino group substituted with one of the above amino-protecting groups.

"Aryl" when used alone or as part of another term means a carbocyclic aromatic group whether or not fused having the number of carbon atoms designated or if no number is designated, up to 14 carbon atoms. Particular aryl groups are phenyl, naphthyl, biphenyl, phenanthrenyl, naphthacenyl, and the like (see e.g., Dean, J. A., ed. *Lange's Handbook of Chemistry*. 13th ed. New York: McGraw-Hill, 1985, Table 7-2). A particular aryl is phenyl. Substituted phenyl or substituted aryl means a phenyl group or aryl group substituted with one, two, three, four or five substituents, for example 1-2, 1-3 or 1-4 substituents chosen, unless otherwise specified, from halogen (F, Cl, Br, I), hydroxy, protected hydroxy, cyano, nitro, alkyl (for example $C_1$-$C_6$ alkyl), alkoxy (for example $C_1$-$C_6$ alkoxy), benzyloxy, carboxy, protected carboxy, carboxymethyl, protected carboxymethyl, hydroxymethyl, protected hydroxymethyl, aminomethyl, protected aminomethyl, trifluoromethyl, alkylsulfonylamino, alkylsulfonylaminoalkyl, arylsulfonylamino, arylsulonylaminoalkyl, heterocyclylsulfonylamino, heterocyclylsulfonylaminoalkyl, heterocyclyl, aryl, or other groups specified. One or more methyne (CH) and/or methylene (CH$_2$) groups in these substituents may in turn be substituted with a similar group as those denoted above. Examples of the term "substituted phenyl" includes but is not limited to a mono- or di(halo)phenyl group, such as 2-chlorophenyl, 2-bromophenyl, 4-chlorophenyl, 2,6-dichlorophenyl, 2,5-dichlorophenyl, 3,4-dichlorophenyl, 3-chlorophenyl, 3-bromophenyl, 4-bromophenyl, 3,4-dibromophenyl, 3-chloro-4-fluorophenyl, 2-fluorophenyl and the like; a mono- or di(hydroxy)phenyl group such as 4-hydroxyphenyl, 3-hydroxyphenyl, 2,4-dihydroxyphenyl, the protected-hydroxy derivatives thereof and the like; a nitrophenyl group such as 3- or 4-nitrophenyl; a cyanophenyl group, for example, 4-cyanophenyl; a mono- or di(lower alkyl)phenyl group such as 4-methylphenyl, 2,4-dimethylphenyl, 2-methylphenyl, 4-(isopropyl)phenyl, 4-ethylphenyl, 3-(n-propyl)phenyl and the like; a mono or di(alkoxy) phenyl group, for example, 3,4-dimethoxyphenyl, 3-methoxy-4-benzyloxyphenyl, 3-methoxy-4-(1-chloromethyl)benzyloxy-phenyl, 3-ethoxyphenyl, 4-(isopropoxy) phenyl, 4-(t-butoxy)phenyl, 3-ethoxy-4-methoxyphenyl and the like; 3- or 4-trifluoromethylphenyl; a mono- or dicarboxyphenyl or (protected carboxy)phenyl group such as 4-carboxyphenyl; a mono- or di(hydroxymethyl)phenyl or (protected hydroxymethyl)phenyl such as 3-(protected hydroxymethyl)phenyl or 3,4-di(hydroxymethyl)phenyl; a mono- or di(aminomethyl)phenyl or (protected aminomethyl)phenyl such as 2-(aminomethyl)phenyl or 2,4-(protected aminomethyl)phenyl; a mono- or di(N-(methylsulfonylamino))phenyl such as 3-(N-methylsulfonylamino))phenyl; disubstituted phenyl groups such as 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy-4-chlorophenyl; trisubstituted phenyl groups such as 3-methoxy-4-benzyloxy-6-methyl sulfonylamino, 3-methoxy-4-benzyloxy-6-phenyl sulfonylamino; and tetrasubstituted phenyl groups such as 3-methoxy-4-benzyloxy-5-methyl-6-phenyl sulfonylamino. Particular substituted phenyl groups include the 2-chlorophenyl, 2-aminophenyl, 2-bromophenyl, 3-methoxyphenyl, 3-ethoxy-phenyl, 4-benzyloxyphenyl, 4-methoxyphenyl, 3-ethoxy-4-benzyloxyphenyl, 3,4-diethoxyphenyl, 3-methoxy-4-benzyloxyphenyl, 3-methoxy-4-(1-chloromethyl)benzyloxy-phenyl, 3-methoxy-4-(1-chloromethyl)benzyloxy-6-methyl sulfonyl aminophenyl groups. Fused aryl rings may also be substituted with any, for example 1, 2 or 3, of the substituents specified herein in the same manner as substituted alkyl groups.

"Carbocyclyl", "carbocyclic", "carbocycle" and "carbocyclo" alone and when used as a moiety in a complex group such as a carbocycloalkyl group, refer to a mono-, bi-, or tricyclic aliphatic ring having 3 to 14 carbon atoms, for example 3 to 7 carbon atoms or 3 to 6 carbon atoms, which may be saturated or unsaturated, aromatic or non-aromatic. Particular saturated carbocyclic groups are cyclopropyl, cyclobutyl, cyclopentyl and cyclohexyl groups. A particular saturated carbocycle is cyclopropyl. Another particular saturated carbocycle is cyclohexyl. Particular unsaturated carbocycles are aromatic e.g. aryl groups as previously defined, for example phenyl. The terms "substituted carbocyclyl", "carbocycle" and "carbocyclo" mean these groups substituted by the same substituents as the "substituted alkyl" group.

"Carboxy-protecting group" as used herein refers to one of the ester derivatives of the carboxylic acid group commonly employed to block or protect the carboxylic acid group while reactions are carried out on other functional groups on the compound. Examples of such carboxylic acid protecting groups include 4-nitrobenzyl, 4-methoxybenzyl, 3,4-dimethoxybenzyl, 2,4-dimethoxybenzyl, 2,4,6- trimethoxybenzyl, 2,4,6-trimethylbenzyl, pentamethylbenzyl, 3,4-methylenedioxybenzyl, benzhydryl, 4,4'-dimethoxybenzhydryl, 2,2',4,4'-tetramethoxybenzhydryl, alkyl such as t-butyl or t-amyl, trityl, 4-methoxytrityl, 4,4'-dimethoxytrityl, 4,4',4''-trimethoxytrityl, 2-phenylprop-2-yl, trimethylsilyl, t-butyldimethylsilyl, phenacyl, 2,2,2-trichloroethyl, beta-(trimethylsilyl)ethyl, beta-(di(n-butyl)methylsilyl)ethyl, p-toluenesulfonylethyl, 4-nitrobenzylsulfonylethyl, allyl, cinnamyl, 1-(trimethylsilylmethyl)prop-1-en-3-yl, and like moieties. The species of carboxy-protecting group employed is not critical so long as the derivatized carboxylic acid is stable to the condition of subsequent reaction(s) on other positions of the molecule and can be removed at the appropriate point without disrupting the remainder of the molecule. In particular, it is important not to subject a carboxy-protected molecule to strong nucleophilic bases, such as lithium hydroxide or NaOH, or reductive conditions employing highly activated metal hydrides such as $LiAH_4$. Such harsh removal conditions are also to be avoided when removing amino-protecting groups and hydroxy-protecting groups, discussed below. Particular carboxylic acid protecting groups are the alkyl (e.g., methyl, ethyl, t-butyl), allyl, benzyl and p-nitrobenzyl groups. Similar carboxy-protecting groups used in the cephalosporin, penicillin and peptide arts can also be used to protect carboxy group substituents. Further examples of these groups are found in Greene, T.W., and P.G.M. Wuts. *Protective Groups in Organic Synthesis*. 2nd ed. New York: John Wiley & Sons, Inc. 1991, Chapter 5; Haslam, E. *Protective Groups in Organic Chemistry*. New York: Plenum Press 1973, Chapter 5; and Greene, T.W. *Protective Groups in Organic Synthesis*. New York: John Wiley & Sons, Inc. 1981, Chapter 5. The term "protected carboxy" refers to a carboxy group substituted with one of the above carboxy-protecting groups.

"Alkoxycarbonyl" means the group —C(=O)OR in which R is alkyl. A particular group is $C_1$-$C_6$ alkoxycarbonyl, wherein the R group is $C_1$-$C_6$ alkyl.

"Guanidine" means the group —NH—C(NH)—NHR in which R is hydrogen, alkyl, a carbocycle, a heterocycle, carbocycle-substituted alkyl or heterocycle-substituted alkyl, wherein the alkyl, alkoxy, carbocycle and heterocycle are as defined herein. A particular guanidine is the group —NH—C(NH)—$NH_2$.

"Hydroxy-protecting group" as used herein refers to a derivative of the hydroxy group commonly employed to block or protect the hydroxy group while reactions are carried out on other functional groups on the compound. Examples of such protecting groups include tetrahydropyranyloxy, benzoyl, acetoxy, carbamoyloxy, benzyl, and silylethers (e.g., TBS, TBDPS) groups. Further examples of these groups are found in Greene, T.W., and P.G.M. Wuts. *Protective Groups in Organic Synthesis*. 2nd ed. New York: John Wiley & Sons, Inc. 1991, Chapters 2-3; Haslam, E. *Protective Groups in Organic Chemistry*. New York: Plenum Press 1973, Chapter 5; and Greene, T.W. *Protective Groups in Organic Synthesis*. New York: John Wiley & Sons, Inc. 1981. The term "protected hydroxy" refers to a hydroxy group substituted with one of the above hydroxy-protecting groups.

"Heterocyclic group", "heterocyclic", "heterocycle", "heterocyclyl", or "heterocyclo" alone and when used as a moiety in a complex group such as a heterocycloalkyl group, are used interchangeably and refer to any mono-, bi-, or tricyclic, saturated or unsaturated, aromatic (heteroaryl) or non-aromatic ring having the number of atoms designated, generally from 5 to about 14 ring atoms, where the ring atoms are carbon and at least one heteroatom (nitrogen, sulfur or oxygen), for example 1 to 4 heteroatoms. Heterocyclic groups include four to seven membered cyclic groups containing one, two or three heteroatoms selected from the group consisting of nitrogen, oxygen and sulfur. Typically, a 5-membered ring has 0 to 2 double bonds and 6- or 7-membered ring has 0 to 3 double bonds. The nitrogen or sulfur heteroatoms may optionally be oxidized (e.g., SO, $SO_2$), and any nitrogen heteroatom may optionally be quaternized. Particular non-aromatic heterocycles are morpholinyl (morpholino), pyrrolidinyl, oxiranyl, oxetanyl, tetrahydrofuranyl, 2,3-dihydrofuranyl, 2H-pyranyl, tetrahydropyranyl, thiiranyl, thietanyl, tetrahydrothietanyl, aziridinyl, azetidinyl, 1-methyl-2-pyrrolyl, piperazinyl and piperidinyl. A "heterocycloalkyl" group is a heterocycle group as defined above covalently bonded to an alkyl group as defined above. Particular 5-membered heterocycles containing a sulfur or oxygen atom and one to three nitrogen atoms are thiazolyl, in particular thiazol-2-yl and thiazol-2-yl N-oxide, thiadiazolyl, in particular 1,3,4-thiadiazol-5-yl and 1,2,4-thiadiazol-5-yl, oxazolyl, for example oxazol-2-yl, and oxadiazolyl, such as 1,3,4-oxadiazol-5-yl, and 1,2,4-oxadiazol-5-yl. Particular 5-membered ring heterocycles containing 2 to 4 nitrogen atoms include imidazolyl, such as imidazol-2-yl; triazolyl, such as 1,3,4-triazol-5-yl; 1,2,3-triazol-5-yl, 1,2,4-triazol-5-yl, and tetrazolyl, such as 1H-tetrazol-5-yl. Particular benzo-fused 5-membered heterocycles are benzoxazol-2-yl, benzthiazol-2-yl and benzimidazol-2-yl. Particular 6-membered heterocycles contain one to three nitrogen atoms and optionally a sulfur or oxygen atom, for example pyridyl, such as pyrid-2-yl, pyrid-3-yl, and pyrid-4-yl; pyrimidyl, such as pyrimid-2-yl and pyrimid-4-yl; triazinyl, such as 1,3,4-triazin-2-yl and 1,3,5-triazin-4-yl; pyridazinyl, in particular pyridazin-3-yl, and pyrazinyl. The pyridine N-oxides and pyridazine N-oxides and the pyridyl, pyrimid-2-yl, pyrimid-4-yl, pyridazinyl and the 1,3,4-triazin-2-yl groups, are a particular group. Substituents for "optionally substituted heterocycles", and further examples of the 5- and 6-membered ring systems discussed above can be found in W. Druckheimer et al., U.S. Pat. No. 4,278,793. In a particular embodiment, such optionally substituted heterocycle groups are substituted with hydroxyl, alkyl, alkoxy, acyl, halogen, mercapto, oxo, carboxyl, acyl, halo-substituted alkyl, amino, cyano, nitro, amidino and guanidino.

"Heteroaryl" alone and when used as a moiety in a complex group such as a heteroaralkyl group, refers to any mono-, bi-, or tricyclic aromatic ring system having the number of atoms designated where at least one ring is a 5-, 6- or 7-membered ring containing from one to four heteroatoms selected from the group nitrogen, oxygen, and sulfur, and in a particular embodiment at least one heteroatom is nitrogen (Lange's Handbook of Chemistry, supra). In one example, the heteroaryl is a five to six membered aromatic ring containing one, two or three heteroatoms selected from nitrogen, oxygen and sulfur. Included in the definition are any bicyclic groups where any of the above heteroaryl rings are fused to a benzene ring. Particular heteroaryls incorporate a nitrogen or oxygen heteroatom. The following ring systems are examples of the heteroaryl (whether substituted or unsubstituted) groups denoted by the term "heteroaryl": thienyl, furyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, thiazinyl, oxazinyl, triazinyl, thiadiazinyl, oxadiazinyl, dithiazinyl, dioxazinyl, oxathiazinyl, tetrazinyl, thiatriazinyl, oxatriazinyl, dithiadiazinyl, imidazolinyl, dihydropyrimidyl, tetrahydropyrimidyl, tetrazolo[1, 5-b]pyridazinyl and purinyl, as well as benzo-fused derivatives, for example benzoxazolyl, benzofuryl, benzothiazolyl, benzothiadiazolyl, benzotriazolyl, benzoimidazolyl and indolyl. A particular "heteroaryl" may be selected from: 1,3-thiazol-2-yl, 4-(carboxymethyl)-5-methyl-1,3-thiazol-2-yl, 4-(carboxymethyl)-5-methyl-1,3-thiazol-2-yl, 1,2,4-thiadiazol-5-yl, 3-methyl-1,2,4-thiadiazol-5-yl, 1,3,4-triazol-5-yl, 2-methyl-1,3,4-triazol-5-yl, 2-hydroxy-1,3,4-triazol-5-yl, 2-carboxy-4-methyl-1,3,4-triazol-5-yl, 2-carboxy-4-methyl-1,3,4-triazol-5-yl, 1,3-oxazol-2-yl, 1,3,4-oxadiazol-5-yl, 2-methyl-1,3,4-oxadiazol-5-yl, 2-(hydroxymethyl)-1,3,4-oxadiazol-5-yl, 1,2,4-oxadiazol-5-yl, 1,3,4-thiadiazol-5-yl, 2-thiol-1,3,4-thiadiazol-5-yl, 2-(methylthio)-1,3,4-thiadiazol-5-yl,2-amino-1,3,4-thiadiazol-5-yl,1H-tetrazol-5-yl,1-methyl-1H-tetrazol-5-yl, 1-(1-(dimethylamino)eth-2-yl)-1H-tetrazol-5-yl, 1-(carboxymethyl)-1H-tetrazol-5-yl, 1-(carboxymethyl)-1H-tetrazol-5-yl, 1-(methylsulfonic acid)-1H-tetrazol-5-yl, 1-(methylsulfonic acid)-1H-tetrazol-5-yl, 2-methyl-1H-tetrazol-5-yl, 1,2,3-triazol-5-yl, 1-methyl-1,2,3-triazol-5-yl, 2-methyl-1,2,3-triazol-5-yl, 4-methyl-1,2,3-triazol-5-yl, pyrid-2-yl N-oxide, 6-methoxy-2-(n-oxide)-pyridaz-3-yl, 6-hydroxypyridaz-3-yl, 1-methylpyrid-2-yl, 1-methylpyrid-4-yl, 2-hydroxypyrimid-4-yl, 1,4,5,6-tetrahydro-5,6-dioxo-4-methyl-as-triazin-3-yl, 1,4,5,6-tetrahydro-4-(formylmethyl)-5,6-dioxo-as-triazin-3-yl, 2,5-dihydro-5-oxo-6-hydroxy-astriazin-3-yl, 2,5-dihydro-5-oxo-6-hydroxy-as-triazin-3-yl, 2,5-dihydro-5-oxo-6-hydroxy-2-methyl-astriazin-3-yl, 2,5-dihydro-5-oxo-6-hydroxy-2-methyl-as-triazin-3-yl, 2,5-dihydro-5-oxo-6-methoxy-2-methyl-as-triazin-3-yl, 2,5-dihydro-5-oxo-as-triazin-3-yl, 2,5-dihydro-5-oxo-2-methyl-as-triazin-3-yl, 2,5-dihydro-5-oxo-2,6-dimethyl-as-triazin-3-yl, tetrazolo[1,5-b]pyridazin-6-yl and 8-aminotetrazolo[1,5-b]-pyridazin-6-yl. An alternative group of "heteroaryl" includes; 4-(carboxymethyl)-5-methyl-1,3-thiazol-2-yl, 4-(carboxymethyl)-5-methyl-1,3-thiazol-2-yl, 1,3,4-triazol-5-yl, 2-methyl-1,3,4-triazol-5-yl, 1H-tetrazol-5-yl, 1-methyl-1H-tetrazol-5-yl, 1-(1-(dimethylamino)eth-2-yl)-1H-tetrazol-5-yl, 1-(carboxymethyl)-1H-tetrazol-5-yl, 1-(carboxymethyl)-1H-tetrazol-5-yl, 1-(methylsulfonic acid)-1H-tetrazol-5-yl, 1-(methylsulfonic acid)-1H-tetrazol-5-yl, 1,2,3-triazol-5-yl, 1,4,5,6-tetrahydro-5,6-dioxo-4-methyl-as-triazin-3-yl, 1,4,5,6-tetrahydro-4-(2-formylmethyl)-5,6-dioxo-as-triazin-3-yl, 2,5-dihydro-5-oxo-6-hydroxy-2-methyl-as-triazin-3-yl, 2,5-dihydro-5-oxo-6-hydroxy-2-methyl-as-triazin-3-yl, tetrazolo[1,5-b]pyridazin-6-yl, and 8-aminotetrazolo[1,5-b] pyridazin-6-yl. Heteroaryl groups are optionally substituted as described for heterocycles.

"Inhibitor" means a compound which reduces or prevents the enzymatic conversion of cortisol to cortisone by HSD2.

"Optionally substituted" unless otherwise specified means that a group may be unsubstituted or substituted by one or more (e.g., 0, 1, 2, 3 or 4) of the substituents listed for that group, as valency allows, in which said substituents may be the same or different. In one embodiment, an optionally substituted group has 1 substituent. In another embodiment, an optionally substituted group has 2 substituents. In another embodiment, an optionally substituted group has 3 substituents.

"Pharmaceutically acceptable salts" include both acid and base addition salts. "Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, carbonic acid, phosphoric acid and the like, and organic acids may be selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, p-toluenesulfonic acid, salicyclic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Particularly base addition salts are the ammonium, potassium, sodium, calcium and magnesium salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, polyamine resins and the like. Particularly organic non-toxic bases are isopropylamine, diethylamine, ethanolamine, trimethamine, dicyclohexylamine, choline, and caffeine.

"Sulfanyl" means —S—R group in which R is alkyl, a carbocycle, a heterocycle, carbocycle-substituted alkyl or heterocycle-substituted alkyl, wherein the alkyl, alkoxy, carbocycle and heterocycle are as defined herein. Particular sulfanyl groups are alkylsulfanyl (i.e., —SO$_2$-alkyl), for example methylsulfanyl; arylsulfanyl, for example phenylsulfanyl; aralkylsulfanyl, for example benzylsulfanyl.

"Sulfinyl" means —SO—R group in which R is hydrogen, alkyl, a carbocycle, a heterocycle, carbocycle-substituted alkyl or heterocycle-substituted alkyl, wherein the alkyl, alkoxy, carbocycle and heterocycle are as defined herein. Particular sulfonyl groups are alkylsulfinyl (i.e., —SO-alkyl), for example methylsulfinyl; arylsulfinyl, for example phenylsulfinyl; aralkylsulfinyl, for example benzylsulfinyl.

"Sulfonyl" means a —SO$_2$—R group in which R is hydrogen, alkyl, a carbocycle, a heterocycle, carbocycle-substituted alkyl or heterocycle-substituted alkyl, wherein the alkyl, alkoxy, carbocycle and heterocycle are as defined herein. Particular sulfonyl groups are alkylsulfonyl (i.e. —SO$_2$-alkyl), for example methylsulfonyl; arylsulfonyl, for example phenylsulfonyl; aralkylsulfonyl, for example benzylsulfonyl.

The phrase "and salts and solvates thereof" as used herein means that compounds of the inventions may exist in one or a mixture of salts and solvate forms. For example a compound of the invention may be substantially pure in one particular salt or solvate form or else may be mixtures of two or more salt or solvate forms.

In particular embodiments of the invention, compounds of Formula I have the structures defined by Formula Ia-Ir:
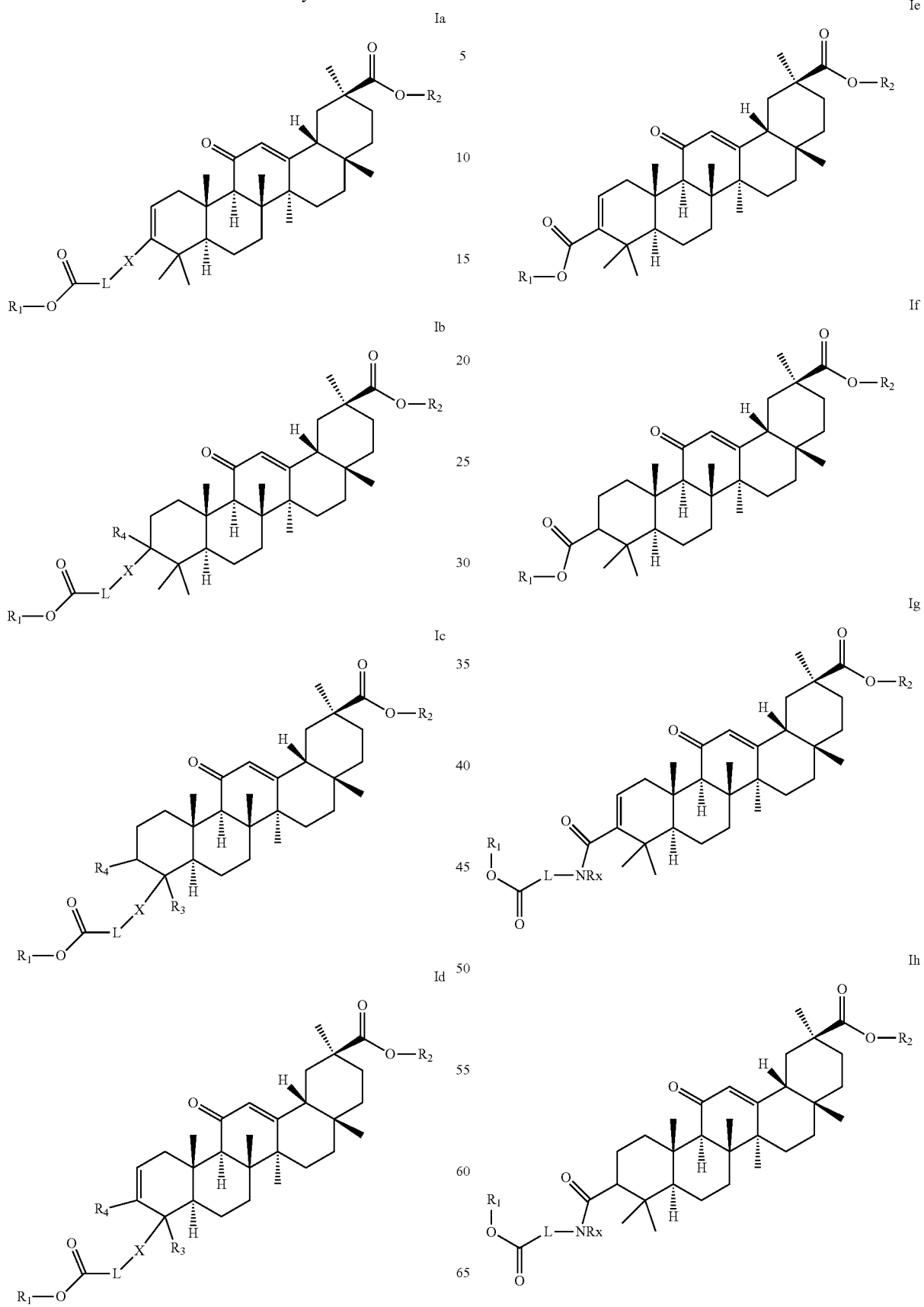

Ii
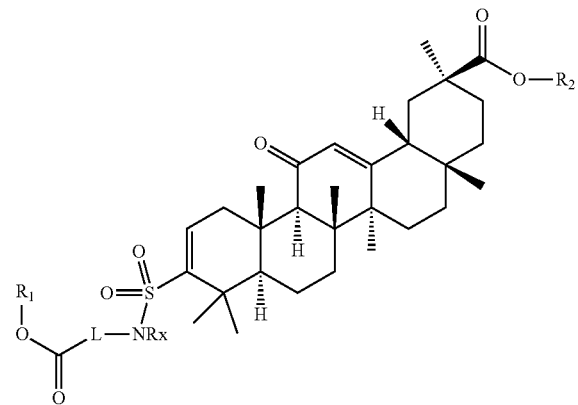
Ij
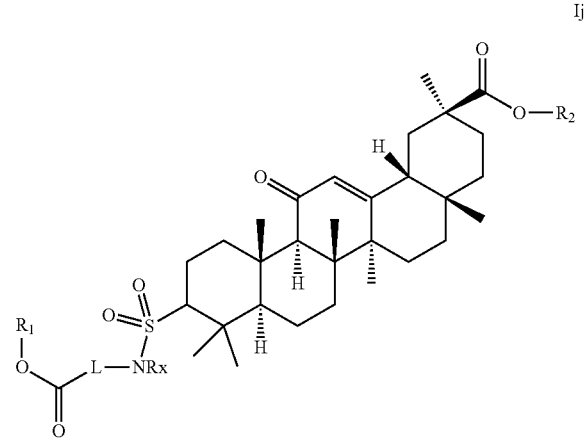
Ik
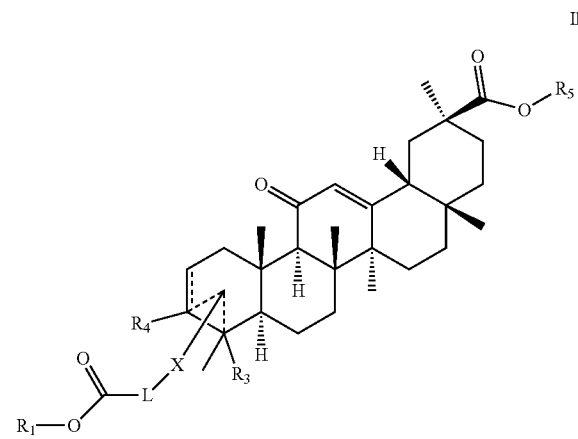
Il
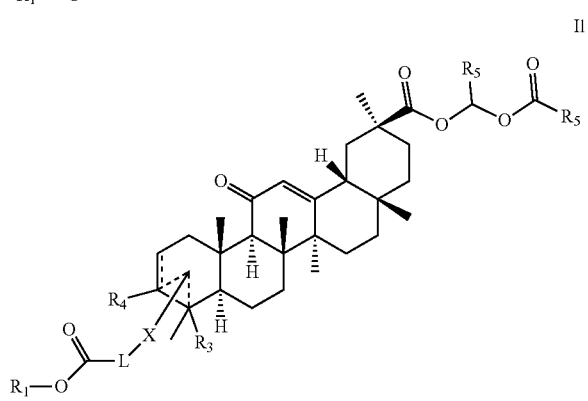
Im
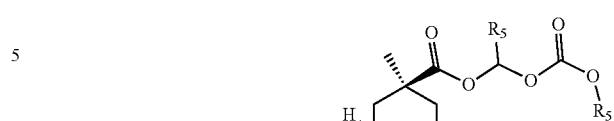
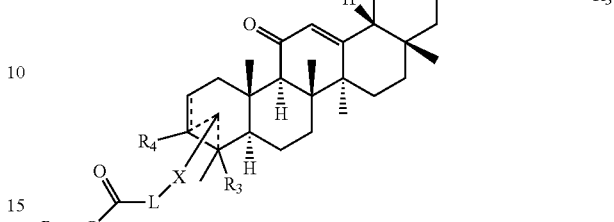
In
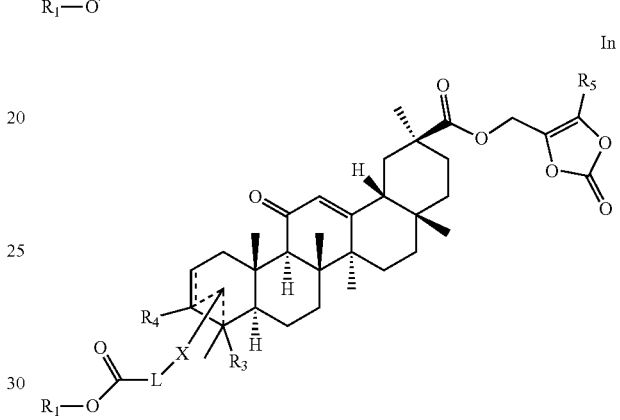
Io
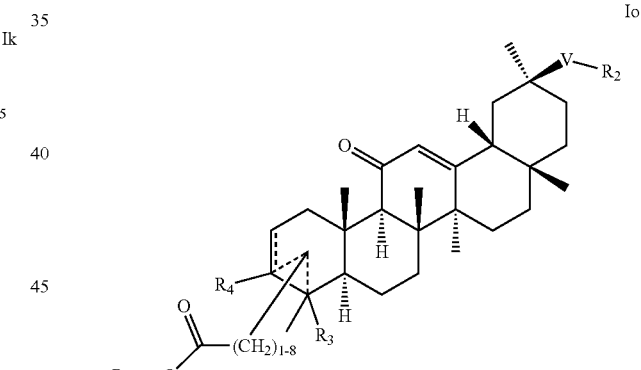
Ip
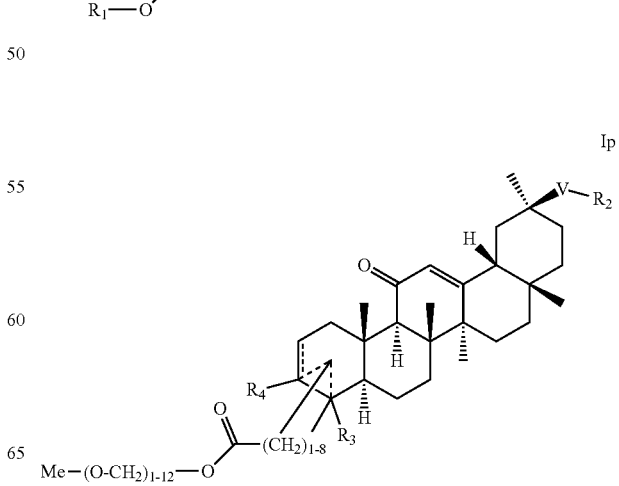

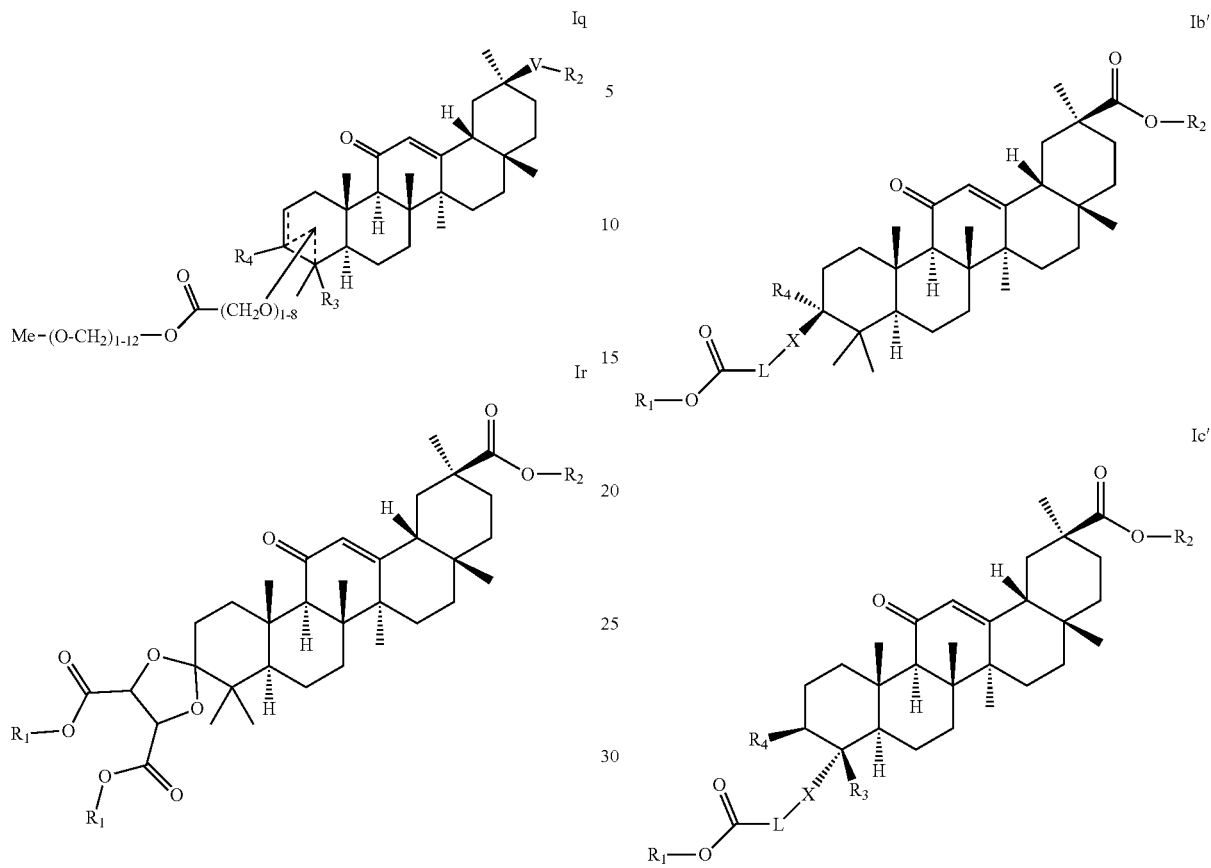

wherein X, L, $R_1$, $R_2$, $R_3$ and $R_4$, are as defined herein. In a particular embodiment, the compounds have the structure according to Formula Ia. In a particular embodiment, the compounds have the structure according to Formula Ib. In a particular embodiment, the compounds have the structure according to Formula Ic. In a particular embodiment, the compounds have the structure according to Formula Id. In a particular embodiment, the compounds have a structure according to Formula Ie. In a particular embodiment, the compounds have a structure according to Formula If. In a particular embodiment, the compounds have a structure according to Formula Ig. In a particular embodiment, the compounds have a structure according to Formula Ih. In a particular embodiment, the compounds have a structure according to Formula Ii. In a particular embodiment, the compounds have a structure according to Formula Ij. In a particular embodiment, the compounds have a structure according to Formula Ik. In a particular embodiment, the compounds have a structure according to Formula Il. In a particular embodiment, the compounds have a structure according to Formula Im. In a particular embodiment, the compounds have a structure according to Formula In. In a particular embodiment, the compounds have a structure according to Formula Io. In a particular embodiment, the compounds have a structure according to Formula Ip. In a particular embodiment, the compounds have a structure according to Formula Iq. In a particular embodiment, the compounds have a structure according to Formula Ir.

In particular embodiments of the invention, compounds of Formula I have the structures defined by Formula Ib', Ic', Id', If', Ih', Ij', Ik', Il', Im', In', Io', Ip' and Iq':

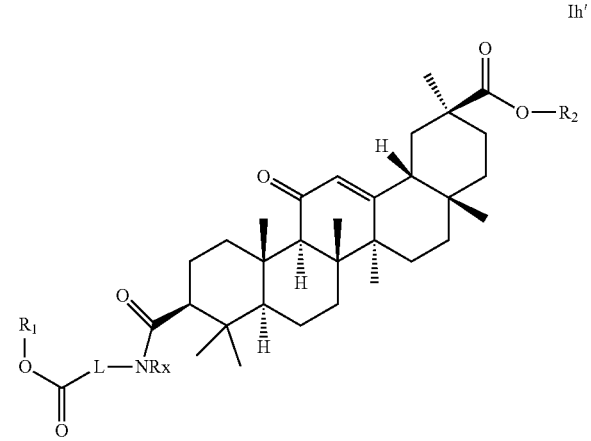
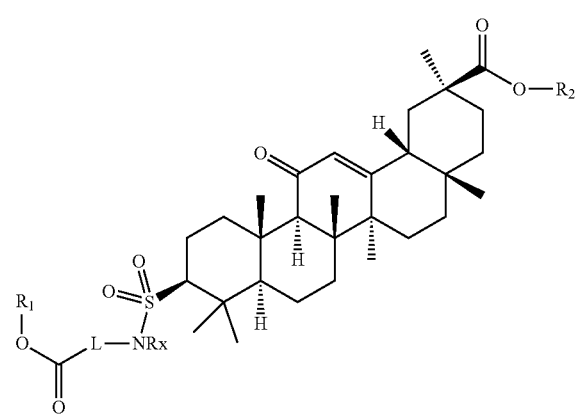
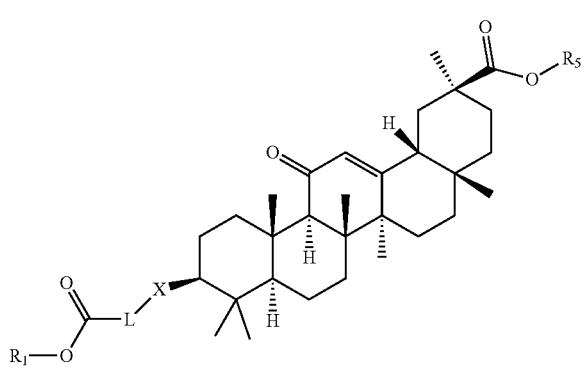
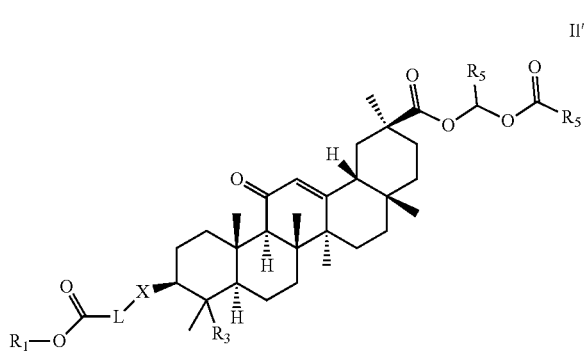
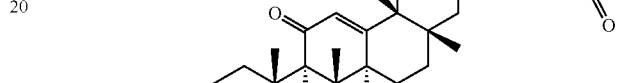
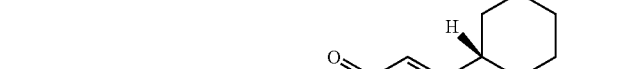
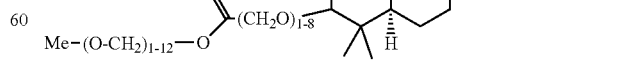
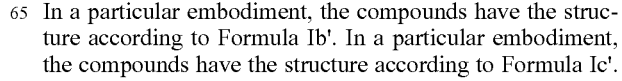
wherein X, L, $R_1$, $R_2$, $R_3$, $R_4$ and $R_5$ are as defined herein.
In a particular embodiment, the compounds have the structure according to Formula Ib'. In a particular embodiment, the compounds have the structure according to Formula Ic'.

In a particular embodiment, the compounds have the structure according to Formula Id'. In a particular embodiment, the compounds have the structure according to Formula If'. In a particular embodiment, the compounds have a structure according to Formula Ih'. In a particular embodiment, the compounds have a structure according to Formula Ij'. In a particular embodiment, the compounds have a structure according to Formula Ik'. In a particular embodiment, the compounds have a structure according to Formula Il'. In a particular embodiment, the compounds have a structure according to Formula Im'. In a particular embodiment, the compounds have a structure according to Formula Io'. In a particular embodiment, the compounds have a structure according to Formula Ip'. In a particular embodiment, the compounds have a structure according to Formula Iq'.

In an embodiment, the compound of the invention has a formula of any one of formula I In an embodiment, X is a bond, —O—, —N($R_x$)—, —C(O)N($R_x$)—, —N($R_x$)—C(O)—, —S(O)$_n$—N($R_x$)— or —N($R_x$)—S(O)$_n$—; wherein $R_x$ is H, —C(O)O—$R_1$, or alkyl optionally substituted with —C(O)O—$R_1$; In an embodiment, X is a bond. In an embodiment, X is —O—. In an embodiment, X is —N($R_x$)—. In an embodiment, X is —NH—. In an embodiment, X is —C(O)N($R_x$)—. In an embodiment, X is —C(O)NH—. In an embodiment, X is —N($R_x$)—C(O)—. In an embodiment, X is —NH—C(O)—. In an embodiment, X is —S(O)$_n$—N($R_x$)—. In an embodiment, X is —S(O)—NH—. In an embodiment, X is —S(O)$_2$—NH—. In an embodiment, X is —N($R_x$)—S(O)$_n$—. In an embodiment, X is —NH—S(O)—. In an embodiment, X is —NH—S(O)$_2$—.

V is —C(O)O—, —C(O)N($R_5$)—, —C(O)N($R_5$)O—, —NH—C(O)—N($R_5$)— or NH—S(O)$_n$—.

In an embodiment, V is —C(O)O—. In an embodiment, V is —C(O)O— and $R_2$ is H. In an embodiment, V is —C(O)O— and $R_2$ is a prodrug group. In an embodiment, V is —C(O)O— and $R_2$ is alkyl. In an embodiment, V is —C(O)O— and $R_2$ is methyl. In another embodiment V is —C(O)O— and $R_2$ is alkyl optionally substituted with oxo, acyloxy, alkoxycarbonyl, alkoxyacyloxy, alkoxycarbonyloxy, a carbocycle optionally substituted with alkyl and oxo, and a heterocycle optionally substituted with alkyl and oxo.

In an embodiment, V is —C(O)N($R_5$)—. In an embodiment, V is —C(O)N($R_5$)— and both $R_2$ and $R_5$ are H. In an embodiment, V is —C(O)N($R_5$)— and $R_2$ and $R_5$ are independently H and alkyl optionally substituted with OH. In an embodiment, V is —C(O)N($R_5$)— and $R_5$ is H and $R_2$ is hydroxyethyl.

In an embodiment, V is —C(O)N($R_5$)O—. In an embodiment, V is —C(O)N($R_5$)O— and $R_2$ and $R_5$ are independently H or alkyl. In an embodiment, V is —C(O)N($R_5$)O— and $R_2$ is methyl and $R_5$ is H.

In an embodiment, V is —NH—C(O)—N($R_5$)— and $R_2$ and $R_5$ are independently H or alkyl. In an embodiment, V is —NH—C(O)—N($R_2$)— and $R_2$ is methyl and $R_5$ is H. In an embodiment, V is —NH—C(O)—N($R_5$)— and both $R_2$ and $R_5$ are H.

In an embodiment, V is NH—S(O)$_n$—. In an embodiment, V is NH—S(O)$_2$—. In an embodiment, V is NH—S(O)$_2$— and $R_2$ is alkyl. In an embodiment, V is NH—S(O)$_2$— and $R_2$ is methyl.

L is a bond, alkylene wherein one or more non-adjacent methylene groups of said alkylene are replaced with —O—; divalent aryl or divalent heteroaryl; or L is alkylene-Y-alkylene wherein Y is O, N$R_x$, S, SO, SO$_2$ or a divalent heterocycle; wherein said alkylene groups are optionally substituted with OH, —C(O)O—$R_1$, alkyl or alkyl substituted with OH or —C(O)O—$R_1$; and wherein a carbon of said alkylene groups and $R_x$ optionally together form a heterocycle; provided that when X is other than a bond, then L is other than a bond;

In an embodiment, L is a bond or alkylene wherein one or more non-adjacent methylene groups of said alkylene are replaced with —O—. In an embodiment, L is a bond. In an embodiment, L is alkylene. In an embodiment, L is alkylene. In an embodiment, L is alkylene in which one or more non-adjacent methylene groups of said alkylene are replaced with —O—. In an embodiment, L is —[(CH$_2$)$_2$—O]$_{1-5}$—. In an embodiment, L is —(CH$_2$)$_2$—O—. In an embodiment, L is —[(CH$_2$)$_2$—O]$_2$—. In an embodiment, L is —[(CH$_2$)$_2$—O]$_3$—. In an embodiment, L is —[(CH$_2$)$_2$—O]$_4$—. In an embodiment, L is —[(CH$_2$)$_2$—O]$_5$—.

In an embodiment, L is alkylene-Y-alkylene wherein Y is O, N$R_x$, S, SO, SO$_2$ or a divalent heterocycle; wherein said alkylene groups are optionally substituted with OH, —C(O)O—$R_1$, alkyl or alkyl substituted with OH or —C(O)O—$R_1$; and wherein a carbon of said alkylene groups and $R_x$ optionally together form a heterocycle; provided that when X is other than a bond, then L is other than a bond. In an embodiment, L is alkylene-Y-alkylene wherein Y is O. In an embodiment, L is alkylene-Y-alkylene wherein Y is N$R_x$. In an embodiment, L is alkylene-Y-alkylene wherein Y is N$R_x$ wherein a carbon of said alkylene groups and $R_x$ together form a heterocycle. In an embodiment, L is alkylene-Y-alkylene wherein Y is S. In an embodiment, L is alkylene-Y-alkylene wherein Y is SO. In an embodiment, L is alkylene-Y-alkylene wherein Y is SO$_2$. In an embodiment, L is alkylene-Y-alkylene wherein Y is divalent heterocycle. In an embodiment, L is a aryl. In an embodiment, L is phenyl. In an embodiment, L is 1,4-phenylene. In an embodiment, L is heteroaryl. In an embodiment, L is triazole. In an embodiment, L is isoxazole.

$R_1$ is alkyl optionally substituted with halogen, OH, amino, oxo, carboxy, acyloxy, alkoxycarbonyl, alkoxyacyloxy, alkoxycarbonyloxy, aminocarbonyl, a carbocycle optionally substituted with alkyl, haloalkyl, oxo, amino and halogen and a heterocycle optionally substituted with alkyl, oxo, amino and halogen; and a carbocycle or heterocycle optionally substituted with alkyl, haloalkyl, oxo, amino and halogen; wherein one or more non-adjacent methylene groups in any of the foregoing alkyl groups is replaced with O. In an embodiment, $R_1$ is alkyl. In an embodiment, $R_1$ is alkyl substituted with OH. In an embodiment, $R_1$ is alkyl substituted with oxo. In an embodiment, $R_1$ is alkyl substituted with carboxy. In an embodiment, $R_1$ is alkyl substituted with acyloxy. In an embodiment, $R_1$ is alkyl substituted with alkoxycarbonyl. In an embodiment, one or more non-adjacent methylene groups in any of the alkyl groups in $R_1$ is replaced with O. In an embodiment, $R_1$ is alkyl substituted with alkoxyacyloxy. In an embodiment, $R_1$ is alkyl substituted with alkoxycarbonyloxy. In an embodiment, $R_1$ is alkyl substituted with aminocarbonyl. In an embodiment, $R_1$ is methyl. In an embodiment, $R_1$ is propyl. In an embodiment, $R_1$ is hydroxyethyl. In an embodiment, $R_1$ is 2,2,2-trifluoroethyl. In an embodiment, $R_1$ is 1,1-trifluoromethylethyl. In an embodiment, $R_1$ is 2-morpholinoethyl. In an embodiment, $R_1$ is 2-(1H-imidazol-1-yl)ethyl. In an embodiment, $R_1$ is 2-(pyridin-2-yl)ethyl. In an embodiment, $R_1$ is —CH$_2$—C(O)OH.

In an embodiment, $R_1$ is —CH$_2$—C(O)O-Me. In an embodiment, $R_1$ is —CH$_2$—C(O)NH$_2$. In an embodiment, $R_1$ is-CH$_2$—C(O)NMe$_2$. In an embodiment, $R_1$ is-CH$_2$—C(O)O-t-butyl. In an embodiment, $R_1$ is (5-methyl-2-oxo-1,3-dioxol-4-yl)methyl. In an embodiment, $R_1$ is (pivaloyloxy)methyl. In an embodiment, $R_1$ is ((isopropoxycarbonyl)oxy)methyl. In an embodiment, $R_1$ is (S)-1-((isopropoxycarbonyl)oxy)ethyl. In an embodiment, $R_1$ is (R)-1-((isopropoxycarbonyl)oxy)ethyl. In an embodiment, $R_1$ is 2-morpholino-2-oxoethyl. In an embodiment, $R_1$ is 2-(4-methylpiperazin-1-yl)-2-oxoethyl. In an embodiment, $R_1$ is (R)-quinuclidin-3-yl.

In an embodiment, $R_1$ is —[(CH$_2$)$_2$—O]$_p$-Me wherein p is 1 to 20. In an embodiment p is 1 to 19. In an embodiment p is 1 to 18. In an embodiment p is 1 to 17. In an embodiment p is 1 to 16. In an embodiment p is 1 to 15. In an embodiment p is 1 to 14. In an embodiment p is 1 to 13. In an embodiment p is 1 to 12. In an embodiment p is 1 to 11. In an embodiment p is 1 to 10. In an embodiment p is 1 to 9. In an embodiment p is 1 to 8. In an embodiment p is 1 to 7. In an embodiment p is 1 to 6. In an embodiment p is 1 to 5. In an embodiment p is 1 to 4. In an embodiment p is 1 to 3. In an embodiment p is 1 to 2. In an embodiment p is 1 to 1.

In an embodiment, $R_2$ is H or $R_1$. In an embodiment, $R_2$ is H. In an embodiment, $R_2$ is $R_1$. In an embodiment, $R_2$ is methyl. In an embodiment, $R_2$ is t-butyl. In an embodiment, $R_2$ is benzhydryl. In an embodiment, $R_2$ is benzyl.

$R_3$ is absent, Me; provided that when X depends from the carbon to which $R_3$ depends then $R_3$ is absent; or $R_3$ is —Z-L-C(O)O—$R_1$ wherein Z is a bond, —O—, —N($R_x$)—, —C(O)N($R_x$)—, —N($R_x$)—C(O)—, —S(O)$_n$—N($R_x$)— or —N($R_x$)—S(O)$_n$—. In an embodiment, $R_3$ is methyl. In an embodiment, $R_3$ is absent and X depends from the carbon to which $R_3$ depends. In an embodiment, $R_3$ is —Z-L-C(O)O—$R_1$ wherein Z is a bond, —O—, —N($R_x$)—, —C(O)N($R_x$)—, —N($R_x$)—C(O)—, —S(O)$_n$—N($R_x$)— or —N($R_x$)—S(O)$_n$—. In an embodiment, Z is —O—. In an embodiment, Z is —N($R_x$)—. In an embodiment, Z is —NH—. In an embodiment, $R_3$ is —C(O)N($R_x$)—. In an embodiment, $R_3$ is —C(O)NH—. In an embodiment, $R_3$ is —N($R_x$)—C(O)—. In an embodiment, $R_3$ is —NH—C(O)—. In an embodiment, $R_3$ is —S(O)$_n$—N($R_x$)—. In an embodiment, $R_3$ is —S(O)—NH—. In an embodiment, $R_3$ is —S(O)$_2$—NH—. In an embodiment, $R_3$ is —N($R_x$)—S(O)$_n$—. In an embodiment, $R_3$ is —NH—S(O)$_1$—. In an embodiment, $R_3$ is —NH—S(O)$_2$—.

$R_4$ is absent, H or OH; provided that when —X-L-C(O)O—$R_1$ depends from the carbon to which $R_4$ depends then $R_4$ is H or absent;

In an embodiment, $R_4$ is H. In an embodiment, $R_4$ is H and the carbon from which it depends is part of a double bond. In an embodiment, $R_4$ is H and the carbon from which it depends is not part of a double bond. In an embodiment, $R_4$ is OH. In an embodiment, $R_4$ is absent and X depends-X-L-C(O)O—$R_1$ depends from the carbon to which $R_4$ depend and said carbon is part of a double bond.

$R_5$ is H or alkyl optionally substituted with a carbocycle or heterocycle wherein said carbocycle and heterocycle are optionally substituted with oxo and alkyl. In an embodiment, $R_5$ is H. In an embodiment, $R_5$ is alkyl. In an embodiment, $R_5$ is methyl. In an embodiment, $R_5$ is In an embodiment, $R_x$ is H. In an embodiment, $R_x$ is —C(O)O—$R_1$. In an embodiment, $R_x$ is alkyl.

In an embodiment, $R_x$ is alkyl optionally substituted with —C(O)O—$R_1$.

In an embodiment 'n' is 1. In another embodiment, 'n' is 2.

In an embodiment, the compound of the invention is one of the following compounds:
(2S,4aS,6aS,6bR,8aS,10S,12aS,12bR,14bR)-10-(Methoxycarbonyl)-2,4a,6a,6b,9,9,12a-heptamethyl-13-oxo-1,2,3,4,4a,5,6,6a,6b,7,8,8a,9,10,11,12,12a,12b,13,14b-icosahydropicene-2-carboxylic acid;
(2S,4aS,6aS,6bR,8aS,10S,12aS,12bR,14bR)-10-(Isopropoxycarbonyl)-2,4a,6a,6b,9,9,12a-heptamethyl-13-oxo-1,2,3,4,4a,5,6,6a,6b,7,8,8a,9,10,11,12,12a,12b,13,14b-icosahydropicene-2-carboxylic acid;
(2S,4aS,6aS,6bR,8aS,10S,12aS,12bR,14bR)-10-(((1,1,1,3,3,3-Hexafluoro-2-methylpropan-2-yl)oxy)carbonyl)-2,4a,6a,6b,9,9,12a-heptamethyl-13-oxo-1,2,3,4,4a,5,6,6a,6b,7,8,8a, 9,10,11,12,12a,12b,13,14b-icosahydropicene-2-carboxylic acid;
(2S,4aS,6aS,6bR,8aS,10S,12aS,12bR,14bR)-10-((2-Hydroxyethoxy)carbonyl)-2,4a,6a,6b,9,9,12a-heptamethyl-13-oxo-1,2,3,4,4a,5,6,6a,6b,7,8,8a,9,10,11,12,12a, 12b, 13,14b-icosahydropicene-2-carboxylic acid;
(2S,4aS,6aS,6bR,8aS,10S,12aS,12bR,14bR)-2,4a,6a,6b,9,9,12a-Heptamethyl-13-oxo-10-((2,2,2-trifluoroethoxy)carbonyl)-1,2,3,4,4a,5,6,6a,6b,7,8,8a,9,10,11,12,12a,12b,13,14b-icosahydropicene-2-carboxylic acid;
(2S,4aS,6aS,6bR,8aS,10S,12aS,12bR,14bR)-10-((2-(1H-Imidazol-1-yl)ethoxy)carbonyl)-2,4a,6a,6b,9,9,12a-heptamethyl-13-oxo-1,2,3,4,4a,5,6,6a,6b,7,8,8a,9,10,11,12, 12a, 12b,13,14b-icosahydropicene-2-carboxylic acid;
(2S,4aS,6aS,6bR,8aS,10S,12aS,12bR,14bR)-2,4a,6a,6b,9,9,12a-Heptamethyl-10-((2-morpholinoethoxy)carbonyl)-13-oxo-1,2,3,4,4a,5,6,6a,6b,7,8,8a,9,10,11,12,12a,12b,13,14b-icosahydropicene-2-carboxylic acid;
(2S,4aS,6aS,6bR,8aS,10S,12aS,12bR,14bR)-2,4a,6a,6b,9,9,12a-Heptamethyl-13-oxo-10-((((R)-quinuclidin-3-yl)oxy)carbonyl)-1,2,3,4,4a,5,6,6a,6b,7,8,8a,9,10,11,12,12a,12b,13,14b-icosahydropicene-2-carboxylic acid;
(2S,4aS,6aS,6bR,8aS,10S,12aS,12bR,14bR)-2,4a,6a,6b,9,9,12a-Heptamethyl-13-oxo-10-((2-(pyridin-2-yl)ethoxy)carbonyl)-1,2,3,4,4a,5,6,6a,6b,7,8,8a,9,10,11,12,12a,12b,13,14b-icosahydropicene-2-carboxylic acid;
(2S,4aS,6aS,6bR,8aS,10S,12aS,12bR,14bR)-10-((2-Amino-2-oxoethoxy)carbonyl)-2,4a,6a,6b,9,9,12a-heptamethyl-13-oxo-1,2,3,4,4a,5,6,6a,6b,7,8,8a,9,10,11,12, 12a,12b, 13,14b-icosahydropicene-2-carboxylic acid;
(2S,4aS,6aS,6bR,8aS,10S,12aS,12bR,14bR)-10-((Carboxymethoxy)carbonyl)-4a,6a,6b,9,9,12a-heptamethyl-13-oxo-1,2,3,4,4a,5,6,6a,6b,7,8,8a,9,10,11,12,12a,12b, 13,14b-icosahydropicene-2-carboxylic acid;
(2S,4aS,6aS,6bR,8aS,10S,12aS,12bR,14bR)-10-((2-methoxy-2-oxoethoxy)carbonyl)-2,4a,6a,6b,9,9,12a-heptamethyl-13-oxo-1,2,3,4,4a,5,6,6a,6b,7,8,8a,9,10,11,12, 12a,12b, 13,14b-icosahydropicene-2-carboxylic acid;
(2S,4aS,6aS,6bR,8aS,10S,12aS,12bR,14bR)-10-((2-(tert-Butoxy)-2-oxoethoxy)carbonyl)-2,4a,6a,6b,9,9,12a-heptamethyl-13-oxo-1,2,3,4,4a,5,6,6a,6b,7,8,8a,9,10,11,12, 12a,12b, 13,14b-icosahydropicene-2-carboxylic acid;
(2S,4aS,6aS,6bR,8aR,12aS,12bR,14bR)-10-(Methoxycarbonyl)-2,4a,6a,6b,9,9,12a-heptamethyl-13-oxo-1,2,3,4,4a,5,6,6a,6b,7,8,8a,9,12,12a,12b,13,14b-octadecahydropicene-2-carboxylic acid;
(2S,4aS,6aS,6bR,8aS,10S,12aS,12bR,14bR)-10-((2-methoxy-2-oxoethyl)carbamoyl)-2,4a,6a,6b,9,9,12a-heptamethyl-13-oxo-1,2,3,4,4a,5,6,6a,6b,7,8,8a,9,10,11,12, 12a,12b, 13,14b-icosahydropicene-2-carboxylic acid;
(2S,4aS,6aS,6bR,8aS,10S,12aS,12bR,14bR)-10-((carboxymethyl)carbamoyl)-2,4a,6a,6b,9,9,12a-heptamethyl-13-oxo-1,2,3,4,4a,5,6,6a,6b,7,8,8a,9,10,11,12,12a,12b, 13,14b-icosahydropicene-2-carboxylic acid;
(2S,4aS,6aS,6bR,8aS,10S,12aS,12bR,14bR)-10-((2-Methoxy-2-oxoethyl)(methyl)-carbamoyl)-2,4a,6a,6b,9, 9,12a-heptamethyl-13-oxo-1,2,3,4,4a,5,6,6a,6b,7,8,8a,9, 10,11,12,12a,12b, 13,14b-icosahydropicene-2-carboxylic acid;

(2S,4aS,6aS,6bR,8aS,10S,12aS,12bR,14bR)-10-((R)-2-(Methoxycarbonyl)pyrrolidine-1-carbonyl)-2,4a,6a,6b,9, 9,12a-heptamethyl-13-oxo-1,2,3,4,4a,5,6,6a,6b,7,8,8a,9, 10,11,12,12a,12b,13,14b-icosahydropicene-2-carboxylic acid;

(2S,4aS,6aS,6bR,8aS,10S,12aS,12bR,14bR)-10-(((S)-1,5-Dimethoxy-1,5-dioxopentan-2-yl)carbamoyl)-2,4a,6a,6b, 9,9,12a-heptamethyl-13-oxo-1,2,3,4,4a,5,6,6a,6b,7,8,8a, 9,10,11,12,12a,12b,13,14b-icosahydropicene-2-carboxylic acid;

(2S,4aS,6aS,6bR,8aS,10S,12aS,12bR,14bR)-10-(((R)-1,4-Dimethoxy-1,4-dioxobutan-2-yl)carbamoyl)-2,4a,6a,6b, 9,9,12a-heptamethyl-13-oxo-1,2,3,4,4a,5,6,6a,6b,7,8,8a, 9,10,11,12,12a,12b,13,14b-icosahydropicene-2-carboxylic acid;

(2S,4aS,6aS,6bR,8aS,10S,12aS,12bR,14bR)-10-(((S)-1-Methoxy-1-oxopropan-2-yl)carbamoyl)-2,4a,6a,6b,9,9, 12a-heptamethyl-13-oxo-1,2,3,4,4a,5,6,6a,6b,7,8,8a, 9,10,11,12,12a, 12b,13,14b-icosahydropicene-2-carboxylic acid;

(2S,4aS,6aS,6bR,8aS,10S,12aS,12bR,14bR)-10-(((S)-3-Hydroxy-1-methoxy-1-oxopropan-2-yl)carbamoyl)-2,4a, 6a,6b,9,9,12a-heptamethyl-13-oxo-1,2,3,4,4a,5,6,6a,6b, 7,8,8a,9,10,11,12,12a,12b,13,14b-icosahydropicene-2-carboxylic acid;

(2S,4aS,6aS,6bR,8aS,10S,12aS,12bR,14bR)-10-((2-(2-(1H-imidazol-1-yl)ethoxy)-2-oxoethyl)carbamoyl)-2,4a,6a, 6b,9,9,12a-heptamethyl-13-oxo-1,2,3,4,4a,5,6,6a,6b,7,8, 8a, 9,10,11,12,12a,12b,13,14b-icosahydropicene-2-carboxylic acid;

(2S,4aS,6aS,6bR,8aS,10S,12aS,12bR,14bR)-10-((2-(2-Hydroxyethoxy)-2-oxoethyl)carbamoyl)-2,4a,6a,6b,9,9,12a-heptamethyl-13-oxo-1,2,3,4,4a,5,6,6a, 6b,7,8,8a,9,10,11, 12,12a, 12b,13,14b-icosahydropicene-2-carboxylic acid;

(2S,4aS,6aS,6bR,8aS,10S,12aS,12bR,14bR)-2,4a,6a,6b,9,9, 12a-heptamethyl-10-((2-(2-morpholinoethoxy)-2-oxoethyl)carbamoyl)-13-oxo-1,2,3,4,4a,5,6,6a,6b,7,8,8a, 9,10,11,12,12a,12b,13,14b-icosahydropicene-2-carboxylic acid;

(2S,4aS,6aS,6bR,8aS,10S,12aS,12bR,14bR)-2,4a,6a,6b,9,9, 12a-Heptamethyl-13-oxo-10-(((pivaloyloxy)methoxy) carbonyl)-1,2,3,4,4a,5,6,6a,6b,7,8,8a,9,10,11,12,12a,12b, 13,14b-icosahydropicene-2-carboxylic acid;

(2S,4aS,6aS,6bR,8aS,10S,12aS,12bR,14bR)-10-((((isopropoxycarbonyl)oxy)methoxy) carbonyl)-2,4a,6a,6b, 9,12a-heptamethyl-13-oxo-1,2,3,4,4a,5,6,6a,6b,7,8,8a,9, 10,11,12,12a,12b,13,14b-icosahydropicene-2-carboxylic acid;

(2S,4aS,6aS,6bR,8aS,10S,12aS,12bR,14bR)-10-(((S)-1-((isopropoxycarbonyl)oxy)-ethoxy)carbonyl)-2,4a,6a,6b, 9,9,12a-heptamethyl-13-oxo-1,2,3,4,4a,5,6, 6a,6b,7,8,8a, 9,10,11,12,12a,12b,13,14b-icosahydropicene-2-carboxylic acid;

(2S,4aS,6aS,6bR,8aS,10S,12aS,12bR,14bR)-10-(((R)-1-((Isopropoxycarbonyl)oxy)ethoxy) carbonyl)-2,4a,6a,6b, 9,9,12a-heptamethyl-13-oxo-1,2,3,4,4a,5,6,6a,6b,7,8,8a, 9,10,11,12,12a,12b,13,14b-icosahydropicene-2-carboxylic acid;

(2S,4aS,6aS,6bR,8aS,10S,12aS,12bR,14bR)-10-((2-(Diethylamino)-2-oxoethoxy)carbonyl)-2,4a,6a,6b,9,9,12a-heptamethyl-13-oxo-1,2,3,4,4a,5,6,6a,6b,7,8,8a,9,10,11,12, 12a,12b, 13,14b-icosahydropicene-2-carboxylic acid;

(2S,4aS,6aS,6bR,8aS,10S,12aS,12bR,14bR)-2,4a,6a,6b,9,9, 12a-Heptamethyl-10-((2-morpholino-2-oxoethoxy)carbonyl)-13-oxo-1,2,3,4,4a,5,6,6a,6b,7,8,8a,9,10,11,12, 12a, 12b,13,14b-icosahydropicene-2-carboxylic acid;

(2S,4aS,6aS,6bR,8aS,10S,12aS,12bR,14bR)-2,4a,6a,6b,9,9, 12a-heptamethyl-10-((2-(4-methylpiperazin-1-yl)-2-oxoethoxy)carbonyl)-13-oxo-1,2,3,4,4a,5,6,6a,6b,7,8,8a,9, 10, 11,12,12a,12b,13,14b-icosahydropicene-2-carboxylic acid;

(2S,4aS,6aS,6bR,8aR,10S,12aS,12bR,14bR)-10-((2-Methoxy-2-oxoethyl)amino)-2,4a,6a,6b,9,9,12a-heptamethyl-13-oxo-1,2,3,4,4a,5,6,6a,6b,7,8,8a,9,10,11,12,12a, 12b, 13,14b-icosahydropicene-2-carboxylic acid;

(2S,4aS,6aS,6bR,8aR,10S,12aS,12bR,14bR)-10-(bis(2-Methoxy-2-oxoethyl)amino)-2,4a,6a,6b,9,9,12a-heptamethyl-13-oxo-1,2,3,4,4a,5,6,6a,6b,7,8,8a,9,10,11,12,12a, 12b, 13,14b-icosahydropicene-2-carboxylic acid;

Dibenzyl 2,2'-(((3 S,4aR,6aR,6bS,8aS,11S,12aR,14aR, 14bS)-11-((benzyloxy)carbonyl)-4,4,6a, 6b,8a,11,14b-heptamethyl-14-oxo-1,2,3,4,4a,5,6,6a,6b,7,8,8a,9,10,11, 12,12a,14,14a,14b-icosahydropicen-3-yl)azanediyl) diacetate;

(2S,4aS,6aS,6bR,8aR,10S,12aS,12bR,14bR)-10-(3-Methoxy-2,2-dimethyl-3-oxopropanamido)-2,4a,6a,6b,9, 9,12a-heptamethyl-13-oxo-1,2,3,4,4a,5,6,6a,6b,7,8,8a,9, 10,11,12,12a,12b, 13,14b-icosahydropicene-2-carboxylic acid;

(2S,4aS,6aS,6bR,8aR,10S,12aS,12bR,14bR)-10-(2-methoxy-2-oxoacetamido)-2,4a,6a,6b,9,9,12a-heptamethyl-13-oxo-1,2,3,4,4a,5,6,6a,6b,7,8,8a,9,10,11,12,12a, 12b, 13,14b-icosahydropicene-2-carboxylic acid;

(2S,4aS,6aS,6bR,8aR,10S,12aS,12bR,14bR)-10-(3-Methoxy-3-oxopropanamido)-2,4a,6a,6b,9,9,12a-heptamethyl-13-oxo-1,2,3,4,4a,5,6,6a,6b,7,8,8a,9,10,11,12, 12a,12b, 13,14b-icosahydropicene-2-carboxylic acid;

(2S,4aS,6aS,6bR,8aR,10S,12aS,12bR,14bR)-10-(4-Methoxy-4-oxobutanamido)-2,4a,6a,6b,9,9,12a-heptamethyl-13-oxo-1,2,3,4,4a,5,6,6a,6b,7,8,8a,9,10,11,12,12a, 12b, 13,14b-icosahydropicene-2-carboxylic acid;

(2S,4aS,6aS,6bR,8aR,10S,12aS,12bR,14bR)-10-((E)-4-Methoxy-4-oxobut-2-enamido)-2,4a,6a,6b,9,9,12a-heptamethyl-13-oxo-1,2,3,4,4a,5,6,6a,6b,7,8,8a,9,10,11,12, 12a, 12b,13,14b-icosahydropicene-2-carboxylic acid;

Benzyl (2S,4aS,6aS,6bR,8aR,10S,12aS,12bR,14bR)-10-(4-methoxy-3,3-dimethyl-4-oxobutan amido)-2,4a,6a,6b,9, 9,12a-heptamethyl-13-oxo-1,2,3,4,4a,5,6,6a,6b,7,8,8a,9, 10,11,12,12a,12b,13,14b-icosahydropicene-2-carboxylate;

(2S,4aS,6aS,6bR,8aR,10S,12aS,12bR,14bR)-10-(4-Methoxy-3,3-dimethyl-4-oxobutanamido)-2,4a,6a,6b,9, 9,12a-heptamethyl-13-oxo-1,2,3,4,4a,5,6,6a,6b,7,8,8a,9, 10,11,12,12a,12b, 13,14b-icosahydropicene-2-carboxylic acid;

(2S,4aS,6aS,6bR,8aR,10S,12aS,12bR,14bR)-10-((2-Methoxy-2-oxoethyl)sulfonamido)-2,4a,6a,6b,9,9,12a-heptamethyl-13-oxo-1,2,3,4,4a,5,6,6a,6b,7,8,8a,9,10,11, 12,12a,12b, 13,14b-icosahydropicene-2-carboxylic acid;

(2S,4aS,6aS,6bR,8aR,10S,12aS,12bR,14bR)-10-((3-Methoxy-3-oxopropyl)sulfonamido)-2,4a,6a,6b,9,9,12a-heptamethyl-13-oxo-1,2,3,4,4a,5,6,6a,6b,7,8,8a,9,10,11, 12,12a,12b, 13,14b-icosahydropicene-2-carboxylic acid;

(2S,4aS,6aS,6bR,8aR,10S,12aS,12bR,14bR)-10-(2-(2-Methoxy-2-oxoethoxy)acetamido)-2,4a,6a,6b,9,9,12a-heptamethyl-13-oxo-1,2,3,4,4a,5,6,6a,6b,7,8,8a,9,10,11, 12,12a,12b, 13,14b-icosahydropicene-2-carboxylic acid;

(2S,4aS,6aS,6bR,8aR,10S,12aS,12bR,14bR)-10-((1-(2-Methoxy-2-oxoethyl)-1H-1,2,3-triazol-4-yl)methoxy)-2, 4a,6a,6b,9,9,12a-heptamethyl-13-oxo-1,2,3,4,4a,5,6,6a, 6b,7,8,8a,9,10, 11,12,12a,12b,13,14b-icosahydropicene-2-carboxylic acid;

(2S,4aS,6aS,6bR,8aR,10S,12aS,12bR,14bR)-10-(2-Methoxy-2-oxoethoxy)-2,4a,6a,6b,9,9,12a-heptamethyl-13-oxo-1,2,3,4,4a,5,6,6a,6b,7,8,8a,9,10,11,12, 12a,12b, 13,14b-icosahydropicene-2-carboxylic acid;

(2S,4aS,6aS,6bR,8aR,10S,12aS,12bR,14bR)-10-((1,3-Dimethoxy-1,3-dioxopropan-2-yl)oxy)-2,4a,6a,6b,9,9,12a-heptamethyl-13-oxo-1,2,3,4,4a,5,6,6a,6b,7,8,8a,9,10,11, 12,12a,12b, 13,14b-icosahydropicene-2-carboxylic acid;

(2S,4aS,6aS,6bR,8aR,10S,12aS,12bR,14bR)-10-(3-(4-(Ethoxycarbonyl)piperidin-1-yl)-2-hydroxypropoxy)-2,4a,6a,6b,9,9,12a-heptamethyl-13-oxo-1,2,3,4,4a,5,6,6a, 6b,7,8,8a,9, 10,11,12,12a,12b,13,14b-icosahydropicene-2-carboxylic acid;

(2S,4aS,6aS,6bR,8aS,10S,12aS,12bR,14bR)-2,4a,6a,6b,9,9, 12a-Heptamethyl-13-oxo-10-((3-oxo-2,6,9,12-tetraoxatetradecan-14-yl)carbamoyl)-1,2,3,4,4a,5,6,6a,6b,7,8,8a, 9,10, 11,12,12a,12b,13,14b-icosahydropicene-2-carboxylic acid;

(2S,4aS,6aS,6bR,8aR,10S,12aS,12bR,14bR)-2,4a,6a,6b,9, 9,12a-Heptamethyl-13-oxo-10-((12-oxo-2,5,8,11-tetraoxatetradecane)sulfonamido)-1,2,3,4,4a,5,6,6a,6b,7,8, 8a,9,10, 11,12,12a,12b,13,14b-icosahydropicene-2-carboxylic acid;

(2S,4aS,6aS,6bR,8aS,10S,12aS,12bR,14bR)-2,4a,6a,6b,9,9, 12a-Heptamethyl-13-oxo-10-(4-oxo-2,8,11,14-tetraoxa-5-azapentadecanoyl)-1,2,3,4,4a,5,6,6a,6b,7,8,8a,9,10,11, 12,12a, 12b,13,14b-icosahydropicene-2-carboxylic acid;

(2S,4aS,6aS,6bR,8aR,9S,10S,12aS,12bR,14bR)-10-Hydroxy-9-(methoxycarbonyl)-2,4a,6a,6b,9,12a-hexamethyl-13-oxo-1,2,3,4,4a,5,6,6a,6b,7,8,8a,9,10,11,12,12a, 12b, 13,14b-icosahydropicene-2-carboxylic acid;

(2S,4aS,6aS,6bR,8aS,10S,12aS,12bR,14bR)-2,4a,6a,6b,9,9, 12a-Heptamethyl-13-oxo-10-((2-oxo-2-(((R)-quinuclidin-3-yl)oxy)ethyl)carbamoyl)-1,2,3,4,4a,5,6,6a,6b,7,8, 8a,9, 10,11,12,12a,12b,13,14b-icosahydropicene-2-carboxylic acid.

In another embodiment, the compound of the invention is one of the following compounds:

(2S,4aS,6aS,6bR,8aR,10S,12aS,12bR,14bR)-2,4a,6a,6b,9, 9,12a-heptamethyl-13-oxo-10-((12-oxo-2,5,8,11-tetraoxatridecan-13-yl)oxy)-1,2,3,4,4a,5,6,6a,6b,7,8,8a,9,10,11, 12, 12a,12b,13,14b-icosahydropicene-2-carboxylic acid;

(2S,4aS,6aS,6bR,8aR,10S,12aS,12bR,14bR)-2,4a,6a,6b,9, 9,12a-heptamethyl-10-((10-methyl-12-oxo-2,5,8,11-tetraoxatridecan-13-yl)oxy)-13-oxo-1,2,3,4,4a,5,6,6a,6b,7, 8,8a,9,10, 11,12,12a,12b,13,14b-icosahydropicene-2-carboxylic acid;

(2S,4aS,6aS,6bR,8aR,10S,12aS,12bR,14bR)-10-(2-(2,5,9, 12-tetraoxatridecan-7-yloxy)-2-oxoethoxy)-2,4a,6a,6b,9, 9,12a-heptamethyl-13-oxo-1,2,3,4,4a,5,6,6a,6b,7,8,8a,9, 10, 11,12,12a,12b,13,14b-icosahydropicene-2-carboxylic acid;

(2S,4aS,6aS,6bR,8aR,10S,12aS,12bR,14bR)-10-(2-(2-ethoxy-2-oxoethoxy)ethoxy)-2,4a,6a,6b,9,9,12a-heptamethyl-13-oxo-1,2,3,4,4a,5,6,6a,6b,7,8,8a,9,10,11,12,12a, 12b,13,14b-icosahydropicene-2-carboxylic acid;

(2S,4aS,6aS,6bR,8aR,10S,12aS,12bR,14bR)-10-(2-(2-(2-methoxyethoxy)-2-oxoethoxy)ethoxy)-2,4a,6a,6b,9,9, 12a-heptamethyl-13-oxo-1,2,3,4,4a,5,6,6a,6b,7,8,8a,9, 10,11,12,12a,12b, 13,14b-icosahydropicene-2-carboxylic acid;

(2S,4aS,6aS,6bR,8aR,10S,12aS,12bR,14bR)-10-(2-(2-(((1-methoxypropan-2-yl)oxy)-2-oxoethoxy)ethoxy)-2,4a,6a, 6b,9,9,12a-heptamethyl-13-oxo-1,2,3,4,4a,5,6,6a,6b,7,8, 8a,9, 10,11,12,12a,12b,13,14b-icosahydropicene-2-carboxylic acid;

(2S,4aS,6aS,6bR,8aR,10S,12aS,12bR,14bR)-10-(bis(2-(2-(2-methoxyethoxy)ethoxy)-2-oxoethyl)amino)-2,4a,6a, 6b,9,9,12a-heptamethyl-13-oxo-1,2,3,4,4a,5,6,6a,6b, 7,8, 8a,9,10,11,12,12a,12b,13,14b-icosahydropicene-2-carboxylic acid;

(2S,4aS,6aS,6bR,8aR,10S,12aS,12bR,14bR)-10-((2-methoxy-2-oxoethyl)(2-(2-(2-methoxyethoxy)ethoxy) ethyl)amino)-2,4a,6a,6b,9,9,12a-heptamethyl-13-oxo-1, 2,3,4,4a,5,6,6a,6b,7,8,8a,9,10,11,12,12a,12b,13,14b-icosahydropicene-2-carboxylic acid;

(2S,4aS,6aS,6bR,8aR,10S,12aS,12bR,14bR)-10-(4-methoxy-N-(2-(2-(2-methoxyethoxy)ethoxy)ethyl)-4-oxobutanamido)-2,4a,6a,6b,9,9,12a-heptamethyl-13-oxo-1,2,3,4,4a,5,6,6a,6b,7,8,8a,9,10,11,12,12a,12b,13,14b-icosahydropicene-2-carboxylic acid;

(2S,4aS,6aS,6bR,8aS,10S,12aS,12bR,14bR)-10-(2,5,8,11-tetraoxadodecan-1-oyl)-2,4a,6a,6b,9,9,12a-heptamethyl-13-oxo-1,2,3,4,4a,5,6,6a,6b,7,8,8a,9,10,11,12,12a,12b, 13,14b-icosahydropicene-2-carboxylic acid;

(2S,4aS,6aS,6bR,8aS,10S,12aS,12bR,14bR)-2,4a,6a,6b,9,9, 12a-heptamethyl-13-oxo-10-(4-oxo-2,5,8,11,14-pentaoxapentadecan-1-oyl)-1,2,3,4,4a,5,6,6a,6b,7,8,8a,9,10, 11,12,12a,12b, 13,14b-icosahydropicene-2-carboxylic acid;

(2S,4aS,6aS,6bR,8aS,10S,12aS,12bR,14bR)-2,4a,6a,6b,9,9, 12a-heptamethyl-10-(5-methyl-4-oxo-2,8,11,14-tetraoxa-5-azapentadecan-1-oyl)-13-oxo-1,2,3,4,4a,5,6,6a,6b,7,8, 8a,9,10, 11,12,12a,12b,13,14b-icosahydropicene-2-carboxylic acid;

(2S,4aS,6aS,6bR,8aS,10S,12aS,12bR,14bR)-2,4a,6a,6b,9,9, 12a-heptamethyl-10-(3-methyl-4-oxo-2,8,11,14-tetraoxa-5-azapentadecan-1-oyl)-13-oxo-1,2,3,4,4a,5,6,6a,6b,7,8, 8a,9, 10,11,12,12a,12b,13,14b-icosahydropicene-2-carboxylic acid;

(2S,4aS,6aS,6bR,8aS,10S,12aS,12bR,14bR)-10-(3,5-dimethyl-4-oxo-2,8,11,14-tetraoxa-5-azapentadecan-1-oyl)-2,4a,6a,6b,9,9,12a-heptamethyl-13-oxo-1,2,3,4,4a,5,6,6a, 6b,7,8, 8a,9,10,11,12,12a,12b,13,14b-icosahydropicene-2-carboxylic acid;

(2S,4aS,6aS,6bR,8aR,10S,12aS,12bR,14bR)-10-(3-(4-(2,5, 8,11,14-pentaoxapentadecan-1-oyl)piperidin-1-yl)-2-hydroxypropoxy)-2,4a,6a,6b,9,9,12a-heptamethyl-13-oxo-1,2,3,4,4a,5,6,6a,6b,7,8,8a,9,10,11,12,12a,12b,13,14b-icosahydropicene-2-carboxylic acid;

(2S,4aS,6aS,6bR,8aR,9S,10S,12aS,12bR,14bR)-10-hydroxy-9-(methoxycarbonyl)-2,4a,6a,6b,9,12a-hexamethyl-13-oxo-1,2,3,4,4a,5,6,6a,6b,7,8,8a,9,10,11,12,12a, 12b,13,14b-icosahydropicene-2-carboxylic acid;

(2S,4aS,6aS,6bR,8aR,9S,10S,12aS,12bR,14bR)-10-(2,5,8, 11-tetraoxatetradecan-14-oyloxy)-9-(methoxycarbonyl)-2,4a,6a,6b,9,12a-hexamethyl-13-oxo-1,2,3,4,4a,5,6,6a, 6b,7,8,8a,9, 10,11,12,12a,12b,13,14b-icosahydropicene-2-carboxylic acid;

(2S,4aS,6aS,6bR,8aR,10S,12aS,12bR,14bR)-10-{3-[4,4-bis (methoxycarbonyl)piperidin-1-yl]-2-hydroxypropoxy}-2, 4a,6a,6b,9,9,12a-heptamethyl-13-oxo-1,2,3,4,4a,5,6,6a, 6b,7, 8,8a,9,10,11,12,12a,12b,13,14b-icosahydropicene-2-carboxylic acid;

(2S,4aS,6aS,6bR,8aR,10S,12aS,12bR,14bR)-10-{[(2-methoxy-2-oxoethyl)carbamoyl]oxy}-2,4a,6a,6b,9,9, 12a-heptamethyl-13-oxo-1,2,3,4,4a,5,6,6a,6b,7,8,8a,9, 10,11,12,12a,12b,13,14b-icosahydropicene-2-carboxylic acid;

(2S,4aS,6aS,6bR,8aR,9S,10S,12aS,12bR,14bR)-10-(acety-loxy)-9-[(ethylsulfanyl)carbonyl]-2,4a,6a,6b,9,12a-hexamethyl-13-oxo-1,2,3,4,4a,5,6,6a,6b,7,8,8a,9,10,11, 12,12a,12b,13,14b-icosahydropicene-2-carboxylic acid;

(2S,4aS,6aS,6bR,8aR,10S,12aS,12bR,14bR)-10-[3-(tert-butoxy)-3-oxopropoxy]-2,4a,6a,6b,9,9,12a-heptamethyl-13-oxo-1,2,3,4,4a,5,6,6a,6b,7,8, 8a,9,10,11,12,12a,12b, 13,14b-icosahydropicene-2-carboxylic acid;

(2S,4aS,6aS,6bR,8aR,9S,10S,12aS,12bR,14bR)-10-[(3R)-3-(methoxycarbonyl)pyrrolidin-1-yl]-2,4a,6a,6b,9,12a-hexamethyl-13-oxo-1,2,3,4,4a,5,6,6a,6b,7,8,8a,9, 10,11, 12,12a,12b,13,14b-icosahydropicene-2,9-dicarboxylic acid; and (2S,4aS,6aS,6bR,8aR,9S,10S,12aS,12bR,14bR)-10-[4-(methoxycarbonyl)piperidin-1-yl]-2,4a,6a,6b,9,12a-hexamethyl-13-oxo-1,2,3,4,4a,5,6,6a,6b,7,8,8a,9,10,11, 12,12a,12b,13,14b-icosahydropicene-2,9-dicarboxylic acid.

Many of the compounds listed above (greater than 50%) were tested in the assays described in examples 59 to determine their activity in inhibiting HSD2 by measuring the amount of cortisol before and after contacting cell lysate (human and rat) or a colon monolayer organoid derived from human colon tissue. HSD2 inhibition for the compounds of the invention as expressed as $pIC_{50}$ ranged from 8.9 to 7.7 (human lysate) and 8.9 to 7.5 (rat lysate) and >8 to 5.9 (human organoid). For reference, glycyrrhetinic acid was tested in the same HSD2 assays: 8.5 (human lysate), 6.4 (human organoid). The $pIC_{50}$ differential between the compounds of the invention and their corresponding acid compound ranged from 2.2 to 0.4 (human lysate), 1.3 to 0.8 (human organoid) with the exception of one compound tested having negative pIC50 differentials (less HSD2 inhibitory activity) in both lysates but 1.3 in the human organoid. The positive differentials demonstrate greater HSD2 inhibitory activity of the compound of the invention compared to the corresponding acid compound.

Compounds of the invention may contain one or more asymmetric or chiral centers. Accordingly, the compounds may exist as diastereomers, enantiomers or mixtures thereof. The syntheses of the compounds may employ racemates, diastereomers or enantiomers as starting materials or as intermediates. Diastereomeric compounds may be separated by chromatographic or crystallization methods. Similarly, enantiomeric mixtures may be separated using the same techniques or others known in the art. Unless specified, each of the asymmetric centers may be in the R or S configuration and both of these configurations are within the scope of the invention. It is intended that all stereoisomeric forms of the compounds described herein, including but not limited to, diastereomers, enantiomers and atropisomers, as well as mixtures thereof, such as racemic mixtures, form part of the present compounds.

It will also be appreciated that certain compounds of Formula I may be used as intermediates for further compounds of Formula I. It will be further appreciated that the compounds described herein may exist in unsolvated, as well as solvated forms with pharmaceutically acceptable solvents, such as water, ethanol, and the like, and it is intended that the compounds embrace both solvated and unsolvated forms.

Compounds of the invention are prepared using standard organic synthetic techniques from commercially available starting materials and reagents. It will be appreciated that synthetic procedures employed in the preparation of compounds of the invention will depend on the particular substituents present in a compound and that various protection and deprotection steps that are standard in organic synthesis may be required but may not be illustrated in the following general schemes. The starting materials are generally available from commercial sources or are readily prepared using methods well known to those skilled in the art. For illustrative purposes, schemes herein shows a general method for preparing the compounds of the invention, as well as key intermediates. Those skilled in the art will appreciate that other synthetic routes may be used to synthesize the compounds. Although specific starting materials and reagents are depicted in the Schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art. In general, the compounds of the invention may be prepared according to scheme 1 starting with a carboxylic acid derivative of glycyrrhetinic acid (i) which is converted to the corresponding acid halide e.g. acid chloride intermediate (ii), for example, with oxalyl chloride catalyzed by dimethylformamide. Intermediate (ii) is then reacted with alcohol intermediate (iii) to give final ester compound of formula I.

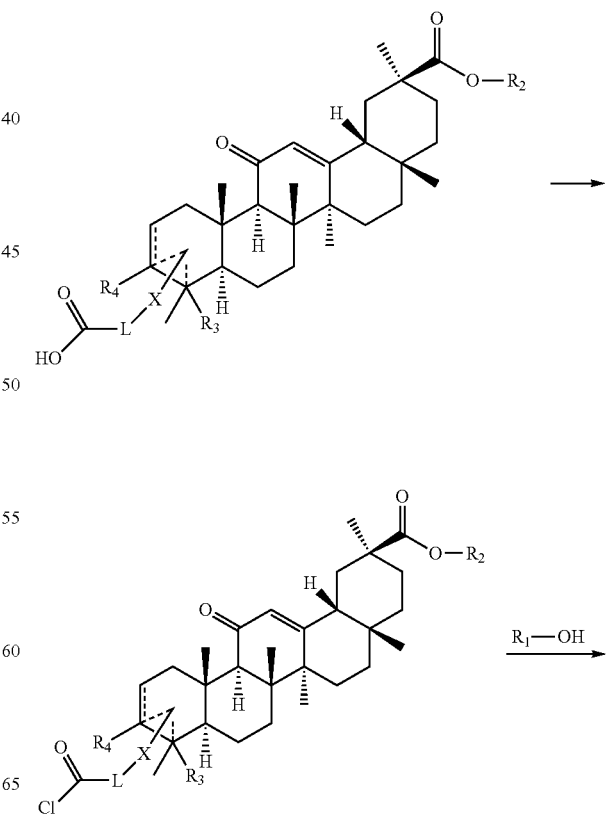

Scheme 1

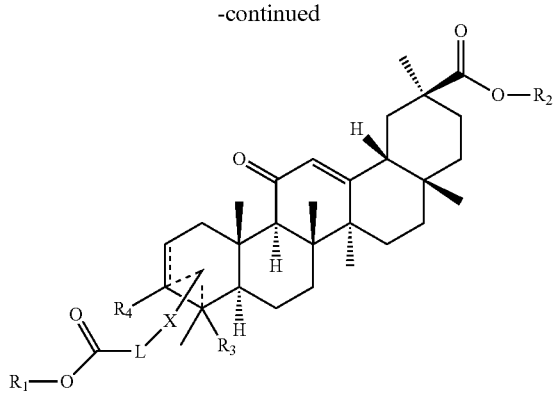

In preparing compounds of Formula I, protection of remote functionalities (e.g., primary or secondary amines, etc.) of intermediates may be necessary. The need for such protection will vary depending on the nature of the remote functionality and the conditions of the preparation methods. The need for such protection is readily determined by one skilled in the art. For a general description of protecting groups and their use, see Greene, T.W., and P.G.M. Wuts. *Greene's Protective Groups in Organic Synthesis.* 4th ed. New York: Wiley-Interscience, 2006.

It may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed ("SMB") and preparative thin or thick layer chromatography, as well as techniques of small scale thin layer and flash chromatography. One skilled in the art will apply techniques most likely to achieve the desired separation.

Diastereomeric and enantiomeric mixtures can be separated into their individual stereoisomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Enantiomers can also be separated by use of a chiral HPLC column.

The invention also includes pharmaceutical compositions or medicaments containing the compounds of the invention and a therapeutically inert carrier, diluent or excipient, as well as methods of using the compounds of the invention to prepare such compositions and medicaments. Typically, the compounds of Formula I used in the methods of the invention are formulated by mixing at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of compound, but may range anywhere from about 3 to about 8. Formulation in an acetate buffer at pH 5 is a suitable embodiment. In one embodiment, formulations comprising compounds of the invention are sterile. The compounds ordinarily will be stored as a solid composition, although lyophilized formulations or aqueous solutions are acceptable.

Compositions comprising compounds of the invention will be formulated, dosed, and administered in a fashion consistent with good medical practice. Factors for consideration in this context include the particular disorder being treated, the particular mammal being treated, the clinical condition of the individual patient, the cause of the disorder, the site of administration, the method of administration, the scheduling of administration, and other factors known to medical practitioners. The "effective amount" of the compound to be administered will be governed by such considerations, and is the minimum amount necessary to inhibit conversion of cortisol to cortisone by HSD2. Such amount may be below the amount that is toxic to normal cells, or the mammal as a whole.

The compound of the invention may be administered by any suitable means. In a particular embodiment, the compounds are administered orally. In a particular embodiment, the compounds are administered rectally.

Generally, the initial pharmaceutically effective amount of the compound of the invention administered parenterally per dose will be in the range of about 0.01-1,000 mg/kg/day, for example about 0.1 to 100 mg/kg of patient body weight per day, with the typical initial range of compound used being 0.5 to 50 mg/kg/day. Oral unit dosage forms, such as tablets and capsules, may contain from about 25 to about 1000 mg of the compound of the invention. In a particular embodiment, an effective amount is the amount of the compound of the invention sufficient to enhance colonic potassium secretion by about 15 mmol/day. In a particular embodiment, an effective amount is the amount of the compound of the invention sufficient to enhance colonic potassium secretion by about 1 mmol/day. In a particular embodiment, an effective amount is the amount of the compound of the invention sufficient to enhance colonic potassium secretion by about 5 mmol/day. In a particular embodiment, an effective amount is the amount of the compound of the invention sufficient to enhance colonic potassium secretion by about 10 mmol/day. In a particular embodiment, an effective amount is the amount of the compound of the invention sufficient to enhance colonic potassium secretion by about 15 mmol/day. In a particular embodiment, an effective amount is the amount of the compound of the invention sufficient to enhance colonic potassium secretion by about 20 mmol/day.

The compounds may be administered in any convenient administrative form, e.g., tablets, capsules, solutions, dispersions, suspensions, syrups, suppositories, gels, emulsions etc. An example of a suitable oral dosage form is a tablet containing about 25 mg, 50 mg, 100 mg, 250 mg, or 500 mg of the compound of the invention compounded with about 90-30 mg anhydrous lactose, about 5-40 mg sodium croscarmellose, about 5-30 mg polyvinylpyrrolidone ("PVP") K30, and about 1-10 mg magnesium stearate. The powdered ingredients are first mixed together and then mixed with a solution of the PVP. The resulting composition can be dried, granulated, mixed with the magnesium stearate and compressed to tablet form using conventional equipment.

Another formulation may be prepared by mixing a compound described herein and a carrier or excipient. Suitable carriers and excipients are well known to those skilled in the art and are described in detail in, e.g., Ansel, Howard C., et al., *Ansel's Pharmaceutical Dosage Forms and Drug Delivery Systems*. Philadelphia: Lippincott, Williams & Wilkins, 2004; Gennaro, Alfonso R., et al. *Remington: The Science and Practice of Pharmacy*. Philadelphia: Lippincott, Williams & Wilkins, 2000; and Rowe, Raymond C. *Handbook of Pharmaceutical Excipients*. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound described herein or pharmaceutical composition thereof) or aid in the manufacturing of the pharmaceutical product (i.e., medicament).

In an embodiment, the formulation releases the compound in response to contact with colonic enzyme, for example, enzymes created by enterobacteria. Certain starch-based capsule coatings may be used that are resistant to digestion in the stomach and small intestine but are degraded by microbial (normal gut flora) enzymes once the dosage form reaches the colon.

In an embodiment, the compound of the invention is administered orally. In another embodiment, the compound is formulated for colonic delivery. Colonic delivery may be effected in response to pH time, microbes, and pressure. In an embodiment, the formulation releases the compound in response to colonic pH. Release of the compound is triggered by the pH increase as the formulation travels through the GI tract. Formulations are based on polymers that are insoluble at the lower pH in the stomach and upper small intestine and soluble in the higher pH found in the distal small intestine, for example, polymers that are derivatives of acrylic acid and cellulose which withstand an environment as low as pH ~1.2. Suitable enteric polymers include, polyvinyl acetate phthalate (PVAP) e.g. Coateric®, cellulose acetate trimellitate (CAT), hydroxypropyl methylcellulose phthalate (HPMCP) e.g. HP-50, HP-55, HP-55S, hydroxypropylmethylcellulose acetate succinate (HPMCAS) e.g. LF grade, MF grade or HF grade, methacrylic acid copolymer e.g. Eudragit® L100-55, L30D-55, L-1000, L12.5, S-100, S12.5, FS30D, cellulose acetate phthalate (CAP) e.g. Aquateric®, and shellac e.g. MarCoat® 125 or 125N.

In an aspect of the invention, there is provided a method of inhibiting conversion of cortisol to cortisone by HSD2 comprising contacting HSD2 with a compound of Formula I. In another aspect of the invention, there is provided a method for promoting activation MR in a mammal, comprising administering to said mammal an effective amount of a compound of Formula I. In another aspect of the invention, there is provided a method of reducing potassium levels in plasma of a mammal, comprising administering to said mammal an effective amount of a compound of Formula I. In another aspect of the invention, there is provided a method for promoting potassium ion secretion into the colonic lumen of a mammal, comprising administering to said mammal an effective amount of a compound of Formula I.

In an aspect of the invention, there is provided a method for treating and/or preventing hyperkalemia in a mammal, comprising administering to said mammal an effective amount of a compound of Formula I. Hyperkalemia occurs especially frequently in patients with chronic kidney disease (CKD), hypertension, heart failure and diabetes. Accordingly, in an embodiment of the invention the methods of treating and/or preventing hyperkalemia is in a patient having CKD hypertension, heart failure and diabetes. Patients suffering for these conditions are often treated with certain classes of medications, such as angiotensin-converting-enzyme (ACE) inhibitors, angiotensin-receptor blockers (ARBs) or other inhibitors of the renin-angiotensin-aldosterone system (RAAS) in order to regulate blood pressure. However such medications promote potassium retention. Accordingly, there is provided a method of treating and/or preventing hyperkalemia in a mammal comprising administering a compound of formula I in combination with an inhibitor of the RAAS system. In an embodiment, the RAAS inhibitor is an ACE inhibitor.

The compounds described herein and stereoisomers, diastereomers, enantiomers, tautomers and pharmaceutically acceptable salts thereof may be employed alone or in combination with other anti-hyperkalemia agents that works by a different mechanism of action. The compound of the invention may be administered together with the other anti-hyperkalemia agent in a unitary pharmaceutical composition or separately and, when administered separately this may occur simultaneously or sequentially in any order. Such sequential administration may be close in time or remote in time.

In an embodiment, the other anti-hyperkalemic compound is a potassium ion binder such as a cross-lined polystyrene sulfonate (PSS) polymer resins. In an embodiment, the PSS resin is crosslinked with divinylbenzene (DVB) co-polymer. DVB-crosslinked PSS is the most common agent used in the management of hyperkalemia in hospitalized patients. PSS is typically provided as a sodium or calcium salt, and in the lumen of the intestine it exchanges sodium or calcium ions for secreted potassium ions. Most of this takes place in the colon, the site of most potassium secretion in the gut. In an embodiment, the anti-hyperkalemic PSS resin is described in WO2016111855 (incorporated herein by reference). In an embodiment, the PSS resin is a calcium salt of a PSS polymer resins crosslinked with DVB co-polymer. In an embodiment, the PSS resin is cross-linked with from 1.0 to 1.9 percent of DVB. In an embodiment, the PSS resin is cross-linked with from 1.6 to 1.9 percent of DVB. In an embodiment, the PSS resin is cross-linked with about 1.8 percent of DVB.

In an embodiment, the other anti-hyperkalemia agent is Kayexalate®, Argamate®, Kionex®, Resonium® or RDX7675. In another embodiment, the other anti-hyperkalemia agent is a fluoroacrylate polymer incorporating a potassium-binding carboxylate group e.g. patiromer (Veltassa®). In an embodiment, the other anti-hyperkalemia agent is an insoluble, non-absorbed zirconium-sodium silicate that traps potassium ions within its crystalline lattice structure e.g. ZS-9 (Lokelma®). In an embodiment, the other anti-hyperkalemia agent is a crosslinked polyacrylic acid e.g. CLP-1001.

In another aspect of the invention, it has been found unexpectedly that HSD2 inhibition in combination with inhibition of sodium-hydrogen exchanger (NHE) synergistically increase excretion of potassium into feces. NHE is found in the tubulus proximal of the nephron of the kidney and in the apical membrane of enterocytes of the intestine. The isoform known as NHE3 is primarily responsible for maintaining the balance of sodium and also indirectly linked to buffering of blood pH. The NHE3 antiporter imports one sodium ion into the cytosol of a cell as it ejects one hydrogen ion from the cell into the intestinal lumen and proximal tubule lumen. As shown in FIG. 1, it has been demonstrated that there is a synergistic effect on fecal potassium excretion when inhibiting HSD2 and NHE. Accordingly, there is provided a method for removing potassium from plasma and/or tissue of a mammal comprising administering to said mammal an effective amount of an HSD2 inhibitor or an MR agonist in combination with a compound that increases fluid volume in the colon. There is also provided a method for removing potassium from plasma and/or tissue of a mammal comprising administering to said mammal an effective amount of an HSD2 inhibitor or an MR agonist in combination with a compound that removes sodium from plasma and/or tissue. There is also provided a method for removing potassium from plasma and/or tissue of a mammal comprising administering to said mammal an effective amount of an HSD2 inhibitor or an MR agonist in combination with a compound that promotes excretions of sodium into the gastrointestinal tract. In an embodiment, the compound is a laxative that increases fluid in the colon. In an embodiment, the laxative is bisacodyl. In an embodiment, the laxative is picosulfate. In an embodiment, the laxative is MgOH. In an embodiment, the laxative is MiraLAX® (PEG 3350). In an embodiment, the laxative is lactulose. In an embodiment, the compound is an activator of intestinal guanylate cyclase. In an embodiment the guanylate cyclase agonist is linaclotide. In an embodiment, the guanylate cyclase agonist is plecanatide. In an embodiment, the compound is an activator of intestinal ClC-2 chloride channel. In an embodiment, the ClC-2 chloride channels activator is lubiprostone.

There is also provided a method for removing potassium from plasma and/or tissue of a mammal comprising administering to said mammal an effective amount of an HSD2 inhibitor or an MR agonist in combination with a an NHE inhibitor. In an embodiment, the HSD2 inhibitor or MR agonist and the NHE inhibitor compounds are administered concurrently. In an embodiment, the HSD2 or MR agonist and the NHE inhibitor compounds are administered sequentially. In an embodiment, the HSD2 inhibitor or MR agonist is administered prior to the NHE inhibitor or MR agonist. In an embodiment, the NHE inhibitor or MR agonist compound is administered prior to the HSD2 inhibitor or MR agonist. In an embodiment, the NHE inhibitor is an NHE3 inhibitor.

In another aspect of the invention, there is provided a pharmaceutical composition comprising an HSD2 inhibitor and an NHE inhibitor. In another aspect, there is provided a pharmaceutical composition comprising an MR agonist and an NHE inhibitor.

In another aspect, there is provided a method for treating hyperkalemia in a mammal comprising administering to said mammal an effective amount of an HSD2 inhibitor or an MR agonist in combination with an NHE inhibitor. In an embodiment, the NHE inhibitor is an NHE3 inhibitor.

In an embodiment, the MR agonist is fludrocortisone.

In another aspect, there is provided a method for treating hyperkalemia in a mammal comprising administering to said mammal an effective amount of an HSD2 inhibitor in combination with an NHE inhibitor. In an embodiment, the NHE inhibitor is an NHE3 inhibitor. In another aspect, there is provided a composition comprising an HSD2 inhibitor and an NHE inhibitor. In an embodiment, the composition is a pharmaceutical composition. In an embodiment there is an effective amount of HSD2 inhibitor compound and the NHE inhibitor compound. In an embodiment, the composition further comprises a pharmaceutically acceptable carrier, excipient and/or diluent. In an embodiment, the HSD2 inhibitor is glycyrrhetinic acid or an analogue thereof. In an embodiment, the HSD2 inhibitor is glycyrrhetinic acid. In an embodiment, the HSD2 inhibitor is glycyrrhizin. In an embodiment, the HSD2 inhibitor is a compound according to formula I herein. In an embodiment, the NHE inhibitor is an NHE3 inhibitor. In an embodiment the NHE3 inhibitor is a compound described in: U.S. Pat. Nos. 5,866,610; 6,399,824; 6,911,453; 6,703,405; 6,005,010; 6,736,705; 6,887,870; 6,737,423; 7,326,705; 5,824,691 (WO94/026709); 6,399,824 (WO02/024637); U.S. Pat. Pub. Nos. 2004/0039001 (WO02/020496); 2005/0020612 (WO03/055490); 2004/0113396 (WO03/051866); 2005/0020612; 2005/0054705; 2008/0194621; 2007/0225323; 2004/0039001; 2004/0224965; 2005/0113396; 2007/0135383; 2007/0135385; 2005/0244367; 2007/0270414; International Publication Nos. WO 01/072742; WO 01/021582 (CA2387529); WO97/024113 (CA02241531) WO2010078449; WO2014029983; WO2014029984; and European Pat. No. EP0744397 (CA2177007); each of which is incorporated herein by reference in their entirety.

In an embodiment, the NHE inhibitor is a compound that is minimally systemic, i.e., it inhibits NHE in the intestine and is substantially non-bioavailable. In an embodiment, the NHE inhibitor is a compound Formula (I) or (IX):

(I)

(IX)

wherein:

NHE is a NHE-binding small molecule that comprises (i) a hetero-atom containing moiety, and (ii) a cyclic or heterocyclic scaffold or support moiety bound directly or indirectly thereto, the heteroatom-containing moiety being selected from a substituted guanidinyl moiety and a substituted heterocyclic moiety, which may optionally be fused with the scaffold or support moiety to form a fused bicyclic structure; and, Z is a moiety having at least one site thereon for attachment to the NHE-binding small molecule, the resulting NHE-Z molecule possessing overall physicochemical properties that render it substantially impermeable or substantially systemically non-bioavailable; and, E is an integer having a value of 1 or more.

In certain embodiments, the total number of freely rotatable bonds in the NHE-Z molecule is at least about 10. In certain embodiments, the total number hydrogen bond donors in the NHE-Z molecule is at least about 5. In some embodiments, the total number of hydrogen bond acceptors in the NHE-Z molecule is at least about 10. In certain embodiments, the total number of hydrogen bond donors and hydrogen bond acceptors in the NHE-Z molecule is at least about 10. In some embodiments, the Log P of the NHE-Z binding compound is at least about 5. In certain embodiments, the log P of the NHE-Z binding compound is less than about 1, or less than about 0. In certain embodiments, the scaffold is a 5-member or 6-member cyclic or heterocyclic moiety. In certain embodiments, the scaffold is aromatic.

In some embodiments, the scaffold of the NHE-binding small molecule is bound to the moiety, Z, the compound having the structure of Formula (II):

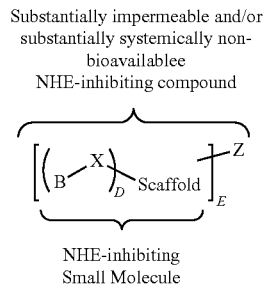

(II)

wherein:

Z is a Core having one or more sites thereon for attachment to one or more NHE-binding small molecules, the resulting NHE-Z molecule possessing overall physicochemical properties that render it substantially impermeable or substantially systemically non-bioavailable;

B is the heteroatom-containing moiety of the NHE-binding small molecule, and is selected from a substituted guanidinyl moiety and a substituted heterocyclic moiety, which may optionally be fused with the Scaffold moiety to form a fused, bicyclic structure;

Scaffold is the cyclic or heterocyclic scaffold or support moiety of the NHE-binding small molecule, which is bound directly or indirectly to heteroatom-containing moiety, B, and which is optionally substituted with one or more additionally hydrocarbyl or heterohydrocarbyl moieties;

X is a bond or a spacer moiety selected from a group consisting of substituted or unsubstituted hydrocarbyl or heterohydrocarbyl moieties, and in particular substituted or unsubstituted $C_{1-7}$ hydrocarbyl or heterohydrocarbyl, and substituted or unsubstituted, saturated or unsaturated, cyclic or heterocyclic moieties, which links B and the Scaffold; and D and E are integers, each independently having a value of 1 or more.

In some embodiments, the compound is an oligomer, dendrimer or polymer, and further wherein Z is a Core moiety having two or more sites thereon for attachment to multiple NHE-binding small molecules, either directly or indirectly through a linking moiety, L, the compound having the structure of Formula (X):

 (X)

wherein L is a bond or linker connecting the Core to the NHE-binding small molecule, and n is an integer of 2 or more, and further wherein each NHE-binding small molecule may be the same or differ from the others.

In some embodiments, the NHE-binding small molecule has the structure of Formula (IV):

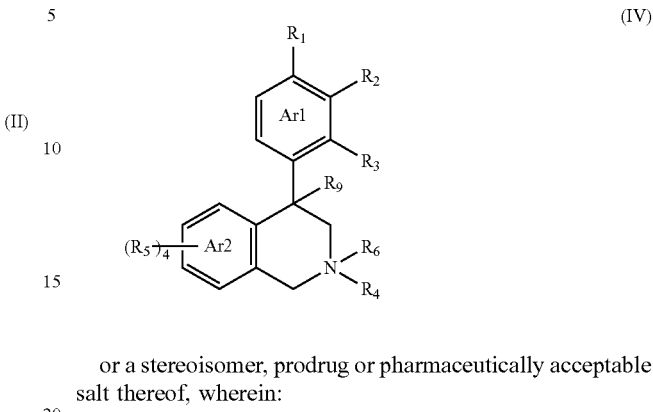

(IV)

or a stereoisomer, prodrug or pharmaceutically acceptable salt thereof, wherein:

each $R_1$, $R_2$, $R_3$, $R_5$ and $R_9$ are independently selected from H, halogen, $-NR_7(CO)R_8$, $-(CO)NR_7R_8$, $-SO_2-NR_7R_8$, $-NR_7SO_2R_8$, $-NR_7R_8$, $-OR_7$, $-SR_7$, $-O(CO)NR_7R_8$, $-NR_7(CO)OR_8$, and $-NR_7SO_2NR_8$, where $R_7$ and $R_8$ are independently selected from H or a bond linking the NHE-binding small molecule to L, provided at least one is a bond linking the NHE-binding small molecule to L;

$R_4$ is selected from H, $C_1$-$C_7$ alkyl, or a bond linking the NHE-binding small molecule to L;

$R_6$ is absent or selected from H and $C_1$-$C_7$ alkyl; and

Ar1 and Ar2 independently represent an aromatic ring or a heteroaromatic ring.

In certain embodiments, the NHE-binding small molecule has the following structure:

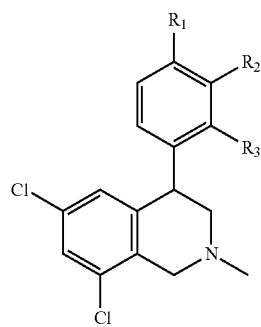

or a stereoisomer, prodrug or pharmaceutically acceptable salt thereof, wherein:

each $R_1$, $R_2$ and $R_3$ are independently selected from H, halogen, $-NR_7(CO)R_8$, $-(CO)NR_7R_8$, $-SO_2-NR_7R_8$, $-NR_7SO_2R_8$, $-NR_7R_8$, $-OR_7$, $-SR_7$, $-O(CO)NR_7R_8$, $-NR_7(CO)OR_8$, and $-NR_7SO_2NR_8$, where $R_7$ and $R_8$ are independently selected from H or a bond linking the NHE-binding small molecule to L, provided at least one is a bond linking the NHE-binding small molecule to L.

In some embodiments, the NHE-binding small molecule has one of the following structures:

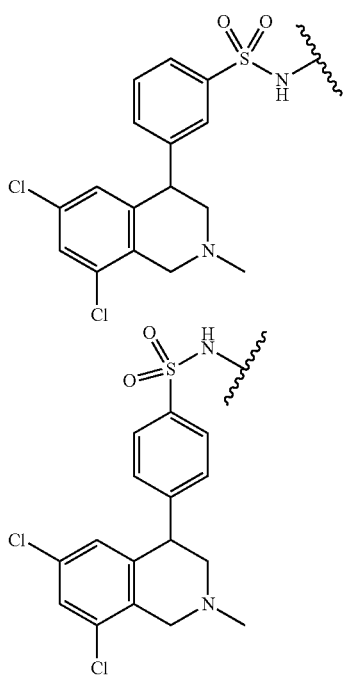

or

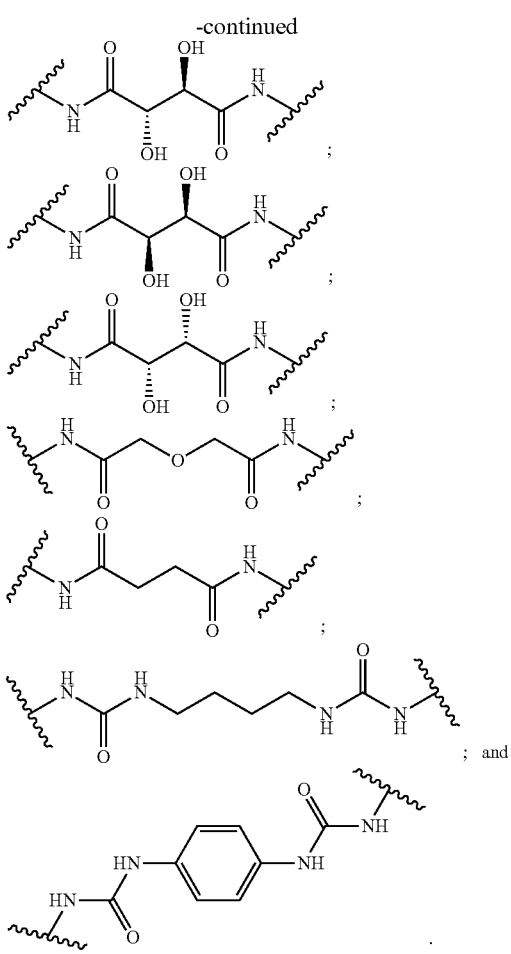

or a stereoisomer, prodrug or pharmaceutically acceptable salt thereof. In certain embodiments, L is a polyalkylene glycol linker. In certain embodiments, L is a polyethylene glycol linker. In some embodiments, n is 2.

In certain embodiments, the Core has the following structure:

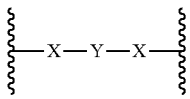

wherein:
X is selected from the group consisting of a bond, —O—, —NH—, —S—, $C_{1-6}$alkylene, —NHC(=O)—, —C(=O)NH—, —NHC(=O)NH—, —SO$_2$NH—, and —NHSO$_2$—;
Y is selected from the group consisting of a bond, optionally substituted $C_{1-8}$-alkylene, optionally substituted aryl, optionally substituted heteroaryl, a polyethylene glycol linker, —(CH$_2$)$_{1-6}$O(CH$_2$)$_{1-6}$— and —(CH$_2$)$_{1-6}$NY$_1$(CH$_2$)$_{1-6}$—; and
Y$_1$ is selected from the group consisting of hydrogen, optionally substituted $C_{1-8}$-alkyl, optionally substituted aryl or optionally substituted heteroaryl.

In some embodiments, the Core is selected from the group consisting of

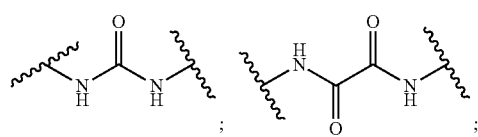

wherein: L is a bond or a linking moiety; NHE is a NHE-binding small molecule; and n is a non-zero integer.

In an embodiment, the NHE inhibitor is:
N,N',N''-(2,2',2''-nitrilotris(ethane-2,1-diyl))tris(3-(6,8-dichloro-2-methyl-1,2,3,4-tetrahydroisoquinolin-4-yl)benzenesulfonamide);
N,N'-(2,2'-(ethane-1,2-diylbis(oxy))bis(ethane-2,1-diyl))bis(3-(6,8-dichloro-2-methyl-1,2,3,4-tetrahydroisoquinolin-4-yl)benzenesulfonamide);
N,N'-(1,4-phenylenebis(methylene))bis(3-(6,8-dichloro-2-methyl-1,2,3,4-tetrahydroisoquinolin-4-yl)benzenesulfonamide);
N,N'-(1,4-phenylenebis(methylene))bis(3-(6,8-dichloro-2-methyl-1,2,3,4-tetrahydroisoquinolin-4-yl)benzenesulfonamide);
N,N'-(butane-1,4-diyl)bis(3-(6,8-dichloro-2-methyl-1,2,3,4-tetrahydroisoquinolin-4-yl)benzenesulfonamide);
N,N'-(dodecane-1,12-diyl)bis(3-(6,8-dichloro-2-methyl-1,2,3,4-tetrahydroisoquinolin-4-yl)benzenesulfonamide);
N,N',N'',N'''-(3,3',3'',3'''-(butane-1,4-diylbis(azanetriyl))tetrakis(propane-3,1-diyl))tetrakis(3-(6,8-dichloro-2-methyl-1,2,3,4-tetrahydroisoquinolin-4-yl)benzenesulfonamide);
N,N'-(butane-1,4-diyl)bis(4-(6,8-dichloro-2-methyl-1,2,3,4-tetrahydroisoquinolin-4-yl)benzenesulfonamide);
N,N'-(dodecane-1,12-diyl)bis(4-(6,8-dichloro-2-methyl-1,2,3,4-tetrahydroisoquinolin-4-yl)benzenesulfonamide);
N,N',N''-(2,2',2''-nitrilotris(ethane-2,1-diyl))tris(4-(6,8-dichloro-2-methyl-1,2,3,4-tetrahydroisoquinolin-4-yl)benzenesulfonamide);

N,N',N'',N'''-(3,3',3'',3'''-(butane-1,4-diylbis(azanetriyl))tetrakis(propane-3,1-diyl))tetrakis(4-(6,8-dichloro-2-methyl-1,2,3,4-tetrahydroisoquinolin-4-yl)benzenesulfonamide);

N,N'-(1,4-phenylenebis(methylene))bis(4-(6,8-dichloro-2-methyl-1,2,3,4-tetrahydroisoquinolin-4-yl)benzenesulfonamide);

N,N'-(2,2'-(ethane-1,2-diylbis(oxy))bis(ethane-2,1-diyl))bis(4-(6,8-dichloro-2-methyl-1,2,3,4-tetrahydroisoquinolin-4-yl)benzenesulfonamide);

N1,N8-bis(2-(2-(2-(2-(3-(6,8-dichloro-2-methyl-1,2,3,4-tetrahydroisoquinolin-4-yl)phenylsulfonamido)ethoxy)ethoxy)ethoxy)ethyl)octanediamide;

2-(N-(4-(6,8-dichloro-2-methyl-1,2,3,4-tetrahydroisoquinolin-4-yl)phenyl)sulfamoylamino)ethylphosphonic acid;

2-(N-(3-(6,8-dichloro-2-methyl-1,2,3,4-tetrahydroisoquinolin-4-yl)phenyl)sulfamoylamino)ethylphosphonic acid;

N,N'-(butane-1,4-diyl)bis[(E)-N-(diaminomethylene)-3-(3,5-difluoro-4-(4-sulfamoylphenoxy)phenyl)-2-methylacrylamide];

N,N'-(1,4-phenylenebis(methylene))bis[(E)-N-(diaminomethylene)-3-(3,5-difluoro-4-(4-sulfamoylphenoxy)phenyl)-2-methylacrylamide];

N,N'-(2,2'-(ethane-1,2-diylbis(oxy))bis(ethane-2,1-diyl))bis[(E)-N-(diaminomethylene)-3-(3,5-difluoro-4-(4-sulfamoylphenoxy)phenyl)-2-methylacrylamide];

N,N'-(2,2'-(2,2'-oxybis(ethane-2,1-diyl)bis(oxy))bis(ethane-2,1-diyl))bis[(E)-N-(diaminomethylene)-3-(3,5-difluoro-4-(4-sulfamoylphenoxy)phenyl)-2-methylacrylamide]

(E)-3-(4-(4-(N-(2-(2-(2-(2-aminoethoxy)ethoxy)ethoxy)ethyl)sulfamoyl)phenoxy)-3,5-difluorophenyl)-N-(diaminomethylene)-2-methylacrylamide;

N,N'-(13-oxo-3,6,9,17,20,23-hexaoxa-12,14-diazapentacosane-1,25-diyl)bis[(E)-N-(diaminomethylene)-3-(3,5-difluoro-4-(4-sulfamoylphenoxy)phenyl)-2-methylacrylamide];

N,N'-(13,20 dioxo-3, 6, 9, 24, 27, 30-hexaoxa-12, 21-diazadotricontane-1,32-diyl)bis[(E)-N-(diaminomethylene)-3-(3,5-difluoro-4-(4-sulfamoylphenoxy)phenyl)-2-methylacrylamide];

N,N'-(2,2'-(2,2'-(2,2'-(2,2'-(4,4'-oxybis(methylene)bis(1H-1,2,3-triazole-4,1-diyl))bis(ethane-2,1-diyl))bis(oxy)bis(ethane-2,1-diyl))bis(oxy)bis(ethane-2,1-diyl))bis(oxy)bis(ethane-2,1-diyl))bis[(E)-N-(diaminomethylene)-3-(3,5-difluoro-4-(4-sulfamoylphenoxy)phenyl)-2-methylacrylamide];

N,N'-(2,2'-(2,2'-(2,2'-(2,2'-(4,4'-oxybis(methylene)bis(1H-1,2,3-triazole-4,1-diyl))bis(ethane-2,1-diyl))bis(oxy)bis(ethane-2,1-diyl))bis(oxy)bis(ethane-2,1-diyl))bis(oxy)bis(ethane-2,1-diyl))bis(3-(6,8-dichloro-2-methyl-1,2,3,4-tetrahydroisoquinolin-4-yl)benzenesulfonamide)

1-(2-(2-(2-(2-(3-(6,8-dichloro-2-methyl-1,2,3,4-tetrahydroisoquinolin-4-yl)phenylsulfonamido)ethoxy)ethoxy)ethyl)-1H-1,2,3-triazole-4,5-dicarboxylic acid;

N1,N4-bis(2-(2-(2-(2-(3-(6,8-dichloro-2-methyl-1,2,3,4-tetrahydroisoquinolin-4-yl)phenylsulfonamido)ethoxy)ethoxy)ethyl)-2,3-dihydroxysuccinamide;

N1,N4-bis(2-(2-(2-(2-(4-(6,8-dichloro-2-methyl-1,2,3,4-tetrahydroisoquinolin-4-yl)phenylsulfonamido)ethoxy)ethoxy)ethyl)-2,3-dihydroxysuccinamide;

N1,N31-bis(2-(2-(2-(2-(3-(6,8-dichloro-2-methyl-1,2,3,4-tetrahydroisoquinolin-4-yl)phenylsulfonamido)ethoxy)ethoxy)ethyl)-4,7,10,13,16,19,22,25,28-nonaoxahentriacontane-1,31-diamide;

N1,N31-bis(2-(2-(2-(2-(4-(6,8-dichloro-2-methyl-1,2,3,4-tetrahydroisoquinolin-4-yl)phenylsulfonamido)ethoxy)ethoxy)ethyl)-4,7,10,13,16,19,22,25,28-nonaoxahentriacontane-1,31-diamide;

N,N'-(13-oxo-3,6,9,17,20,23-hexaoxa-12,14-diazapentacosane-1,25-diyl)bis(3-(6,8-dichloro-2-methyl-1,2,3,4-tetrahydroisoquinolin-4-yl)benzenesulfonamide);

N1,N31-bis(2-(2-(2-(2-(4-(4-((E)-3-(diaminomethyleneamino)-2-methyl-3-oxoprop-1-enyl)-2,6-difluorophenoxy)phenylsulfonamido)ethoxy)ethoxy)ethoxy)ethyl)-4,7,10,13,16,19,22,25,28-nonaoxahentriacontane-1,31-diamide;

N,N'-(13-oxo-3,6,9,17,20,23-hexaoxa-12,14-diazapentacosane-1,25-diyl)bis(4-(6,8-dichloro-2-methyl-1,2,3,4-tetrahydroisoquinolin-4-yl)benzenesulfonamide);

N1,N4-bis(20-(4-(4-((E)-3-(diaminomethyleneamino)-2-methyl-3-oxoprop-1-enyl)-2,6-difluorophenoxy)phenylsulfonamido)-3,6,9,12,15,18-hexaoxaicosyl)-2,3-dihydroxysuccinamide;

N1,N4-bis(2-(3-(6,8-dichloro-2-methyl-1,2,3,4-tetrahydroiso-quinolin-4-yl)phenylsulfonamido)ethyl)-2,3-dihydroxysuccinamide;

N1,N4-bis(2-(2-(2-(2-(3-(6,8-dichloro-2-ethyl-1,2,3,4-tetrahydroisoquinolin-4-yl)phenylsulfonamido)ethoxy)ethoxy)ethoxy)ethyl)-2,3-dihydroxysuccinamide; 3,3'-(2,2'-(2,2'-(2,2'-oxybis(ethane-2,1-diyl)bis(oxy))bis(ethane-2,1-diyl))bis(6,8-dichloro-1,2,3,4-tetrahydroisoquinoline-4,2-diyl))dianiline;

N1,N4-bis(2-(2-(2-(2-(3-(6,8-dichloro-2-methyl-1,2,3,4-tetrahydroisoquinolin-4-yl)phenylsulfonamido)ethoxy)ethoxy)ethyl)-2,3-dihydroxysuccinamide;

N1,N4-bis(2-(2-(2-(2-(3-(6,8-dichloro-2-methyl-1,2,3,4-tetrahydroisoquinolin-4-yl)phenylamino)ethoxy)ethoxy)ethoxy)ethyl)-2,3-dihydroxysuccinamide;

N1,N4-bis(1-(3-(6,8-dichloro-2-methyl-1,2,3,4-tetrahydroisoquinolin-4-yl)phenylamino)-1-oxo-5,8,11-trioxa-2-azatridecan-13-yl)-2,3-dihydroxysuccinamide;

N1,N2-bis(2-(2-(2-(4-(6,8-dichloro-2-methyl-1,2,3,4-tetrahydroisoquinolin-4-yl)phenylsulfonamido)ethoxy)ethoxy)ethyl)oxalamide;

N1,N4-bis(2-(2-(3-(6,8-dichloro-2-methyl-1,2,3,4-tetrahydroisoquinolin-4-yl)phenylsulfonamido)ethoxy)ethyl)-2,3-dihydroxysuccinamide;

N1,N4-bis(2-(2-(4-(6,8-dichloro-2-methyl-1,2,3,4-tetrahydroisoquinolin-4-yl)phenylsulfonamido)ethoxy)ethoxy)ethyl)succinamide;

2,2'-oxybis(N-(2-(2-(2-(4-(6,8-dichloro-2-methyl-1,2,3,4-tetrahydroisoquinolin-4-yl)phenylsulfonamido)ethoxy)ethoxy)ethyl)acetamide);

(2R,3R)—N1,N4-bis(2-(2-(2-(3-(3-(6,8-dichloro-2-methyl-1,2,3,4-tetrahydroisoquinolin-4-yl)phenylamino)-3-oxopropoxy)ethoxy)ethoxy)ethyl)-2,3-dihydroxysuccinamide;

N1,N2-bis(2-(2-(2-(2-(3-(6,8-dichloro-2-methyl-1,2,3,4-tetrahydroisoquinolin-4-yl)phenylsulfonamido)ethoxy)ethoxy)ethoxy)ethyl)oxalamide;

N1,N4-bis(2-(2-(2-(2-(3-(6,8-dichloro-2-methyl-1,2,3,4-tetrahydroisoquinolin-4-yl)phenylsulfonamido)ethoxy)ethoxy)ethyl)succinamide;

N1,N3-bis(2-(2-(2-(2-(3-(6,8-dichloro-2-methyl-1,2,3,4-tetrahydroisoquinolin-4-yl)phenylsulfonamido)ethoxy)ethoxy)ethyl)-2,2-dimethylmalonamide;

N1,N3-bis(2-(2-(2-(4-(6,8-dichloro-2-methyl-1,2,3,4-tetrahydroisoquinolin-4-yl)phenylsulfonamido)ethoxy)ethyl)-2,2-dimethylmalonamide;

N,N'-(2,2'-(2,2'-(2,2'-(pyridine-2,6-diylbis(oxy))bis(ethane-2,1-diyl))bis(oxy)bis(ethane-2,1-diyl))bis(oxy)

bis(ethane-2,1-diyl))bis(oxy)bis(ethane-2,1-diyl))bis(3-(6,8-dichloro-2-methyl-1,2,3,4-tetrahydroisoquinolin-4-yl)benzenesulfonamide);

2,2'-(methylazanediyl)bis(N-(2-(2-(2-(4-(6,8-dichloro-2-methyl-1,2,3,4-tetrahydroisoquinolin-4-yl)phenylsulfonamido)ethoxy)ethoxy)ethyl)acetamide) tris(2,2,2-trifluoroacetate); 5-amino-N1,N3-bis(2-(2-(2-(4-(6,8-dichloro-2-methyl-1,2,3,4-tetrahydroisoquinolin-4-yl)phenylsulfonamido)ethoxy)ethoxy)ethyl)isophthalamide tris(2,2,2-trifluoroacetate);

2,2'-oxybis(N-(2-(2-(2-(2-(3-(6,8-dichloro-2-methyl-1,2,3,4-tetrahydroisoquinolin-4-yl)phenylsulfonamido)ethoxy)ethoxy)ethoxy)ethyl)acetamide);

5-bromo-N1,N3-bis(2-(2-(2-(4-(6,8-dichloro-2-methyl-1,2,3,4-tetrahydroisoquinolin-4-yl)phenylsulfonamido)ethoxy)ethoxy)ethyl)isophthalamide bis(2,2,2-trifluoroacetate);

N1,N3-bis(2-(2-(2-(4-(6,8-dichloro-2-methyl-1,2,3,4-tetrahydroisoquinolin-4-yl)phenylsulfonamido)ethoxy)ethoxy)ethyl)-2-hydroxymalonamide bis(2,2,2-trifluoroacetate);

N1,N2-bis(2-(2-(2-(3-(6,8-dichloro-2-methyl-1,2,3,4-tetrahydroisoquinolin-4-yl)phenylsulfonamido)ethoxy)ethoxy)ethyl)oxalamide;

N1,N4-bis(2-(2-(2-(3-(6,8-dichloro-2-methyl-1,2,3,4-tetrahydroisoquinolin-4-yl)phenylsulfonamido)ethoxy)ethoxy)ethyl)succinamide; 3,5-bis(2-(2-(2-(4-(6,8-dichloro-2-methyl-1,2,3,4-tetrahydroisoquinolin-4-yl)phenylsulfonamido)ethoxy)ethoxy)ethylcarbamoyl)benzenesulfonic acid;

N1,N3-bis(2-(2-(2-(4-(6,8-dichloro-2-methyl-1,2,3,4-tetrahydroisoquinolin-4-yl)phenylsulfonamido)ethoxy)ethoxy)ethyl)-5-hydroxyisophthalamide;

(2R,3R)—N1,N4-bis(3-((3-(3-(6,8-dichloro-2-methyl-1,2,3,4-tetrahydroisoquinolin-4-yl)phenylsulfonamido)propyl)(methyl)amino)propyl)-2,3-dihydroxysuccinamide;

2,2'-oxybis(N-(2-(2-(2-(3-(6,8-dichloro-2-methyl-1,2,3,4-tetrahydroisoquinolin-4-yl)phenylsulfonamido)ethoxy)ethoxy)ethyl)acetamide);

N1,N3-bis(2-(2-(2-(3-(6,8-dichloro-2-methyl-1,2,3,4-tetrahydroisoquinolin-4-yl)phenylsulfonamido)ethoxy)ethoxy)ethyl)-2,2-dimethylmalonamide;

N1,N2-bis(2-(2-(2-(4-(6,8-dichloro-2-methyl-1,2,3,4-tetrahydroisoquinolin-4-yl)phenylsulfonamido)ethoxy)ethoxy)ethyl)oxalamide;

2,2'-oxybis(N-(2-(2-(2-(2-(4-(6,8-dichloro-2-methyl-1,2,3,4-tetrahydroisoquinolin-4-yl)phenylsulfonamido)ethoxy)ethoxy)ethoxy)ethyl)acetamide);

N1,N4-bis(2-(2-(2-(2-(4-(6,8-dichloro-2-methyl-1,2,3,4-tetrahydroisoquinolin-4-yl)phenylsulfonamido)ethoxy)ethoxy)ethoxy)ethyl)succinamide;

N1,N4-bis(2-(2-(2-(4-((S or R)-6,8-dichloro-2-methyl-1,2,3,4-tetrahydroisoquinolin-4-yl)phenylsulfonamido)ethoxy)ethoxy)ethyl)succinamide;

2,2'-oxybis(N-(2-(2-(2-(4-((S or R)-6,8-dichloro-2-methyl-1,2,3,4-tetrahydroisoquinolin-4-yl)phenylsulfonamido)ethoxy)ethoxy)ethyl)acetamide);

(S or R)—N,N'-(10,17-dioxo-3,6,21,24-tetraoxa-9,11,16,18-tetraazahexacosane-1,26-diyl)bis(3-((S)-6,8-dichloro-2-methyl-1,2,3,4-tetrahydroisoquinolin-4-yl)benzenesulfonamide);

(S or R)—N,N'-(2,2'-(2,2'-(2,2'-(1,4-phenylenebis(azanediyl))bis(oxomethylene)bis(azanediyl)bis(ethane-2,1-diyl))bis(oxy)bis(ethane-2,1-diyl))bis(oxy)bis(ethane-2,1-diyl))bis(3-((S or R)-6,8-dichloro-2-methyl-1,2,3,4-tetrahydroisoquinolin-4-yl)benzenesulfonamide);

N,N'-(butane-1,4-diyl)bis(2-(2-(2-(4-(6,8-dichloro-2-methyl-1,2,3,4-tetrahydroisoquinolin-4-yl)phenylsulfonamido)acetamido)acetamide);

N1,N4-bis(2-(2-(2-(4-(6,8-dichloro-2-methyl-1,2,3,4-tetrahydroisoquinolin-4-yl)phenylsulfonamido)ethoxy)ethoxy)ethyl)-2,3-dihydroxysuccinamide;

N,N'-(2,2'-(2,2'-(2,2'-(1,4-phenylenebis(methylene))bis(azanediyl))bis(ethane-2,1-diyl))bis(oxy)bis(ethane-2,1-diyl))bis(oxy)bis(ethane-2,1-diyl))bis(3-(6,8-dichloro-2-methyl-1,2,3,4-tetrahydroisoquinolin-4-yl)benzenesulfonamide);

(2R,3R)—N1,N4-bis(2-(2-(2-(4-(6,8-dichloro-2-methyl-1,2,3,4-tetrahydroisoquinolin-4-yl)phenylsulfonamido)ethoxy)ethoxy)ethyl)-2,3-dihydroxysuccinamide;

N,N'-(13,20-dioxo-3,6,9,24,27,30-hexaoxa-12,14,19,21-tetraazadotriacontane-1,32-diyl)bis(3-(6,8-dichloro-2-methyl-1,2,3,4-tetrahydroisoquinolin-4-yl)benzenesulfonamide);

N,N'-(1,1'-(1,4-phenylenebis(azanediyl))bis(1-oxo-5,8,11-trioxa-2-azatridecane-13,1-diyl))bis(3-(6,8-dichloro-2-methyl-1,2,3,4-tetrahydroisoquinolin-4-yl)benzenesulfonamide);

(2R,3R)—N1,N4-bis(20-(4-(4-((E)-3-(diaminomethyleneamino)-2-methyl-3-oxoprop-1-enyl)-2,6-difluorophenoxy)phenylsulfonamido)-3,6,9,12,15,18-hexaoxaicosyl)-2,3-dihydroxysuccinamide;

(E)-3-(4-(4-(N-(20-amino-3,6,9,12,15,18-hexaoxaicosyl)sulfamoyl)phenoxy)-3,5-difluorophenyl)-N-(diaminomethylene)-2-methylacrylamide;

(2R,3R)—N1,N4-bis(2-(2-(2-(2-(4-(4-((E)-3-(diaminomethyleneamino)-2-methyl-3-oxoprop-1-enyl)-2,6-difluorophenoxy)phenylsulfonamido)ethoxy)ethoxy)ethoxy)ethyl)-2,3-dihydroxysuccinamide;

2,2',2''-nitrilotris(N-(2-(2-(2-(2-(3-(6,8-dichloro-2-methyl-1,2,3,4-tetrahydroisoquinolin-4-yl)phenylsulfonamido)ethoxy)ethoxy)ethoxy)ethyl)acetamide);

N-(32-amino-3,6,9,12,15,18,21,24,27,30-decaoxadotriacontyl)-3-(6,8-dichloro-2-methyl-1,2,3,4-tetrahydroisoquinolin-4-yl)benzenesulfonamide;

N1,N3,N5-tris(2-(2-(2-(2-(3-(6,8-dichloro-2-methyl-1,2,3,4-tetrahydroisoquinolin-4-yl)phenylsulfonamido)ethoxy)ethoxy)ethoxy)ethyl)benzene-1,3,5-tricarboxamide;

N1,N4-bis(2-(2-(2-(2-(3-(6,8-dichloro-2-methyl-1,2,3,4-tetrahydroisoquinolin-4-yl)phenylsulfonamido)ethoxy)ethoxy)ethoxy)ethyl)terephthalamide;

N1,N31-bis(32-(3-(6,8-dichloro-2-methyl-1,2,3,4-tetrahydroisoquinolin-4-yl)phenylsulfonamido)-3,6,9,12,15,18,21,24,27,30-decaoxadotriacontyl)-4,7,10,13,16,19,22,25,28-nonaoxahentriacontane-1,31-diamide;

2R,3R)—N1,N4-bis(2-(2-(2-(3-(6,8-dichloro-2-methyl-1,2,3,4-tetrahydroisoquinolin-4-yl)phenylsulfonamido)ethoxy)ethoxy)ethyl)-2,3-dihydroxysuccinamide;

N1,N3-bis(2-(2-(2-(2-(3-(6,8-dichloro-2-methyl-1,2,3,4-tetrahydroisoquinolin-4-yl)phenylsulfonamido)ethoxy)ethoxy)ethoxy)ethyl)benzene-1,3-disulfonamide;

N4,N4'-bis(2-(2-(2-(3-(6,8-dichloro-2-methyl-1,2,3,4-tetrahydroisoquinolin-4-yl)phenylsulfonamido)ethoxy)ethoxy)ethyl)biphenyl-4,4'-disulfonamide;

(14R,15R)-1-(3-(6,8-dichloro-2-methyl-1,2,3,4-tetrahydroisoquinolin-4-yl)phenylsulfonamido)-14,15-dihydroxy-13-oxo-3,6,9-trioxa-12-azahexadecan-16-oic acid;

(2S,3S)—N1,N4-bis(2-(2-(2-(2-(3-(6,8-dichloro-2-methyl-1,2,3,4-tetrahydroisoquinolin-4-yl)phenylsulfonamido)ethoxy)ethoxy)ethoxy)ethyl)-2,3-dihydroxysuccinamide;

N1,N4-bis(2-(2-(2-(2-(3-((R)-6,8-dichloro-2-methyl-1,2,3,4-tetrahydroisoquinolin-4-yl)phenylsulfonamido)ethoxy)ethoxy)ethyl)-2,3-dihydroxysuccinamide;

N1,N4-bis(2-(2-(2-(2-(3-((S or R)-6,8-dichloro-2-methyl-1,2,3,4-tetrahydroisoquinolin-4-yl)phenylsulfonamido)ethoxy)ethoxy)ethoxy)ethyl)-2,3-dihydroxysuccinamide;

N1,N4-bis(2-(2-(2-(2-(4-((S or R)-6,8-dichloro-2-methyl-1,2,3,4-tetrahydroisoquinolin-4-yl)phenylsulfonamido)ethoxy)ethoxy)ethoxy)ethyl)-2,3-dihydroxysuccinamide;

N1,N4-bis(2-(2-(2-(2-(4-((R or S)-6,8-dichloro-2-methyl-1,2,3,4-tetrahydroisoquinolin-4-yl)phenylsulfonamido)ethoxy)ethoxy)ethoxy)ethyl)-2,3-dihydroxysuccinamide;

N1,N4-bis(2-(2-(2-(2-(4-(6,8-dichloro-2-methyl-1,2,3,4-tetrahydroisoquinolin-4-yl)phenylsulfonamido)ethoxy)ethoxy)ethoxy)ethyl)-2,3-dihydroxysuccinamide;

N1,N3-bis(2-(2-(2-(2-(3-(6,8-dichloro-2-methyl-1,2,3,4-tetrahydroisoquinolin-4-yl)phenylsulfonamido)ethoxy)ethoxy)ethoxy)ethyl)isophthalamide;

(2R,3S)—N1,N4-bis(2-(2-(2-(2-(3-(6,8-dichloro-2-methyl-1,2,3,4-tetrahydroisoquinolin-4-yl)phenylsulfonamido)ethoxy)ethoxy)ethoxy)ethyl)-2,3-dihydroxysuccinamide;

N1,N2-bis(2-(2-(2-(2-(3-(6,8-dichloro-2-methyl-1,2,3,4-tetrahydroisoquinolin-4-yl)phenylsulfonamido)ethoxy)ethoxy)ethoxy)ethyl)phthalamide;

N1,N4-bis(2-(2-(2-(4-(6,8-dichloro-2-methyl-1,2,3,4-tetrahydroisoquinolin-4-yl)phenylsulfonamido)ethoxy)ethoxy)ethyl)terephthalamide;

N,N'-(10-oxo-3,6,14,17-tetraoxa-9,11-diazanonadecane-1,19-diyl)bis(4-(6,8-dichloro-2-methyl-1,2,3,4-tetrahydroisoquinolin-4-yl)benzenesulfonamide);

N1,N4-bis(2-(2-(2-(2-(4-(6,8-dichloro-2-methyl-1,2,3,4-tetrahydroisoquinolin-4-yl)phenylsulfonamido)ethoxy)ethoxy)ethoxy)ethyl)terephthalamide;

N1,N4-bis(2-(2-(2-(3-(6,8-dichloro-2-methyl-1,2,3,4-tetrahydroisoquinolin-4-yl)phenylsulfonamido)ethoxy)ethoxy)ethyl)terephthalamide;

N,N'-(10-oxo-3,6,14,17-tetraoxa-9,11-diazanonadecane-1,19-diyl)bis(3-(6,8-dichloro-2-methyl-1,2,3,4-tetrahydroisoquinolin-4-yl)benzenesulfonamide);

N,N'-(10,17-dioxo-3,6,21,24-tetraoxa-9,11,16,18-tetraazahexacosane-1,26-diyl)bis(3-(6,8-dichloro-2-methyl-1,2,3,4-tetrahydroisoquinolin-4-yl)benzenesulfonamide);

N,N'-(2,2'-(2,2'-(2,2'-(1,4-phenylenebis(azanediyl))bis(oxomethylene)bis(azanediyl)bis(ethane-2,1-diyl))bis(oxy)bis(ethane-2,1-diyl))bis(oxy)bis(ethane-2,1-diyl))bis(3-(6,8-dichloro-2-methyl-1,2,3,4-tetrahydroisoquinolin-4-yl)benzenesulfonamide);

N,N'-(10,17-dioxo-3,6,21,24-tetraoxa-9,11,16,18-tetraazahexacosane-1,26-diyl)bis(4-(6,8-dichloro-2-methyl-1,2,3,4-tetrahydroisoquinolin-4-yl)benzenesulfonamide);

Phenylenebis(azanediyl))bis(oxomethylene)bis(azanediyl)bis(ethane-2,1-diyl))bis(oxy)bis(ethane-2,1-diyl))bis(oxy)bis(ethane-2,1-diyl))bis(4-(6,8-dichloro-2-methyl-1,2,3,4-tetrahydroisoquinolin-4-yl)benzenesulfonamide);

(2S,3S)—N1,N4-bis(2-(2-(2-(2-(3-((S or R)-6,8-dichloro-2-methyl-1,2,3,4-tetrahydroisoquinolin-4-yl)phenylsulfonamido)ethoxy)ethoxy)ethoxy)ethyl)-2,3-dihydroxysuccinamide;

(2R,3R)—N1,N4-bis(2-(2-(2-(2-(3-((S or R)-6,8-dichloro-2-methyl-1,2,3,4-tetrahydroisoquinolin-4-yl)phenylsulfonamido)ethoxy)ethoxy)ethoxy)ethyl)-2,3-dihydroxysuccinamide;

(2S,3S)—N1,N4-bis(2-(2-(2-(2-(4-((S or R)-6,8-dichloro-2-methyl-1,2,3,4-tetrahydroisoquinolin-4-yl)phenylsulfonamido)ethoxy)ethoxy)ethoxy)ethyl)-2,3-dihydroxysuccinamide;

(2R,3R)—N1,N4-bis(2-(2-(2-(2-(4-((S or R)-6,8-dichloro-2-methyl-1,2,3,4-tetrahydroisoquinolin-4-yl)phenylsulfonamido)ethoxy)ethoxy)ethoxy)ethyl)-2,3-dihydroxysuccinamide;

(S or R)—N,N'-(13,20-dioxo-3,6,9,24,27,30-hexaoxa-12,14,19,21-tetraazadotriacontane-1,32-diyl)bis(3-((S or R)-6,8-dichloro-2-methyl-1,2,3,4-tetrahydroisoquinolin-4-yl)benzenesulfonamide);

(S or R)—N,N'-(1,1'-(1,4-phenylenebis(azanediyl))bis(1-oxo-5,8,11-trioxa-2-azatridecane-13,1-diyl))bis(3-((S or R)-6,8-dichloro-2-methyl-1,2,3,4-tetrahydroisoquinolin-4-yl)benzenesulfonamide);

N1,N4-bis(2-(2-(2-(2-(4-((S or R)-6,8-dichloro-2-methyl-1,2,3,4-tetrahydroisoquinolin-4-yl)phenylsulfonamido)ethoxy)ethoxy)ethoxy)ethyl)-terephthalamide;

N1-(2-(2-(2-(2-(3-(6,8-dichloro-2-methyl-1,2,3,4-tetrahydroisoquinolin-4-yl)phenylsulfonamido)ethoxy)ethoxy)ethoxy)ethyl)succinamide;

N,N'-(13,20-dioxo-3,6,9,24,27,30-hexaoxa-12,14,19,21-tetraazadotriacontane-1,32-diyl)bis(4-(6,8-dichloro-2-methyl-1,2,3,4-tetrahydroisoquinolin-4-yl)benzenesulfonamide);

N,N'-(1,1'-(1,4-phenylenebis(azanediyl))bis(1-oxo-5,8,11-trioxa-2-azatridecane-13,1-diyl))bis(4-(6,8-dichloro-2-methyl-1,2,3,4-tetrahydroisoquinolin-4-yl)benzenesulfonamide);

(S or R)—N,N'-(13-oxo-3,6,9,17,20,23-hexaoxa-12,14-diazapentacosane-1,25-diyl)bis(4-((S or R)-6,8-dichloro-2-methyl-1,2,3,4-tetrahydroisoquinolin-4-yl)benzenesulfonamide);

(S or R)—N,N'-(13,20-dioxo-3,6,9,24,27,30-hexaoxa-12,14,19,21-tetraazadotriacontane-1,32-diyl)bis(4-((S or R)-6,8-dichloro-2-methyl-1,2,3,4-tetrahydroisoquinolin-4-yl)benzenesulfonamide); or (S or R)—N,N'-(1,1'-(1,4-phenylenebis(azanediyl))bis(1-oxo-5,8,11-trioxa-2-azatridecane-13,1-diyl))bis(4-((S or R)-6,8-dichloro-2-methyl-1,2,3,4-tetrahydroisoquinolin-4-yl)benzenesulfonamide).

In an embodiment, the NHE inhibitor is:

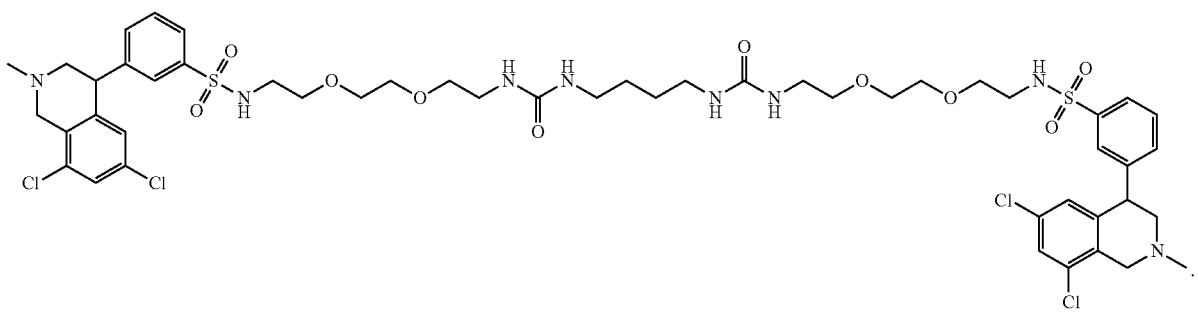

In some embodiments, the compound has the following structure of Formula (I-H):

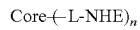   (I-H)

or a stereoisomer, prodrug or pharmaceutically acceptable salt thereof, wherein:

(a) n is an integer of 2 or more;

(b) Core is a Core moiety having two or more sites thereon for attachment to two or more NHE-binding small molecule moieties;

(c) L is a bond or linker connecting the Core moiety to the two or more NHE-binding small molecule moieties; and (d) NHE is a NHE-binding small molecule moiety having the following structure of Formula (XI-H):

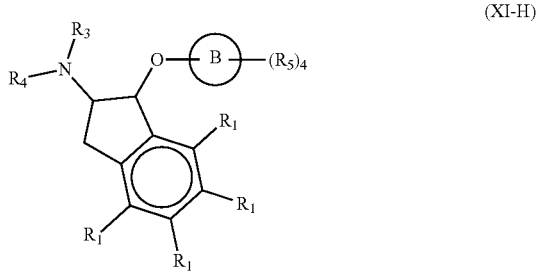   (XI-H)

wherein:

B is selected from the group consisting of aryl and heterocyclyl;

each $R_5$ is independently selected from the group consisting of hydrogen, halogen, optionally substituted $C_{1-4}$alkyl, optionally substituted $C_{1-4}$alkoxy, optionally substituted $C_{1-4}$ thioalkyl, optionally substituted heterocyclyl, optionally substituted heterocyclylalkyl, optionally substituted aryl, optionally substituted heteroaryl, hydroxyl, oxo, cyano, nitro, —$NR_7R_8$, —$NR_7C(=O)R_8$, —$NR_7C(=O)OR_8$, —$NR_7C(=O)NR_8R_9$, —$NR_7SO_2R_8$, —$NR_7S(O)_2NR_8R_9$, —$C(=OR_7)$, —$C(=O)NR_7R_8$, —$S(O)_{1-2}R_7$, and —$SO_2NR_7R_8$, wherein $R_7$, $R_8$, and $R_9$ are independently selected from the group consisting of hydrogen, $C_{1-4}$alkyl, or a bond linking the NHE-binding small molecule moiety to L, provided at least one is a bond linking the NHE-binding small molecule moiety to L;

$R_3$ and $R_4$ are independently selected from the group consisting of hydrogen, optionally substituted $C_{1-4}$alkyl, optionally substituted cycloalkyl, optionally substituted cycloalkylalkyl, optionally substituted aryl, optionally substituted aralkyl, optionally substituted heterocyclyl and optionally substituted heteroaryl; or $R_3$ and $R_4$ form together with the nitrogen to which they are bonded an optionally substituted 4-8 membered heterocyclyl; and each $R_1$ is independently selected from the group consisting of hydrogen, halogen, optionally substituted $C_{1-6}$alkyl and optionally substituted $C_{1-6}$alkoxy. In some embodiments, n is 2. In certain embodiments, L is a polyalkylene glycol linker. In certain embodiments, L is a polyethylene glycol linker.

In certain embodiments, the Core has the following structure:

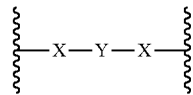

wherein:

X is selected from the group consisting of a bond, —O—, —NH—, —S—, $C_{1-6}$alkylene, —NHC(=O)—, —C(=O)NH—, —NHC(=O)NH—, —SO_2NH—, and —NHSO_2—;

Y is selected from the group consisting of a bond, optionally substituted $C_{1-6}$-alkylene, optionally substituted aryl, optionally substituted heteroaryl, a polyethylene glycol linker, —$(CH_2)_{1-6}O(CH_2)_{1-6}$— and —$(CH_2)_{1-6}NY_1(CH_2)_{1-6}$—; and $Y_1$ is selected from the group consisting of hydrogen, optionally substituted $C_{1-8}$-alkyl, optionally substituted aryl or optionally substituted heteroaryl.

In some embodiments, the Core is selected from the group consisting of

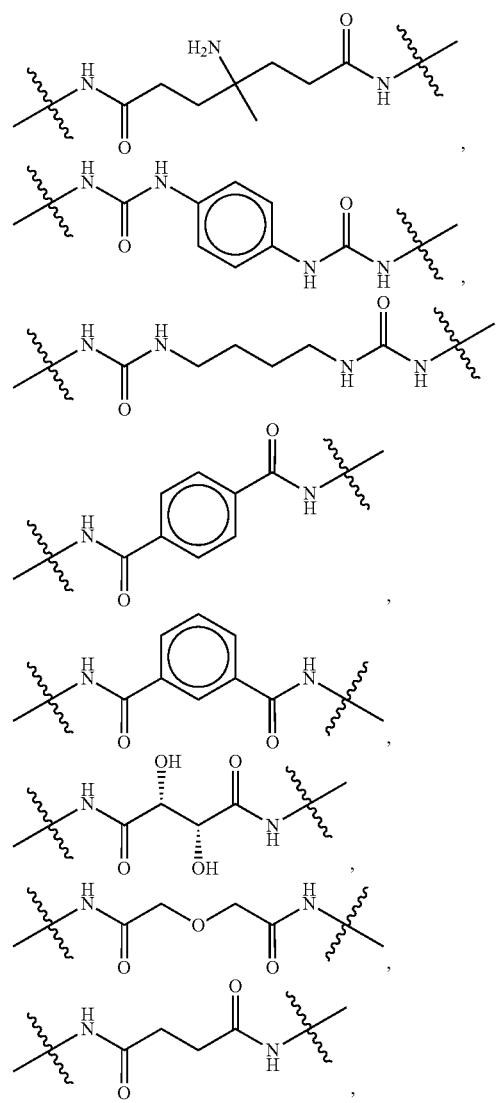

-continued

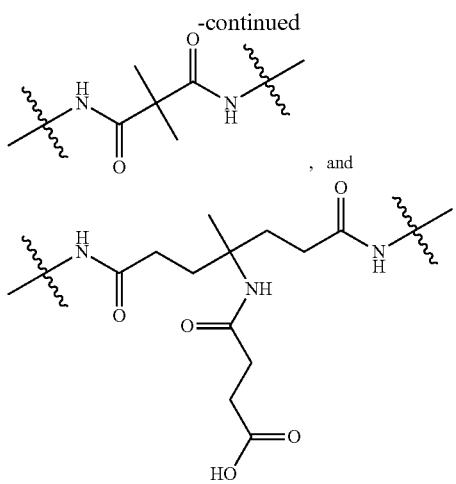

, and

In certain embodiments, the NHE-binding small molecule moiety has the following structure of Formula (XII-H):

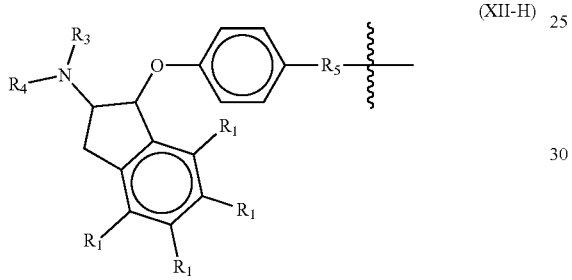

(XII-H)

wherein:
each $R_3$ and $R_4$ are independently selected from the group consisting of hydrogen and optionally substituted $C_{1-4}$alkyl, or $R_3$ and $R_4$, taken together with the nitrogen to which they are bonded, form an optionally substituted 4-8 membered heterocyclyl;
each $R_1$ is independently selected from the group consisting of hydrogen, halogen, $C_{1-6}$alkyl, and $C_{1-6}$haloalkyl; and
$R_5$ is selected from the group consisting of —$SO_2$—$NR_7$— and —NHC(=O)NH—, wherein $R_7$ is hydrogen or $C_{1-4}$alkyl.

In some embodiments, $R_3$ and $R_4$, taken together with the nitrogen to which they are bonded, form an optionally substituted 5 or 6 membered heterocyclyl. In certain embodiments, the optionally substituted 5 or 6 membered heterocyclyl is pyrrolidinyl or piperidinyl. In certain embodiments, the optionally substituted 5 or 6 membered heterocyclyl is pyrrolidinyl or piperidinyl, each substituted with at least one amino or hydroxyl. In some embodiments, $R_3$ and $R_4$ are independently $C_{1-4}$alkyl. In certain embodiments, $R_3$ and $R_4$ are methyl. In some embodiments, each $R_1$ is independently selected from the group consisting of hydrogen or halogen. In certain embodiments, each $R_1$ is independently selected from the group consisting of hydrogen, F and Cl.

In certain embodiments, the compound has the following structure of Formula (I-I):

Core—(L-NHE)$_3$  (I-I)

or a stereoisomer, prodrug or pharmaceutically acceptable salt thereof, wherein:
(a) NHE is a NHE-binding small molecule moiety having the following structure of Formula (A-I):

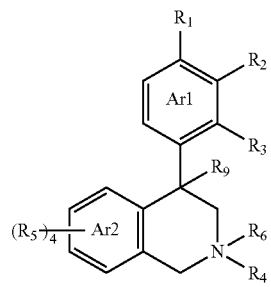

(A-I)

wherein:
each $R_1$, $R_2$, $R_3$, $R_5$ and $R_9$ are independently selected from H, halogen, —$NR_7(CO)R_8$, —$(CO)NR_7R_8$, —$SO_2$—$NR_7R_8$, —$NR_7SO_2R_8$, —$NR_7R_8$, —$OR_7$, —$SR_7$, —$O(CO)NR_7R_8$, —$NR_7(CO)OR_8$, and —$NR_7SO_2NR_8$, where $R_7$ and $R_8$ are independently selected from H, $C_{1-6}$alkyl, —$C_{1-6}$alkyl-OH or a bond linking the NHE-binding small molecule to L, provided at least one is a bond linking the NHE-binding small molecule to L;
$R_4$ is selected from H, $C_1$-$C_7$ alkyl, or a bond linking the NHE-binding small molecule to L;
$R_6$ is absent or selected from H and $C_1$-$C_7$ alkyl; and
Ar1 and Ar2 independently represent an aromatic ring or a heteroaromatic ring;
(b) Core is a Core moiety having the following structure of Formula (B-I):

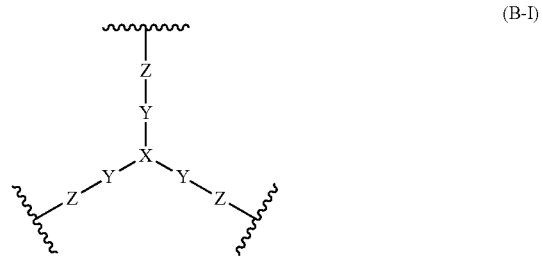

(B-I)

wherein:
X is selected from $C(X_1)$, N and $N(C_{1-6}$alkyl);
$X_1$ is selected from hydrogen, optionally substituted alkyl, —$NX_aX_b$, —$NO_2$, —$NX_c$—$C(=O)$—$NX_c$—$X_a$, —$C(=O)NX_c$—$X_a$, —$NX_c$—$C(=O)$—$X_a$, —$NX_c$—$SO_2$—$X_a$, —$C(=O)$—$X_a$ and —$OX_a$,
each $X_a$ and $X_b$ are independently selected from hydrogen, optionally substituted alkyl, optionally substituted cycloalkyl, optionally substituted cycloalkylalkyl, optionally substituted heterocyclyl, optionally substituted heterocyclylalkyl, optionally substituted aryl, optionally substituted aralkyl, optionally substituted heteroaryl and optionally substituted heteroarylalkyl;
Y is $C_{1-6}$alkylene;
Z is selected from —$NZ_a$—$C(=O)$—$NZ_a$—, —$C(=O)NZ_a$—, —$NZ_a$—$C(=O)$— and heteroaryl when X is $CX_1$;

Z is selected from $-NZ_a-C(=O)-NZ_a-$, $-NZ_a-C(=O)-$ and heteroaryl when X is N or N($C_{1-6}$alkyl); and each $X_c$ and $Z_a$ is independently selected from hydrogen and $C_{1-6}$alkyl; and (c) L is a bond or linker connecting the Core moiety to the NHE-binding small molecule moieties.

In some embodiments, the NHE-binding small molecule moiety has the following structure:

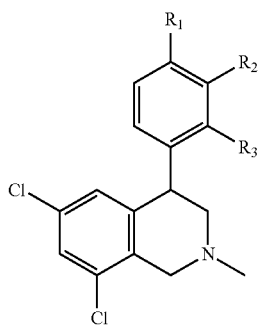

wherein:
each $R_1$, $R_2$ and $R_3$ are independently selected from H, halogen, $-NR_7(CO)R_8$, $-(CO)NR_7R_8$, $-SO_2-NR_7R_8$, $-NR_7SO_2R_8$, $-NR_7R_8$, $-OR_7$, $-SR_7$, $-O(CO)NR_7R_8$, $-NR_7(CO)OR_8$, and $-NR_7SO_2NR_8$, where $R_7$ and $R_8$ are independently selected from H, $C_{1-6}$alkyl, $-C_{1-6}$alkyl-OH or a bond linking the NHE-binding small molecule to L, provided at least one is a bond linking the NHE-binding small molecule to L.

In some embodiments, the NHE-binding small molecule moiety has one of the following structures:

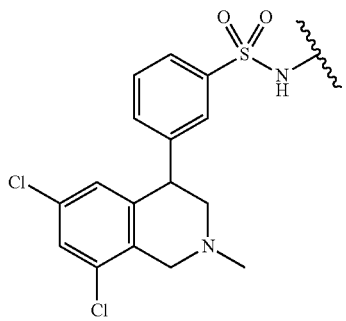

or

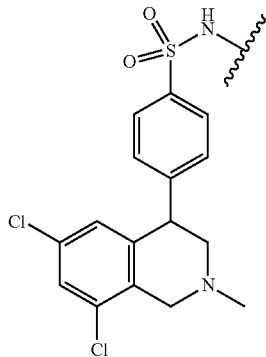

In some embodiments, L is a polyalkylene glycol linker.
In certain embodiments, L is a polyethylene glycol linker. In some embodiments, X is C($X_1$). In some embodiments, each $X_c$ is hydrogen. In certain embodiments, X is N. In certain embodiments, each $Z_a$ is hydrogen.

In some embodiments, the compound has the structure of Formula (II):

Core—(—L-NHE)$_4$ (II-I)

or a stereoisomer, prodrug or pharmaceutically acceptable salt thereof, wherein:
(a) NHE is a NHE-binding small molecule moiety having the structure of Formula (A-I):

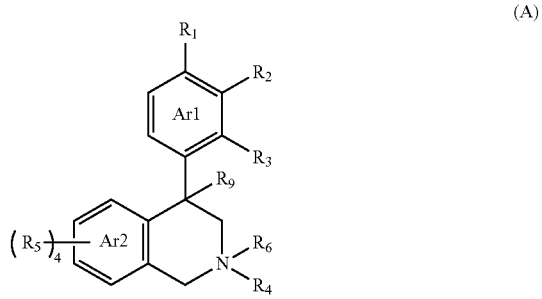

wherein:

each $R_1$, $R_2$, $R_3$, $R_5$ and $R_9$ are independently selected from H, halogen, —$NR_7(CO)R_8$, —$(CO)NR_7R_8$, —$SO_2$—$NR_7R_8$, —$NR_7SO_2R_8$, —$NR_7R_8$, —$OR_7$, —$SR_7$, —$O(CO)NR_7R_8$, —$NR_7(CO)OR_8$, and —$NR_7SO_2NR_8$, where $R_7$ and $R_8$ are independently selected from H, $C_{1-6}$alkyl, —$C_{1-6}$alkyl-OH or a bond linking the NHE-binding small molecule to L, provided at least one is a bond linking the NHE-binding small molecule to L;

$R_4$ is selected from H, $C_1$-$C_7$ alkyl, or a bond linking the NHE-binding small molecule to L;

$R_6$ is absent or selected from H and $C_1$-$C_7$ alkyl; and

Ar1 and Ar2 independently represent an aromatic ring or a heteroaromatic ring;

(b) Core is a Core moiety having the following structure of Formula (C-I):

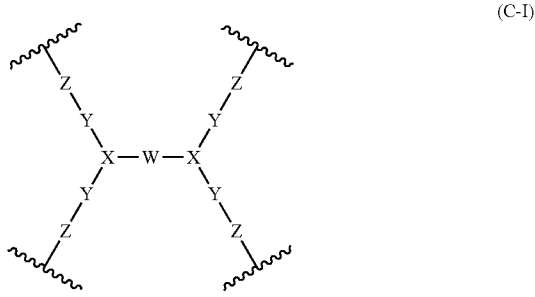

(C-I)

wherein:

W is selected from alkylene, polyalkylene glycol, —C(=O)—NH-(alkylene)-NH—C(=O)—, —C(=O)—NH-(polyalkylene glycol)-NH—C(=O)—, —C(=O)-(alkylene)-C(=O)—, —C(=O)-(polyalkylene glycol)-C(=O)— and cycloalkyl, X is N;

Y is $C_{1-6}$alkylene;

Z is selected from —$NZ_a$—C(=O)—$NZ_a$—, —C(=O)$NZ_a$—, —$NZ_a$—C(=O)— and heteroaryl;

each $Z_a$ is independently selected from hydrogen and $C_{1-6}$alkyl; and (c) L is a bond or linker connecting the Core moiety to the NHE-binding small molecules.

In certain embodiments, the NHE-binding small molecule moiety has the following structure:

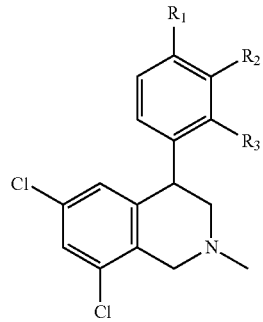

wherein:

each $R_1$, $R_2$ and $R_3$ are independently selected from H, halogen, —$NR_7(CO)R_8$, —$(CO)NR_7R_8$, —$SO_2$—$NR_7R_8$, —$NR_7SO_2R_8$, —$NR_7R_8$, —$OR_7$, —$SR_7$, —$O(CO)NR_7R_8$, —$NR_7(CO)OR_8$, and —$NR_7SO_2NR_8$, where $R_7$ and $R_8$ are independently selected from H, $C_{1-6}$alkyl, —$C_{1-6}$alkyl-OH or a bond linking the NHE-binding small molecule to L, provided at least one is a bond linking the NHE-binding small molecule to L.

In certain embodiments, the NHE-binding small molecule moiety has one of the following structures:

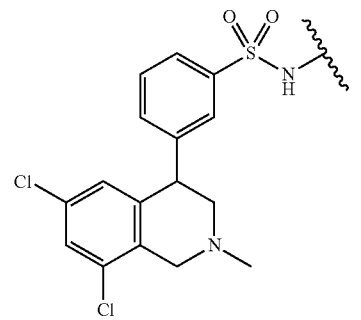

or

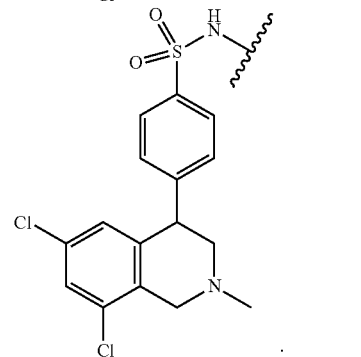

In another embodiment, the NHE inhibitor is:

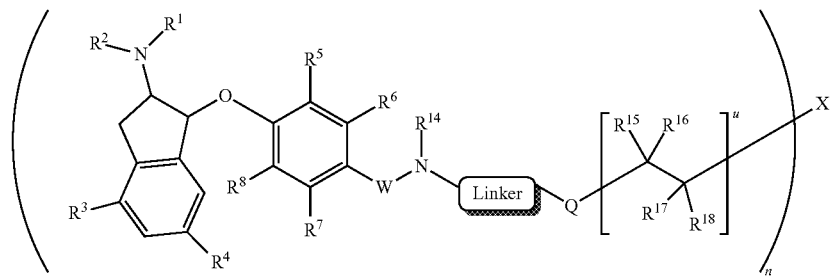

and pharmaceutically acceptable salts, prodrugs, solvates, hydrates, isomers, and tautomers thereof, wherein:

Linker is $-(CHR^{13})_p-[Y-(CH_2)_r]_s-Z-R^{13}-(CH_2)_t-Z-$;

W is independently, at each occurrence, $S(O)_2$, $C(O)$, or $-(CH_2)_m-$;

Z is independently, at each occurrence, a bond, $C(O)$, or $-C(O)NH-$;

Y is independently, at each occurrence, O, S, NH, N(C1-C3alkyl), or $-C(O)NH-$; Q is a bond, NH, $-C(O)NH-$, $-NHC(O)NH-$, $-NHC(O)N(CH_3)-$, or $-NHC(O)NH-(CHR^{13})$; m is an integer from 1 to 2; n is an integer from 1 to 4;

r and p are independently, at each occurrence, integers from 0 to 8;

s is an integer from 0 to 4;

t is an integer from 0 to 4;

u is an integer from 0 to 2;

$R_1$ and $R^2$ are independently H, $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl containing 1-5 heteroatoms selected from the group consisting of N, S, P and O, wherein each alkyl, alkenyl, cycloalkenyl, alkynyl, cycloalkyl, heterocyclyl, aryl, or heteroaryl is optionally substituted with one or more halogen, OH, CN, $-NO_2$, oxo, $-SR^9$, $-OR^9$, $-NHR^9$, $-NR^9R^{10}$, $-S(O)_2N(R^9)_2-$, $-S(O)_2R_9$, $-C(O)R^9$, $-C(O)OR^9$, $-C(O)NR^9R^{10}$, $-NR^9S(O)_2R^{10}$, $-S(O)R^9$, $-S(O)NR^9R^{10}$, $-NR'S(O)R^9$, $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, heterocycle, aryl, or heteroaryl; or $R^1$ and $R^2$ together with the nitrogen to which they are attached can form a heterocyclyl or heteroaryl containing 1-5 heteroatoms selected from the group consisting of N, S, P and O, wherein the heterocyclyl or heteroaryl group is optionally substituted with one or more halogen, OH, CN, $-NO_2$, oxo, $-SR^9$, $-OR^9$, $-NHR^9$, $-NR^9R^{10}$, $-S(O)_2N(R^9)_2-$, $-S(O)_2R_9$, $-C(O)R^9$, $-C(O)OR^9$, $-C(O)NR^9R^{10}$, $-NR^9S(O)_2R^{10}$, $-S(O)R^9$, $-S(O)NR^9R^{10}$, $-NR^9S(O)R^{10}$, $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, heterocycle, aryl, or heteroaryl;

$R^3$ and $R^4$ are independently halogen, OH, CN, $C_1$-$C_6$alkyl, $C_1$-$C_6$alkoxy, $C_1$-$C_6$haloalkyl, $C_1$-$C_6$haloalkoxy, or $-C(O)NR^9R^{10}$;

$R^5$, $R^6$, $R^7$, and $R^8$ are independently H, halogen, OH. CN, $-NO_2$, $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl containing 1-5 heteroatoms selected from the group consisting of N, S, P and O, $-SR^9$, $-OR^9$, $-NHR^9$, $-NR^9R^{10}$, $-S(O)_2N(R^9)_2-$, $-S(O)_2R_9$, $-C(O)R^9$, $-C(O)OR^9$, $-NR^9S(O)_2R^{10}$, $-S(O)R^9$, $-S(O)NR^9R_{10}$, $-NR^8S(O)R^9$;

$R^9$ and $R^{10}$ are independently H, $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, or heteroaryl containing 1-5 heteroatoms selected from the group consisting of N, S, P and O X is a bond, H, N, O, $CR^{11}R^{12}$, CR, C, $-NHC(O)NH-$, or $C_3$-$C_6$cyclolakyl;

$R^{11}$ and $R^{12}$ are independently H, $C_1$-$C_6$alkyl, OH, $NH_2$, CN, or $NO_2$;

$R^{13}$ is independently, at each occurrence, a bond, H, $C_1$-$C_6$alkyl, $C_4$-$C_8$cycloalkenyl, $C_3$-$C_8$cycloalkyl, heterocyclyl, aryl, or heteroaryl, wherein each cycloalkenyl, cycloalkyl, heterocyclyl, aryl, or heteroaryl is optionally substituted with one or more $R_{19}$;

$R^{14}$ is independently, at each occurrence, H, $C_1$-$C_6$alkyl, or $C_1$-$C_6$haloalkyl; or $R^6$ and $R^{14}$ together with the atoms to which they are attached may combine to form, independently, at each occurrence, 5-to-6 membered heterocyclyl, wherein each $C_3$-$C_8$ cycloalkyl, or heterocyclyl is optionally substituted with one or more $R^{19}$; or $R^{13}$ and $R^{14}$ together with the atoms to which they are attached may combine to form independently, at each occurrence, $C_3$-$C_8$ cycloalkyl, heterocyclyl, aryl, or heteroaryl containing 1-5 heteroatoms selected from the group consisting of N, S, P and O, wherein each heterocyclyl or heteroaryl is optionally substituted with one or more $R_{19}$ $R^{15}$, $R^{16}$, $R^{17}$, and $R^{18}$ are independently, at each occurrence, H, OH, $NH_2$, or $C_1$-$C_3$ alkyl, wherein the alkyl is optionally substituted with one or more $R^{19}$; and $R_{19}$ are independently, at each occurrence, H, OH, $NH_2$, oxo, $C_1$-$C_6$alkyl, $C_1$-$C_6$Hhaloalkyl, $C_1$-$C_6$alkoxy.

In an embodiment, the NHE3 inhibitor is a compound according to the foregoing formula provided that:

(1) when X is H, n is 1;

(2) when X is a bond, O, or $CR^{11}R^{12}$, n is 2;

(3) when n is 3, X is $CR^{11}$ or N;

(4) when n is 4 X is C;

(5) only one of Q or X is $-NHC(O)NH-$ at the time, (6) $R^1$ and $R^2$ together with the nitrogen to which they are attached, cannot form a pyrrolidinyl;

(7) when $R^1$ and $R^2$ are methyl, $R^3$ and $R^4$ are halogen, and $R^5$ and $R^8$ are H, Linker is not

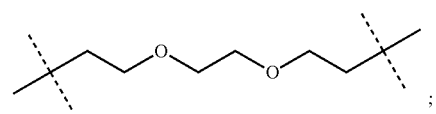

(8) when $R^1$ and $R^2$ together with the nitrogen to which they are attached form a piperidinyl, $R^3$ and $R^4$ are halogen, and $R^5$ and $R^8$ are H, Linker is not

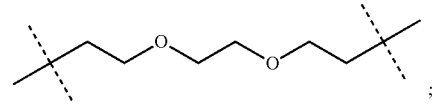

or (9) when R and $R^2$, together with the nitrogen to which they are attached, form 3-aminopiperidin-1-yl, $R^3$ and $R^4$ are halogen, and $R^5$, $R^6$, $R^7$, and $R^8$ are H, Linker is not

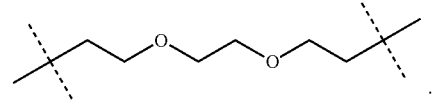

In an embodiment, the NHE3 compound has a structure according to the following formula:

[Chemical structure diagram showing a compound with R³, R⁴, R⁵, R⁶, R⁷, R¹, R², and a Linker with R¹³, R¹⁴, R¹⁵, R¹⁶ groups connected to X, with subscript n]

and pharmaceutically acceptable salts, prodrugs, solvates, hydrates, isomers, and tautomers thereof, wherein:

Linker is —(CHR$^8$)$_p$—[Y—(CH$_2$)$_r$]$_s$—Z—R$^8$—(CH$_2$)$_t$—Z—;

Q is a bond or —NHC(O)NH—;

Z is independently, at each occurrence, a bond, C(O), or —C(O)NH—;

Y is independently, at each occurrence, O, S, NH, N(C$_1$-C$_3$alkyl), or —C(O)NH—;

X is a bond, N, O, CR$^{11}$R$^{12}$, CR$^{11}$, C, or —NHC(O)NH—;

n is an integer from 2 to 4;

r and p are independently, at each occurrence, integers from 0 to 8;

s is an integer from 0 to 4;

t is an integer from 0 to 4;

u is an integer from 0 to 2;

R$^1$ and R$^2$ are independently halogen, OH, CN, C$_1$-C$_6$alkyl, C$_1$-C$_6$alkoxy, C$_1$-C$_6$haloalkyl, C$_1$-C$_6$haloalkoxy, or —C(O)NR$^9$R$^{10}$;

R$^3$, R$^4$, R$^5$, and R$^6$ are independently H, halogen, OH. CN, —NO$_2$, C$_1$-C$_6$alkyl, C$_2$-C$_6$alkenyl, C$_4$-C$_8$cycloalkenyl, C$_2$-C$_6$alkynyl, C$_3$-C$_8$cycloalkyl, heterocyclyl, aryl, heteroaryl containing 1-5 heteroatoms selected from the group consisting of N, S, P and O, —SR$^9$, —OR$^9$, —NHR$^9$, —NR$^9$R$_{10}$, —S(O)$_2$N(R$^9$)$_2$—, —S(O)$_2$R$_9$, —C(O)R$^9$, —C(O)OR$^9$, —NR$^9$S(O)$_2$R$^{10}$, —S(O)R$^9$, —S(O)NR$^9$R$_{10}$, —NR$^8$S(O)R$^9$;

R$^7$ is independently, at each occurrence, H, C$_1$-C$_6$alkyl, or C$_1$-C$_6$haloalkyl;

R$^8$ is independently, at each occurrence, a bond, H, C$_1$-C$_6$alkyl, C$_4$-C$_8$cycloalkenyl, C$_3$-C$_8$cycloalkyl, heterocyclyl, aryl, or heteroaryl, wherein each cycloalkenyl, cycloalkyl, heterocyclyl, aryl, or heteroaryl is optionally substituted with one or more R$^{17}$; or R$^7$ and R$^8$ together with the atoms to which they are attached may combine to form independently, at each occurrence, heterocyclyl or heteroaryl containing 1-5 heteroatoms selected from the group consisting of N, S, P and O, wherein each heterocyclyl or heteroaryl is optionally substituted with one or more R$^{17}$;

R$^9$ and R$^{10}$ are independently H, C$_1$-C$_6$alkyl, C$_2$-C$_6$alkenyl, C$_4$-C$_8$cycloalkenyl, C$_2$-C$_6$alkynyl, C$_3$-C$_8$cycloalkyl, heterocyclyl, aryl, or heteroaryl containing 1-5 heteroatoms selected from the group consisting of N, S, P and O;

R$^{11}$ and R$^{12}$ are independently H, C$_1$-C$_6$alkyl, OH, NH$_2$, CN, or NO$_2$;

R$^{13}$, R$^{14}$, R$^{15}$, and R$^{16}$ are independently, at each occurrence, H, OH, NH$_2$, or C$_1$-C$_3$ alkyl, wherein the alkyl is optionally substituted with one or more R$^{17}$; and R$^{17}$ is independently, at each occurrence, H, OH, NH$_2$, oxo, C$_1$-C$_6$alkyl, C$_1$-C$_6$haloalkyl, or C$_1$-C$_6$alkoxy.

In an embodiment, the NHE3 inhibitor compound has a structure according to the foregoing formula provided that:
(1) when X is a bond, O, or CR$^{11}$R$^{12}$, n is 2;
(2) when n is 3, X is CR$^{11}$ or N;
(3) when n is 4 X is C;
(4) only one of Q or X is —NHC(O)NH— at the time;
(5) when R$^1$ and R$^2$ are chloro, Q is —NHC(O)NH—, and R$^3$, R$^4$, R$^5$, and R$^6$ are H, Linker is not

[Chemical structure fragment showing linker with O-CH2CH2-O-CH2CH2-O linkage];

(6) when R$^1$ and R$^2$ are chloro, Q is —NHC(O)NH—, and R$^3$, R$^4$, R$^5$, and R$^6$ are H, Linker is not

[Chemical structure fragment showing linker with O-CH2CH2-O-CH2CH2-O-CH2CH2 linkage].

In an embodiment, the NHE3 inhibitor compound has a structure according to the following formula:

N,N'-(10,17-Dioxo-3,6,21,24-tetraoxa-9,11,16,18-tetraaza-hexacosane-1,26-diyl)bis[3-(6-chloro-2,8-dimethyl-1,2,3,4-tetrahydroisoquinolin-4-yl)benzenesulfonamide];

N,N'-(10,17-Dioxo-3,6,21,24-tetraoxa-9,11,16,18-tetraaza-hexacosane-1,26-diyl)bis[3-(6-chloro-8-cyano-2-methyl-1,2,3,4-tetrahydroisoquinolin-4-yl)benzenesulfonamide];

N,N'-(10,17-Dioxo-3,6,21,24-tetraoxa-9,11,16,18-tetraaza-hexacosane-1,26-diyl)bis[3-(6,8-dichloro-2-methyl-1,2,3,4-tetrahydroisoquinolin-4-yl)-4-methylbenzenesulfonamide];

N,N'-(10,17-Dioxo-3,6,21,24-tetraoxa-9,11,16,18-tetraaza-hexacosane-1,26-diyl)bis[3-(6-chloro-2,8-dimethyl-1,2,3,4-tetrahydroisoquinolin-4-yl)-4-methylbenzenesulfonamide];

N,N'-(10,17-Dioxo-3,6,21,24-tetraoxa-9,11,16,18-tetraaza-hexacosane-1,26-diyl)bis[3-(6-chloro-8-cyano-2-methyl-1,2,3,4-tetrahydroisoquinolin-4-yl)-4-methylbenzenesulfonamide];

N,N'-(10,17-Dioxo-3,6,21,24-tetraoxa-9,11,16,18-tetraaza-hexacosane-1,26-diyl)bis[5-(6,8-dichloro-2-methyl-1,2,3,4-tetrahydroisoquinolin-4-yl)-2-methylbenzenesulfonamide];

N,N'-(10,17-Dioxo-3,6,21,24-tetraoxa-9,11,16,18-tetraaza-hexacosane-1,26-diyl)bis[5-(6-chloro-2,8-dimethyl-1,2,3,4-tetrahydroisoquinolin-4-yl)-2-methylbenzenesulfonamide];

N,N'-(10,17-Dioxo-3,6,21,24-tetraoxa-9,11,16,18-tetraaza-hexacosane-1,26-diyl)bis(5-(6-chloro-8-cyano-2-methyl-1,2,3,4-tetrahydroisoquinolin-4-yl)-2-methylbenzenesulfonamide);

N,N'-(10,17-Dioxo-3,6,21,24-tetraoxa-9,11,16,18-tetraaza-hexacosane-1,26-diyl)bis[3-(6,8-dichloro-2-methyl-1,2,3,4-tetrahydroisoquinolin-4-yl)-4-fluorobenzenesulfonamide];

N,N'-(10,17-Dioxo-3,6,21,24-tetraoxa-9,11,16,18-tetraaza-hexacosane-1,26-diyl)bis[3-(6-chloro-2,8-dimethyl-1,2,3,4-tetrahydroisoquinolin-4-yl)-4-fluorobenzenesulfonamide];

N,N'-(10,17-Dioxo-3,6,21,24-tetraoxa-9,11,16,18-tetraaza-hexacosane-1,26-diyl)bis[3-(6-chloro-8-cyano-2-methyl-1,2,3,4-tetrahydroisoquinolin-4-yl)-4-fluorobenzenesulfonamide];

N,N'-[(3S,3'S)-(7,14-Dioxo-3,18-dioxa-6,8,13,15-tetraazaicosane-1,20-diyl)bis(pyrrolidine-1,3-diyl)]bis[3-(6,8-dichloro-2-methyl-1,2,3,4-tetrahydroisoquinolin-4-yl)benzenesulfonamide];

N,N'-[(3S,3'S)-(7,14-Dioxo-3,18-dioxa-6,8,13,15-tetraazaicosane-1,20-diyl)bis(pyrrolidine-1,3-diyl)]bis[3-(6-chloro-2,8-dimethyl-1,2,3,4-tetrahydroisoquinolin-4-yl)benzenesulfonamide];

N,N'-[(3S,3'S)-(7,14-Dioxo-3,18-dioxa-6,8,13,15-tetraazaicosane-1,20-diyl)bis(pyrrolidine-1,3-diyl)]bis[3-(6-chloro-8-cyano-2-methyl-1,2,3,4-tetrahydroisoquinolin-4-yl)benzenesulfonamide];

N,N'-[(3S,3'S)-(7,14-Dioxo-3,18-dioxa-6,8,13,15-tetraazaicosane-1,20-diyl)bis(pyrrolidine-1,3-diyl)]bis[3-(6,8-dichloro-2-methyl-1,2,3,4-tetrahydroisoquinolin-4-yl)-4-methylbenzenesulfonamide];

N,N'-[(3S,3'S)-(7,14-Dioxo-3,18-dioxa-6,8,13,15-tetraazaicosane-1,20-diyl)bis(pyrrolidine-1,3-diyl)]bis[3-(6-chloro-2,8-dimethyl-1,2,3,4-tetrahydroisoquinolin-4-yl)-4-methylbenzenesulfonamide];

N,N'-[(3S,3'S)-(7,14-Dioxo-3,18-dioxa-6,8,13,15-tetraazaicosane-1,20-diyl)bis(pyrrolidine-1,3-diyl)]bis[3-(6-chloro-8-cyano-2-methyl-1,2,3,4-tetrahydroisoquinolin-4-yl)-4-methylbenzenesulfonamide];

N,N'-[(3S,3'S)-(7,14-Dioxo-3,18-dioxa-6,8,13,15-tetraazaicosane-1,20-diyl)bis(pyrrolidine-1,3-diyl)]bis[5-(6,8-dichloro-2-methyl-1,2,3,4-tetrahydroisoquinolin-4-yl)-2-methylbenzenesulfonamide];

N,N'-[(3S,3'S)-(7,14-Dioxo-3,18-dioxa-6,8,13,15-tetraazaicosane-1,20-diyl)bis(pyrrolidine-1,3-diyl)]bis[5-(6-chloro-2,8-dimethyl-1,2,3,4-tetrahydroisoquinolin-4-yl)-2-methylbenzenesulfonamide];

N,N'-[(3S,3'S)-(7,14-Dioxo-3,18-dioxa-6,8,13,15-tetraazaicosane-1,20-diyl)bis(pyrrolidine-1,3-diyl)]bis[5-(6-chloro-8-cyano-2-methyl-1,2,3,4-tetrahydroisoquinolin-4-yl)-2-methylbenzenesulfonamide];

N,N'-[(3S,3'S)-(7,14-Dioxo-3,18-dioxa-6,8,13,15-tetraazaicosane-1,20-diyl)bis(pyrrolidine-1,3-diyl)]bis[3-(6,8-dichloro-2-methyl-1,2,3,4-tetrahydroisoquinolin-4-yl)-4-fluorobenzenesulfonamide];

N,N'-[(3S,3'S)-(7,14-Dioxo-3,18-dioxa-6,8,13,15-tetraazaicosane-1,20-diyl)bis(pyrrolidine-1,3-diyl)]bis[3-(6-chloro-2,8-dimethyl-1,2,3,4-tetrahydroisoquinolin-4-yl)-4-fluorobenzenesulfonamide];

N,N'-[(3S,3'S)-(7,14-Dioxo-3,18-dioxa-6,8,13,15-tetraazaicosane-1,20-diyl)bis(pyrrolidine-1,3-diyl)]bis[3-(6-chloro-8-cyano-2-methyl-1,2,3,4-tetrahydroisoquinolin-4-yl)-4-fluorobenzenesulfonamide];

N,N'-[(3R,3'R)-(7,14-Dioxo-3,18-dioxa-6,8,13,15-tetraazaicosane-1,20-diyl)bis(pyrrolidine-1,3-diyl)]bis[3-(6,8-dichloro-2-methyl-1,2,3,4-tetrahydroisoquinolin-4-yl)benzenesulfonamide];

N,N'-[(3R,3'R)-(7,14-Dioxo-3,18-dioxa-6,8,13,15-tetraazaicosane-1,20-diyl)bis(pyrrolidine-1,3-diyl)]bis[3-(6-chloro-2,8-dimethyl-1,2,3,4-tetrahydroisoquinolin-4-yl)benzenesulfonamide];

N,N'-[(3R,3'R)-(7,14-Dioxo-3,18-dioxa-6,8,13,15-tetraazaicosane-1,20-diyl)bis(pyrrolidine-1,3-diyl)]bis[3-(6-chloro-8-cyano-2-methyl-1,2,3,4-tetrahydroisoquinolin-4-yl)benzenesulfonamide];

N,N'-[(3R,3'R)-(7,14-Dioxo-3,18-dioxa-6,8,13,15-tetraazaicosane-1,20-diyl)bis(pyrrolidine-1,3-diyl)]bis[3-(6,8-dichloro-2-methyl-1,2,3,4-tetrahydroisoquinolin-4-yl)-4-methylbenzenesulfonamide];

N,N'-[(3R,3'R)-(7,14-Dioxo-3,18-dioxa-6,8,13,15-tetraazaicosane-1,20-diyl)bis(pyrrolidine-1,3-diyl)]bis[3-(6-chloro-2,8-dimethyl-1,2,3,4-tetrahydroisoquinolin-4-yl)-4-methylbenzenesulfonamide];

N,N'-[(3R,3'R)-(7,14-Dioxo-3,18-dioxa-6,8,13,15-tetraazaicosane-1,20-diyl)bis(pyrrolidine-1,3-diyl)]bis[3-(6-chloro-8-cyano-2-methyl-1,2,3,4-tetrahydroisoquinolin-4-yl)-4-methylbenzenesulfonamide];

N,N'-[(3R,3'R)-(7,14-Dioxo-3,18-dioxa-6,8,13,15-tetraazaicosane-1,20-diyl)bis(pyrrolidine-1,3-diyl)]bis[5-(6,8-dichloro-2-methyl-1,2,3,4-tetrahydroisoquinolin-4-yl)-2-methylbenzenesulfonamide];

N,N'-[(3R,3'R)-(7,14-Dioxo-3,18-dioxa-6,8,13,15-tetraazaicosane-1,20-diyl)bis(pyrrolidine-1,3-diyl)]bis[5-(6-chloro-2,8-dimethyl-1,2,3,4-tetrahydroisoquinolin-4-yl)-2-methylbenzenesulfonamide];

N,N'-[(3R,3'R)-(7,14-Dioxo-3,18-dioxa-6,8,13,15-tetraazaicosane-1,20-diyl)bis(pyrrolidine-1,3-diyl)]bis[5-(6-chloro-8-cyano-2-methyl-1,2,3,4-tetrahydroisoquinolin-4-yl)-2-methylbenzenesulfonamide];

N,N'-[(3R,3'R)-(7,14-Dioxo-3,18-dioxa-6,8,13,15-tetraazaicosane-1,20-diyl)bis(pyrrolidine-1,3-diyl)]bis[3-(6,8-dichloro-2-methyl-1,2,3,4-tetrahydroisoquinolin-4-yl)-4-fluorobenzenesulfonamide];

N,N'-[(3R,3'R)-(7,14-Dioxo-3,18-dioxa-6,8,13,15-tetraazaicosane-1,20-diyl)bis(pyrrolidine-1,3-diyl)]bis[3-(6-chloro-2,8-dimethyl-1,2,3,4-tetrahydroisoquinolin-4-yl)-4-fluorobenzenesulfonamide];

N,N'-[(3R,3'R)-(7,14-Dioxo-3,18-dioxa-6,8,13,15-tetraazaicosane-1,20-diyl)bis(pyrrolidine-1,3-diyl)]bis[3-(6-chloro-8-cyano-2-methyl-1,2,3,4-tetrahydroisoquinolin-4-yl)-4-fluorobenzenesulfonamide];

N,N'-[(7,14-Dioxo-3,18-dioxa-6,8,13,15-tetraazaicosane-1,20-diyl)bis(piperidine-1,4-diyl)]bis[3-(6-chloro-2,8-dimethyl-1,2,3,4-tetrahydroisoquinolin-4-yl)benzenesulfonamide];

N,N'-[(7,14-Dioxo-3,18-dioxa-6,8,13,15-tetraazaicosane-1,20-diyl)bis(piperidine-1,4-diyl)]bis[3-(6-chloro-8-cyano-2-methyl-1,2,3,4-tetrahydroisoquinolin-4-yl)benzenesulfonamide];

1,1'-[(3R,3'R)-(7,14-Dioxo-3,18-dioxa-6,8,13,15-tetraazaicosane-1,20-diyl)bis(pyrrolidine-1,3-diyl)]bis[N-([3-(6-chloro-2,8-dimethyl-1,2,3,4-tetrahydroisoquinolin-4-yl)phenyl]sulfonyl)formamide];

1,1'-[(3R,3'R)-(7,14-Dioxo-3,18-dioxa-6,8,13,15-tetraazaicosane-1,20-diyl)bis(pyrrolidine-1,3-diyl)]bis[N-([3-(6-chloro-8-cyano-2-methyl-1,2,3,4-tetrahydroisoquinolin-4-yl)phenyl]sulfonyl)formamide];

1,1'-(5,12-Dioxo-4,6,11,13-tetraazahexadecane-1,16-diyl)bis[N-([3-(6,8-dichloro-2-methyl-1,2,3,4-tetrahydroisoquinolin-4-yl)phenyl]sulfonyl)piperidine-4-carboxamide];

1,1'-(5,12-Dioxo-4,6,11,13-tetraazahexadecane-1,16-diyl)bis[N-([3-(6,8-dichloro-2-methyl-1,2,3,4-tetrahydroisoquinolin-4-yl)phenyl]sulfonyl)piperidine-3-carboxamide];

$N^1,N^{18}$-Bis([3-(6,8-Dichloro-2-dimethyl-1,2,3,4-tetrahydroisoquinolin-4-yl)phenyl]sulfonyl)-6,13-dioxo-5,7,12,14-tetraazaoctadecanediamide;

N,N'-[(3S,3'S)-(6,13-Dioxo-5,7,12,14-tetraazaoctadecanedioyl)bis(pyrrolidine-1,3-diyl)]bis[3-(6-chloro-2,8-dimethyl-1,2,3,4-tetrahydroisoquinolin-4-yl)benzenesulfonamide];

N,N'-[(3S,3'S)-(6,13-Dioxo-5,7,12,14-tetraazaoctadecanedioyl)bis(pyrrolidine-1,3-diyl)]bis[3-(6-chloro-8-cyano-2-methyl-1,2,3,4-tetrahydroisoquinolin-4-yl)benzenesulfonamide];

1-[2-(2-[(1-[(3-[(S)-6,8-Dichloro-2-methyl-1,2,3,4-tetrahydroisoquinolin-4-yl]phenyl)sulfonyl]piperidin-4-yl)oxy]

ethoxy)ethyl]-3-[4-(3-[2-(2-[(1-[(3-[(S)-6,8-dichloro-2-methyl-1,2,3,4-tetrahydroisoquinolin-4-yl]phenyl)sulfonyl]piperidin-4-yl)oxy]ethoxy)ethyl]ureido)butyl]urea;

1-(2-(2-(((R)-1-((3-((S)-6,8-dichloro-2-methyl-1,2,3,4-tetrahydroisoquinolin-4-yl)phenyl)sulfonyl)pyrrolidin-3-yl)oxy)ethoxy)ethyl)-3-(4-(3-(2-(2-(((R)-1-((3-((S)-6,8-dichloro-2-methyl-1,2,3,4-tetrahydroisoquinolin-4-yl)phenyl)sulfonyl)pyrrolidin-3-yl)oxy)ethoxy)ethyl)ureido)butyl)urea;

1-(2-[2-([(S)-1-[(3-[(S)-6,8-dichloro-2-methyl-1,2,3,4-tetrahydroisoquinolin-4-yl]phenyl)sulfonyl]pyrrolidin-3-yl]oxy)ethoxy]ethyl)-3-(4-[3-(2-[2-([(S)-1-[(3-[(S)-6,8-dichloro-2-methyl-1,2,3,4-tetrahydroisoquinolin-4-yl]phenyl)sulfonyl]pyrrolidin-3-yl]oxy)ethoxy]ethyl)ureido]butyl)urea;

3-[(S)-6,8-Dichloro-2-methyl-1,2,3,4-tetrahydroisoquinolin-4-yl]-N-[(3R,28R)-28-[(3-[(S)-6,8-dichloro-2-methyl-1,2,3,4-tetrahydroisoquinolin-4-yl]phenyl)sulfonamido]-2,29-dimethyl-12,19-dioxo-5,8,23,26-tetraoxa-11,13,18,20-tetraazatriacontan-3-yl]benzenesulfonamide;

N,N'-(10-Oxo-3,6,14,17-tetraoxa-9,11-diazanonadecane-1,19-diyl)bis[3-(6,8-dichloro-2-methyl-1,2,3,4-tetrahydroisoquinolin-4-yl)benzenesulfonamide];

N,N'-[(3S,3'S)-(7-Oxo-3,11-dioxa-6,8-diazatridecane-1,13-diyl]bis[pyrrolidine-1,3-diyl])bis(3-(6,8-dichloro-2-methyl-1,2,3,4-tetrahydroisoquinolin-4-yl)benzenesulfonamide];

$N^1,N^{18}$-Bis(1-[(3-[(S)-6,8-dichloro-2-methyl-1,2,3,4-tetrahydroisoquinolin-4-yl]phenyl)sulfonyl]piperidin-4-yl)-6,13-dioxo-5,7,12,14-tetraazaoctadecanediamid;

$N^1,N^{18}$-Bis(1-[(3-[(S)-6-chloro-8-cyano-2-methyl-1,2,3,4-tetrahydroisoquinolin-4-yl]phenyl)sulfonyl]piperidin-4-yl)-6,13-dioxo-5,7,12,14-tetraazaoctadecanediamide; or $N^1,N^{18}$-Bis(1-[(3-[(S)-6-chloro-2,8-dimethyl-1,2,3,4-tetrahydroisoquinolin-4-yl]phenyl)sulfonyl]piperidin-4-yl)-6,13-dioxo-5,7,12,14-tetraazaoctadecanediamide.

In one embodiment of the invention, the NHE3 inhibitor is a compound according to the formula:

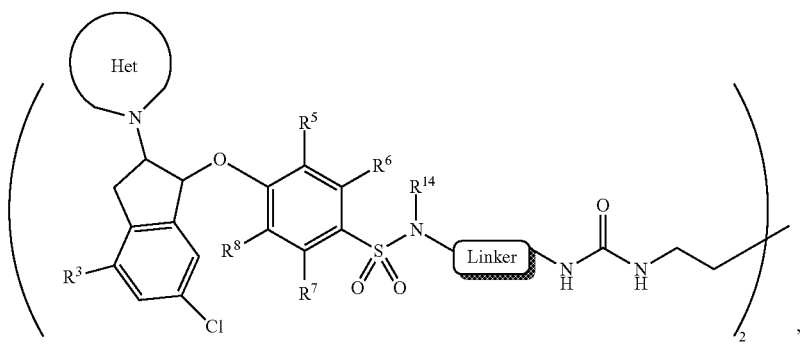

(Ia)

In one embodiment of the invention, the NHE3 inhibitor is a compound according to the formula:

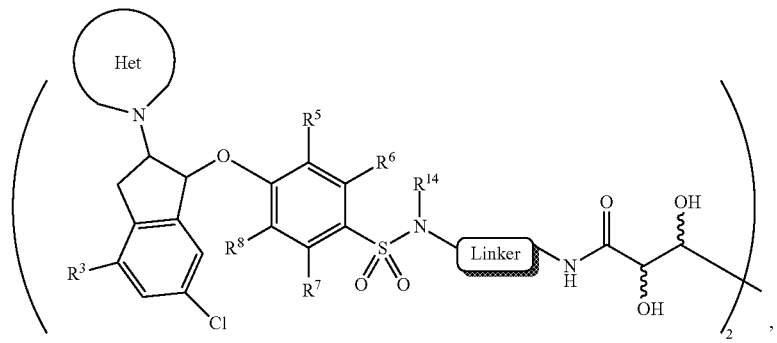

(Ib)

In an embodiment the NHE3 inhibitor is one of the following compounds:

1-[2-(2-[2-[(4-[[(1S,2S)-2-[(3R)-3-Aminopiperidin-1-yl]-4,6-dichloro-2,3-dihydro-1H-inden-1-yl]oxy]-3-methylbenzene)sulfonamido]ethoxy]ethoxy)ethyl]-3-[4-([[2-(2-[2-[(4-[[(1S,2S)-2-[(3R)-3-aminopiperidin-1-yl]-4,6-dichloro-2,3-dihydro-1H-inden-1-yl]oxy]-3-methylbenzene)sulfonamido]ethoxy]ethoxy)ethyl]carbamoyl]amino)butyl]urea;

3-[2-(2-[2-[(4-[[(1S,2S)-2-[(3R)-3-Aminopiperidin-1-yl]-4,6-dichloro-2,3-dihydro-1H-inden-1-yl]oxy]-3-fluorobenzene)sulfonamido]ethoxy]ethoxy)ethyl]-1-[4-([[2-(2-[2-[(4-[[(1S,2S)-2-[(3R)-3-aminopiperidin-1-yl]-4,6-dichloro-2,3-dihydro-1H-inden-1-yl]oxy]-3-fluorobenzene)sulfonamido]ethoxy]ethoxy)ethyl]carbamoyl]amino)butyl]urea;

3-[2-(2-[2-[(4-[[(1S,2S)-2-[(3R)-3-Aminopiperidin-1-yl]-6-chloro-4-methyl-2,3-dihydro-1H-inden-1-yl]oxy]benzene)sulfonamido]ethoxy]ethoxy)ethyl]-1-[4-([[2-(2-[2-[(4-[[(1S,2S)-2-[(3R)-3-aminopiperidin-1-yl]-6-chloro-4-methyl-2,3-dihydro-1H-inden-1-yl]oxy]benzene)sulfonamido]ethoxy]ethoxy)ethyl]carbamoyl]amino)butyl]urea;

3-[2-(2-[2-[(4-[[(1S,2S)-2-[(3R)-3-Aminopiperidin-1-yl]-6-chloro-4-cyano-2,3-dihydro-1H-inden-1-yl]oxy]benzene)sulfonamido]ethoxy]ethoxy)ethyl]-1-[4-([[2-(2-[2-[(4-[[(1S,2S)-2-[(3R)-3-aminopiperidin-1-yl]-6-chloro-4-cyano-2,3-dihydro-1H-inden-1-yl]oxy]benzene)sulfonamido]ethoxy]ethoxy)ethyl]carbamoyl]amino)butyl]urea;

3-[2-(2-[2-[(4-[[(1S,2S)-2-[(3R)-3-Aminopiperidin-1-yl]-6-chloro-4-methoxy-2,3-dihydro-1H-inden-1-yl]oxy]benzene)sulfonamido]ethoxy]ethoxy)ethyl]-1-[4-([[2-(2-[2-[(4-[[(1S,2S)-2-[(3R)-3-aminopiperidin-1-yl]-6-chloro-4-methoxy-2,3-dihydro-1H-inden-1-yl]oxy]benzene)sulfonamido]ethoxy]ethoxy)ethyl]carbamoyl]amino)butyl]urea;

1-[2-(2-[2-[(4-[[(1S,2S)-2-[(3R)-3-Aminopiperidin-1-yl]-6-chloro-4-fluoro-2,3-dihydro-1H-inden-1-yl]oxy]-3-methylbenzene)sulfonamido]ethoxy]ethoxy)ethyl]-3-[4-([[2-(2-[2-[(4-[[(1S,2S)-2-[(3R)-3-aminopiperidin-1-yl]-6-chloro-4-fluoro-2,3-dihydro-1H-inden-1-yl]oxy]-3-methylbenzene)sulfonamido]ethoxy]ethoxy)ethyl]carbamoyl]amino)butyl]urea;

3-[2-(2-[2-[(4-[[(1S,2S)-2-[(3R)-3-Aminopiperidin-1-yl]-6-chloro-4-methyl-2,3-dihydro-1H-inden-1-yl]oxy]-3-methylbenzene)sulfonamido]ethoxy]ethoxy)ethyl]-1-[4-([[2-(2-[2-[(4-[[(1S,2S)-2-[(3R)-3-aminopiperidin-1-yl]-6-chloro-4-methyl-2,3-dihydro-1H-inden-1-yl]oxy]-3-methylbenzene)sulfonamido]ethoxy]ethoxy)ethyl]carbamoyl]amino)butyl]urea;

3-[2-(2-[2-[(4-[[(1S,2S)-2-[(3R)-3-Aminopiperidin-1-yl]-6-chloro-4-cyano-2,3-dihydro-1H-inden-1-yl]oxy]-3-methylbenzene)sulfonamido]ethoxy]ethoxy)ethyl]-1-[4-([[2-(2-[2-[(4-[[(1S,2S)-2-[(3R)-3-aminopiperidin-1-yl]-6-chloro-4-cyano-2,3-dihydro-1H-inden-1-yl]oxy]-3-methylbenzene)sulfonamido]ethoxy]ethoxy)ethyl]carbamoyl]amino)-butyl]urea;

3-[2-(2-[2-[(4-[[(1S,2S)-2-[(3R)-3-Aminopiperidin-1-yl]-6-chloro-4-methoxy-2,3-dihydro-1H-inden-1-yl]oxy]-3-methylbenzene)sulfonamido]ethoxy]ethoxy)ethyl]-1-[4-([[2-(2-[2-[(4-[[(1S,2S)-2-[(3R)-3-aminopiperidin-1-yl]-6-chloro-4-methoxy-2,3-dihydro-1H-inden-1-yl]oxy]-3-methylbenzene)sulfonamido]ethoxy]ethoxy)ethyl]carbamoyl]amino)-butyl]urea;

3-[2-(2-[2-[(4-[[(1S,2S)-2-[(3R)-3-Aminopiperidin-1-yl]-6-chloro-4-methyl-2,3-dihydro-1H-inden-1-yl]oxy]-3-fluoro benzene)sulfonamido]ethoxy]ethoxy)ethyl]-1-[4-([[2-(2-[2-[(4-[[(1S,2S)-2-[(3R)-3-aminopiperidin-1-yl]-6-chloro-4-methyl-2,3-dihydro-1H-inden-1-yl]oxy]-3-fluorobenzene)sulfonamido]ethoxy]ethoxy)ethyl]carbamoyl]amino)butyl]urea;

3-[2-(2-[2-[(4-[[(1S,2S)-6-Chloro-2-(dimethylamino)-4-methyl-2,3-dihydro-1H-inden-1-yl]oxy]benzene)sulfonamido]ethoxy]ethoxy) ethyl]-1-[4-([[2-(2-[2-[(4-[[(1S,2S)-6-chloro-2-(dimethylamino)-4-methyl-2,3-dihydro-1H-inden-1-yl]oxy]benzene)sulfonamido]ethoxy]ethoxy)ethyl]carbamoyl]amino)butyl]urea;

3-[2-(2-[2-[(4-[[(1S,2S)-6-Chloro-4-cyano-2-(dimethylamino)-2,3-dihydro-1H-inden-1-yl]oxy]benzene)sulfonamido]ethoxy]ethoxy)ethyl]-1-[4-([[2-(2-[2-[(4-[[(1S,2S)-6-chloro-4-cyano-2-(dimethylamino)-2,3-dihydro-1H-inden-1-yl]oxy]benzene)sulfonamido]ethoxy]ethoxy)ethyl]carbamoyl]amino)butyl]urea;

3-[2-(2-[2-[(4-[[(1S,2S)-6-Chloro-2-(dimethylamino)-4-(trifluoromethyl)-2,3-dihydro-1H-inden-1-yl]oxy]benzene)sulfonamido]ethoxy]ethoxy)ethyl]-1-[4-([[2-(2-[2-[(4-[[(1S,2S)-6-chloro-2-(dimethylamino)-4-(trifluoromethyl)-2,3-dihydro-1H-inden-1-yl]oxy]benzene)sulfonamido]ethoxy]ethoxy)ethyl]carbamoyl]amino)butyl]urea;

1-[2-(2-[2-[(4-[[(1S,2S)-6-Chloro-2-(dimethylamino)-4-(trifluoromethoxy)-2,3-dihydro-1H-inden-1-yl]oxy]benzene)sulfonamido]ethoxy]ethoxy)ethyl]-3-[4-([[2-(2-[2-[(4-[[(1S,2S)-6-chloro-2-(dimethylamino)-4-(trifluoromethoxy)-2,3-dihydro-1H-inden-1-yl]oxy]benzene)sulfonamido]ethoxy]ethoxy)ethyl]carbamoyl]amino)butyl]urea;

3-[2-(2-[2-[(4-[[(1S,2S)-6-Chloro-2-(dimethylamino)-4-methoxy-2,3-dihydro-1H-inden-1-yl]oxy]benzene)sulfonamido]ethoxy]ethoxy)ethyl]-1-[4-([[2-(2-[2-[(4-[[(1S,2S)-6-chloro-2-(dimethylamino)-4-methoxy-2,3-dihydro-1H-inden-1-yl]oxy]benzene)sulfonamido]ethoxy]ethoxy)ethyl]carbamoyl]amino)butyl]urea;

3-[2-(2-[2-[(4-[[(1S,2S)-6-Chloro-2-(dimethylamino)-4-fluoro-2,3-dihydro-1H-inden-1-yl]oxy]-3-methylbenzene)sulfonamido]ethoxy]ethoxy)ethyl]-1-[4-([[2-(2-[2-[(4-[[(1S,2S)-6-chloro-2-(dimethylamino)-4-fluoro-2,3-dihydro-1H-inden-1-yl]oxy]-3-methylbenzene)sulfonamido]ethoxy]ethoxy)ethyl]carbamoyl]amino)butyl]urea;

3-[2-(2-[2-[(4-[[(1S,2S)-6-Chloro-2-(dimethylamino)-4-methyl-2,3-dihydro-1H-inden-1-yl]oxy]-3-methyl benzene)sulfonamido]ethoxy]ethoxy)ethyl]-1-[4-([[2-(2-[2-[(4-[[(1S,2S)-6-chloro-2-(dimethylamino)-4-methyl-2,3-dihydro-1H-inden-1-yl]oxy]-3-methylbenzene)sulfonamido]ethoxy]ethoxy)ethyl]carbamoyl]amino)butyl]urea;

3-[2-(2-[2-[(4-[[(1S,2S)-6-Chloro-4-cyano-2-(dimethylamino)-2,3-dihydro-1H-inden-1-yl]oxy]-3-methylbenzene)sulfonamido]ethoxy]ethoxy)ethyl]-1-[4-([[2-(2-[2-[(4-[[(1S,2S)-6-chloro-4-cyano-2-(dimethylamino)-2,3-dihydro-1H-inden-1-yl]oxy]-3-methylbenzene)sulfonamido]ethoxy]ethoxy) ethyl]carbamoyl]amino)butyl]urea;

3-[2-(2-[2-[(4-[[(1S,2S)-6-Chloro-2-(dimethylamino)-4-(trifluoromethyl)-2,3-dihydro-1H-inden-1-yl]oxy]-3-methylbenzene)sulfonamido]ethoxy]ethoxy)ethyl]-1-[4-([[2-(2-[2-[(4-[[(1S,2S)-6-chloro-2-(dimethylamino)-4-(trifluoromethyl)-2,3-dihydro-1H-inden-1-yl]oxy]-3-methylbenzene)sulfonamido]ethoxy]ethoxy)ethyl]carbamoyl]-amino)butyl]urea;

1-[2-(2-[2-[(4-[[(1S,2S)-6-Chloro-2-(dimethylamino)-4-(trifluoromethoxy)-2,3-dihydro-1H-inden-1-yl]oxy]-3- methylbenzene)sulfonamido]ethoxy]ethoxy)ethyl]-3-[4-([[2-(2-[2-[(4-[[(1S,2S)-6-chloro-2-(dimethylamino)-4-(trifluoromethoxy)-2,3-dihydro-1H-inden-1-yl]oxy]-3-methylbenzene)sulfonamido]ethoxy]ethoxy)ethyl]carbamoyl]amino)butyl]urea;

3-[2-(2-[2-[(4-[[(1S,2S)-6-Chloro-2-(dimethylamino)-4-methoxy-2,3-dihydro-1H-inden-1-yl]oxy]-3-methylbenzene)sulfonamido]ethoxy]ethoxy)ethyl]-1-[4-([[2-(2-[2-[(4-[[(1S,2S)-6-chloro-2-(dimethylamino)-4-methoxy-2,3-dihydro-1H-inden-1-yl]oxy]-3-methylbenzene)sulfonamido]ethoxy]ethoxy)ethyl]carbamoyl]amino)butyl]urea;

3-[2-(2-[2-[(4-[[(1S,2S)-4,6-Dichloro-2-(dimethylamino)-2,3-dihydro-1H-inden-1-yl]oxy]-3-methylbenzene)sulfonamido]ethoxy]ethoxy)ethyl]-1-[4-([[2-(2-[2-[(4-[[(1S,2S)-4,6-dichloro-2-(dimethylamino)-2,3-dihydro-1H-inden-1-yl]oxy]-3-methyl benzene)sulfonamido]ethoxy]ethoxy)ethyl]carbamoyl]amino)butyl]urea dihydrochloride;

3-[2-(2-[2-[(4-[[(1S,2S)-4,6-Dichloro-2-(dimethylamino)-2,3-dihydro-1H-inden-1-yl]oxy]-3-fluorobenzene)sulfonamido]ethoxy]ethoxy)ethyl]-1-[4-([[2-(2-[2-[(4-[[(1S,2S)-4,6-dichloro-2-(dimethylamino)-2,3-dihydro-1H-inden-1-yl]oxy]-3-fluorobenzene)sulfonamido]ethoxy]ethoxy)ethyl]carbamoyl]amino)butyl]urea;

3-[2-(2-[2-[(4-[[(1S,2S)-6-Chloro-2-(dimethylamino)-4-methyl-2,3-dihydro-1H-inden-1-yl]oxy]-3-fluorobenzene)sulfonamido]ethoxy]ethoxy)ethyl]-1-[4-([[2-(2-[2-[(4-[[(1S,2S)-6-chloro-2-(dimethylamino)-4-methyl-2,3-dihydro-1H-inden-1-yl]oxy]-3-fluorobenzene)sulfonamido]ethoxy]ethoxy)ethyl]carbamoyl]amino)butyl]urea;

3-[2-(2-[2-[(4-[[(1S,2S)-4,6-Dichloro-2-[(3R)-3-(dimethylamino)piperidin-1-yl]-2,3-dihydro-1H-inden-1-yl]oxy]benzene)sulfonamido]ethoxy]ethoxy)ethyl]-1-[4-([[2-(2-[2-[(4-[[(1S,2S)-4,6-dichloro-2-[(3R)-3-(dimethylamino)piperidin-1-yl]-2,3-dihydro-1H-inden-1-yl]oxy]benzene)sulfonamido]ethoxy]ethoxy)ethyl]carbamoyl]amino)butyl]urea;

3-[2-(2-[2-[(4-[[(1S,2S)-4,6-Dichloro-2-[(3R)-3-(dimethylamino)piperidin-1-yl]-2,3-dihydro-1H-inden-1-yl]oxy]-3-methylbenzene)sulfonamido]ethoxy]ethoxy)ethyl]-1-[4-([[2-(2-[2-[(4-[[(1S,2S)-4,6-dichloro-2-[(3R)-3-(dimethylamino)piperidin-1-yl]-2,3-dihydro-1H-inden-1-yl]oxy]-3-methylbenzene)sulfonamido]ethoxy]ethoxy)ethyl]carbamoyl]-amino)butyl]urea;

3-[2-(2-[2-[(4-[[(1S,2S)-4,6-Dichloro-2-[(3R)-3-(dimethylamino)piperidin-1-yl]-2,3-dihydro-1H-inden-1-yl]oxy]-3-fluorobenzene)sulfonamido]ethoxy]ethoxy)ethyl]-1-[4-([[2-(2-[2-[(4-[[(1S,2S)-4,6-dichloro-2-[(3R)-3-(dimethylamino)piperidin-1-yl]-2,3-dihydro-1H-inden-1-yl]oxy]-3-fluorobenzene)sulfonamido]ethoxy]ethoxy)ethyl-carbamoyl]amino)butyl]urea;

3-[2-(2-[2-[(4-[[(1S,2S)-6-Chloro-2-[(3R)-3-(dimethylamino)piperidin-1-yl]-4-methyl-2,3-dihydro-1H-inden-1-yl]oxy]benzene)sulfonamido]ethoxy]ethoxy)ethyl]-1-[4-([[2-(2-[2-[(4-[[(1S,2S)-6-chloro-2-[(3R)-3-(dimethylamino)piperidin-1-yl]-4-methyl-2,3-dihydro-1H-inden-1-yl]oxy]benzene)sulfonamido]ethoxy]ethoxy)ethyl]-carbamoyl]amino)butyl]urea;

3-[2-(2-[2-[(4-[[(1S,2S)-6-Chloro-2-[(3R)-3-(dimethylamino)piperidin-1-yl]-4-methyl-2,3-dihydro-1H-inden-1-yl]oxy]-3-methylbenzene)sulfonamido]ethoxy]ethoxy)ethyl]-1-[4-([[2-(2-[2-[(4-[[(1S,2S)-6-chloro-2-[(3R)-3-(dimethylamino)piperidin-1-yl]-4-methyl-2,3-dihydro-1H-inden-1-yl]oxy]-3-methylbenzene)sulfonamido]ethoxy]ethoxy)ethyl]carbamoyl]amino)butyl]urea;

3-[2-(2-[2-[(4-[[(1S,2S)-6-Chloro-2-[(3R)-3-(dimethylamino)piperidin-1-yl]-4-methyl-2,3-dihydro-1H-inden-1-yl]oxy]-3-fluorobenzene)sulfonamido]ethoxy]ethoxy)ethyl]-1-[4-([[2-(2-[2-[(4-[[(1S,2S)-6-chloro-2-[(3R)-3-(dimethylamino)piperidin-1-yl]-4-methyl-2,3-dihydro-1H-inden-1-yl]oxy]-3-fluorobenzene)sulfonamido]ethoxy]ethoxy)ethyl]carbamoyl]amino)butyl]urea;

3-[2-(2-[2-[(4-[[(1S,2S)-4,6-Dichloro-2-(piperazin-1-yl)-2,3-dihydro-1H-inden-1-yl]oxy]benzene)sulfonamido]ethoxy]ethoxy)ethyl]-1-[4-([[2-(2-[2-[(4-[[(1S,2S)-4,6-dichloro-2-(piperazin-1-yl)-2,3-dihydro-1H-inden-1-yl]oxy]benzene)sulfonamido]-ethoxy]ethoxy)ethyl]carbamoyl]amino)butyl]urea;

3-[2-(2-[2-[(4-[[(1S,2S)-4,6-Dichloro-2-(piperazin-1-yl)-2,3-dihydro-1H-inden-1-yl]oxy]-3-methylbenzene)sulfonamido]ethoxy]ethoxy)ethyl]-1-[4-([[2-(2-[2-[(4-[[(1S,2S)-4,6-dichloro-2-(piperazin-1-yl)-2,3-dihydro-1H-inden-1-yl]oxy]-3-methylbenzene)-sulfonamido]ethoxy]ethoxy)ethyl]carbamoyl]amino)butyl]urea;

3-[2-(2-[2-[(4-[[(1S,2S)-4,6-Dichloro-2-(piperazin-1-yl)-2,3-dihydro-1H-inden-1-yl]oxy]-3-fluorobenzene)sulfonamido]ethoxy]ethoxy)ethyl]-1-[4-([[2-(2-[2-[(4-[[(1S,2S)-4,6-dichloro-2-(piperazin-1-yl)-2,3-dihydro-1H-inden-1-yl]oxy]-3-fluorobenzene)sulfonamido]ethoxy]ethoxy)ethyl]carbamoyl]amino)butyl]urea;

3-[2-(2-[2-[(4-[[(1S,2S)-6-Chloro-4-methyl-2-(piperazin-1-yl)-2,3-dihydro-1H-inden-1-yl]oxy]benzene)sulfonamido]ethoxy]ethoxy)ethyl]-1-[4-([[2-(2-[2-[(4-[[(1S,2S)-6-chloro-4-methyl-2-(piperazin-1-yl)-2,3-dihydro-1H-inden-1-yl]oxy]benzene)-sulfonamido]ethoxy]ethoxy)ethyl]carbamoyl]amino)butyl]urea;

3-[2-(2-[2-[(4-[[(1S,2S)-6-Chloro-4-methyl-2-(piperazin-1-yl)-2,3-dihydro-1H-inden-1-yl]oxy]-3-methylbenzene)sulfonamido]ethoxy]ethoxy)ethyl]-1-[4-([[2-(2-[2-[(4-[[(1S,2S)-6-chloro-4-methyl-2-(piperazin-1-yl)-2,3-dihydro-1H-inden-1-yl]oxy]-3-methylbenzene)sulfonamido]ethoxy]ethoxy)ethyl]carbamoyl]amino)butyl]urea;

3-[2-(2-[2-[(4-[[(1S,2S)-6-Chloro-4-methyl-2-(piperazin-1-yl)-2,3-dihydro-1H-inden-1-yl]oxy]-3-fluorobenzene)sulfonamido]ethoxy]ethoxy)ethyl]-1-[4-([[2-(2-[2-[(4-[[(1S,2S)-6-chloro-4-methyl-2-(piperazin-1-yl)-2,3-dihydro-1H-inden-1-yl]oxy]-3-fluorobenzene)sulfonamido]ethoxy]ethoxy)ethyl]carbamoyl]amino)butyl]urea;

3-[2-(2-[2-[(4-[[(1S,2S)-6-Chloro-4-cyano-2-(dimethylamino)-2,3-dihydro-1H-inden-1-yl]oxy]-3-fluorobenzene)sulfonamido]ethoxy]ethoxy)ethyl]-1-[4-([[2-(2-[2-[(4-[[(1S,2S)-6-chloro-4-cyano-2-(dimethylamino)-2,3-dihydro-1H-inden-1-yl]oxy]-3-fluorobenzene)sulfonamido]ethoxy]ethoxy)ethyl]carbamoyl]amino)butyl]urea;

3-[2-(2-[2-[(4-[[(1S,2S)-2-[(3R)-3-Aminopiperidin-1-yl]-6-chloro-4-methyl-2,3-dihydro-1H-inden-1-yl]oxy]-3-fluorobenzene)sulfonamido]ethoxy]ethoxy)ethyl]-1-[4-([[2-(2-[2-[(4-[[(1S,2S)-2-[(3R)-3-aminopiperidin-1-yl]-6-chloro-4-methyl-2,3-dihydro-1H-inden-1-yl]oxy]-3-fluorobenzene)sulfonamido]ethoxy]ethoxy)ethyl]carbamoyl]amino)butyl]urea;

3-[2-(2-[2-[(4-[[(1S,2S)-6-Chloro-4-cyano-2-[(3R)-3-(dimethylamino)piperidin-1-yl]-2,3-dihydro-1H-inden-1-yl]oxy]-3-methylbenzene)sulfonamido]ethoxy]ethoxy)ethyl]-1-[4-([[2-(2-[2-[(4-[[(1S,2S)-6-chloro-4-cyano-2-[(3R)-3-(dimethylamino)piperidin-1-yl]-2,3-dihydro-1H-inden-1-yl]oxy]-3-methylbenzene)sulfonamido]ethoxy]ethoxy)ethyl]-carbamoyl]amino)butyl]urea;

3-[2-(2-[2-[(4-[[(1S,2S)-6-Chloro-4-cyano-2-[(3R)-3-(dimethylamino)piperidin-1-yl]-2,3-dihydro-1H-inden-1-yl]oxy]-3-fluorobenzene)sulfonamido]ethoxy]ethoxy)ethyl]-1-[4-([[2-(2-[2-[(4-[[(1S,2S)-6-chloro-4-cyano-2-[(3R)-3-(dimethylamino)piperidin-1-yl]-2,3-dihydro-1H-inden-1-yl]oxy]-3-fluorobenzene)sulfon amido]ethoxy]ethoxy)ethyl]-carbamoyl]amino)butyl]urea;

3-[2-(2-[2-[(4-[[(1S,2S)-6-Chloro-4-cyano-2-(piperazin-1-yl)-2,3-dihydro-1H-inden-1-yl]oxy]benzene)sulfonamido]ethoxy]ethoxy)ethyl]-1-[4-([[2-(2-[2-[(4-[[(1S,2S)-6-chloro-4-cyano-2-(piperazin-1-yl)-2,3-dihydro-1H-inden-1-yl]oxy]benzene)-sulfonamido]ethoxy]ethoxy)ethyl]carbamoyl]amino)butyl]urea;

3-[2-(2-[2-[(4-[[(1S,2S)-6-Chloro-4-cyano-2-(piperazin-1-yl)-2,3-dihydro-1H-inden-1-yl]oxy]-3-methylbenzene)sulfonamido]ethoxy]ethoxy)ethyl]-1-[4-([[2-(2-[2-[(4-[[(1S,2S)-6-chloro-4-cyano-2-(piperazin-1-yl)-2,3-dihydro-1H-inden-1-yl]oxy]-3-methylbenzene)sulfonamido]ethoxy]ethoxy)ethyl]carbamoyl]amino)butyl]urea;

3-[2-(2-[2-[(4-[[(1S,2S)-6-Chloro-4-cyano-2-(piperazin-1-yl)-2,3-dihydro-1H-inden-1-yl]oxy]-3-fluorobenzene)sulfonamido]ethoxy]ethoxy)ethyl]-1-[4-([[2-(2-[2-[(4-[[(1S,2S)-6-chloro-4-cyano-2-(piperazin-1-yl)-2,3-dihydro-1H-inden-1-yl]oxy]-3-fluorobenzene)sulfonamido]ethoxy]ethoxy)ethyl]carbamoyl]amino)butyl]urea;

3-[2-(2-[[(3 S)-1-[(4-[[(1S,2S)-4,6-dichloro-2-(dimethylamino)-2,3-dihydro-1H-inden-1-yl]oxy]-3-methylbenzene)sulfonyl]pyrrolidin-3-yl]methoxy]ethoxy)ethyl]-1-[4-([[2-(2-[[(3S)-1-[(4-[[(1S,2S)-4,6-dichloro-2-(dimethylamino)-2,3-dihydro-1H-inden-1-yl]oxy]-3-methylbenzene)sulfonyl]pyrrolidin-3-yl]methoxy]ethoxy)ethyl]carbamoyl]amino) butyl]urea;

3-[2-(2-[[(3R)-1-[(4-[[(1S,2S)-4,6-Dichloro-2-(dimethylamino)-2,3-dihydro-1H-inden-1-yl]oxy]-3-methylbenzene)sulfonyl]pyrrolidin-3-yl]methoxy]ethoxy)ethyl]-1-[4-([[2-(2-[[(3R)-1-[(4-[[(1S,2S)-4,6-dichloro-2-(dimethylamino)-2,3-dihydro-1H-inden-1-yl]oxy]-3-methylbenzene) sulfonyl]pyrrolidin-3-yl]methoxy]ethoxy)ethyl]carbamoyl]amino)butyl]urea;

3-[2-(2-[[(3 S)-1-[(4-[[(1S,2S)-6-Chloro-4-cyano-2-(dimethylamino)-2,3-dihydro-1H-inden-1-yl]oxy]-3-methylbenzene)sulfonyl]pyrrolidin-3-yl]methoxy]ethoxy)ethyl]-1-[4-([[2-(2-[[(3S)-1-[(4-[[(1S,2S)-6-chloro-4-cyano-2-(dimethylamino)-2,3-dihydro-1H-inden-1-yl]oxy]-3-methylbenzene)sulfonyl]pyrrolidin-3-yl]methoxy]ethoxy)ethyl]carbamoyl]-amino)butyl]urea;

3-[2-(2-[[(3R)-1-[(4-[[(1S,2S)-6-Chloro-4-cyano-2-(dimethylamino)-2,3-dihydro-1H-inden-1-yl]oxy]-3-methylbenzene)sulfonyl]pyrrolidin-3-yl]methoxy]ethoxy)ethyl]-1-[4-([[2-(2-[[(3R)-1-[(4-[[(1S,2S)-6-chloro-4-cyano-2-(dimethylamino)-2,3-dihydro-1H-inden-1-yl]oxy]-3-methylbenzene)sulfonyl]pyrrolidin-3-yl]methoxy]ethoxy)ethyl]carbamoyl]-amino)butyl]urea;

3-[(4-[[(3 S)-1-[(4-[[(1S,2S)-4,6-Dichloro-2-(dimethylamino)-2,3-dihydro-1H-inden-1-yl]oxy]-3-methylbenzene)sulfonyl]pyrrolidin-3-yl]methoxy]pyridin-2-yl)methyl]-1-[4-([[(4-[[(3S)-1-[(4-[[(1S,2S)-4,6-dichloro-2-(dimethylamino)-2,3-dihydro-1H-inden-1-yl]oxy]-3-methylbenzene)sulfonyl]pyrrolidin-3-yl]methoxy]pyridin-2-yl)methyl]carbamoyl]-amino)butyl]urea;

3-[(4-[[(3R)-1-[(4-[[(1S,2S)-4,6-Dichloro-2-(dimethylamino)-2,3-dihydro-1H-inden-1-yl]oxy]-3-methylbenzene)sulfonyl]pyrrolidin-3-yl]methoxy]pyridin-2-yl)methyl]-1-[4-([[(4-[[(3R)-1-[(4-[[(1S,2S)-4,6-dichloro-2-(dimethylamino)-2,3-dihydro-1H-inden-1-yl]oxy]-3-methylbenzene)sulfonyl]pyrrolidin-3-yl]methoxy]pyridin-2-yl)methyl]carbamoyl]-amino)butyl]urea;

3-[(4-[[(3S)-1-[(4-[[(1S,2S)-6-Chloro-4-cyano-2-(dimethylamino)-2,3-dihydro-1H-inden-1-yl]oxy]-3-methylbenzene)sulfonyl]pyrrolidin-3-yl]methoxy]pyridin-2-yl)methyl]-1-[4-([[(4-[[(3S)-1-[(4-[[(1S,2S)-6-chloro-4-cyano-2-(dimethylamino)-2,3-dihydro-1H-inden-1-yl]oxy]-3-methylbenzene)sulfonyl]pyrrolidin-3-yl]methoxy]pyridin-2-yl)methyl]carbamoyl]amino)butyl]urea;

3-[(4-[[(3R)-1-[(4-[[(1S,2S)-6-Chloro-4-cyano-2-(dimethylamino)-2,3-dihydro-1H-inden-1-yl]oxy]-3-methylbenzene)sulfonyl]pyrrolidin-3-yl]methoxy]pyridin-2-yl)methyl]-1-[4-([[(4-[[(3R)-1-[(4-[[(1S,2S)-6-chloro-4-cyano-2-(dimethylamino)-2,3-dihydro-1H-inden-1-yl]oxy]-3-methylbenzene)sulfonyl]pyrrolidin-3-yl]methoxy]pyridin-2-yl)methyl]carbamoyl]amino)butyl]urea;

3-(2-[2-[(3S)-3-[(4-[[(1S,2S)-4,6-Dichloro-2-(dimethylamino)-2,3-dihydro-1H-inden-1-yl]oxy]-3-methylbenzene) sulfonamido]pyrrolidin-1-yl]ethoxy]ethyl)-1-(4-[[(2-[2-[(3S)-3-[(4-[[(1S,2S)-4,6-dichloro-2-(dimethylamino)-2,3-dihydro-1H-inden-1-yl]oxy]-3-methylbenzene)sulfonamido]pyrrolidin-1-yl]ethoxy]ethyl) carbamoyl]amino]butyl)urea;

3-(2-[2-[(3R)-3-[(4-[[(1S,2S)-4,6-Dichloro-2-(dimethylamino)-2,3-dihydro-1H-inden-1-yl]oxy]-3-methylbenzene)sulfonamido]pyrrolidin-1-yl]ethoxy]ethyl)-1-(4-[[(2-[2-[(3R)-3-[(4-[[(1S,2S)-4,6-dichloro-2-(dimethylamino)-2,3-dihydro-1H-inden-1-yl]oxy]-3-methylbenzene)sulfonamido]pyrrolidin-1-yl]ethoxy]ethyl)carbamoyl]amino]butyl)urea;

3-(2-[2-[(3S)-3-[(4-[[(1S,2S)-6-Chloro-4-cyano-2-(dimethylamino)-2,3-dihydro-1H-inden-1-yl]oxy]-3-methylbenzene)sulfonamido]pyrrolidin-1-yl]ethoxy]ethyl)-1-(4-[[(2-[2-[(3S)-3-[(4-[[(1S,2S)-6-chloro-4-cyano-2-(dimethylamino)-2,3-dihydro-1H-inden-1-yl]oxy]-3-methylbenzene)sulfonamido]pyrrolidin-1-yl]ethoxy]ethyl)carbamoyl]amino]butyl)urea;

3-(2-[2-[(3R)-3-[(4-[[(1S,2S)-6-Chloro-4-cyano-2-(dimethylamino)-2,3-dihydro-1H-inden-1-yl]oxy]-3-methylbenzene)sulfonamido]pyrrolidin-1-yl]ethoxy]ethyl)-1-(4-[[(2-[2-[(3R)-3-[(4-[[(1S,2S)-6-chloro-4-cyano-2-(dimethylamino)-2,3-dihydro-1H-inden-1-yl]oxy]-3-methylbenzene)sulfonamido]pyrrolidin-1-yl]ethoxy]ethyl)carbamoyl]amino]butyl)urea;

1-([1-[2-(2-[2-[(4-[[(1S,2S)-2-[(3R)-3-Aminopiperidin-1-yl]-4,6-dichloro-2,3-dihydro-1H-inden-1-yl]oxy]benzene) sulfonamido]ethoxy]ethoxy)ethyl]-1H-1,2,3-triazol-4-yl]methyl)-3-(4-[[(1-[2-(2-[2-[(4-[[(1S,2S)-2-[(3R)-3-aminopiperidin-1-yl]-4,6-dichloro-2,3-dihydro-1H-inden-1-yl]oxy]benzene)sulfonamido]ethoxy]ethoxy)ethyl]-1H-1,2,3-triazol-4-yl]methyl)carbamoyl]amino]butyl)urea;

(2R,3S,4R,5S)—N1,N6-Bis([1-[2-(2-[2-[(4-[[(1S,2S)-2-[(3R)-3-aminopiperidin-1-yl]-4,6-dichloro-2,3-dihydro-1H-inden-1-yl]oxy]benzene)sulfonamido]ethoxy]ethoxy)ethyl]-1H-1,2,3-triazol-4-yl]methyl)-2,3,4,5-tetrahydroxyhexanediamide;

3-[(1-[4-[(4-[[(1S,2S)-2-[(3R)-3-Aminopiperidin-1-yl]-4,6-dichloro-2,3-dihydro-1H-inden-1-yl]oxy]benzene)sulfonamido]butyl]-1H-1,2,3-triazol-4-yl)methyl]-1-[4-([[(1-[4-[(4-[[(1S,2S)-2-[(3R)-3-aminopiperidin-1-yl]-4,6-dichloro-2,3-dihydro-1H-inden-1-yl]oxy]benzene)sulfonamido]butyl]-1H-1,2,3-triazol-4-yl)methyl]carbamoyl]amino)-butyl]urea;

3-[(1-[6-[(4-[[(1S,2S)-2-[(3R)-3-Aminopiperidin-1-yl]-4,6-dichloro-2,3-dihydro-1H-inden-1-yl]oxy]benzene)sulfonamido]hexyl]-1H-1,2,3-triazol-4-yl)methyl]-1-[4-([[(1-[6-[(4-[[(1S,2S)-2-[(3R)-3-aminopiperidin-1-yl]-4,6-dichloro-2,3-dihydro-1H-inden-1-yl]oxy]benzene)sulfonamido]hexyl]-1H-1,2,3-triazol-4-yl)methyl]carbamoyl]amino)-butyl]urea;

(4R,4aS,8S,8aR)—N4,N8-Bis([1-(4-[4-((1S,2S)-2-[(3R)-3-aminopiperidin-1-yl]-4,6-dichloro-2,3-dihydro-1H-inden-1-yloxy)phenyl sulfonamide]butyl)-1H-1,2,3-triazol-4-yl]methyl)-2,2,6,6-tetramethyl-tetrahydro-[1,3]dioxino[5,4-d][1,3]dioxine-4,8-dicarboxamide;

(4R,4aS,8S,8aR)—N4,N8-Bis([1-(6-[4-((1S,2S)-2-[(3R)-3-amino piperidin-1-yl]-4,6-dichloro-2,3-dihydro-1H-inden-1-yloxy)phenylsulfonamido]hexyl)-1H-1,2,3-triazol-4-yl]methyl)-2,2,6,6-tetramethyl-tetrahydro-[1,3]dioxino[5,4-d][1,3]dioxine-4,8-dicarboxamide;

3-[8-[(4-[[(1S,2S)-2-[(3R)-3-Aminopiperidin-1-yl]-4,6-dichloro-2,3-dihydro-1H-inden-1-yl]oxy]benzene)sulfonamido]octyl]-1-[4-[([8-[(4-[[(1S,2S)-2-[(3R)-3-aminopiperidin-1-yl]-4,6-dichloro-2,3-dihydro-1H-inden-1-yl]oxy]benzene) sulfonamido]octyl]-carbamoyl)amino]butyl]urea;

3-[8-[(4-[[(1S,2S)-2-[(3R)-3-Aminopiperidin-1-yl]-4,6-dichloro-2,3-dihydro-1H-inden-1-yl]oxy]-3-methylbenzene) sulfonamido]octyl]-1-[4-[([8-[(4-[[(1S,2S)-2-[(3R)-3-aminopiperidin-1-yl]-4,6-dichloro-2,3-dihydro-1H-inden-1-yl]oxy]-3-methylbenzene)sulfonamido]octyl]carbamoyl)amino]butyl]urea;

3-[8-[(4-[[(1S,2S)-4,6-Dichloro-2-(dimethylamino)-2,3-dihydro-1H-inden-1-yl]oxy]benzene)sulfonamido]octyl]-1-[4-[([8-[(4-[[(1S,2S)-4,6-dichloro-2-(dimethylamino)-2,3-dihydro-1H-inden-1-yl]oxy]benzene) sulfonamido]octyl]-carbamoyl)amino]butyl]urea;

3-[8-[(4-[[(1S,2S)-4,6-Dichloro-2-(dimethylamino)-2,3-dihydro-1H-inden-1-yl]oxy]-3-methylbenzene)sulfonamido]octyl]-1-[4-[([8-[(4-[[(1S,2S)-4,6-dichloro-2-(dimethylamino)-2,3-dihydro-1H-inden-1-yl]oxy]-3-methylbenzene) sulfonamido]octyl]carbamoyl)amino]butyl]urea;

3-[2-(2-[2-[(4-[[(1S,2S)-4,6-Dichloro-2-[(2R)-2-methylpiperidin-1-yl]-2,3-dihydro-1H-inden-1-yl]oxy]benzene)sulfonamido]ethoxy]ethoxy)ethyl]-1-[4-([[2-(2-[2-[(4-[[(1S,2S)-4,6-dichloro-2-[(2R)-2-methylpiperidin-1-yl]-2,3-dihydro-1H-inden-1-yl]oxy]benzene)-sulfonamido]ethoxy]ethoxy)ethyl]carbamoyl]amino)butyl]urea;

3-[2-(2-[2-[(4-[[(1S,2S)-4,6-Dichloro-2-[(2S)-2-methylpiperidin-1-yl]-2,3-dihydro-1H-inden-1-yl]oxy]benzene)sulfonamido]ethoxy]ethoxy)ethyl]-1-[4-([[2-(2-[2-[(4-[[(1S,2S)-4,6-dichloro-2-[(2S)-2-methylpiperidin-1-yl]-2,3-dihydro-1H-inden-1-yl]oxy]benzene)sulfonamido]ethoxy]ethoxy)ethyl]carbamoyl]amino)butyl]urea;

3-[2-(2-[2-[(4-[[(1S,2S)-2-[2-Azabicyclo[2.2.1]heptan-2-yl]-4,6-dichloro-2,3-dihydro-1H-inden-1-yl]oxy]benzene)sulfonamido]ethoxy]ethoxy)ethyl]-1-[4-([[2-(2-[2-[(4-[[(1S,2S)-2-[2-azabicyclo[2.2.1]heptan-2-yl]-4,6-dichloro-2,3-dihydro-1H-inden-1-yl]oxy]benzene)sulfonamido]ethoxy]ethoxy)ethyl]carbamoyl]amino)butyl]urea;

1-[2-(2-[2-[(4-[[(1S,2S)-2-[2-Azabicyclo[2.2.2]octan-2-yl]-4,6-dichloro-2,3-dihydro-1H-inden-1-yl]oxy]benzene)sulfonamido]ethoxy]ethoxy)ethyl]-3-[4-([[2-(2-[2-[(4-[[(1S,2S)-2-[2-azabicyclo[2.2.2]octan-2-yl]-4,6-dichloro-2,3-dihydro-1H-inden-1-yl]oxy]benzene)-sulfonamido]ethoxy]ethoxy)ethyl]carbamoyl]amino)butyl]urea;

3-[2-(2-[2-[(4-[[(1S,2S)-2-[8-azabicyclo[3.2.1]octan-8-yl]-4,6-dichloro-2,3-dihydro-1H-inden-1-yl]oxy]benzene) sulfonamido]ethoxy]ethoxy)ethyl]-1-[4-([[2-(2-[2-[(4-[[(1S,2S)-2-[8-azabicyclo[3.2.1]octan-8-yl]-4,6-dichloro-2,3-dihydro-1H-inden-1-yl]oxy]benzene)-sulfonamido]ethoxy]ethoxy)ethyl]carbamoyl]amino)butyl]urea;

1-[2-(2-[2-[(4-[[(1S,2S)-2-[9-Azabicyclo[3.3.1]nonan-9-yl]-4,6-dichloro-2,3-dihydro-1H-inden-1-yl]oxy]benzene)sulfonamido]ethoxy]ethoxy)ethyl]-3-[4-([[2-(2-[2-[(4-[[(1S,2S)-2-[9-azabicyclo[3.3.1]nonan-9-yl]-4,6-dichloro-2,3-dihydro-1H-inden-1-yl]oxy]benzene)-sulfonamido]ethoxy]ethoxy)ethyl]carbamoyl]amino)butyl]urea;

3-[2-(2-[2-[(4-[[(1S,2S)-4,6-Dichloro-2-(4-methylpiperazin-1-yl)-2,3-dihydro-1H-inden-1-yl]oxy]benzene)sulfonamido]ethoxy]ethoxy)ethyl]-1-[4-([[2-(2-[2-[(4-[[(1S,2S)-4,6-dichloro-2-(4-methylpiperazin-1-yl)-2,3-dihydro-1H-inden-1-yl]oxy]benzene)sulfonamido]ethoxy]ethoxy)ethyl]carbamoyl]amino)butyl]urea;

3-[2-(2-[2-[(4-[[(1S,2S)-4,6-Dichloro-2-(4-methylpiperazin-1-yl)-2,3-dihydro-1H-inden-1-yl]oxy]-3-methylbenzene)sulfonamido]ethoxy]ethoxy)ethyl]-1-[4-([[2-(2-[2-[(4-[[(1S,2S)-4,6-dichloro-2-(4-methylpiperazin-1-yl)-2,3-dihydro-1H-inden-1-yl]oxy]-3-methylbenzene)sulfonamido]ethoxy]ethoxy)ethyl]carbamoyl]amino)butyl]urea;

3-[2-(2-[2-[(4-[[(1S,2S)-2-(4-Acetylpiperazin-1-yl)-4,6-dichloro-2,3-dihydro-1H-inden-1-yl]oxy]benzene)sulfonamido]ethoxy]ethoxy)ethyl]-1-[4-([[2-(2-[2-[(4-[[(1S,2S)-2-(4-acetylpiperazin-1-yl)-4,6-dichloro-2,3-dihydro-1H-inden-1-yl]oxy]benzene)-sulfonamido]ethoxy]ethoxy)ethyl]carbamoyl]amino)butyl]urea;

3-[2-(2-[2-[(4-[[(1S,2S)-2-(4-Acetylpiperazin-1-yl)-4,6-dichloro-2,3-dihydro-1H-inden-1-yl]oxy]-3-methylbenzene)sulfonamido]ethoxy]ethoxy)ethyl]-1-[4-([[2-(2-[2-[(4-[[(1S,2S)-2-(4-acetylpiperazin-1-yl)-4,6-dichloro-2,3-dihydro-1H-inden-1-yl]oxy]-3-methylbenzene)sulfonamido]ethoxy]ethoxy)ethyl]carbamoyl]amino)butyl]urea;

4-[(1S,2S)-4,6-dichloro-1-[4-[(2-[2-[2-([[4-([[2-(2-[2-[(4-[[(1S,2S)-4,6-dichloro-2-[4-(dimethylcarbamoyl)piperazin-1-yl]-2,3-dihydro-1H-inden-1-yl]oxy]benzene)sulfonamido]ethoxy]ethoxy)ethyl]carbamoyl]amino)butyl]carbamoyl]amino)ethoxy]ethoxy]ethyl)sulfamoyl]phenoxy]-2,3-dihydro-1H-inden-2-yl]-N,N-dimethylpiperazine-1-carboxamide;

4-[(1S,2S)-4,6-dichloro-1-[4-[(2-[2-[2-([[4-([[2-(2-[2-[(4-[[(1S,2S)-4,6-dichloro-2-[4-(dimethylcarbamoyl)piperazin-1-yl]-2,3-dihydro-1H-inden-1-yl]oxy]-3-methylbenzene)sulfonamido]ethoxy]ethoxy)ethyl]carbamoyl]amino)butyl]carbamoyl]amino)ethoxy]ethoxy]ethyl)sulfamoyl]-2-methylphenoxy]-2,3-dihydro-1H-inden-2-yl]-N,N-dimethylpiperazine-1-carboxamide;

3-[2-(2-[2-[(4-[[(1S,2S)-4,6-Dichloro-2-[(3R)-3-[methyl(propan-2-yl)amino]piperidin-1-yl]-2,3-dihydro-1H-inden-1-yl]oxy]benzene) sulfonamido]ethoxy]ethoxy)ethyl]-1-[4-([[2-(2-[2-[(4-[[(1S,2S)-4,6-dichloro-2-[(3R)-3-[methyl(propan-2-yl)amino]piperidin-1-yl]-2,3-dihydro-1H-inden-1-yl]oxy]benzene)sulfonamido]ethoxy]ethoxy)ethyl]carbamoyl]amino)butyl]urea;

3-[2-(2-[2-[(4-[[(1S,2S)-2-[(3R)-3-Aminopiperidin-1-yl]-4,6-dichloro-2,3-dihydro-1H-inden-1-yl]oxy]-3,5-dimethyl benzene)sulfonamido]ethoxy]ethoxy)ethyl]-1-[4-([[2-(2-[2-[(4-[[(1S,2S)-2-[(3R)-3-aminopiperidin-1-yl]-4,6-dichloro-2,3-dihydro-1H-inden-1-yl]oxy]-3,5-dimethyl-benzene)sulfonamido]ethoxy]ethoxy)ethyl]carbamoyl]amino)butyl]urea; hydrochloride;

1-[2-(2-[2-[(3-[[(1S,2S)-4,6-dichloro-2-(dimethylamino)-2,3-dihydro-1H-inden-1-yl]oxy]-2,4-dimethylbenzene)

sulfonamido]ethoxy]ethoxy) ethyl]-3-[4-([[2-(2-[2-[(4-[[(1S,2S)-4,6-dichloro-2-(dimethylamino)-2,3-dihydro-1H-inden-1-yl]oxy]-3,5-dimethylbenzene)-sulfonamido]ethoxy]ethoxy)ethyl]carbamoyl]amino)butyl]urea;

3-[2-(2-[2-[(4-[[(1S,2S)-2-[(3R)-3-Aminopiperidin-1-yl]-4,6-dichloro-2,3-dihydro-1H-inden-1-yl]oxy]-2,5-dimethylbenzene) sulfonamido]ethoxy]ethoxy)ethyl]-1-[4-([[2-(2-[2-[(4-[[(1S,2S)-2-[(3R)-3-aminopiperidin-1-yl]-4,6-dichloro-2,3-dihydro-1H-inden-1-yl]oxy]-2,5-dimethylbenzene)sulfonamido]ethoxy]ethoxy)ethyl]carbamoyl]amino)butyl]urea;

3-[2-(2-[2-[(4-[[(1S,2S)-4,6-Dichloro-2-(dimethylamino)-2,3-dihydro-1H-inden-1-yl]oxy]-2,5-dimethylbenzene)sulfonamido]ethoxy]ethoxy)ethyl]-1-[4-([[2-(2-[2-[(4-[[(1S,2S)-4,6-dichloro-2-(dimethylamino)-2,3-dihydro-1H-inden-1-yl]oxy]-2,5-dimethylbenzene)sulfonamido]ethoxy]ethoxy)ethyl]carbamoyl]amino)butyl]urea;

1-[2-(2-[2-[(4-[[(1S,2S)-2-[(3R)-3-Aminopiperidin-1-yl]-4,6-dichloro-2,3-dihydro-1H-inden-1-yl]oxy]-3-fluoro-5-methylbenzene)sulfonamido]ethoxy]ethoxy)ethyl]-3-[4-([[2-(2-[2-[(4-[[(1S,2S)-2-[(3R)-3-aminopiperidin-1-yl]-4,6-dichloro-2,3-dihydro-1H-inden-1-yl]oxy]-3-fluoro-5-methylbenzene)sulfonamido]ethoxy]ethoxy)ethyl]-carbamoyl]amino)butyl]urea; hydrochloride;

1-[2-(2-[2-[(4-[[(1S,2S)-4,6-Dichloro-2-(dimethylamino)-2,3-dihydro-1H-inden-1-yl]oxy]-3-fluoro-5-methylbenzene)sulfonamido]ethoxy]ethoxy)ethyl]-3-[4-([[2-(2-[2-[(4-[[(1S,2S)-4,6-dichloro-2-(dimethylamino)-2,3-dihydro-1H-inden-1-yl]oxy]-3-fluoro-5-methylbenzene)sulfonamido]ethoxy]ethoxy)ethyl]carbamoyl]amino)butyl]urea;

3-[2-(2-[2-[(4-[[(1S,2S)-2-[(3R)-3-Aminopiperidin-1-yl]-4,6-dichloro-2,3-dihydro-1H-inden-1-yl]oxy]-3,5-difluorobenzene) sulfonamido]ethoxy]ethoxy)ethyl]-1-[4-([[2-(2-[2-[(4-[[(1S,2S)-2-[(3R)-3-aminopiperidin-1-yl]-4,6-dichloro-2,3-dihydro-1H-inden-1-yl]oxy]-3,5-difluorobenzene)sulfonamido]ethoxy]ethoxy)ethyl]carbamoyl]amino)butyl]urea;

4-([[(1S,2S)-4,6-dichloro-2-(dimethylamino)-2,3-dihydro-1H-inden-1-yl]oxy)-N-[26-([4-([[(1S,2S)-4,6-dichloro-2-(dimethylamino)-2,3-dihydro-1H-inden-1-yl]oxy)-3,5-difluorophenyl]sulfonamido)-10,17-dioxo-3,6,21,24-tetraoxa-9,11,16,18-tetraazahexacosyl]-3,5-difluorobenzenesulfonamide;

3-[2-(2-[2-[(4-[[(1S,2S)-2-[(3R)-3-Aminopiperidin-1-yl]-4,6-dichloro-2,3-dihydro-1H-inden-1-yl]oxy]-5-fluoro-2-methylbenzene)sulfonamido]ethoxy]ethoxy)ethyl]-1-[4-([[2-(2-[2-[(4-[[(1S,2S)-2-[(3R)-3-aminopiperidin-1-yl]-4,6-dichloro-2,3-dihydro-1H-inden-1-yl]oxy]-5-fluoro-2-methylbenzene)sulfonamido]ethoxy]ethoxy)ethyl]carbamoyl]amino)butyl]urea;

3-[2-(2-[2-[(4-[[(1S,2S)-4,6-Dichloro-2-(dimethylamino)-2,3-dihydro-1H-inden-1-yl]oxy]-5-fluoro-2-methylbenzene)sulfonamido]ethoxy]ethoxy)ethyl]-1-[4-([[2-(2-[2-[(4-[[(1S,2S)-4,6-dichloro-2-(dimethylamino)-2,3-dihydro-1H-inden-1-yl]oxy]-5-fluoro-2-methylbenzene)sulfonamido]ethoxy]ethoxy)ethyl]carbamoyl]amino)butyl]urea;

3-[2-(2-[2-[(4-[[(1S,2S)-2-[(3R)-3-Aminopiperidin-1-yl]-4,6-dichloro-2,3-dihydro-1H-inden-1-yl]oxy]-2-fluoro-5-methylbenzene)sulfonamido]ethoxy]ethoxy)ethyl]-1-[4-([[2-(2-[2-[(4-[[(1S,2S)-2-[(3R)-3-aminopiperidin-1-yl]-4,6-dichloro-2,3-dihydro-1H-inden-1-yl]oxy]-2-fluoro-5-methylbenzene)sulfonamido]ethoxy]ethoxy)ethyl]-carbamoyl]amino)butyl]urea;

3-[2-(2-[2-[(4-[[(1S,2S)-4,6-Dichloro-2-(dimethylamino)-2,3-dihydro-1H-inden-1-yl]oxy]-2-fluoro-5-methylbenzene)sulfonamido]ethoxy]ethoxy)ethyl]-1-[4-([[2-(2-[2-[(4-[[(1S,2S)-4,6-dichloro-2-(dimethylamino)-2,3-dihydro-1H-inden-1-yl]oxy]-2-fluoro-5-methylbenzene)sulfonamido]ethoxy]ethoxy)ethyl]carbamoyl]amino)butyl]urea;

1-(2-[2-[(3S)-3-[(4-[[(1S,2S)-4,6-Dichloro-2-(dimethylamino)-2,3-dihydro-1H-inden-1-yl]oxy]-3-methylbenzene)sulfonamido]-2-oxopyrrolidin-1-yl]ethoxy]ethyl)-3-(4-[[(2-[2-[(3S)-3-[(4-[[(1S,2S)-4,6-dichloro-2-(dimethylamino)-2,3-dihydro-1H-inden-1-yl]oxy]-3-methylbenzene)sulfonamido]-2-oxopyrrolidin-1-yl]ethoxy]ethyl)carbamoyl]amino]-butyl)urea;

1-(2-[2-[(3S)-3-[(4-[[(1S,2S)-6-Chloro-4-cyano-2-(dimethylamino)-2,3-dihydro-1H-inden-1-yl]oxy]-3-methylbenzene)sulfonamido]-2-oxopyrrolidin-1-yl]ethoxy]ethyl)-3-(4-[[(2-[2-[(3S)-3-[(4-[[(1S,2S)-6-chloro-4-cyano-2-(dimethylamino)-2,3-dihydro-1H-inden-1-yl]oxy]-3-methylbenzene)sulfonamido]-2-oxopyrrolidin-1-yl]ethoxy]ethyl)carbamoyl-amino]butyl)urea;

3-[2-(2-[[(3R)-1-[(4-[[(1S,2S)-2-[(3R)-3-Aminopiperidin-1-yl]-4,6-dichloro-2,3-dihydro-1H-inden-1-yl]oxy]benzene)sulfonyl]pyrrolidin-3-yl]oxy]ethoxy)ethyl]-1-[4-([[2-(2-[[(3R)-1-[(4-[[(1S,2S)-2-[(3R)-3-aminopiperidin-1-yl]-4,6-dichloro-2,3-dihydro-1H-inden-1-yl]oxy]benzene)sulfonyl]pyrrolidin-3-yl]oxy]ethoxy)ethyl]carbamoyl]amino)butyl]urea;

3-[2-(2-[[(3S)-1-[(4-[[(1S,2S)-2-[(3R)-3-Aminopiperidin-1-yl]-4,6-dichloro-2,3-dihydro-1H-inden-1-yl]oxy]benzene)sulfonyl]pyrrolidin-3-yl]oxy]ethoxy)ethyl]-1-[4-([[2-(2-[[(3S)-1-[(4-[[(1S,2S)-2-[(3R)-3-aminopiperidin-1-yl]-4,6-dichloro-2,3-dihydro-1H-inden-1-yl]oxy]benzene)sulfonyl]pyrrolidin-3-yl]oxy]ethoxy)ethyl]carbamoyl]amino)butyl]urea;

3-[2-[2-([1-[(4-[[(1S,2S)-2-[(3R)-3-Aminopiperidin-1-yl]-4,6-dichloro-2,3-dihydro-1H-inden-1-yl]oxy]benzene)sulfonyl]piperidin-4-yl]oxy)ethoxy]ethyl]-1-[4-[([2-[2-([1-[(4-[[(1S,2S)-2-[(3R)-3-aminopiperidin-1-yl]-4,6-dichloro-2,3-dihydro-1H-inden-1-yl]oxy]benzene)-sulfonyl]piperidin-4-yl]oxy)ethoxy]ethyl]carbamoyl)amino]butyl]urea;

1-(2-[2-[(2S)-2-[(4-[[(1S,2S)-2-[(3R)-3-Aminopiperidin-1-yl]-4,6-dichloro-2,3-dihydro-1H-inden-1-yl]oxy]benzene)sulfonamido]propoxy]ethyl)-3-(4-[[(2-[2-[(2S)-2-[(4-[[(1S,2S)-2-[(3R)-3-aminopiperidin-1-yl]-4,6-dichloro-2,3-dihydro-1H-inden-1-yl]oxy]benzene)sulfonamido]propoxy]ethyl)carbamoyl]amino]butyl)urea; hydrochloride;

3-(2-[2-[(2R)-2-[(4-[[(1S,2S)-2-[(3R)-3-Aminopiperidin-1-yl]-4,6-dichloro-2,3-dihydro-1H-inden-1-yl]oxy]benzene)sulfonamido]propoxy]ethyl)-1-(4-[[(2-[2-[(2R)-2-[(4-[[(1S,2S)-2-[(3R)-3-aminopiperidin-1-yl]-4,6-dichloro-2,3-dihydro-1H-inden-1-yl]oxy]benzene)sulfonamido]propoxy]ethyl)carbamoyl]amino]butyl)urea;

3-(2-[2-[(2S)-2-[(4-[[(1S,2S)-2-[(3R)-3-Aminopiperidin-1-yl]-4,6-dichloro-2,3-dihydro-1H-inden-1-yl]oxy]benzene)sulfonamido]-3-methylbutoxy]ethoxy]ethyl)-1-(4-[[(2-[2-[(2S)-2-[(4-[[(1S,2S)-2-[(3R)-3-aminopiperidin-1-yl]-4,6-dichloro-2,3-dihydro-1H-inden-1-yl]oxy]benzene) sulfonamido]-3-methylbutoxy]ethoxy]ethyl)carbamoyl]amino]butyl)-urea dihydrochloride;

3-(2-[2-[(2R)-2-[(4-[[(1S,2S)-2-[(3R)-3-Aminopiperidin-1-yl]-4,6-dichloro-2,3-dihydro-1H-inden-1-yl]oxy]benzene)sulfonamido]-3-methylbutoxy]ethoxy]ethyl)-1-(4-[[(2-[2-[(2R)-2-[(4-[[(1S,2S)-2-[(3R)-3-aminopiperidin-1-yl]-4,6-dichloro-2,3-dihydro-1H-inden-1-yl]oxy]

benzene)sulfonamido]-3-methylbutoxy]ethoxy]ethyl)
carbamoyl]-amino]butyl]urea;

1-[2-(2-[2-[(4-[[(1S,2S)-2-[(3R)-3-Aminopiperidin-1-yl]-4,
6-dichloro-2,3-dihydro-1H-inden-1-yl]oxy]benzene)
sulfonamido]-2-methylpropoxy]ethoxy]ethyl]-3-[4-([[2-
(2-[2-[(4-[[(1S,2S)-2-[(3R)-3-aminopiperidin-1-yl]-4,6-
dichloro-2,3-dihydro-1H-inden-1-yl]oxy]benzene)
sulfonamido]-2-methylpropoxy]ethoxy]ethyl]carbamoyl]
amino)butyl]urea; hydrochloride;

1-[2-(2-[2-[(4-[[(1S,2S)-2-[(3R)-3-Aminopiperidin-1-yl]-4,
6-dichloro-2,3-dihydro-1H-inden-1-yl]oxy]-2-methoxy-
benzene)sulfonamido]ethoxy]ethoxy]ethyl]-3-[4-([[2-(2-
[2-[(4-[[(1S,2S)-2-[(3R)-3-aminopiperidin-1-yl]-4,6-
dichloro-2,3-dihydro-1H-inden-1-yl]oxy]-2-
methoxybenzene)sulfonamido]ethoxy]ethoxy]ethyl]
carbamoyl]amino)butyl]urea;

3-[2-(2-[2-[(4-[[(1S,2S)-2-[(3R)-3-Aminopiperidin-1-yl]-4,
6-dichloro-2,3-dihydro-1H-inden-1-yl]oxy]-2-methyl-
benzene)sulfonamido]ethoxy]ethoxy]ethyl]-1-[4-([[2-(2-
[2-[(4-[[(1S,2S)-2-[(3R)-3-aminopiperidin-1-yl]-4,6-
dichloro-2,3-dihydro-1H-inden-1-yl]oxy]-2-
methylbenzene)sulfonamido]ethoxy]ethoxy]ethyl]
carbamoyl]amino)butyl]urea;

1-[2-(2-[2-[(4-[[(1S,2S)-2-[(3R)-3-Aminopiperidin-1-yl]-4,
6-dichloro-2,3-dihydro-1H-inden-1-yl]oxy]-2-fluoroben-
zene)sulfonamido]ethoxy]ethoxy]ethyl]-3-[4-([[2-(2-[2-
[(4-[[(1S,2S)-2-[(3R)-3-aminopiperidin-1-yl]-4,6-
dichloro-2,3-dihydro-1H-inden-1-yl]oxy]-2-
fluorobenzene)sulfonamido]ethoxy]ethoxy]ethyl]
carbamoyl]amino)butyl]urea;

4-([[(1S,2S)-2-[(R)-3-Aminopiperidin-1-yl]-4,6-dichloro-2,
3-dihydro-1H-inden-1-yl]oxy)-N-[26-([4-([[(1S,2S)-2-
[(R)-3-aminopiperidin-1-yl]-4,6-dichloro-2,3-dihydro-
1H-inden-1-yl]oxy)-2-chlorophenyl]sulfonamido)-10,17-
dioxo-3,6,21,24-tetraoxa-9,11,16,18-tetraazahexacosyl]-
2-chlorobenzenesulfonamide;

4-([[(1S,2S)-4,6-Dichloro-2-(piperazin-1-yl)-2,3-dihydro-
1H-inden-1-yl]oxy)-N—[(R)-1-(20-[(R)-3-([4-([[(1S,2S)-
4,6-dichloro-2-(piperazin-1-yl)-2,3-dihydro-1H-inden-1-
yl]oxy)-3-fluorophenyl]sulfonamido)pyrrolidin-1-yl]-7,
14-dioxo-3,18-dioxa-6,8,13,15-tetraazaicosyl)pyrrolidin-
3-yl]-3-fluorobenzenesulfonamide; tetra(trifluoroacetate);

4-([[(1S,2S)-4,6-Dichloro-2-(piperazin-1-yl)-2,3-dihydro-
1H-inden-1-yl]oxy)-N—[(S)-1-(20-[(S)-3-([4-([[(1S,2S)-
4,6-dichloro-2-(piperazin-1-yl)-2,3-dihydro-1H-inden-1-
yl]oxy)-3-fluorophenyl]sulfonamido)pyrrolidin-1-yl]-7,
14-dioxo-3,18-dioxa-6,8,13,15-tetraazaicosyl)pyrrolidin-
3-yl]-3-fluorobenzenesulfonamide; tetra(trifluoroacetate);

4-([[(1S,2S)-6-Chloro-4-cyano-2-(piperazin-1-yl)-2,3-di-
hydro-1H-inden-1-yl]oxy)-N—[(S)-1-(20-[(S)-3-[(4-
([[(1S,2S)-6-chloro-4-cyano-2-(piperazin-1-yl)-2,3-di-
hydro-1H-inden-1-yl]oxy)phenyl]sulfonamido)
pyrrolidin-1-yl]-7,14-dioxo-3,18-dioxa-6,8,13,15-
tetraazaicosyl)pyrrolidin-3-yl]benzenesulfonamide; tetra
(trifluoroacetate);

4-([[(1S,2S)-6-Chloro-4-cyano-2-(piperazin-1-yl)-2,3-di-
hydro-1H-inden-1-yl]oxy)-N—[(R)-1-(20-[(R)-3-[(4-
([[(1S,2S)-6-chloro-4-cyano-2-(piperazin-1-yl)-2,3-di-
hydro-1H-inden-1-yl]oxy)phenyl]sulfonamido)
pyrrolidin-1-yl]-7,14-dioxo-3,18-dioxa-6,8,13,15-
tetraazaicosyl)pyrrolidin-3-yl]benzenesulfonamide; tetra
(trifluoroacetate);

4-([[(1S,2S)-6-Chloro-4-cyano-2-(piperazin-1-yl)-2,3-di-
hydro-1H-inden-1-yl]oxy)-N—[(R)-1-(20-[(R)-3-[(4-
([[(1S,2S)-6-chloro-4-cyano-2-(piperazin-1-yl)-2,3-di-
hydro-1H-inden-1-yl]oxy)-3-fluorophenyl)sulfonamido)
pyrrolidin-1-yl]-7,14-dioxo-3,18-dioxa-6,8,13,15-
tetraazaicosyl)pyrrolidin-3-yl]-3-
fluorobenzenesulfonamide; tetra(trifluoroacetate);

4-([[(1S,2S)-6-Chloro-4-cyano-2-(piperazin-1-yl)-2,3-di-
hydro-1H-inden-1-yl]oxy)-N—[(S)-1-(20-[(S)-3-[(4-
([[(1S,2S)-6-chloro-4-cyano-2-(piperazin-1-yl)-2,3-di-
hydro-1H-inden-1-yl]oxy)-3-fluorophenyl)sulfonamido)
pyrrolidin-1-yl]-7,14-dioxo-3,18-dioxa-6,8,13,15-
tetraazaicosyl)pyrrolidin-3-yl]-3-
fluorobenzenesulfonamide; tetra(trifluoroacetate);

4-([[(1S,2S)-4,6-Dichloro-2-(dimethylamino)-2,3-dihydro-
1H-inden-1-yl]oxy)-N—[(S)-1-(20-[(S)-3-([4-([[(1S,2S)-
4,6-dichloro-2-(dimethylamino)-2,3-dihydro-1H-inden-
1-yl]oxy)-3-fluorophenyl]sulfonamido)pyrrolidin-1-yl]-
7,14-dioxo-3,18-dioxa-6,8,13,15-tetraazaicosyl)
pyrrolidin-3-yl]-3-fluorobenzenesulfonamide; tetra
(trifluoroacetate);

4-([[(1S,2S)-4,6-Dichloro-2-(dimethylamino)-2,3-dihydro-
1H-inden-1-yl]oxy)-N—[(R)-1-(20-[(R)-3-([4-([[(1S,2S)-
4,6-dichloro-2-(dimethylamino)-2,3-dihydro-1H-inden-
1-yl]oxy)-3-fluorophenyl]sulfonamido)pyrrolidin-1-yl]-
7,14-dioxo-3,18-dioxa-6,8,13,15-tetraazaicosyl)
pyrrolidin-3-yl]-3-fluorobenzenesulfonamide; tetra
(trifluoroacetate);

4-([[(1S,2S)-6-Chloro-2-[(R)-3-(dimethylamino)piperidin-1-
yl]-4-methyl-2,3-dihydro-1H-inden-1-yl]oxy)-N—[(R)-
1-(20-[(R)-3-([4-([[(1S,2S)-6-chloro-2-[(R)-3-(dimethyl-
amino)piperidin-1-yl]-4-methyl-2,3-dihydro-1H-inden-1-
yl]oxy)-3-methylphenyl]sulfonamido)pyrrolidin-1-yl]-7,
14-dioxo-3,18-dioxa-6,8,13,15-tetraazaicosyl)pyrrolidin-
3-yl]-3-methylbenzenesulfonamide; tetra
(trifluoroacetate);

4-([[(1S,2S)-6-Chloro-2-[(R)-3-(dimethylamino)piperidin-1-
yl]-4-methyl-2,3-dihydro-1H-inden-1-yl]oxy)-N—[(S)-
1-(20-[(S)-3-([4-([[(1S,2S)-6-chloro-2-[(R)-3-(dimethyl-
amino)piperidin-1-yl]-4-methyl-2,3-dihydro-1H-inden-1-
yl]oxy)-3-methylphenyl]sulfonamido)pyrrolidin-1-yl]-7,
14-dioxo-3,18-dioxa-6,8,13,15-tetraazaicosyl)pyrrolidin-
3-yl]-3-methylbenzenesulfonamide; tetra
(trifluoroacetate);

4-([[(1S,2S)-6-Chloro-4-cyano-2-(piperazin-1-yl)-2,3-di-
hydro-1H-inden-1-yl]oxy)-N-[1-(18-[4-([[(1S,2S)-6-
chloro-4-cyano-2-(piperazin-1-yl)-2,3-dihydro-1H-in-
den-1-yl]oxy)phenyl]sulfonamido)piperidin-1-yl]-6,13,
18-trioxo-5,7,12,14-tetraazaoctadecanoyl)piperidin-4-yl]
benzenesulfonamide;

4-([[(1S,2S)-6-Chloro-4-cyano-2-(piperazin-1-yl)-2,3-di-
hydro-1H-inden-1-yl]oxy)-N—[(S)-1-(14-[(S)-3-([4-
([[(1S,2S)-6-chloro-4-cyano-2-(piperazin-1-yl)-2,3-di-
hydro-1H-inden-1-yl]oxy)phenyl]sulfonamido)
pyrrolidin-1-yl]-4,11,14-trioxo-3,5,10,12-
tetraazatetradecanoyl)pyrrolidin-3-yl]
benzenesulfonamide;

4-([[(1S,2S)-6-Chloro-4-cyano-2-(piperazin-1-yl)-2,3-di-
hydro-1H-inden-1-yl]oxy)-N—[(S)-1-[(2S,13S)-14-[(S)-
3-([4-([[(1S,2S)-6-chloro-4-cyano-2-(piperazin-1-yl)-2,3-
dihydro-1H-inden-1-yl]oxy)phenyl]sulfonamido)
pyrrolidin-1-yl]-2,13-dimethyl-4,11,14-trioxo-3,5,10,12-
tetraazatetradecanoyl]pyrrolidin-3-yl]
benzenesulfonamide;

N1,N14-bis(2-[(S)-3-([4-([[(1S,2S)-6-chloro-4-cyano-2-
(piperazin-1-yl)-2,3-dihydro-1H-inden-1-yl]oxy)phenyl]
sulfonamido)pyrrolidin-1-yl]-2-oxoethyl)-4,11-dioxo-3,
5,10,12-tetraazatetradecanediamide;

N1,N14-bis(2-[(R)-3-([4-([[(1S,2S)-6-chloro-4-cyano-2-
(piperazin-1-yl)-2,3-dihydro-1H-inden-1-yl]oxy)phenyl]
sulfonamido)pyrrolidin-1-yl]-2-oxoethyl)-4,11-dioxo-3,
5,10,12-tetraazatetradecanediamide;

N1,N18-Bis(1-([4-([(1S,2S)-6-chloro-4-cyano-2-(piperazin-1-yl)-2,3-dihydro-1H-inden-1-yl]oxy)phenyl]sulfonyl)piperidin-4-yl)-6,13-dioxo-5,7,12,14-tetraazaoctadecanediamide;

4-([(1S,2S)-6-Chloro-4-cyano-2-[(R)-3-(dimethylamino)piperidin-1-yl]-2,3-dihydro-1H-inden-1-yl]oxy)-N-[26-([4-([(1S,2S)-6-chloro-4-cyano-2-[(R)-3-(dimethylamino)piperidin-1-yl]-2,3-dihydro-1H-inden-1-yl]oxy)phenyl]sulfonamido)-10,17-dioxo-3,6,21,24-tetraoxa-9,11,16,18-tetraazahexacosyl]benzenesulfonamide;

-([(1S,2S)-6-Chloro-4-cyano-2-[(S)-3-(dimethylamino)piperidin-1-yl]-2,3-dihydro-1H-inden-1-yl]oxy)-N-[26-([4-([(1S,2S)-6-chloro-4-cyano-2-[(S)-3-(dimethylamino)piperidin-1-yl]-2,3-dihydro-1H-inden-1-yl]oxy)phenyl]sulfonamido)-10,17-dioxo-3,6,21,24-tetraoxa-9,11,16,18-tetraazahexacosyl]benzenesulfonamide;

4-([(1S,2S)-6-chloro-4-cyano-2-(piperazin-1-yl)-2,3-dihydro-1H-inden-1-yl]oxy)-N-[1-(20-[4-([(1S,2S)-6-chloro-4-cyano-2-(piperazin-1-yl)-2,3-dihydro-1H-inden-1-yl]oxy)phenyl]sulfonamide]piperidin-1-yl)-7,14-dioxo-3,18-dioxa-6,8,13,15-tetraazaicosyl]piperidin-4-yl)benzenesulfonamide;

N1,N18-Bis([4-([(1S,2S)-6-chloro-4-cyano-2-(piperazin-1-yl)-2,3-dihydro-1H-inden-1-yl]oxy)phenyl]sulfonyl)-6,13-dioxo-5,7,12,14-tetraazaoctadecanediamide;

N-([4-([(1S,2S)-6-chloro-4-cyano-2-(piperazin-1-yl)-2,3-dihydro-1H-inden-1-yl]oxy)phenyl]sulfonyl)-1-[16-(4-[([4-([(1S,2S)-6-chloro-4-cyano-2-(piperazin-1-yl)-2,3-dihydro-1H-inden-1-yl]oxy)phenyl]sulfonyl)carbamoyl]piperidin-1-yl)-5,12-dioxo-4,6,11,13-tetraazahexadecyl]piperidine-4-carboxamide;

4-([(1S,2S)-6-chloro-4-cyano-2-(1,4-diazepan-1-yl)-2,3-dihydro-1H-inden-1-yl]oxy)-N—[(S)-1-(20-[(S)-3-([4-([(1S,2S)-6-chloro-4-cyano-2-(1,4-diazepan-1-yl)-2,3-dihydro-1H-inden-1-yl]oxy)phenyl]sulfonamido)pyrrolidin-1-yl]-7,14-dioxo-3,18-dioxa-6,8,13,15-tetraazaicosyl)pyrrolidin-3-yl]benzenesulfonamide;

4-([(1S,2S)-6-chloro-4-cyano-2-(1,4-diazepan-1-yl)-2,3-dihydro-1H-inden-1-yl]oxy)-N—[(R)-1-(20-[(R)-3-([4-([(1S,2S)-6-chloro-4-cyano-2-(1,4-diazepan-1-yl)-2,3-dihydro-1H-inden-1-yl]oxy)phenyl]sulfonamido)pyrrolidin-1-yl]-7,14-dioxo-3,18-dioxa-6,8,13,15-tetraazaicosyl)pyrrolidin-3-yl]benzenesulfonamide;

4-([(1S,2S)-6-chloro-4-cyano-2-(4-methyl-1,4-diazepan-1-yl)-2,3-dihydro-1H-inden-1-yl]oxy)-N—[(S)-1-(20-[(S)-3-([4-([(1S,2S)-6-chloro-4-cyano-2-(4-methyl-1,4-diazepan-1-yl)-2,3-dihydro-1H-inden-1-yl]oxy)phenyl]sulfonamido)pyrrolidin-1-yl]-7,14-dioxo-3,18-dioxa-6,8,13,15-tetraazaicosyl)pyrrolidin-3-yl]benzenesulfonamide;

4-([(1S,2S)-6-chloro-4-cyano-2-(4-methyl-1,4-diazepan-1-yl)-2,3-dihydro-1H-inden-1-yl]oxy)-N—[(R)-1-(20-[(R)-3-([4-([(1S,2S)-6-chloro-4-cyano-2-(4-methyl-1,4-diazepan-1-yl)-2,3-dihydro-1H-inden-1-yl]oxy)phenyl]sulfonamido)pyrrolidin-1-yl]-7,14-dioxo-3,18-dioxa-6,8,13,15-tetraazaicosyl)pyrrolidin-3-yl]benzenesulfonamide;

4-([(1S,2S)-2-[(1S,4S)-2,5-diazabicyclo[2.2.1]heptan-2-yl]-6-chloro-4-cyano-2,3-dihydro-1H-inden-1-yl]oxy)-N—[(S)-1-(20-[(S)-3-([4-([(1S,2S)-2-[(1S,4S)-2,5-diazabicyclo[2.2.1]-heptan-2-yl]-6-chloro-4-cyano-2,3-dihydro-1H-inden-1-yl]oxy)phenyl]sulfonamido)-pyrrolidin-1-yl]-7,14-dioxo-3,18-dioxa-6,8,13,15-tetraazaicosyl)pyrrolidin-3-yl]benzenesulfonamide;

4-([(1S,2S)-2-[(1S,4S)-2,5-diazabicyclo[2.2.1]heptan-2-yl]-6-chloro-4-cyano-2,3-dihydro-1H-inden-1-yl]oxy)-N—[(R)-1-(20-[(R)-3-([4-([(1S,2S)-2-[(1S,4S)-2,5-diazabicyclo[2.2.1]-heptan-2-yl]-6-chloro-4-cyano-2,3-dihydro-1H-inden-1-yl]oxy)phenyl]sulfonamido)-pyrrolidin-1-yl]-7,14-dioxo-3,18-dioxa-6,8,13,15-tetraazaicosyl)pyrrolidin-3-yl]benzenesulfonamide;

4-([(1S,2S)-6-chloro-4-cyano-2-[(R)-3-methylpiperazin-1-yl]-2,3-dihydro-1H-inden-1-yl]oxy)-N—(S)-1-(20-[(S)-3-([4-([(1S,2S)-6-chloro-4-cyano-2-[(R)-3-methylpiperazin-1-yl]-2,3-dihydro-1H-inden-1-yl]oxy)phenyl]sulfonamido)pyrrolidin-1-yl]-7,14-dioxo-3,18-dioxa-6,8,13,15-tetraazaicosyl)pyrrolidin-3-yl]benzenesulfonamide;

4-([(1S,2S)-6-chloro-4-cyano-2-[(R)-3-methylpiperazin-1-yl]-2,3-dihydro-1H-inden-1-yl]oxy)-N—[(R)-1-(20-[(R)-3-([4-([(1S,2S)-6-chloro-4-cyano-2-[(R)-3-methylpiperazin-1-yl]-2,3-dihydro-1H-inden-1-yl]oxy)phenyl]sulfonamido)pyrrolidin-1-yl]-7,14-dioxo-3,18-dioxa-6,8,13,15-tetraazaicosyl)pyrrolidin-3-yl]benzenesulfonamide;

4-([(1S,2S)-6-chloro-4-cyano-2-[(S)-3-methylpiperazin-1-yl]-2,3-dihydro-1H-inden-1-yl]oxy)-N—[(S)-1-(20-[(S)-3-([4-([(1S,2S)-6-chloro-4-cyano-2-[(S)-3-methylpiperazin-1-yl]-2,3-dihydro-1H-inden-1-yl]oxy)phenyl]sulfonamido)pyrrolidin-1-yl]-7,14-dioxo-3,18-dioxa-6,8,13,15-tetraazaicosyl)pyrrolidin-3-yl]benzenesulfonamide;

4-([(1S,2S)-6-chloro-4-cyano-2-[(S)-3-methylpiperazin-1-yl]-2,3-dihydro-1H-inden-1-yl]oxy)-N—[(R)-1-(20-[(R)-3-([4-([(1S,2S)-6-chloro-4-cyano-2-[(S)-3-methylpiperazin-1-yl]-2,3-dihydro-1H-inden-1-yl]oxy)phenyl]sulfonamido)pyrrolidin-1-yl]-7,14-dioxo-3,18-dioxa-6,8,13,15-tetraazaicosyl)pyrrolidin-3-yl]benzenesulfonamide;

4-([(1S,2S)-6-chloro-4-cyano-2-[(3S,5R)-3,5-dimethylpiperazin-1-yl]-2,3-dihydro-1H-inden-1-yl]oxy)-N—[(S)-1-(20-[(S)-3-([4-([(1S,2S)-6-chloro-4-cyano-2-[(3S,5R)-3,5-dimethylpiperazin-1-yl]-2,3-dihydro-1H-inden-1-yl]oxy)phenyl]sulfonamido)pyrrolidin-1-yl]-7,14-dioxo-3,18-dioxa-6,8,13,15-tetraazaicosyl)pyrrolidin-3-yl]benzenesulfonamide;

4-([(1S,2S)-6-chloro-4-cyano-2-[(3S,5R)-3,5-dimethylpiperazin-1-yl]-2,3-dihydro-1H-inden-1-yl]oxy)-N—[(R)-1-(20-[(R)-3-([4-([(1S,2S)-6-chloro-4-cyano-2-[(3S,5R)-3,5-dimethylpiperazin-1-yl]-2,3-dihydro-1H-inden-1-yl]oxy)phenyl]sulfonamido)pyrrolidin-1-yl]-7,14-dioxo-3,18-dioxa-6,8,13,15-tetraazaicosyl)pyrrolidin-3-yl]benzenesulfonamide;

4-([(1S,2S)-6-chloro-4-cyano-2-(piperazin-1-yl)-2,3-dihydro-1H-inden-1-yl]oxy)-N—[(S)-1-(20-[(S)-3-([4-([(1S,2S)-6-chloro-4-cyano-2-(piperazin-1-yl)-2,3-dihydro-1H-inden-1-yl]oxy)phenyl]sulfonamido)-2-oxopiperidin-1-yl]-7,14-dioxo-3,18-dioxa-6,8,13,15-tetraazaicosyl)-2-oxopiperidin-3-yl]benzenesulfonamide;

4-([(1S,2S)-6-Chloro-4-cyano-2-(piperazin-1-yl)-2,3-dihydro-1H-inden-1-yl]oxy)-N-[2-(2-[2-(3-[(1r,4r)-4-(3-[2-(2-[2-(4-([(1S,2S)-6-chloro-4-cyano-2-(piperazin-1-yl)-2,3-dihydro-1H-inden-1-yl]oxy)phenyl]sulfonamido)ethoxy]ethoxy)ethyl]ureido)cyclohexyl]ureido)-ethoxy]ethoxy)ethyl]benzenesulfonamide;

4-([(1S,2S)-6-Chloro-4-cyano-2-(piperazin-1-yl)-2,3-dihydro-1H-inden-1-yl]oxy)-N—[(R)-1-(18-[(R)-3-([4-([(1S,2S)-6-chloro-4-cyano-2-(piperazin-1-yl)-2,3-dihydro-1H-inden-1-yl]oxy)phenyl]sulfonamido)pyrrolidin-1-yl]-6,13,18-trioxo-5,7,12,14-tetraazaoctadecanoyl)pyrrolidin-3-yl]benzenesulfonamide;

4-([(1S,2S)-6-Chloro-4-cyano-2-(piperazin-1-yl)-2,3-dihydro-1H-inden-1-yl]oxy)benzenesulfonamide;

N-(2-[2-(2-Aminoethoxy)ethoxy]ethyl)-4-([(1S,2S)-6-chloro-4-cyano-2-(piperazin-1-yl)-2,3-dihydro-1H-inden-1-yl]oxy)benzenesulfonamide; N-[1-(4-Aminobutanoyl)piperidin-4-yl]-4-([(1S,2S)-6-chloro-4-cyano-2-(piperazin-1-yl)-2,3-dihydro-1H-inden-1-yl]oxy) benzenesulfonamide;

4-([(1S,2S)-6-Chloro-4-cyano-2-(piperazin-1-yl)-2,3-dihydro-1H-inden-1-yl]oxy)-N-(3-oxo-7,10-dioxa-2,4-diazadodecan-12-yl)benzenesulfonamide;

4-([(1S,2S)-6-Chloro-4-cyano-2-(piperazin-1-yl)-2,3-dihydro-1H-inden-1-yl]oxy)-N-(1-[4-(3-methylureido)butanoyl]piperidin-4-yl)benzenesulfonamide;

4-([(1S,2S)-6-Chloro-4-cyano-2-(piperazin-1-yl)-2,3-dihydro-1H-inden-1-yl]oxy)-N-[(2S,3R,4S,5R)-1,3,4,5,6-pentahydroxyhexan-2-yl]benzenesulfonamide;

4-([4-([(1S,2S)-6-Chloro-4-cyano-2-(piperazin-1-yl)-2,3-dihydro-1H-inden-1-yl]oxy)phenyl]sulfonamido)-N-[(2S,3R,4S,5R)-1,3,4,5,6-pentahydroxyhexan-2-yl]piperidine-1-carboxamide;

4-(3-[4-([4-([(1S,2S)-6-Chloro-4-cyano-2-(piperazin-1-yl)-2,3-dihydro-1H-inden-1-yl]oxy)phenyl]sulfonamido)-4-oxobutyl]ureido)-N-([4-([(1S,2S)-6-chloro-4-cyano-2-(piperazin-1-yl)-2,3-dihydro-1H-inden-1-yl]oxy)phenyl]sulfonyl)butanamide;

4-([(1S,2S)-6-Chloro-4-cyano-2-(piperazin-1-yl)-2,3-dihydro-1H-inden-1-yl]oxy)-N-[1-(4-[3-(4-[4-([(1S,2S)-6-chloro-4-cyano-2-(piperazin-1-yl)-2,3-dihydro-1H-inden-1-yl]oxy)phenyl]sulfonamido)piperidin-1-yl]-4-oxobutyl)ureido]butanoyl)piperidin-4-yl]benzenesulfonamide;

4-([(1S,2S)-6-Chloro-4-cyano-2-(piperazin-1-yl)-2,3-dihydro-1H-inden-1-yl]oxy)-N-[19-([4-([(1S,2S)-6-chloro-4-cyano-2-(piperazin-1-yl)-2,3-dihydro-1H-inden-1-yl]oxy)phenyl]sulfonamido)-10-oxo-3,6,14,17-tetraoxa-9,11-diazanonadecyl]benzenesulfonamide;

4-([(1S,2S)-6-Chloro-4-amido-2-(piperazin-1-yl)-2,3-dihydro-1H-inden-1-yl]oxy)-N-[26-([4-([(1S,2S)-6-chloro-4-amido-2-(piperazin-1-yl)-2,3-dihydro-1H-inden-1-yl]oxy)phenyl]sulfonamido)-10,17-dioxo-3,6,21,24-tetraoxa-9,11,16,18-tetraazahexacosyl]benzenesulfonamide;

4-([(1S,2S)-4-Cyano-6-methyl-2-(piperazin-1-yl)-2,3-dihydro-1H-inden-1-yl]oxy)-N-[26-([4-([(1S,2S)-4-cyano-6-methyl-2-(piperazin-1-yl)-2,3-dihydro-1H-inden-1-yl]oxy)phenyl]sulfonamido)-10,17-dioxo-3,6,21,24-tetraoxa-9,11,16,18-tetraazahexacosyl]benzenesulfonamide;

1,1'-(Butane-1,4-diyl)bis[3-(4-[6-([(1S,2S)-6-chloro-4-cyano-2-(piperazin-1-yl)-2,3-dihydro-1H-inden-1-yl]oxy)-3,4-dihydroisoquinolin-2(1H)-yl]-4-oxobutyl)urea];

1,1'-(Butane-1,4-diyl)bis[3-(4-[7-([(1S,2S)-6-chloro-4-cyano-2-(piperazin-1-yl)-2,3-dihydro-1H-inden-1-yl]oxy)-3,4-dihydroisoquinolin-2(1H)-yl]-4-oxobutyl)urea];

N,N'-(6,14-Dioxo-10-oxa-5,7,13,15-tetraazanonadecane-1,19-diyl)bis[6-([(1S,2S)-6-chloro-4-cyano-2-(piperazin-1-yl)-2,3-dihydro-1H-inden-1-yl]oxy)-3,4-dihydroisoquinoline-2(1H)-carboxamide];

N,N'-(6,14-Dioxo-10-oxa-5,7,13,15-tetraazanonadecane-1,19-diyl)bis[7-([(1S,2S)-6-chloro-4-cyano-2-(piperazin-1-yl)-2,3-dihydro-1H-inden-1-yl]oxy)-3,4-dihydroisoquinoline-2(1H)-carboxamide];

4-([(1S,2S)-6-Chloro-4-cyano-2-[(R)-3-methylpiperazin-1-yl]-2,3-dihydro-1H-inden-1-yl]oxy)-N—[(S)-1-(18-[(S)-3-([4-([(1S,2S)-6-chloro-4-cyano-2-[(R)-3-methylpiperazin-1-yl]-2,3-dihydro-1H-inden-1-yl]oxy)phenyl] sulfonamido)pyrrolidin-1-yl]-6,13,18-trioxo-5,7,12,14-tetraazaoctadecanoyl)pyrrolidin-3-yl]benzenesulfonamide;

4-([(1S,2S)-6-Chloro-4-cyano-2-[(R)-3-methylpiperazin-1-yl]-2,3-dihydro-1H-inden-1-yl]oxy)-N—[(R)-1-(18-[(R)-3-([4-([(1S,2S)-6-chloro-4-cyano-2-[(R)-3-methylpiperazin-1-yl]-2,3-dihydro-1H-inden-1-yl]oxy)phenyl] sulfonamido)pyrrolidin-1-yl]-6,13,18-trioxo-5,7,12,14-tetraazaoctadecanoyl)pyrrolidin-3-yl]benzenesulfonamide;

4-([(1S,2S)-6-Chloro-4-cyano-2-[(R)-3-methylpiperazin-1-yl]-2,3-dihydro-1H-inden-1-yl]oxy)-N-[1-(18-[4-([4-([(1S,2S)-6-chloro-4-cyano-2-[(R)-3-methylpiperazin-1-yl]-2,3-dihydro-1H-inden-1-yl]oxy)phenyl]sulfonamido) piperidin-1-yl]-6,13,18-trioxo-5,7,12,14-tetraazaoctadecanoyl)piperidin-4-yl]benzenesulfonamide;

N1,N14-Bis(2-[(S)-3-([4-([(1S,2S)-6-chloro-4-cyano-2-[(R)-3-methylpiperazin-1-yl]-2,3-dihydro-1H-inden-1-yl]oxy)phenyl]sulfonamido)pyrrolidin-1-yl]-2-oxoethyl)-4,11-dioxo-3,5,10,12-tetraazatetradecanediamide;

4-([(1S,2S)-6-Chloro-4-cyano-2-[(R)-3-methylpiperazin-1-yl]-2,3-dihydro-1H-inden-1-yl]oxy)-N-[1-(20-[4-([4-([(1S,2S)-6-chloro-4-cyano-2-[(R)-3-methylpiperazin-1-yl]-2,3-dihydro-1H-inden-1-yl]oxy)phenyl]sulfonamido) piperidin-1-yl]-7,14-dioxo-3,18-dioxa-6,8,13,15-tetraazaicosyl)piperidin-4-yl]benzenesulfonamide;

4-([(1S,2S)-4,6-Dichloro-2-[(R)-3-methylpiperazin-1-yl]-2,3-dihydro-1H-inden-1-yl]oxy)-N—[(S)-1-(20-[(S)-3-([4-([(1S,2S)-4,6-dichloro-2-[(R)-3-methylpiperazin-1-yl]-2,3-dihydro-1H-inden-1-yl]oxy)phenyl]sulfonamido) pyrrolidin-1-yl]-7,14-dioxo-3,18-dioxa-6,8,13,15-tetraazaicosyl)pyrrolidin-3-yl]benzenesulfonamide;

N1,N14-Bis(2-[(S)-3-([4-([(1S,2S)-4,6-dichloro-2-[(R)-3-methylpiperazin-1-yl]-2,3-dihydro-1H-inden-1-yl]oxy) phenyl]sulfonamido)pyrrolidin-1-yl]-2-oxoethyl)-4,11-dioxo-3,5,10,12-tetraazatetradecanediamide;

1,1'-(Butane-1,4-diyl)bis(3-[2-(2-[6-([(1S,2S)-6-chloro-4-cyano-2-(piperazin-1-yl)-2,3-dihydro-1H-inden-1-yl]oxy)-1-oxoisoindolin-2-yl]ethoxy)ethyl]urea); and 1,1'-(Butane-1,4-diyl)bis(3-[2-(2-[5-([(1S,2S)-6-chloro-4-cyano-2-(piperazin-1-yl)-2,3-dihydro-1H-inden-1-yl]oxy)-1-oxoisoindolin-2-yl]ethoxy)ethyl]urea).

EXAMPLES

The invention will be more fully understood by reference to the following examples. They should not, however, be construed as limiting the scope of the invention. For example, the synthesis of non-exemplified compounds may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds described herein.

Example 1 (2S,4aS,6aS,6bR,8aS,10S,12aS,12bR, 14bR)-10-(Methoxycarbonyl)-2,4a,6a,6b, 9,9,12a-heptamethyl-13-oxo-1,2,3,4,4a,5,6,6a,6b,7,8,8a,9,10, 11,12,12a,12b,13,14b-icosahydro picene-2-carboxylic acid (1-9)
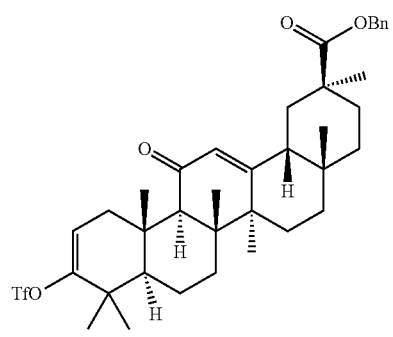
1-1
CO
Pd(PPh₃)₄
―――――
THF, H₂O
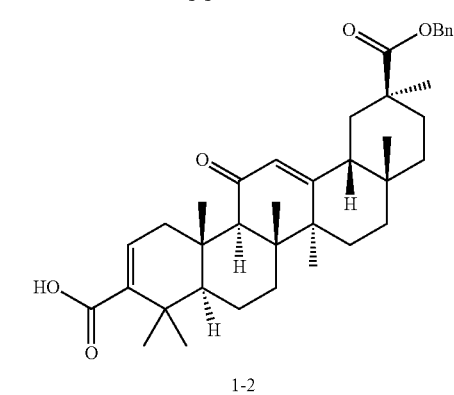
1-2
SEMCl
DMAP
TEA
―――
DMF
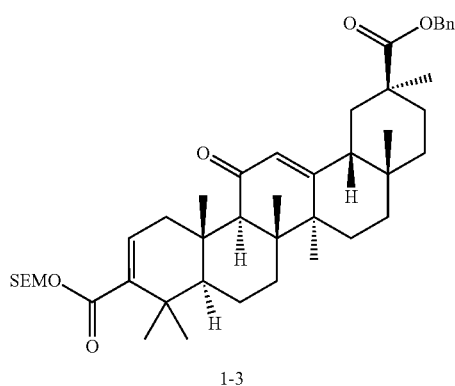
1-3
Pd/C
―――
acetone
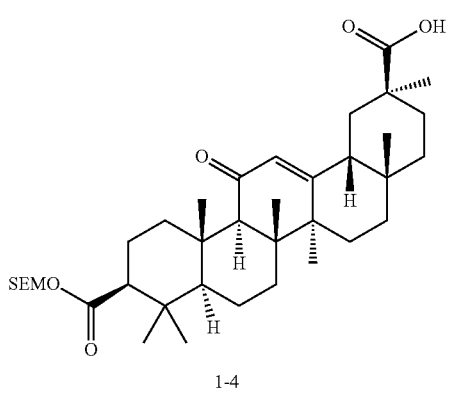
1-4
Cs₂CO₃,
BnBr
―――
DMF
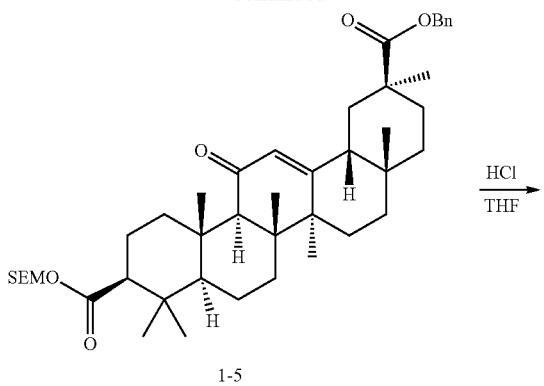
1-5
HCl
―――
THF
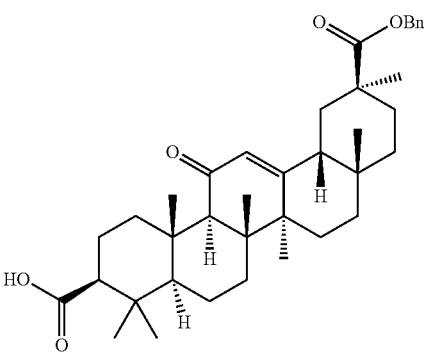
1-6
(COCl)₂
DMF (cat.)
―――――
DCM
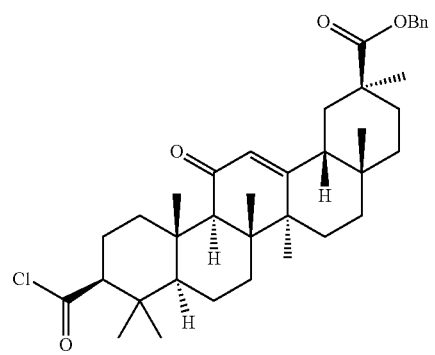
1-7
MeOH
TEA
―――
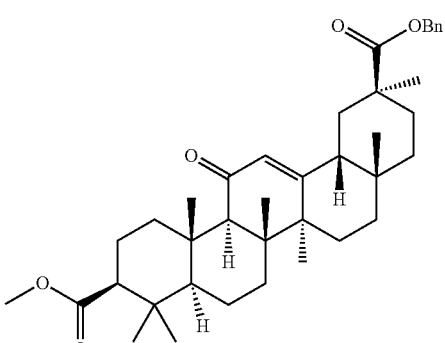
1-8
H2, Pd/C
―――――
MeOH

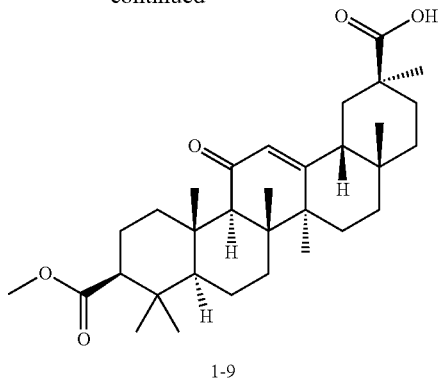

1-9

Synthesis of (4aR,6aR,6bS,8aS,11S,12aR,14aR,14bS)-11-((Benzyloxy)carbonyl)-4,4,6a,6b,8a, 11,14b-heptamethyl-14-oxo-1,4,4a,5,6,6a,6b,7,8,8a,9,10,11,12,12a,14,14a, 14b-octadecahydro picene-3-carboxylic acid (1-2). Into a 1-L pressure tank reactor (10 atm) purged and maintained with an inert atmosphere of CO, was placed benzyl (2S,4aS, 6aS,6bR,8aR,12aS,12bR,14bR)-2,4a,6a,6b,9,9,12a-heptamethyl-13-oxo-10-(((trifluoromethyl)sulfonyl)oxy)-1,2,3,4, 4a,5,6,6a,6b, 7,8,8a,9,12,12a,12b,13,14b-octadecahydropicene-2-carboxylate (prepared according to the method described in US Patent 20160151387) (11 g, 15.92 mmol, 1.00 equiv.), Pd(PPh$_3$)$_4$ (4 g, 3.46 mmol, 0.20 equiv.), THF (250 mL), and water (150 mL). The resulting solution was stirred for 2 days at 50° C. The resulting solution was extracted with 3×150 mL of DCM and the organic layers combined. The resulting mixture was washed with 3×150 mL of brine. The mixture was dried over anhydrous sodium sulfate and concentrated under vacuum. The residue was applied onto a silica gel column with EtOAc/petroleum ether (1:10). The crude product (20 mL) was purified by Flash-Prep-HPLC with the following conditions (CombiFlash-1): Column, C$_{18}$ silica gel; mobile phase, ACN:water=100:0; Detector, UV 254 nm. 1 L product was obtained. This resulted in 6.5 g (69.6%) of 1-2 as a light yellow solid.

Synthesis of 2-Benzyl 10-((2-(trimethylsilyl)ethoxy)methyl) (2S,4aS,6aS,6bR,8aR,12aS, 12bR,14bR)-2,4a,6a, 6b,9,9,12a-heptamethyl-13-oxo-1,2,3,4,4a,5,6,6a,6b,7,8,8a, 9,12,12a,12b, 13,14b-octadecahydropicene-2,10-dicarboxylate (1-3). Into a 250-mL round-bottom flask, was placed 1-2 (3 g, 5.11 mmol, 1.00 equiv.), DMF (30 mL), DMAP (102.4 mg, 0.84 mmol, 0.10 equiv.). This was followed by the addition of TEA (3 mL, 5.80 equiv.) dropwise with stirring at 0° C. To this was added SEMCl (4.2 mL, 4.80 equiv.) dropwise with stirring at 0° C. The resulting solution was stirred for 1.5 h at room temperature. The reaction was then quenched by the addition of 50 mL of aq. K$_2$CO$_3$. The resulting solution was diluted with 250 mL of DCM. The resulting mixture was washed with 3×150 mL of brine. The mixture was dried over anhydrous sodium sulfate and concentrated under vacuum. The residue was applied onto a silica gel column with EtOAc/petroleum ether (1:10). This resulted in 3.5 g (95.5%) of 1-3 as a light-yellow oil.

Synthesis of (2S,4aS,6aS,6bR,8aS,10S,12aS,12bR,14bR)-2,4a,6a,6b,9,9,12a-Heptamethyl-13-oxo-10-(((2-(trimethylsilyl)ethoxy)methoxy)carbonyl)-1,2,3,4,4a,5,6,6a, 6b,7,8,8a,9,10,11,12, 12a,12b,13,14b-icosahydropicene-2-carboxylic acid (1-4). Into a 300-mL pressure tank reactor (40 atm) purged and maintained with an inert atmosphere of H$_2$, was placed 1-3 (6.6 g, 9.20 mmol, 1.00 equiv.), palladium on dried and activated carbon (1.32 g, 0.20 equiv.), acetone (150 mL). The resulting solution was stirred overnight at 50° C. The solids were collected by filtration. The resulting mixture was concentrated under vacuum. This resulted in 4.2 g (73%) of 1-4 as a white solid.

Synthesis of 2-Benzyl 10-((2-(trimethylsilyl)ethoxy)methyl) (2S,4aS,6aS,6bR,8aS,10S,12aS, 12bR,14bR)-2,4a, 6a,6b,9,9,12a-heptamethyl-13-oxo-1,2,3,4,4a,5,6,6a,6b,7,8, 8a,9,10,11,12,12a, 12b,13,14b-icosahydropicene-2,10-dicarboxylate (1-5). Into a 250-mL round-bottom flask, was placed 1-4 (5.25 g, 8.35 mmol, 1.00 equiv.), DMF (70 mL), Cs$_2$CO$_3$ (4.1 g, 12.58 mmol, 1.50 equiv.), BnBr (2.86 g, 16.72 mmol, 2.00 equiv.). The resulting solution was stirred for 2 h at 60° C. The resulting solution was diluted with 250 mL of DCM. The resulting solution was extracted with 2×100 mL of DCM and the organic layers combined and dried in an oven under reduced pressure. The resulting residue was applied onto a silica gel column with EtOAc/petroleum ether (1:10). This resulted in 6 g (99%) of 1-5 as an off-white solid.

Synthesis of (3S,4aS,6aR,6bS,8aS,11S,12aR,14aR,14bS)-11-((Benzyloxy)carbonyl)-4,4,6a,6b, 8a,11,14b-heptamethyl-14-oxo-1,2,3,4,4a,5,6,6a,6b,7,8,8a,9,10,11,12,12a, 14,14a,14b-icosa hydropicene-3-carboxylic acid (1-6). Into a 250-mL round-bottom flask, was placed 1-5 (5.6 g, 7.79 mmol, 1.00 equiv.), THF (40 mL). This was followed by the addition of hydrogen chloride (4M, 30 mL). The resulting solution was stirred for 2 h at 60° C. The pH value of the solution was adjusted to 3 with sodium bicarbonate (sat.). The resulting solution was extracted with 3×100 mL of DCM and the organic layers combined. The resulting mixture was washed with 2×150 mL of Brine. The mixture was dried over anhydrous sodium sulfate. The crude product (20 mL) was purified by Flash-Prep-HPLC with the following conditions (CombiFlash-1): Column, C$_{18}$ silica gel; mobile phase, ACN:water=100:0; Detector, UV 254 nm. 1 L product was obtained. This resulted in 3.1 g (68%, 97% purity) of 1-6 as a white solid. MS (ES, m/z): [M+H]$^+$=589.4; $^1$H-NMR (400 MHz, Chloroform-d): δ 0.76 (s, 4H), 0.91 (s, 5H), 1.01-1.21 (m, 12H), 1.24-1.49 (m, 9H), 1.56-1.75 (m, 4H), 1.83 (td, J=13.6, 4.6 Hz, 1H), 1.91-2.10 (m, 5H), 2.23 (d, J=8.2 Hz, 1H), 2.37 (s, 1H), 2.86 (d, J=13.2 Hz, 1H), 5.11 (d, J=12.0 Hz, 1H), 5.23 (d, J=12.4 Hz, 1H), 5.57 (s, 1H), 7.30-7.45 (m, 5H).

Synthesis of Benzyl (2S,4aS,6aS,6bR,8aS,10S,12aS, 12bR,14bR)-10-(chlorocarbonyl)-2,4a,6a, 6b,9,9,12a-heptamethyl-13-oxo-1,2,3,4,4a,5,6,6a,6b,7,8,8a,9,10,11,12,12a, 12b,13,14b-icosa hydropicene-2-carboxylate (1-7). Oxalyl chloride (0.144 mL, 1.70 mmol) was added dropwise to 1-6 (0.50 g, 0.85 mmol) and DMF (1 drop) in DCM (50 mL) at room temperature. The mixture was stirred at room temperature for 1 hour and then evaporated to dryness. The material was used in the following steps without purification.

Synthesis of 2-Benzyl 10-methyl (2S,4aS,6aS,6bR,8aS, 10S,12aS,12bR,14bR)-2,4a,6a,6b, 9,9,12a-heptamethyl-13-oxo-1,2,3,4,4a,5,6,6a,6b,7,8,8a,9,10,11,12,12a,12b,13,14b-icosahydro picene-2,10-dicarboxylate (1-8). Into a 250-mL round-bottom flask, was placed 1-7 (200 mg, 0.33 mmol, 1.00 equiv.), MeOH (20 mL), TEA (0.274 mL, 6.00 equiv.). The resulting solution was stirred overnight at room temperature. The resulting mixture was concentrated under vacuum. This resulted in 198 mg (100%) of 1-8 as a light yellow crude solid.

Synthesis of (2S,4aS,6aS,6bR,8aS,10S,12aS,12bR, 14bR)-10-(Methoxycarbonyl)-2,4a,6a,6b, 9, 9,12a-heptamethyl-13-oxo-1,2,3,4,4a,5,6,6a,6b,7,8,8a,9,10,11,12,12a,12b,13,14b-icosahydro picene-2-carboxylic acid (1-9). Into a 250-mL round-bottom flask purged and maintained with an inert atmosphere of $H_2$, was placed 1-8 (198 mg, 0.33 mmol, 1.00 equiv.), MeOH (40 mL), Pd/C (20 mg). The resulting solution was stirred for 1 h at room temperature. The solids were filtered out. The resulting mixture was concentrated under vacuum. The crude product (200 mg) was purified by Prep-HPLC with the following conditions: Column, XBridge Prep C18 OBD Column, 190*150 mm 5 um; mobile phase, water (10 mmol/L $NH_4HCO_3$+0.1% $NH_3.H_2O$) and ACN (50.0% ACN up to 62.0% in 7 min); Detector, UV 254/220 nm. 111.8 mg product was obtained. This resulted in 111.8 mg (66%) of 1-9 as a light yellow solid. MS (ES, m/z): $[M+H]^+$=513.60; $^1$H NMR (400 MHz, Chloroform-d) δ 0.76 (d, J=11.2 Hz, 1H), 0.84 (s, 3H), 0.88-0.96 (m, 4H), 0.99-1.08 (m, 4H), 1.18 (s, 3H), 1.19-1.28 (m, 7H), 1.31-1.39 (m, 4H), 1.40-1.48 (m, 4H), 1.50-1.59 (m, 1H), 1.60-1.72 (m, 3H), 1.79-1.89 (m, 1H), 1.91-2.09 (m, 4H), 2.15-2.25 (m, 2H), 2.37 (s, 1H), 2.82 (dt, J=10.4, 3.2 Hz, 1H), 3.65 (s, 3H), 5.70 (s, 1H), 9.89 (s, 1H).

Example 2 (2S,4aS,6aS,6bR,8aS,10S,12aS,12bR,14bR)-2,4a,6a,6b,9,9,12a-Heptamethyl-13-oxo-1,2,3,4,4a,5,6,6a,6b,7,8,8a,9,10,11,12,12a,12b,13,14b-icosahydropicene-2,10-dicarboxylic acid (2-1)

Into a 50-mL round-bottom flask, was placed 1-6 (300 mg, 0.51 mmol, 1.00 equiv.), MeOH (30 mL), Pd/C (30 mg, 0.10 equiv.). To the above hydrogen (1 atm) was introduced in. The resulting solution was stirred for 2 h at room temperature. The solids were filtered out. The crude product was purified by Prep-HPLC with the following conditions; mobile phase, water (0.05% TFA) and ACN (60.0% ACN up to 77.0% in 8 min); Detector, UV 254 nm. This resulted in 110 mg (43%) of 2-1 as a white solid. MS (ES, m/z): $[M+H]^+$=499.25; $^1$H-NMR (400 MHz, MeOH-$d_4$): δ 0.81 (s, 4H), 0.91 (s, 3H), 0.93-1.01 (m, 2H), 1.11 (s, 3H), 1.13-1.20 (m, 9H), 1.21-1.31 (m, 1H), 1.32-1.54 (m, 9H), 1.63-1.81 (m, 3H), 1.81-2.00 (m, 4H), 2.09-2.26 (m, 3H), 2.50 (s, 1H), 2.75 (d, J=13.2 Hz, 1H), 3.34 (s, 2H), 5.59 (s, 1H).

Example 3 (2S,4aS,6aS,6bR,8aS,10S,12aS,12bR,14bR)-10-(Isopropoxycarbonyl)-2,4a,6a,6b,9,9,12a-heptamethyl-13-oxo-1,2,3,4,4a,5,6,6a,6b,7,8,8a,9,10,11,12,12a,12b,13,14b-icosahydropicene-2-carboxylic acid (3-2)

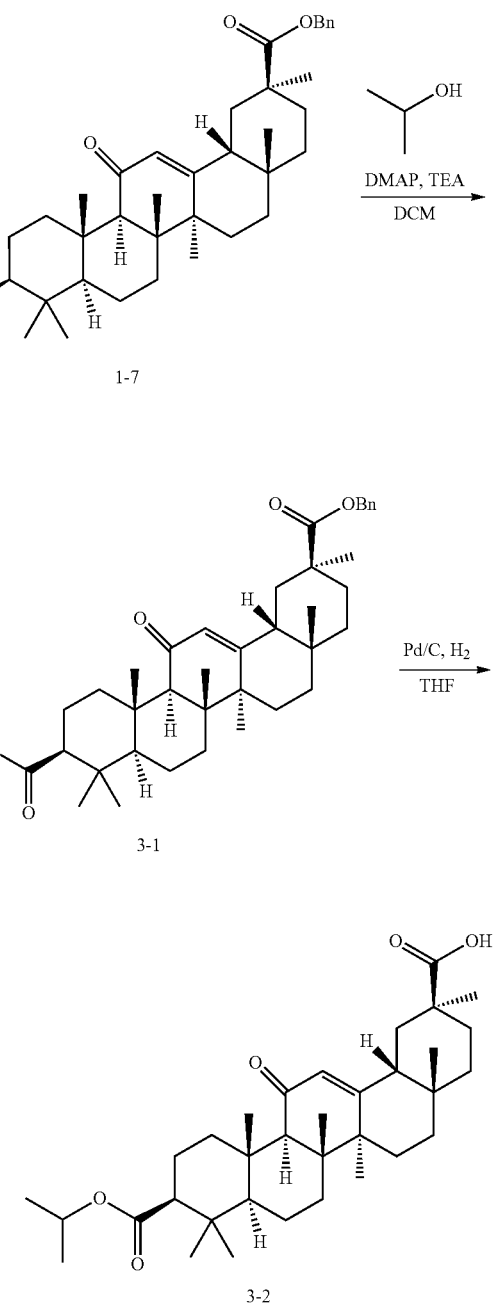

Synthesis of 2-Benzyl 10-isopropyl (2S,4aS,6aS,6bR, 8aS,10S,12aS,12bR,14bR)-2,4a,6a,6b,9,9,12a-Heptamethyl-13-oxo-1,2,3,4,4a,5,6,6a,6b,7,8,8a,9,10,11,12,12a, 12b,13,14b-icosahydropicene-2,10-dicarboxylate (3-1). Into a 25-mL round-bottom flask, was placed 1-7 (154 mg, 0.25 mmol, 1.00 equiv.), DCM (10 mL), propan-2-ol (46 mg, 0.77 mmol, 3.00 equiv.), DMAP (3 mg, 0.02 mmol, 0.10 equiv.), TEA (0.05 mL, 1.50 equiv.). The resulting solution was stirred for 2 days at room temperature. The resulting mixture was concentrated under vacuum. The residue was applied onto a silica gel column with EtOAc/petroleum ether (1:5). This resulted in 114 mg (71%) 3-1 as a white solid.

Synthesis of (2S,4aS,6aS,6bR,8aS,10S,12aS,12bR, 14bR)-10-(Isopropoxycarbonyl)-2,4a,6a,6b, 9,9,12a-heptamethyl-13-oxo-1,2,3,4,4a,5,6,6a,6b,7,8,8a,9,10,11,12,12a, 12b,13,14b-icosahydro picene-2-carboxylic acid (3-2). Into a 50-mL round-bottom flask purged and maintained with an inert atmosphere of $H_2$, 3-1 (114 mg, 0.18 mmol, 1.00 equiv.), THF (10 mL), Pd/C (12 mg). The resulting solution was stirred overnight at room temperature. The solids were filtered out. The resulting mixture was concentrated under vacuum. The crude product (100 mg) was purified by Prep-HPLC with the following conditions: Column, XBridge Shield RP18 OBD Column, 5 um, 19*150 mm; mobile phase, water (0.05% $NH_3H_2O$) and ACN (41.0% ACN up to 57.0% in 8 min); Detector, uv 254 nm. 34.9 mg product was obtained. This resulted in 34.9 mg (36%) of 3-2 as a white solid. MS (ES, m/z): $[M+H]^+$=541.40; $^1$H NMR (400 MHz, Chloroform-d) δ 0.74 (d, J=11.2 Hz, 1H), 0.83-0.94 (m, 7H), 1.01-1.05 (m, 4H), 1.13-1.17 (m, 3H), 1.18-1.27 (m, 13H), 1.32-1.52 (m, 9H), 1.60-1.70 (m, 3H), 1.78-1.88 (m, 1H), 1.91-2.07 (m, 4H), 2.11-2.21 (m, 2H), 2.37 (s, 1H), 2.83 (d, J=13.2 Hz, 1H), 4.97-5.04 (m, 1H), 5.70 (s, 1H), 9.9 (s, 1H).

Example 4 (2S,4aS,6aS,6bR,8aS,10S,12aS,12bR, 14bR)-10-(((1,1,1,3,3,3-Hexafluoro-2-methylpropan-2-yl)oxy)carbonyl)-2,4a,6a,6b,9,9,12a-heptamethyl-13-oxo-1,2,3,4,4a,5,6,6a,6b,7,8,8a,9,10,11,12, 12a,12b,13,14b-icosahydropicene-2-carboxylic acid (4-2)

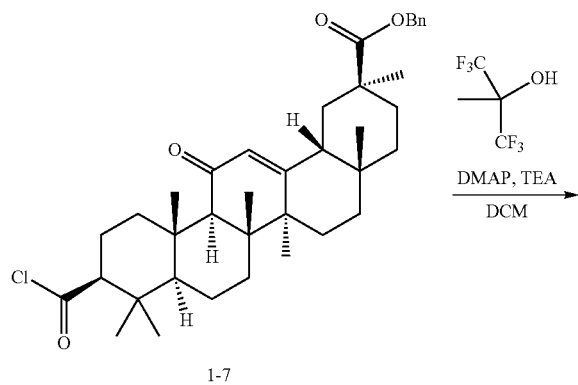

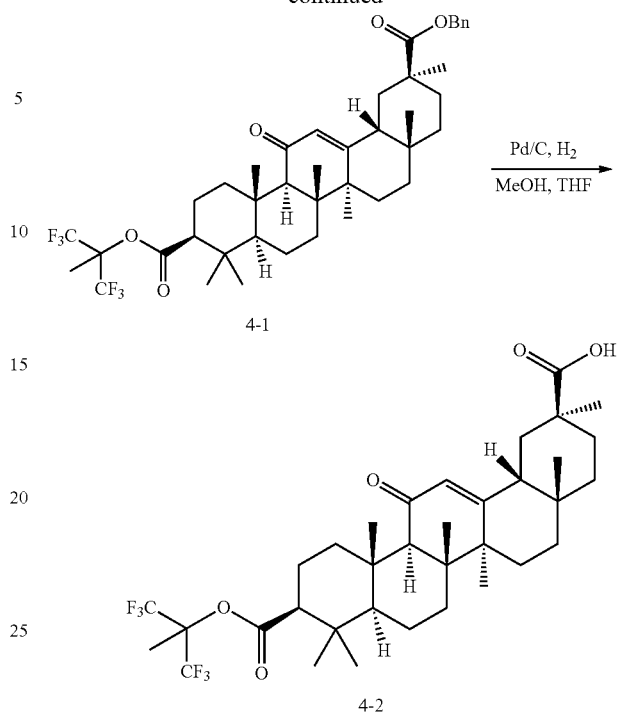

Synthesis of 2-Benzyl 10-(1,1,1,3,3,3-hexafluoro-2-methylpropan-2-yl) (2S,4aS,6aS,6bR, 8aS,10S,12aS,12bR, 14bR)-2,4a,6a,6b,9,9,12a-heptamethyl-13-oxo-1,2,3,4,4a,5, 6,6a,6b,7,8,8a, 9,10,11,12,12a,12b,13,14b-icosahydropicene-2,10-dicarboxylate (4-1). Into a 50-mL round-bottom flask, was placed 1-7 (154 mg, 0.25 mmol, 1.00 equiv.), DCM (10 mL), 1,1,1,3,3,3-hexafluoro-2-methylpropan-2-ol (93 mg, 0.51 mmol, 2.00 equiv.), DMAP (3 mg, 0.02 mmol, 0.10 equiv.), TEA (0.053 mL, 1.50 equiv.). The resulting solution was stirred for 2 h at room temperature. The resulting mixture was concentrated under vacuum. The residue was applied onto a silica gel column with EtOAc/petroleum ether (1:5). This resulted in 226 mg (118%) of 4-1 as a white crude solid.

Synthesis of (2S,4aS,6aS,6bR,8aS,10S,12aS,12bR, 14bR)-10-(((1,1,1,3,3,3-Hexafluoro-2-methyl propan-2-yl) oxy)carbonyl)-2,4a,6a,6b,9,9,12a-heptamethyl-13-oxo-1,2, 3,4,4a,5,6,6a,6b,7,8,8a,9, 10,11,12,12a,12b,13,14b-icosahydropicene-2-carboxylic acid (4-2). Into a 100-mL round-bottom flask purged and maintained with an inert atmosphere of $H_2$, was placed 4-1 (226 mg, 0.30 mmol, 1.00 equiv.), MeOH (10 mL), THF (10 mL), Pd/C (23 mg). The resulting solution was stirred overnight at room temperature. The solids were filtered out. The resulting mixture was concentrated under vacuum. The crude product (190 mg) was purified by Prep-HPLC with the following conditions: Column, XBridge Shield RP18 OBD Column, 5 um, 19*150 mm; mobile phase, water (10 mmol/L $NH_4HCO_3$+0.1% $NH_3.H_2O$) and ACN (5.0% ACN up to 55.0% in 1 min, up to 68.0% in 7 min); Detector, UV 254 nm. 80.9 mg product was obtained. This resulted in 80.9 mg (41%) of 4-2 as a white solid. MS (ES, m/z): $[M+H]^+$=663.30; $^1$H NMR (400 MHz, MeOH-$d_4$) δ 0.82-0.98 (m, 7H), 1.00-1.13 (m, 5H), 1.17-1.30 (m, 10H), 1.39-1.61 (m, 9H), 1.65-1.83 (m, 3H), 1.84-2.09 (m, 7H), 2.12-2.28 (m, 2H), 2.35 (dd, J=12.8, 3.2 Hz, 1H), 2.53 (s, 1H), 2.81 (dt, J=10.4, 3.6 Hz, 1H), 5.62 (s, 1H).

Example 5 (2S,4aS,6aS,6bR,8aS,10S,12aS,12bR, 14bR)-10-((2-Hydroxyethoxy)carbonyl)-2,4a,6a,6b, 9,9,12a-heptamethyl-13-oxo-1,2,3,4,4a,5,6,6a,6b,7, 8,8a,9,10,11,12,12a,12b,13,14b-icosahydropicene-2-carboxylic acid (5-2)

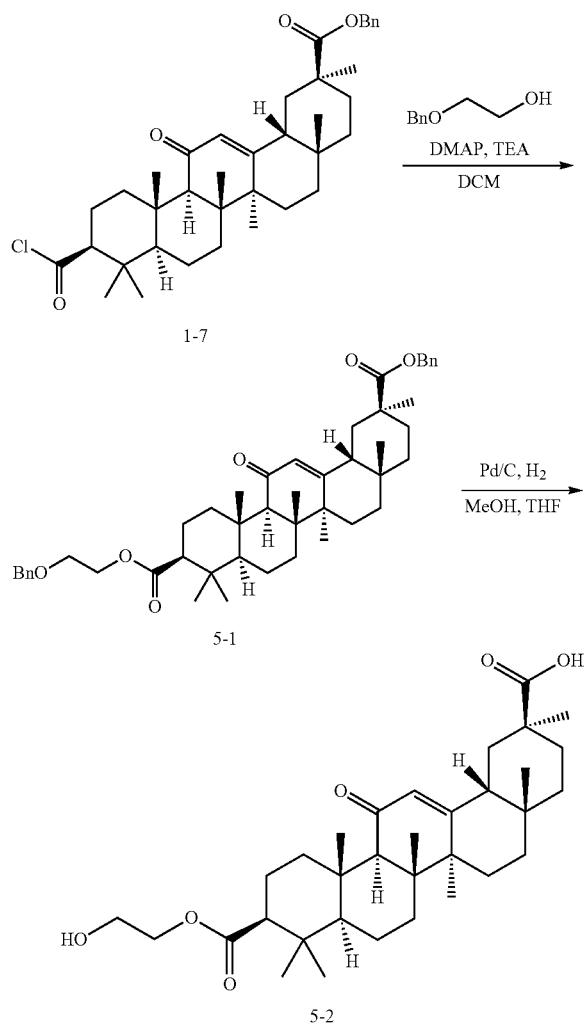

Synthesis of 2-Benzyl 10-(2-(benzyloxy)ethyl) (2S,4aS, 6aS,6bR,8aS,10S,12aS,12bR,14bR)-2,4a,6a,6b,9,9,12a-heptamethyl-13-oxo-1,2,3,4,4a,5,6,6a,6b,7,8,8a,9,10,11,12, 12a,12b,13,14b-icosahydropicene-2,10-dicarboxylate (5-1). Into a 25-mL round-bottom flask, was placed 1-7 (154 mg, 0.25 mmol, 1.00 equiv.), DCM (10 mL), 2-(benzyloxy)ethan-1-ol (58 mg, 0.38 mmol, 1.50 equiv.), DMAP (3 mg, 0.02 mmol, 0.10 equiv.), TEA (0.05 mL, 1.50 equiv.). The resulting solution was stirred overnight at room temperature. The resulting mixture was concentrated under vacuum. The residue was applied onto a silica gel column with EtOAc/petroleum ether (1:5). This resulted in 107 mg (58%) of 5-1 as a white solid.

Synthesis of (2S,4aS,6aS,6bR,8aS,10S,12aS,12bR, 14bR)-10-((2-Hydroxyethoxy)carbonyl)-2,4a,6a,6b,9,9, 12a-heptamethyl-13-oxo-1,2,3,4,4a,5,6,6a,6b,7,8,8a,9,10, 11,12,12a,12b,13,14b-icosahydropicene-2-carboxylic acid (5-2). Into a 100-mL round-bottom flask purged and maintained with an inert atmosphere of H₂, was placed 5-1 (107 mg, 0.15 mmol, 1.00 equiv.), MeOH (10 mL), THF (10 mL), Pd/C (20 mg). The resulting solution was stirred for 7 days at room temperature. The solids were filtered out. The resulting mixture was concentrated under 30 vacuum. The crude product (100 mg) was purified by Prep-HPLC with the following conditions: Column, XBridge Shield RP18 OBD Column, 5 um, 19*150 mm; mobile phase, water (10 mmol/L NH₄HCO₃+0.1% NH₃.H₂O) and ACN (40.0% ACN up to 70.0% in 8 min); Detector, uv 254 nm. 23.2 mg product was obtained. This resulted in 23.2 mg (29%) of 5-2 as a white solid. MS (ES, m/z): [M+H]$^+$=543.35; $^1$H NMR (400 MHz, MeOH-d₄): δ 0.74 (s, 3H), 0.77-0.83 (m, 4H), 0.89-0.95 (m, 5H), 1.05-1.09 (m, 9H), 1.13-1.17 (m, 1H), 1.26-1.44 (m, 9H), 1.55-1.71 (m, 3H), 1.72-1.81 (m, 2H), 1.82-1.94 (m, 2H), 1.96-2.10 (m, 1H), 2.11-2.24 (m, 2H), 2.40 (s, 1H), 2.67 (d, J=13.2 Hz, 1H), 3.63 (t, J=5.0 Hz, 2H), 4.03 (t, J=5.0 Hz, 2H), 5.51 (s, 1H).

Example 6 (2S,4aS,6aS,6bR,8aS,10S,12aS,12bR, 14bR)-2,4a,6a,6b,9,9,12a-Heptamethyl-13-oxo-10-((2,2,2-trifluoroethoxy)carbonyl)-1,2,3,4,4a,5,6,6a, 6b,7,8,8a,9,10,11,12,12a,12b,13,14b-icosahydropicene-2-carboxylic acid (6-2)

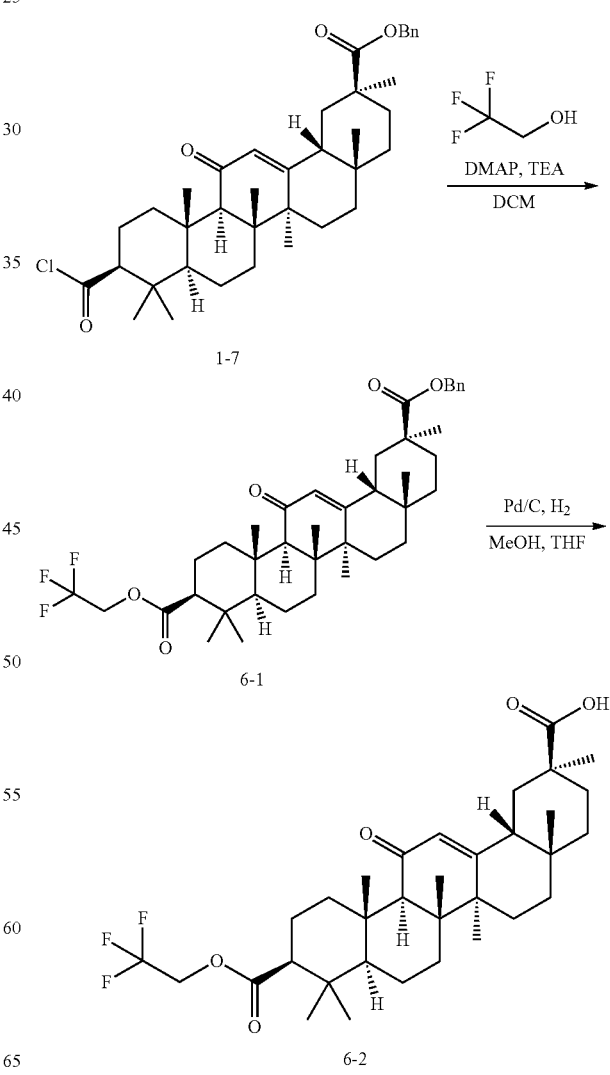

Synthesis of 2-Benzyl 10-(2,2,2-trifluoroethyl) (2S,4aS, 6aS,6bR,8aS,10S,12aS,12bR,14bR)-2,4a,6a,6b,9,9,12a-heptamethyl-13-oxo-1,2,3,4,4a,5,6,6a,6b,7,8,8a,9,10,11,12, 12a,12b,13,14b-icosahydropicene-2,10-dicarboxylate (6-1). Into a 25-mL round-bottom flask, was placed 1-7 (154 mg, 0.25 mmol, 1.00 equiv.), DCM (10 g, 117.74 mmol, 464.30 equiv.), 2,2,2-trifluoroethan-1-ol (51 mg, 0.51 mmol, 2.00 equiv.), DMAP (3 mg, 0.02 mmol, 0.10 equiv.), TEA (0.053 mL, 1.50 equiv.). The resulting solution was stirred for 2 h at room temperature. The resulting mixture was concentrated under vacuum. The residue was applied onto a silica gel column with EtOAc/petroleum ether (1:5). This resulted in 256 mg (150%) of 6-1 as a white crude solid.

Synthesis of (2S,4aS,6aS,6bR,8aS,10S,12aS,12bR, 14bR)-2,4a,6a,6b,9,9,12a-Heptamethyl-13-oxo-10-((2,2,2-trifluoroethoxy)carbonyl)-1,2,3,4,4a,5,6,6a,6b,7,8,8a,9,10, 11,12,12a,12b,13,14b-icosahydropicene-2-carboxylic acid (6-2). Into a 100-mL round-bottom flask purged and maintained with an inert atmosphere of $H_2$, was placed 6-1 (256 mg, 0.38 mmol, 1.00 equiv.), MeOH (10 mL), THF (10 mL), Pd/C (26 mg). The resulting solution was stirred overnight at room temperature. The solids were filtered out. The resulting mixture was concentrated under vacuum. The crude product (200 mg) was purified by Prep-HPLC with the following conditions: Column, XBridge Prep OBD C18 Column, 19*250 mm, 5 um; mobile phase, water (0.05% TFA) and ACN (82.0% ACN up to 89.0% in 8 min); Detector, UV 254 nm. 96.9 mg product was obtained. This resulted in 96.9 mg (44%) of 6-2 as a white solid. MS (ES, m/z): [M+H]$^+$=581.30; $^1$H NMR (400 MHz, MeOH-d$_4$): δ 0.82-1.00 (m, 7H), 1.01-1.11 (m, 5H), 1.17-1.37 (m, 10H), 1.38-1.60 (m, 9H), 1.67-1.81 (m, 3H), 1.82-1.92 (m, 2H), 1.93-2.09 (m, 2H), 2.11-2.27 (m, 2H), 2.38 (dd, J=12.8, 3.6 Hz, 1H), 2.54 (s, 1H), 2.81 (dt, J=13.5, 3.4 Hz, 1H), 4.50-4.76 (m, 2H), 5.61 (s, 1H).

Example 7 (2S,4aS,6aS,6bR,8aS,10S,12aS,12bR, 14bR)-10-((2-(1H-Imidazol-1-yl)ethoxy) carbonyl)-2,4a,6a,6b,9,9,12a-heptamethyl-13-oxo-1,2,3,4,4a,5, 6,6a,6b,7,8,8a,9,10,11,12,12a, 12b,13,14b-icosahydropicene-2-carboxylic acid (7-2)

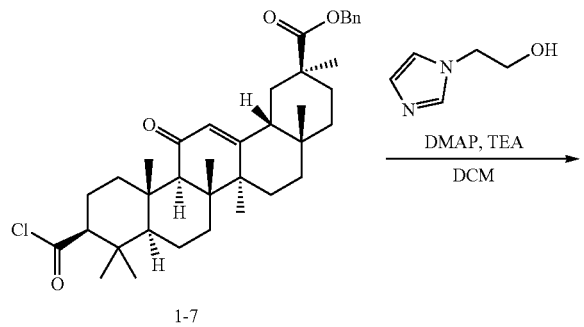

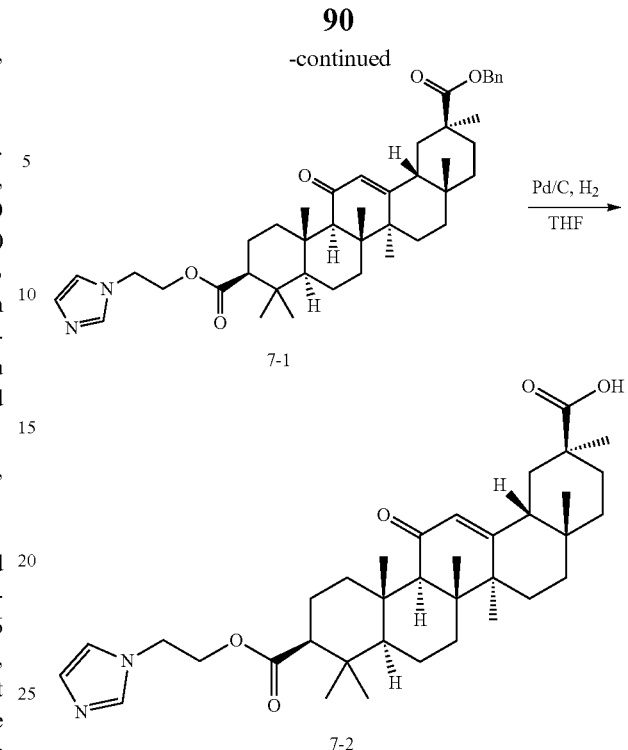

Synthesis of 10-(2-(1H-Imidazol-1-yl)ethyl) 2-benzyl (2S,4aS,6aS,6bR,8aS,10S,12aS, 12bR,14bR)-2,4a,6a,6b,9, 9,12a-heptamethyl-13-oxo-1,2,3,4,4a,5,6,6a,6b,7,8,8a,9,10, 11,12,12a, 12b,13,14b-icosahydropicene-2,10-dicarboxylate (7-1). Into a 25-mL round-bottom flask, was placed 1-7 (137 mg, 0.23 mmol, 1.00 equiv.), DCM (10 mL), 2-(1H-imidazol-1-yl)ethan-1-ol (51 mg, 0.45 mmol, 2.00 equiv.), DMAP (3 mg, 0.02 mmol, 0.10 equiv.), TEA (0.047 mL, 1.50 equiv.). The resulting solution was stirred overnight at room temperature. The resulting mixture was concentrated under vacuum. The residue was applied onto a silica gel column with DCM/MeOH (20:1). This resulted in 140 mg (91%) of 7-1 as a white solid.

Synthesis of (2S,4aS,6aS,6bR,8aS,10S,12aS,12bR, 14bR)-10-((2-(1H-Imidazol-1-yl)ethoxy) carbonyl)-2,4a,6a, 6b,9,9,12a-heptamethyl-13-oxo-1,2,3,4,4a,5,6,6a,6b,7,8,8a, 9,10,11,12,12a, 12b,13,14b-icosahydropicene-2-carboxylic acid (7-2). Into a 50-mL round-bottom flask purged and maintained with an inert atmosphere of $H_2$, was placed 7-1 (140 mg, 0.20 mmol, 1.00 equiv.), THF (10 mL), Pd/C (14 mg). The resulting solution was stirred overnight at room temperature. The solids were filtered out. The resulting mixture was concentrated under vacuum. The crude product (120 mg) was purified by Prep-HPLC with the following conditions: Column, XBridge Prep C18 OBD Column, 19*150 mm 5 um; mobile phase, water (10 mmol/L $NH_4HCO_3$+0.1% $NH_3.H_2O$) and ACN (30.0% ACN up to 66.0% in 7 min); Detector, UV 254/220 nm. 67.4 mg product was obtained. This resulted in 67.4 mg (55%) of 7-2 as a white solid. MS (ES, m/z): [M+H]$^+$=593.40; $^1$H NMR (400 MHz, MeOH-d$_4$): δ 0.69 (s, 3H), 0.71-0.75 (m, 4H), 0.80 (s, 3H), 0.84-0.98 (m, 2H), 1.04-1.09 (m, 9H), 1.10-1.21 (m, 2H), 1.27-1.30 (m, 3H), 1.31-1.32 (m, 4H), 1.35-1.38 (m, 1H), 1.49-1.58 (m, 1H), 1.58-1.69 (m, 2H), 1.70-1.90 (m, 4H), 1.99-2.19 (m, 3H), 2.39 (s, 1H), 2.64 (d, J=13.6 Hz, 1H), 4.20-4.33 (m, 4H), 5.49 (s, 1H), 6.87 (s, 1H), 7.07 (s, 1H), 7.69 (s, 1H).

Example 8 (2S,4aS,6aS,6bR,8aS,10S,12aS,12bR, 14bR)-2,4a,6a,6b,9,9,12a-Heptamethyl-10-((2-morpholinoethoxy)carbonyl)-13-oxo-1,2,3,4,4a,5,6,6a, 6b,7,8,8a,9,10,11,12,12a,12b,13,14b-icosahydropicene-2-carboxylic acid (8-2)

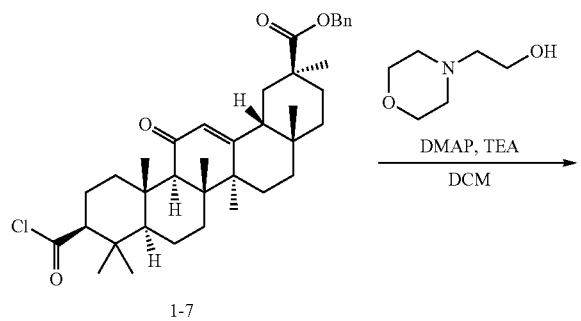

1-7

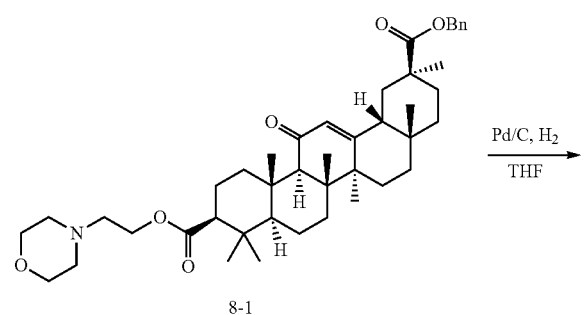

8-1

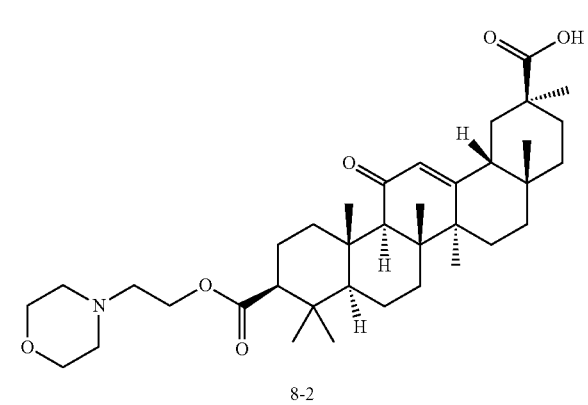

8-2

Synthesis of 2-Benzyl 10-(2-morpholinoethyl) (2S,4aS, 6aS,6bR,8aS,10S,12aS,12bR,14bR)-2,4a,6a,6b,9,9,12a-heptamethyl-13-oxo-1,2,3,4,4a,5,6,6a,6b,7,8,8a,9,10,11,12, 12a,12b,13,14b-icosahydropicene-2,10-dicarboxylate (8-1). Into a 25-mL round-bottom flask, was placed 1-7 (137 mg, 0.23 mmol, 1.00 equiv.), DCM (10 mL), 2-(morpholin-4-yl)ethan-1-ol (59 mg, 0.45 mmol, 2.00 equiv.), DMAP (3 mg, 0.02 mmol, 0.10 equiv.), TEA (0.047 mL, 1.50 equiv.). The resulting solution was stirred overnight at room temperature. The resulting mixture was concentrated under vacuum. The residue was applied onto a silica gel column with DCM/MeOH (20:1). This resulted in 151 mg (95%) of 8-1 as a white solid.

Synthesis of (2S,4aS,6aS,6bR,8aS,10S,12aS,12bR, 14bR)-2,4a,6a,6b,9,9,12a-Heptamethyl-10-((2-morpholinoethoxy)carbonyl)-13-oxo-1,2,3,4,4a,5,6,6a,6b,7,8,8a,9,10, 11,12,12a,12b,13,14b-icosahydropicene-2-carboxylic acid (8-2). Into a 50-mL round-bottom flask purged and maintained with an inert atmosphere of $H_2$, was placed 8-1 (151 mg, 0.22 mmol, 1.00 equiv.), THF (10 mL), Pd/C (15 mg). The resulting solution was stirred overnight at room temperature. The solids were filtered out. The resulting mixture was concentrated under vacuum. The crude product (150 mg) was purified by Prep-HPLC with the following conditions: Column, XBridge Prep C18 OBD Column, 19*150 mm 5 um; mobile phase, water (10 mmol/L $NH_4HCO_3$) and ACN (30.0% ACN up to 66.0% in 7 min); Detector, UV 254/220 nm. 28.6 mg product was obtained. This resulted in 28.6 mg (22%) of 8-2 as a white solid. MS (ES, m/z): $[M+H]^+$=612.70; $^1$H NMR (300 MHz, Chloroform-d): δ 0.49-0.98 (m, 8H), 1.02 (s, 4H), 1.09-1.28 (m, 10H), 1.29-1.48 (m, 8H), 1.49-1.75 (m, 4H), 1.77-2.12 (m, 5H), 2.20 (d, J=12.9 Hz, 2H), 2.37 (s, 1H), 2.44-2.75 (m, 6H), 2.83 (d, J=13.5 Hz, 1H), 3.72 (s, 4H), 4.00-4.70 (m, 2H), 5.70 (s, 1H).

Example 9 (2S,4aS,6aS,6bR,8aS,10S,12aS,12bR, 14bR)-2,4a,6a,6b,9,9,12a-Heptamethyl-13-oxo-10-((((R)-quinuclidin-3-yl)oxy)carbonyl)-1,2,3,4,4a,5,6, 6a,6b,7,8,8a,9,10,11,12,12a,12b,13, 14b-icosahydropicene-2-carboxylic acid (10-2)

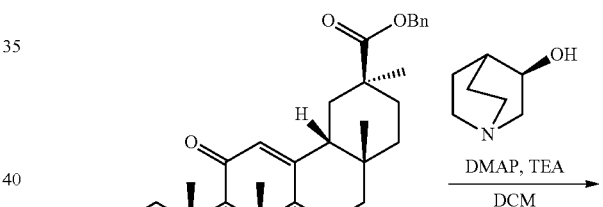

1-7

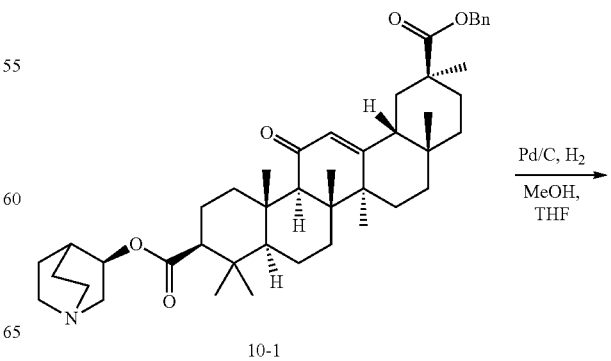

10-1

93

-continued

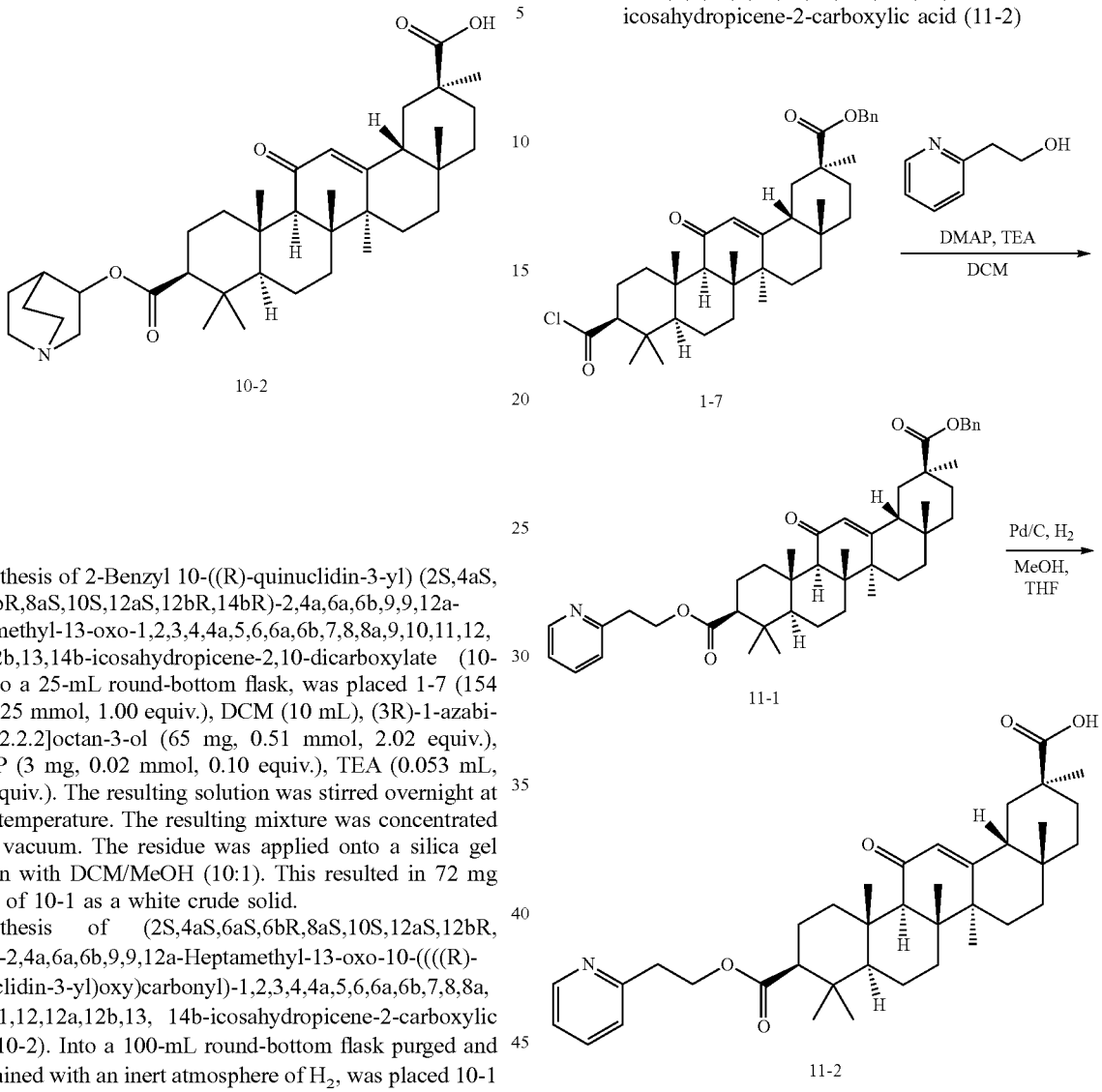

10-2

Synthesis of 2-Benzyl 10-((R)-quinuclidin-3-yl) (2S,4aS,6aS,6bR,8aS,10S,12aS,12bR,14bR)-2,4a,6a,6b,9,9,12a-heptamethyl-13-oxo-1,2,3,4,4a,5,6,6a,6b,7,8,8a,9,10,11,12,12a,12b,13,14b-icosahydropicene-2,10-dicarboxylate (10-1). Into a 25-mL round-bottom flask, was placed 1-7 (154 mg, 0.25 mmol, 1.00 equiv.), DCM (10 mL), (3R)-1-azabicyclo[2.2.2]octan-3-ol (65 mg, 0.51 mmol, 2.02 equiv.), DMAP (3 mg, 0.02 mmol, 0.10 equiv.), TEA (0.053 mL, 1.50 equiv.). The resulting solution was stirred overnight at room temperature. The resulting mixture was concentrated under vacuum. The residue was applied onto a silica gel column with DCM/MeOH (10:1). This resulted in 72 mg (41%) of 10-1 as a white crude solid.

Synthesis of (2S,4aS,6aS,6bR,8aS,10S,12aS,12bR,14bR)-2,4a,6a,6b,9,9,12a-Heptamethyl-13-oxo-10-((((R)-quinuclidin-3-yl)oxy)carbonyl)-1,2,3,4,4a,5,6,6a,6b,7,8,8a,9,10,11,12,12a,12b,13, 14b-icosahydropicene-2-carboxylic acid (10-2). Into a 100-mL round-bottom flask purged and maintained with an inert atmosphere of $H_2$, was placed 10-1 (72 mg, 0.10 mmol, 1.00 equiv.), MeOH (10 mL), THE (10 mL), Pd/C (7 mg). The resulting solution was stirred overnight at room temperature. The solids were filtered out. The resulting mixture was concentrated under vacuum. The crude product (50 mg) was purified by Prep-HPLC with the following conditions: Column, XBridge Shield RP18 OBD Column, 5 um, 19*150 mm; mobile phase, water (0.05% TFA) and ACN (40.0% ACN up to 54.0% in 8 min); Detector, UV 254 nm. 11.3 mg product was obtained. This resulted in 11.3 mg (18%) of 10-2 as a white solid. MS (ES, m/z): [M+H]$^+$=608.40; $^1$H NMR (400 MHz, MeOH-d$_4$): δ 0.84-1.93 (m, 4H), 0.95 (s, 3H), 0.99-1.12 (m, 5H), 1.16-1.23 (m, 9H), 1.24-1.38 (m, 2H), 1.39-1.53 (m, 8H), 1.54-1.65 (m, 1H), 1.68-1.80 (m, 3H), 1.81-2.05 (m, 6H), 2.06-2.19 (m, 2H), 2.20-2.29 (m, 2H), 2.31-2.41 (m, 2H), 2.53 (s, 1H), 2.82 (dt, J=13.2, 3.4 Hz, 1H), 3.21-3.30 (m, 2H), 3.38-3.44 (m, 2H), 3.78 (ddd, J=14.0, 8.7, 2.1 Hz, 1H), 5.12 (dt, J=7.8, 3.5 Hz, 1H), 5.61 (s, 1H).

94

Example 10 (2S,4aS,6aS,6bR,8aS,10S,12aS,12bR,14bR)-2,4a,6a,6b,9,9,12a-Heptamethyl-13-oxo-10-((2-(pyridin-2-yl)ethoxy)carbonyl)-1,2,3,4,4a,5,6,6a,6b,7,8,8a,9,10,11,12,12a,12b,13, 14b-icosahydropicene-2-carboxylic acid (11-2)

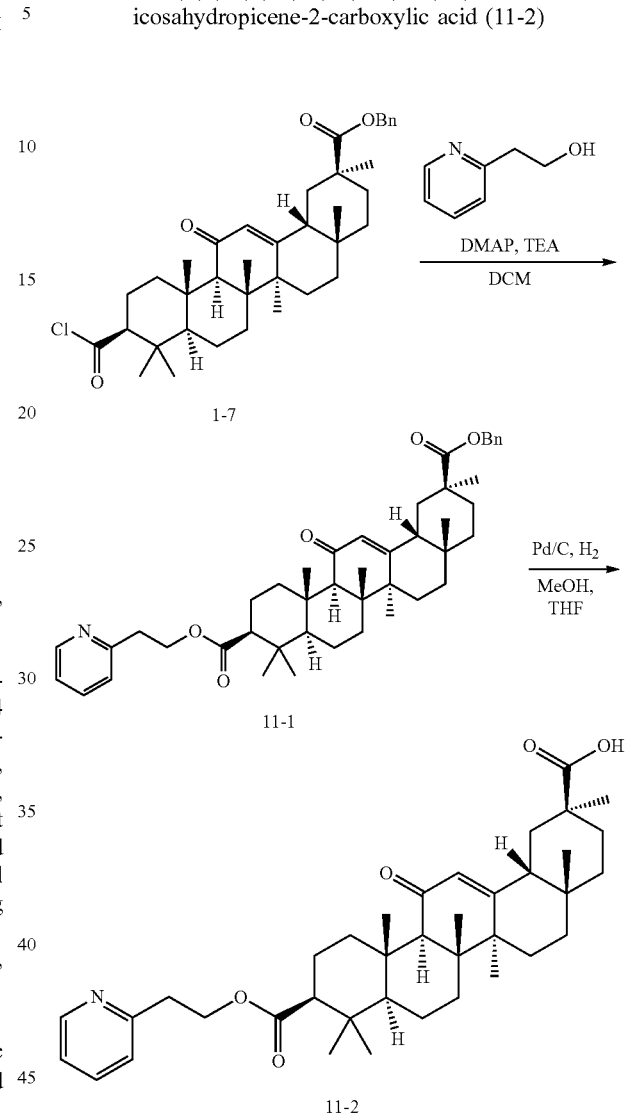

Synthesis of 2-Benzyl 10-(2-(pyridin-2-yl)ethyl) (2S,4aS,6aS,6bR,8aS,10S,12aS,12bR,14bR)-2,4a,6a,6b,9,9,12a-heptamethyl-13-oxo-1,2,3,4,4a,5,6,6a,6b,7,8,8a,9,10,11,12,12a,12b,13,14b-icosahydropicene-2,10-dicarboxylate (11-1). Into a 25-mL round-bottom flask, was placed 1-7 (154 mg, 0.25 mmol, 1.00 equiv.), DCM (10 mL), 2-(pyridin-2-yl)ethan-1-ol (63 mg, 0.51 mmol, 2.00 equiv.), DMAP (3 mg, 0.02 mmol, 0.10 equiv.), TEA (0.053 mL, 1.50 equiv.). The resulting solution was stirred overnight at room temperature. The resulting mixture was concentrated under vacuum. The residue was applied onto a silica gel column with EtOAc/petroleum ether (1:1). This resulted in 217 mg (123%) of 11-1 as a white crude solid.

Synthesis of (2S,4aS,6aS,6bR,8aS,10S,12aS,12bR,14bR)-2,4a,6a,6b,9,9,12a-Heptamethyl-13-oxo-10-((2-(pyridin-2-yl)ethoxy)carbonyl)-1,2,3,4,4a,5,6,6a,6b,7,8,8a,9,10,11,12,12a,12b,13, 14b-icosahydropicene-2-carboxylic acid (11-2). Into a 25-mL round-bottom flask, was placed 11-1 (176 mg, 0.25 mmol, 1.00 equiv.), MeOH (10 mL), THF (10 mL), Pd/C (18 mg). The resulting solution was stirred overnight at room temperature. The solids were filtered out. The resulting mixture was concentrated under vacuum. The crude product (150 mg) was purified by Prep-HPLC with the following conditions: Column, XBridge Shield RP18 OBD Column, 5 um, 19*150 mm; mobile phase, water (0.05% TFA) and ACN (40.0% ACN up to 55.0% in 8 min); Detector, UV 254 nm. 35.8 mg product was obtained. This resulted in 35.8 mg (23%) of 11-2 as a white solid. MS (ES, m/z): [M]$^+$=604.35; $^1$H NMR (400 MHz, MeOH-d$_4$): δ 0.77 (s, 3H), 0.79-0.90 (m, 7H), 0.91-1.01 (m, 1H), 1.03-1.10 (m, 1H), 1.17 (d, J=14.4 Hz, 9H), 1.25-1.33 (m, 1H), 1.37-1.50 (m, 9H), 1.58-1.82 (m, 3H), 1.82-2.08 (m, 4H), 2.09-2.30 (m, 3H), 2.49 (s, 1H), 2.75 (dt, J=13.6, 3.5 Hz, 1H), 3.39 (t, J=6.2 Hz, 2H), 4.50 (t, J=6.2 Hz, 2H), 5.60 (s, 1H), 7.87 (t, J=6.8 Hz, 1H), 7.97 (d, J=8.0 Hz, 1H), 8.45 (td, J=8.0, 1.6 Hz, 1H), 8.75 (dd, J=6.0, 0.8 Hz, 1H).

Example 11 (2S,4aS,6aS,6bR,8aS,10S,12aS,12bR, 14bR)-10-((2-Amino-2-oxoethoxy) carbonyl)-2,4a, 6a,6b,9,9,12a-heptamethyl-13-oxo-1,2,3,4,4a,5,6,6a, 6b,7,8,8a,9,10,11,12,12a, 12b,13,14b-icosahydropicene-2-carboxylicacid (12-2)

Synthesis of 10-(2-Amino-2-oxoethyl) 2-benzyl (2S,4aS, 6aS,6bR,8aS,10S,12aS,12bR,14bR)-2,4a,6a,6b,9,9,12a-heptamethyl-13-oxo-1,2,3,4,4a,5,6,6a,6b,7,8,8a,9,10,11,12, 12a,12b,13,14b-icosahydropicene-2,10-dicarboxylate (12-1). Into a 50-mL round-bottom flask, was placed 1-6 (59 mg, 0.10 mmol, 1 equiv.), DMF (5 mL, 0.07 mmol, 0.683 equiv.), TBAI (18 mg, 0.05 mmol, 0.486 equiv.), 2-chloro-acetamide (11 mg, 0.12 mmol, 1.174 equiv.), K$_2$CO$_3$ (17 mg, 0.12 mmol, 1.228 equiv.). The resulting solution was stirred for 2 hr at 65° C. The resulting solution was diluted with 30 mL of DCM. The resulting mixture was washed with 2×15 mL of brine. The mixture was dried over anhydrous sodium sulfate. The solids were filtered out. The resulting mixture was concentrated. The residue was applied onto a silica gel column with EA. This resulted in 50 mg (77.26%) of 12-1 as a white solid.

Synthesis of (2S,4aS,6aS,6bR,8aS,10S,12aS,12bR, 14bR)-10-((2-Amino-2-oxoethoxy)carbonyl)-2,4a,6a,6b,9, 9,12a-heptamethyl-13-oxo-1,2,3,4,4a,5,6,6a,6b,7,8,8a,9,10, 11,12,12a,12b,13,14b-icosahydropicene-2-carboxylic acid (12-2). Into a 100-mL round-bottom flask purged and maintained with an inert atmosphere of H$_2$, was placed 12-1 (200 mg, 0.31 mmol, 1 equiv.), MeOH (10 mL, 0.31 mmol, 1.008 equiv.), Pd/C (20 mg, 0.19 mmol, 0.607 equiv.). The resulting solution was stirred for 1 hr at room temperature. The solids were filtered out. The crude product was purified by Prep-HPLC with the following conditions (2 # -AnalyseHPLC-SHIMADZU(HPLC-10)): Column, XBridge Shield RP18 OBD Column, 5 um, 19*150 mm; mobile phase, water (0.05% TFA) and ACN (5% Phase B up to 54% in 1 min, up to 68% in 7 min); Detector, uv 254 nm. This resulted in 84.6 mg (49.16%) of 12-2 as a white solid. MS (ES, m/z): [M+H]$^+$=556.46; $^1$H-NMR (400 MHz, MeOH-d$_4$): δ 0.82-0.96 (m, 7H), 0.99-1.08 (m, 5H), 1.13-1.19 (m, 9H), 1.23 (d, J=3.2 Hz, 1H), 1.40-1.49 (m, 8H), 1.55-1.60 (m, 1H), 1.67-1.76 (m, 3H), 1.83-2.00 (m, 4H), 2.15-2.19 (m, 2H), 2.35 (d, J=0.4 Hz, 1H), 2.50 (s, 1H), 2.78 (d, J=1.6 Hz, 1H), 4.51 (q, J=4.8 Hz, 2H), 5.58 (s, 1H).

Example 12 (2S,4aS,6aS,6bR,8aS,10S,12aS,12bR, 14bR)-10-((Carboxymethoxy)carbonyl)-2,4a,6a,6b, 9,9,12a-heptamethyl-13-oxo-1,2,3,4,4a,5,6,6a,6b,7, 8,8a,9,10,11,12,12a,12b,13,14b-icosahydropicene-2-carboxylic acid (13-3)

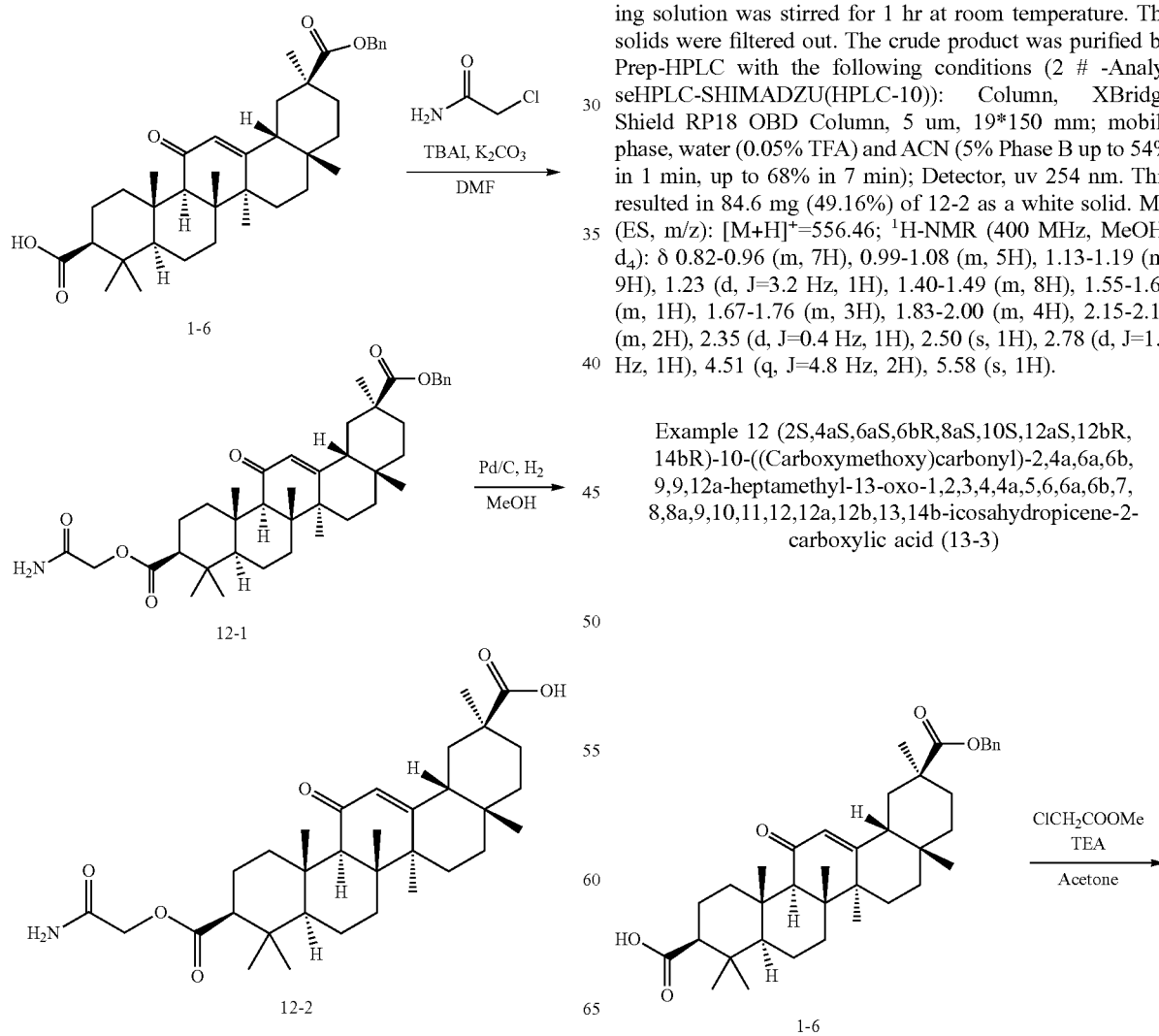

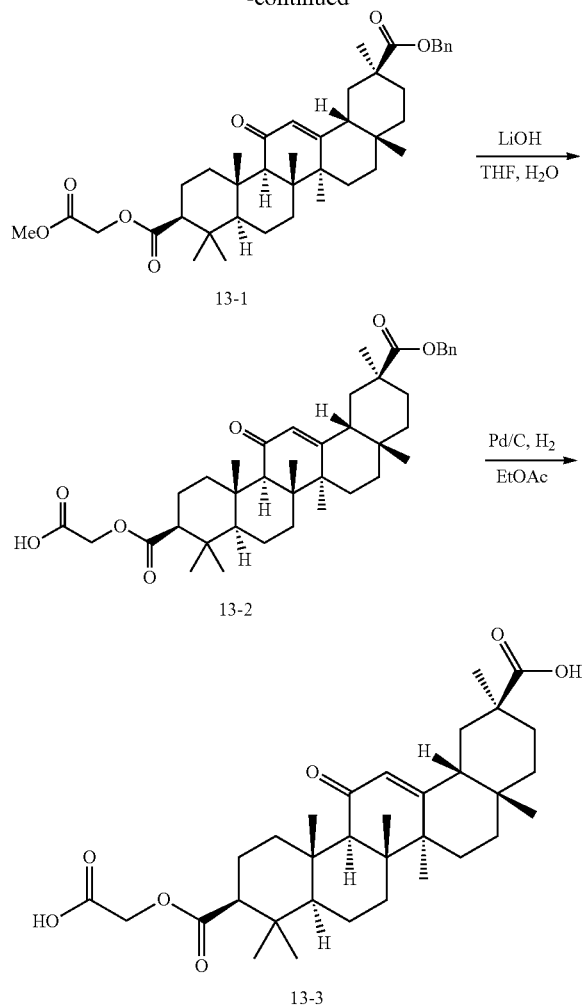

13-1

13-2

13-3

Synthesis of 2-Benzyl 10-(2-methoxy-2-oxoethyl)(2S, 4aS,6aS,6bR,8aS,10S,12aS,12bR,14bR)-2,4a,6a,6b,9,9, 12a-heptamethyl-13-oxo-1,2,3,4,4a,5,6,6a,6b,7,8,8a,9,10, 11,12,12a,12b,13,14b-icosahydropicene-2,10-dicarboxylate (13-1). Into a 50-mL round-bottom flask, was placed 1-6 (590 mg, 1.00 mmol, 1.00 equiv.), Acetone (20 mL), TEA (510 mg, 5.04 mmol, 5.00 equiv.), methyl 2-chloroacetate (440 mg, 4.05 mmol, 4.00 equiv.). The resulting solution was heated to reflux for 4 hr. The resulting mixture was concentrated under vacuum. The resulting solid was washed with 3×10 mL of Hexane. This resulted in 600 mg (91%) of 13-1 as a white solid.

Synthesis of 2-(((3S,4aS,6aR,6bS,8aS,11S,12aR,14aR, 14bS)-11-((Benzyloxy)carbonyl)-4,4,6a, 6b,8a,11,14b-heptamethyl-14-oxo-1,2,3,4,4a,5,6,6a,6b,7,8,8a,9,10,11,12,12a, 14,14a,14b-icosa hydropicene-3-carbonyl)oxy)acetic acid (13-2). Into a 50-mL round-bottom flask, was placed benzyl 13-1 (600 mg, 0.91 mmol, 1.00 equiv.), THF (10 mL), water (10 mL), LiOH.H₂O (190 mg, 4.52 mmol, 5.00 equiv.). The resulting solution was stirred for 3 h at room temperature. The resulting solution was diluted with 30 mL of water. The pH value of the solution was adjusted to 2-3 with 1.0 M hydrogen chloride. The resulting solution was extracted with 3×30 mL of DCM and the organic layers combined. The resulting mixture was washed with 1×40 mL of water and 1×40 mL of sodium chloride sat. The mixture was dried over anhydrous sodium sulfate and concentrated under vacuum. This resulted in 520 mg (89%) of 13-2 as a white solid.

Synthesis of (2S,4aS,6aS,6bR,8aS,10S,12aS,12bR, 14bR)-10-((Carboxymethoxy)carbonyl)-2,4a,6a,6b,9,9,12a-heptamethyl-13-oxo-1,2,3,4,4a,5,6,6a,6b,7,8,8a,9,10,11,12, 12a,12b,13,14b-icosahydropicene-2-carboxylic acid (13-3). Into a 100-mL round-bottom flask, was placed 13-2 (150 mg, 0.23 mmol, 1 equiv.), EA (16 mL), Pd/C (4.9 mg, 0.05 mmol, 0.199 equiv.). To the above H₂ (g) was introduced in. The resulting solution was stirred for 1 overnight at room temperature. The solids were filtered out. The resulting mixture was concentrated. The crude product (130 mg) was purified by Prep-HPLC with the following conditions: Column, XBridge Prep C18 OBD Column, 19*150 mm 5 um; mobile phase, water (0.05% T FA) and ACN (5% Phase B up to 62% in 1 min, up to 76% in 7 min); Detector, uv. product was obtained. This resulted in 89.2 mg (69.09%) of 13-3 as a white solid. MS (ES, m/z): [M+H]⁺=557.30; ¹H NMR (400 MHz, MeOH-d₄): δ 0.84 (s, 3H), 0.85-0.89 (m, 1H), 0.93 (s, 3H), 0.95-1.09 (m, 2H), 1.10 (s, 3H), 1.17 (t, J=4.5 Hz, 9H), 1.20-1.30 (m, 1H), 1.38-1.62 (m, 9H), 1.63-1.79 (m, 3H), 1.80-2.09 (m, 4H), 2.10-2.28 (m, 2H), 2.33 (q, J=5.5 Hz, 1H), 2.51 (s, 1H), 2.78 (d, J=13.2 Hz, 1H), 4.58 (q, J=13.2 Hz, 2H), 5.58 (s, 1H).

Example 13 (2S,4aS,6aS,6bR,8aS,10S,12aS,12bR, 14bR)-10-((2-methoxy-2-oxoethoxy) carbonyl)-2,4a, 6a,6b,9,9,12a-heptamethyl-13-oxo-1,2,3,4,4a,5,6,6a, 6b,7,8,8a,9,10,11,12,12a, 12b,13,14b-icosahydropicene-2-carboxylic acid (14-1)

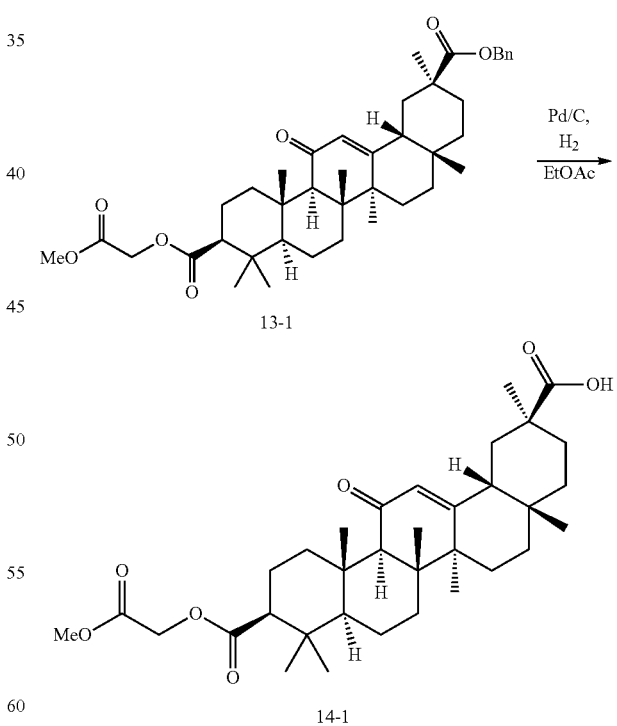

13-1

14-1

Into a 100-mL round-bottom flask, was placed 13-1 (125 mg, 0.19 mmol, 1 equiv.), EA (12 mL), Pd/C (25 mg, 0.23 mmol, 1.242 equiv.). To the above H₂ (g) was introduced in. The resulting solution was stirred for 1 overnight at room temperature. The solids were filtered out. The resulting mixture was concentrated. The crude product (100 mg) was purified by Prep-HPLC with the following conditions: Column, XBridge Prep C18 OBD Column, 5 um, 19*150 mm; mobile phase, water (0.05% TFA) and ACN (66% Phase B up to 83% in 8 min); Detector, uv. product was obtained. This resulted in 127.6 mg (118.20%) of 14-1 as a white solid. MS (ES, m/z): [M+H]$^+$=571.30; $^1$H NMR (400 MHz, MeOH-d$_4$) δ: 0.84 (s, 3H), 0.85-0.89 (m, 1H), 0.93 (s, 3H), 0.98-1.31 (m, 16H), 1.32-1.59 (m, 9H), 1.65-1.79 (m, 3H), 1.80-2.04 (m, 4H), 2.08-2.27 (m, 2H), 2.51 (s, 1H), 2.78 (d, J=13.2 Hz, 1H), 3.73 (s, 3H), 4.62 (q, J=14.5 Hz, 2H), 5.58 (s, 1H).

Example 14 (2S,4aS,6aS,6bR,8aS,10S,12aS,12bR, 14bR)-10-((2-(tert-Butoxy)-2-oxoethoxy) carbonyl)-2,4a,6a,6b,9,9,12a-heptamethyl-13-oxo-1,2,3,4,4a,5, 6,6a,6b,7,8,8a,9,10,11,12,12a, 12b,13,14b-icosahydropicene-2-carboxylic acid (15-2)

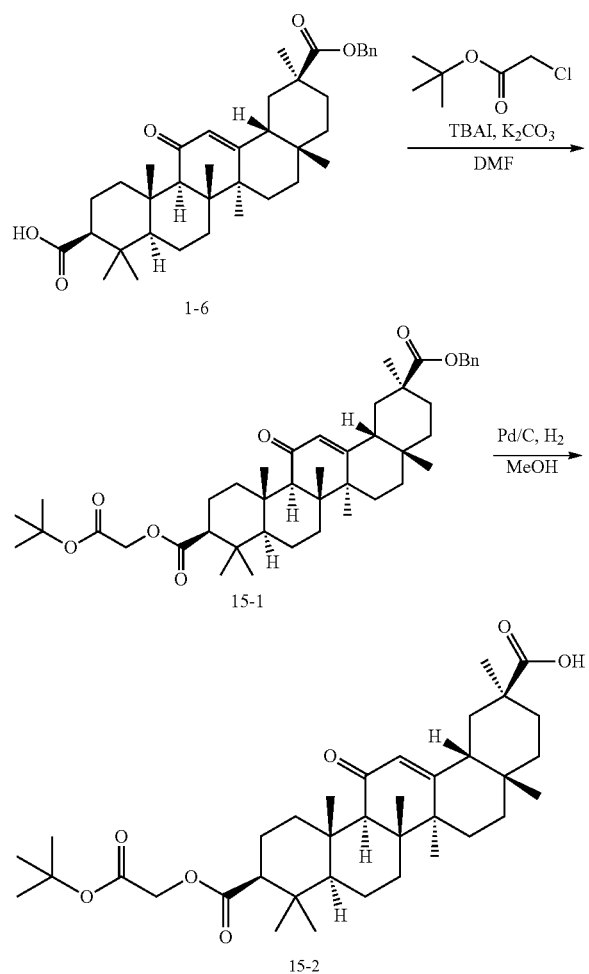

Synthesis of 2-Benzyl 10-(2-(tert-butoxy)-2-oxoethyl) (2S,4aS,6aS,6bR,8aS,10S,12aS, 12bR,14bR)-2,4a,6a,6b,9, 9,12a-heptamethyl-13-oxo-1,2,3,4,4a,5,6,6a,6b,7,8,8a,9,10, 11,12,12a, 12b,13,14b-icosahydropicene-2,10-dicarboxylate (15-1). Into a 100-mL round-bottom flask, was placed 1-6 (295 mg, 0.50 mmol, 1 equiv.), DMF (5 mL, 0.07 mmol), TBAI (92 mg, 0.25 mmol, 0.497 equiv.), K$_2$CO$_3$ (83 mg, 0.60 mmol, 1.199 equiv.), tert-butyl 2-chloroacetate (91 mg, 0.60 mmol, 1.206 equiv.). The resulting solution was stirred for 2 hr at 65° C. The resulting solution was diluted with 50 mL of DCM. The resulting mixture was washed with 2×15 mL of brine. The mixture was dried over anhydrous sodium sulfate. The solids were filtered out. The resulting mixture was concentrated. The residue was applied onto a silica gel column with EtOAc/petroleum ether (1:3). This resulted in 200 mg (56.79%) of 15-1 as yellow oil.

Synthesis of (2S,4aS,6aS,6bR,8aS,10S,12aS,12bR, 14bR)-10-((2-(tert-Butoxy)-2-oxoethoxy) carbonyl)-2,4a, 6a,6b,9,9,12a-heptamethyl-13-oxo-1,2,3,4,4a,5,6,6a,6b,7,8, 8a,9,10,11,12,12a, 12b,13,14b-icosahydropicene-2-carboxylic acid (15-2). Into a 100-mL round-bottom flask purged and maintained with an inert atmosphere of H$_2$, was placed benzyl 15-1 (200 mg, 0.28 mmol, 1 equiv.), MeOH (10 mL, 0.31 mmol), Pd/C (30 mg, 0.28 mmol). The resulting solution was stirred overnight at room temperature. The resulting mixture was concentrated. The crude product was purified by Prep-HPLC with the following conditions (2 # -AnalyseHPLC-SHIMADZU(HPLC-10)): Column, XBridge Shield RP18 OBD Column, 5 um, 19*150 mm; mobile phase, water (0.05% TFA) and ACN (5% Phase B up to 80% in 1 min, up to 90% in 7 min); Detector, UV 254 nm. product was obtained. This resulted in 21 mg (12.04%) of 15-2 as a white solid. MS (ES, m/z): [M+H]$^+$=613.40; $^1$H-NMR (400 MHz, MeOH-d$_4$): δ 0.72-0.99 (m, 8H), 1.00-1.29 (m, 15H), 1.32-1.59 (m, 17H), 1.63-1.68 (m, 4H), 1.91-2.17 (m, 5H), 2.20-2.27 (m, 1H), 2.29 (d, J=1.6 Hz, 1H), 2.38 (s, 1H), 2.84 (d, J=1.6 Hz, 1H), 4.47 (q, J=5.6 Hz, 2H), 5.71 (s, 1H).

Example 15 (2S,4aS,6aS,6bR,8aR,12aS,12bR, 14bR)-10-(Methoxycarbonyl)-2,4a,6a,6b, 9,9,12a-heptamethyl-13-oxo-1,2,3,4,4a,5,6,6a,6b,7,8,8a,9,12, 12a,12b,13,14b-octadecahydro picene-2-carboxylic acid (27-2)

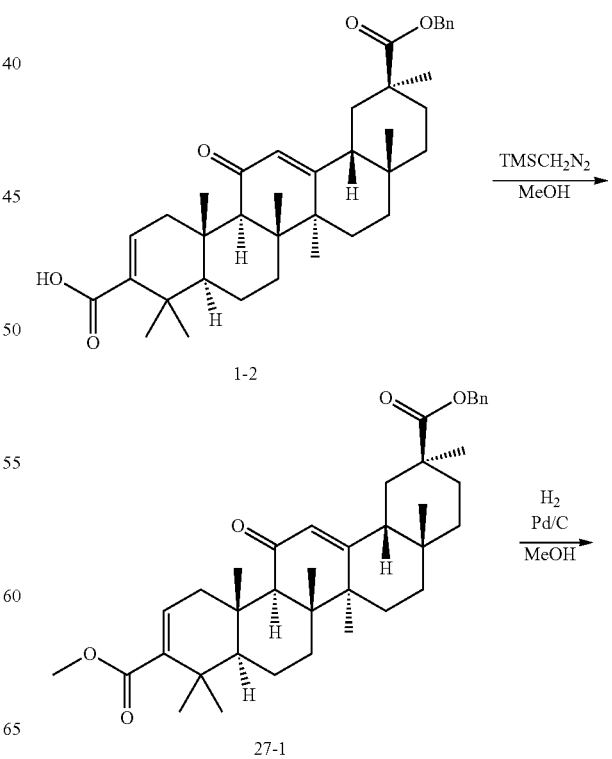

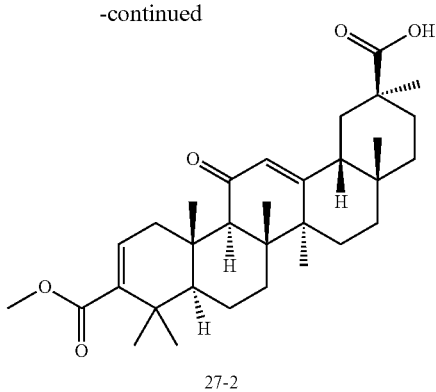

27-2

Synthesis of 2-Benzyl 10-methyl (2S,4aS,6aS,6bR,8aR, 12aS,12bR,14bR)-2,4a,6a,6b,9,9,12a-heptamethyl-13-oxo-1,2,3,4,4a,5,6,6a,6b,7,8,8a,9,12,12a,12b,13,14b-octadeca-hydropicene-2,10-dicarboxylate (27-1). (Trimethylsilyl) diazomethane in ether (2M) was added dropwise to 1-2 (100 mg, 0.170 mmol) in MeOH (3 mL) until yellow color persisted (~1.2 mmol added). The reaction was stirred at room temperature for 30 minutes and then evaporated to provide 27-1 (0.1 g, quantitative) as a white solid.

Synthesis of (2S,4aS,6aS,6bR,8aR,12aS,12bR,14bR)-10-(Methoxycarbonyl)-2,4a,6a,6b,9,9,12a-heptamethyl-13-oxo-1,2,3,4,4a,5,6,6a,6b,7,8,8a,9,12,12a,12b,13,14b-octa-decahydropicene-2-carboxylic acid (27-2). Into a 100-mL round-bottom flask purged and maintained with an inert atmosphere of hydrogen (1 atm), was placed 27-1 (100 mg, 0.17 mmol, 1.00 equiv.), MeOH (25 mL), Pd/C (20 mg). The resulting solution was stirred overnight at room temperature. The solids were filtered out. The crude product was purified by Prep-HPLC with the following conditions: Column, XBridge Shield RP18 OBD Column, 5 um, 19*150 mm; mobile phase, water (0.05% TFA) and ACN (70.0% ACN up to 82.0% in 7 min); Detector, UV 254 nm. This resulted in 25.7 mg (30%) of 27-2 as a white solid. MS (ES, m/z): [M+H]$^+$=511.25; $^1$H-NMR (400 MHz, MeOH-d$_4$, ppm): δ 0.73-0.83 (m, 3H), 0.91-0.97 (m, 1H), 1.03-1.17 (m, 15H), 1.18-1.23 (m, 2H), 1.28-1.35 (m, 6H), 1.41-1.52 (m, 2H), 1.53-1.69 (m, 3H), 1.71-1.93 (m, 4H), 2.03-2.18 (m, 2H), 2.45 (s, 1H), 3.15-3.21 (m, 1H), 3.58 (s, 3H), 5.54 (s, 1H), 6.76 (d, J=2.0 Hz, 1H).

Example 16 (2S,4aS,6aS,6bR,8aS,10S,12aS,12bR, 14bR)-10-((2-methoxy-2-oxoethyl) carbamoyl)-2,4a, 6a,6b,9,9,12a-heptamethyl-13-oxo-1,2,3,4,4a,5,6,6a, 6b,7,8,8a,9,10,11,12,12a, 12b,13,14b-icosahydropicene-2-carboxylic acid (29-2)

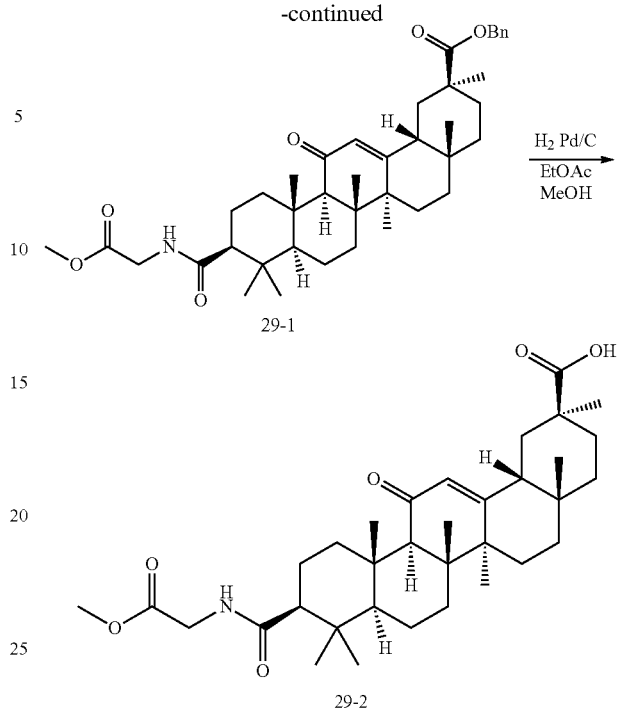

Synthesis of benzyl (2S,4aS,6aS,6bR,8aS,10S,12aS, 12bR,14bR)-10-((2-methoxy-2-oxoethyl) carbamoyl)-2,4a, 6a,6b,9,9,12a-heptamethyl-13-oxo-1,2,3,4,4a,5,6,6a,6b,7,8, 8a,9,10,11,12,12a, 12b,13,14b-icosahydropicene-2-carboxylate (29-1). Into a 250-mL round-bottom flask, was placed methyl 2-aminoacetate hydrochloride (540 mg, 4.30 mmol, 3.00 equiv.), DCM (60 mL), TEA (0.59 mL, 3.00 equiv.), a solution of PH-RDX-013-291-4 (860 mg, 1.42 mmol, 1.00 equiv.) in DCM (30 mL). The resulting solution was stirred for 1 h at room temperature. The resulting mixture was concentrated under vacuum. This resulted in 900 mg (96%) of 29-1 as a white solid.

Synthesis of (2S,4aS,6aS,6bR,8aS,10S,12aS,12bR, 14bR)-10-((2-methoxy-2-oxoethyl) carbamoyl)-2,4a,6a,6b, 9,9,12a-heptamethyl-13-oxo-1,2,3,4,4a,5,6,6a,6b,7,8,8a,9, 10,11,12,12a, 12b,13,14b-icosahydropicene-2-carboxylic acid (29-2). Into a 250-mL round-bottom flask, was placed 29-1 (500 mg, 0.76 mmol, 1.00 equiv.) EtOAc (15 mL), MeOH (15 mL), Pd/C (50 mg).

To the above hydrogen (1 atm) was introduced in. The resulting solution was stirred for 1 h at room temperature. The solids were filtered out. The resulting mixture was concentrated under vacuum. The residue was dissolved in 8 mL of THF-MeOH (1:1). The crude product was purified by Prep-HPLC with the following conditions: Column, XBridge Shield RP18 OBD Column, 5 um, 19*150 mm; mobile phase, water (0.05% TFA) and ACN (52.0% ACN up to 70.0% in 8 min); Detector, UV 254 nm. This resulted in 284.1 mg (66%) of 29-2 as a white solid. MS-PH (ES, m/z): [M+H]$^+$=570.30; $^1$H NMR (400 MHz, MeOH-d$_4$, ppm): δ 0.74 (s, 3H), 0.76 (s, 1H), 0.83 (s, 3H), 0.90-0.95 (m, 2H), 0.97 (s, 3H), 1.06 (s, 6H), 1.08 (s, 3H), 1.16 (d, J=13.6 Hz, 1H), 1.27-1.29 (m, 4H), 1.31 (s, 3H), 1.34-1.38 (m, 2H), 1.56-1.67 (m, 3H), 1.77 (d, J=13.6 Hz, 2H), 1.85-1.92 (m, 2H), 1.98-2.06 (m, 2H), 2.11-2.15 (m, 1H), 2.40 (s, 1H), 2.67-2.71 (m, 1H), 3.61 (s, 3H), 3.75 (d, J=17.6 Hz, 1H), 3.85 (d, J=17.2 Hz, 1H), 5.49 (s, 1H).

Example 17 (2S,4aS,6aS,6bR,8aS,10S,12aS,12bR,14bR)-10-((carboxymethyl)carbamoyl)-2,4a,6a,6b,9,9,12a-heptamethyl-13-oxo-1,2,3,4,4a,5,6,6a,6b,7,8,8a,9,10,11,12,12a,12b,13,14b-icosahydropicene-2-carboxylic acid (30-3)

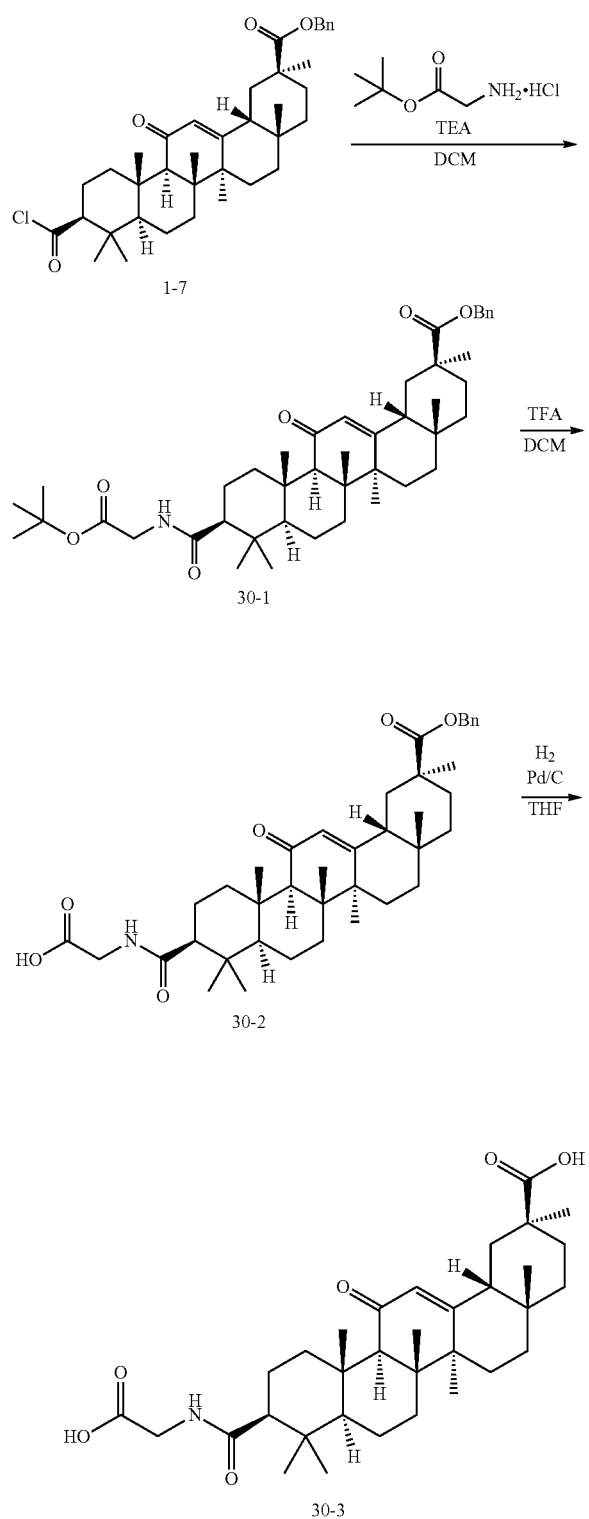

Synthesis of benzyl (2S,4aS,6aS,6bR,8aS,10S,12aS,12bR,14bR)-10-((2-(tert-Butoxy)-2-oxoethyl)carbamoyl)-2,4a,6a,6b,9,9,12a-heptamethyl-13-oxo-1,2,3,4,4a,5,6,6a,6b,7,8,8a,9,10,11,12,12a,12b,13,14b-icosahydropicene-2-carboxylate (30-1). Into a 250-mL round-bottom flask, was placed tert-butyl 2-aminoacetate hydrochloride (828 mg, 4.94 mmol, 3.00 equiv.), DCM (80 mL), TEA (0.728 mL, 6.00 equiv.), a solution of 1-7 (1.0 g, 1.65 mmol, 1.00 equiv.) in DCM (20 mL). The resulting solution was stirred for 2 h at room temperature. The resulting mixture was concentrated under vacuum. The residue was applied onto a silica gel column with EtOAc/petroleum ether (1:1). This resulted in 1.19 g (99%) of 30-1 as a light yellow solid.

Synthesis of ((3S,4aS,6aR,6bS,8aS,11S,12aR,14aR,14bS)-11-((Benzyloxy)carbonyl)-4,4,6a,6b,8a,11,14b-heptamethyl-14-oxo-1,2,3,4,4a,5,6,6a,6b,7,8,8a,9,10,11,12,12a,14,14a,14b-icosa hydropicene-3-carbonyl)glycine (30-2). Into a 100-mL round-bottom flask, was placed 30-1 (1.19 g, 1.70 mmol, 1.00 equiv.), DCM (10 mL), trifluoroacetic acid (10 mL). The resulting solution was stirred for 1 h at room temperature. The resulting mixture was concentrated under vacuum. The resulting mixture was washed with 2×100 mL of n-hexane. This resulted in 1.0 g (91%) of 30-2 as an off-white solid.

Synthesis of (2S,4aS,6aS,6bR,8aS,10S,12aS,12bR,14bR)-10-((Carboxymethyl)carbamoyl)-2,4a,6a,6b,9,9,12a-heptamethyl-13-oxo-1,2,3,4,4a,5,6,6a,6b,7,8,8a,9,10,11,12,12a,12b,13,14b-icosahydropicene-2-carboxylic acid (30-3). Into a 100-mL round-bottom flask, was placed 30-2 (560 g, 848.62 mmol, 1.00 equiv.), Pd/C (50 mg), THF (30 mL). To the above hydrogen (1 atm) was introduced in. The resulting solution was stirred for 1 h at room temperature. The solids were filtered out. The crude product was purified by Prep-HPLC with the following conditions: Column, XBridge Prep OBD C18 Column, 19*250 mm, 5 um; mobile phase, water (0.05% TFA) and ACN (45.0% ACN up to 65.0% in 8 min); Detector, UV 254 nm. This resulted in 289 mg of 30-3 as a white solid. MS (ES, m/z): [M+H]$^+$=556.30; $^1$H NMR (300 MHz, MeOH-d$_4$, ppm): δ 0.87 (s, 3H), 0.90 (s, 1H), 0.96 (s, 3H), 1.02 (d, J=14.0 Hz, 2H), 1.10 (s, 3H), 1.19 (s, 3H), 1.20 (s, 3H), 1.22 (s, 3H), 1.28 (d, J=14.4 Hz, 1H), 1.40-1.56 (m, 9H), 1.67-2.22 (m, 10H), 2.50 (s, 1H), 2.78 (dt, J=13.4 Hz, 3.3 Hz, 1H), 3.82 (d, J=17.4 Hz, 1H), 3.92 (d, J=17.4 Hz, 1H), 5.58 (s, 1H).

Example 18 (2S,4aS,6aS,6bR,8aS,10S,12aS,12bR,14bR)-10-((2-Methoxy-2-oxoethyl) (methyl)carbamoyl)-2,4a,6a,6b,9,9,12a-heptamethyl-13-oxo-1,2,3,4,4a,5,6,6a,6b,7,8,8a,9,10,11,12,12a,12b,13,14b-icosahydropicene-2-carboxylic acid (31-2)

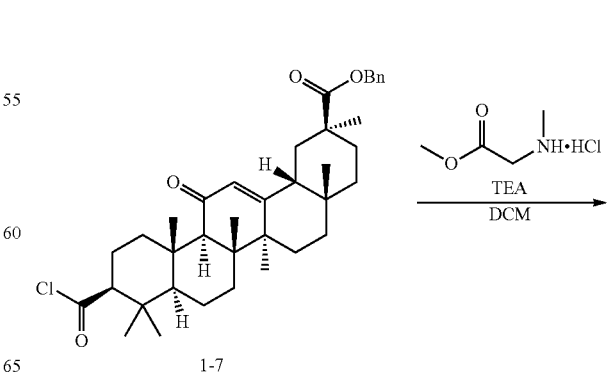

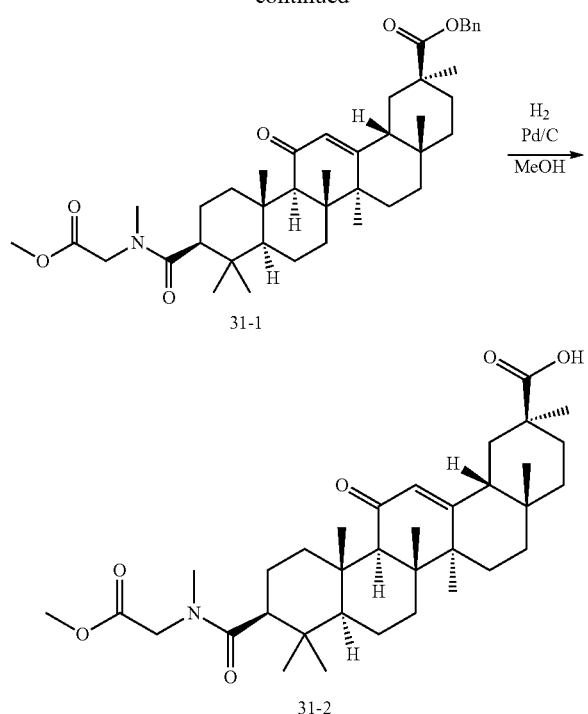

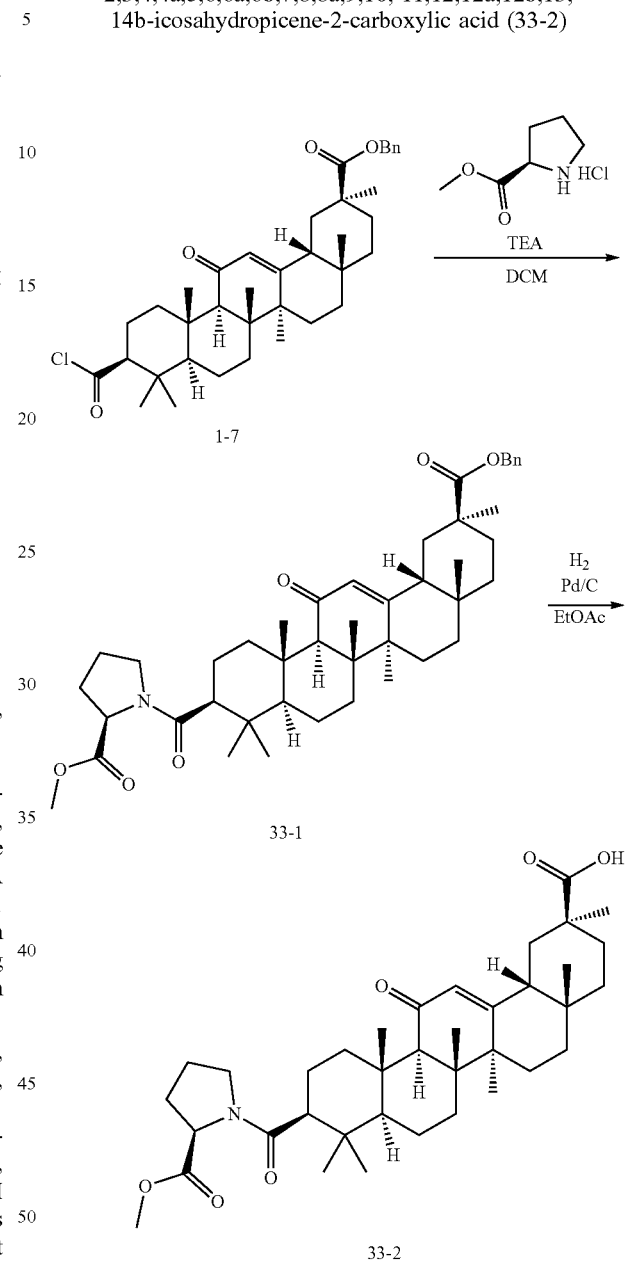

Example 19 (2S,4aS,6aS,6bR,8aS,10S,12aS,12bR, 14bR)-10-((R)-2-(Methoxycarbonyl) pyrrolidine-1-carbonyl)-2,4a,6a,6b,9,9,12a-heptamethyl-13-oxo-1, 2,3,4,4a,5,6,6a,6b,7,8,8a,9,10, 11,12,12a,12b,13, 14b-icosahydropicene-2-carboxylic acid (33-2)

Synthesis of Benzyl (2S,4aS,6aS,6bR,8aS,10S,12aS, 12bR,14bR)-10-((2-Methoxy-2-oxoethyl)(methyl)carbamoyl)-2,4a,6a,6b,9,9,12a-heptamethyl-13-oxo-1,2,3,4,4a,5,6, 6a,6b,7,8, 8a,9,10,11,12,12a,12b,13,14b-icosahydropicene-2-carboxylate (31-1). Into a 100-mL round-bottom flask, was placed methyl 2-(methylamino)acetate hydrochloride (172 mg, 1.23 mmol, 3.00 equiv.), DCM (15 mL), TEA (0.171 mL, 3.00 equiv.), a solution of 1-7 (250 mg, 0.41 mmol, 1.00 equiv.) in DCM (5 mL). The resulting solution was stirred for 1 h at room temperature. The resulting mixture was concentrated under vacuum. This resulted in 0.25 g (90%) of 31-1 as an off-white solid.

Synthesis of (2S,4aS,6aS,6bR,8aS,10S,12aS,12bR, 14bR)-10-((2-Methoxy-2-oxoethyl)(methyl) carbamoyl)-2, 4a,6a,6b,9,9,12a-heptamethyl-13-oxo-1,2,3,4,4a,5,6,6a,6b, 7,8,8a,9,10,11,12,12a, 12b,13,14b-icosahydropicene-2-carboxylic acid (31-2). Into a 100-mL round-bottom flask, was placed 31-1 (250 mg, 0.37 mmol, 1.00 equiv.), MeOH (15 mL), Pd/C (25 mg). To the above hydrogen (1 atm) was introduced in. The resulting solution was stirred for 1 h at room temperature. The solids were filtered out. The crude product was purified by Prep-HPLC with the following conditions: Column, XBridge Shield RP18 OBD Column, 5 um, 19*150 mm; mobile phase, water (0.05% TFA) and ACN (58.0% ACN up to 74.0% in 8 min); Detector, UV 254 nm. This resulted in 28.6 mg (13%) of 31-2 as a white solid. MS (ES, m/z): [M+H]$^+$=584.35; $^1$H NMR (400 MHz, MeOH-d$_4$, ppm): δ 0.84 (s, 3H), 0.92 (s, 3H), 0.93-0.98 (m, 2H), 1.05 (s, 3H), 1.06-1.08 (m, 1H), 1.15 (d, J=4.0 Hz, 3H), 1.17 (s, 3H), 1.19 (d, J=2.4 Hz, 3H), 1.26 (d, J=12.0 Hz, 1H), 1.33-1.43 (m, 5H), 1.45 (s, 3H), 1.48-1.49 (m, 1H), 1.69-1.79 (m, 3H), 1.84-1.90 (m, 2H), 1.92-2.03 (m, 2H), 2.18-2.21 (m, 2H), 2.54 (s, 1H), 2.74-2.80 (m, 2H), 2.93 (s, 1H), 3.19 (s, 2H), 3.70 (s, 3H), 3.98 (d, J=17.2 Hz, 1H), 4.23 (d, J=17.2 Hz, 1H), 5.55 (s, 1H).

Synthesis of Methyl ((3S,4aS,6aR,6bS,8aS,11S,12aR, 14aR,14bS)-11-((benzyloxy)carbonyl)-4,4,6a,6b,8a,11,14b-heptamethyl-14-oxo-1,2,3,4,4a,5,6,6a,6b,7,8,8a,9,10,11,12, 12a,14,14a,14b-icosahydropicene-3-carbonyl)-D-prolinate (33-1). Into a 100-mL round-bottom flask, was placed (2R)-pyrrolidine-2-carboxylic acid hydrochloride (245 mg, 1.62 mmol, 3.00 equiv.), DCM (15 mL), TEA (0.206 mL, 3.00 equiv.), a solution of 1-7 (300 mg, 0.49 mmol, 1.00 equiv.) in DCM (5 mL). The resulting solution was stirred for 1 h at room temperature. The resulting mixture was concentrated under vacuum. This resulted in 320 mg (93%) of 33-1 as a white solid.

Synthesis of (2S,4aS,6aS,6bR,8aS,10S,12aS,12bR, 14bR)-10-((R)-2-(Methoxycarbonyl) pyrrolidine-1-carbonyl)-2,4a,6a,6b,9,9,12a-heptamethyl-13-oxo-1,2,3,4,4a,5,6, 6a,6b,7,8,8a,9, 10,11,12,12a,12b,13,14b-icosahydropicene-2-carboxylic acid (33-2). Into a 100-mL round-bottom flask, was placed 33-1 (320 mg, 0.46 mmol, 1.00 equiv.), EtOAc (20 mL), Pd/C (32 mg).

To the above hydrogen (1 atm) was introduced in. The resulting solution was stirred overnight at room temperature. The solids were filtered out. The resulting mixture was concentrated under vacuum. The residue was dissolved in 8 mL of MeOH. The crude product was purified by Prep-HPLC with the following conditions: Column, XBridge Shield RP18 OBD Column, 5 um, 19*150 mm; mobile phase, water (10 mmol/L $NH_4HCO_3$+0.1% $NH_3.H_2O$) and ACN (35.0% ACN up to 65.0% in 8 min); Detector, UV 254 nm. This resulted in 26 mg (9%) of 33-2 as a white solid. MS (ES, m/z): $[M+H]^+$=610.4; $^1H$ NMR (400 MHz, MeOH-$d_4$, ppm): δ 0.86 (s, 3H), 0.93 (s, 1H), 0.97 (s, 3H), 1.00 (s, 3H), 1.05-1.09 (m, 2H), 1.17 (s, 3H), 1.18 (s, 3H), 1.21 (s, 3H), 1.27 (d, J=14.3 Hz, 1H), 1.35-1.45 (m, 4H), 1.47 (s, 3H), 1.48-1.51 (m, 2H), 1.65-1.87 (m, 3H), 1.90-2.03 (m, 7H), 2.05-2.26 (m, 3H), 2.51-2.55 (m, 2H), 2.81 (dt, J=13.4, 3.3 Hz, 1H), 3.71-3.76 (m, 5H), 4.44 (dd, J=8.6, 3.8 Hz, 1H), 5.62 (s, 1H).

Example 20 (2S,4aS,6aS,6bR,8aS,10S,12aS,12bR,14bR)-10-(((S)-1,5-Dimethoxy-1,5-dioxopentan-2-yl)carbamoyl)-2,4a,6a,6b,9,9,12a-heptamethyl-13-oxo-1,2,3,4,4a,5,6,6a,6b,7,8, 8a,9,10,11,12,12a,12b, 13,14b-icosahydropicene-2-carboxylic acid (35-2)

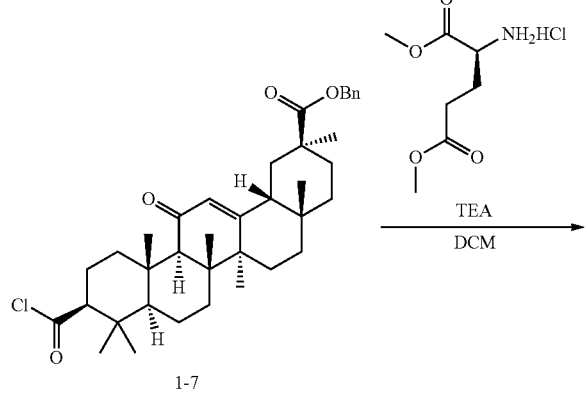

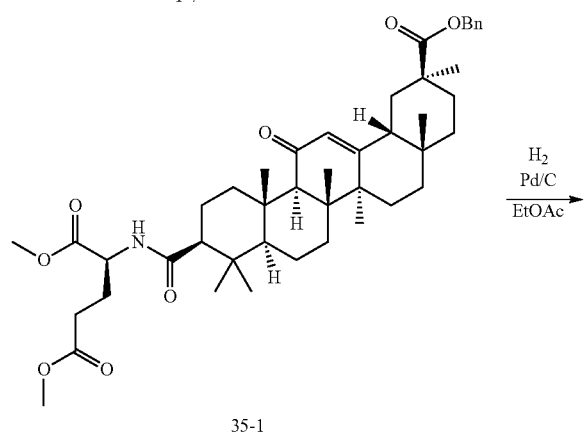

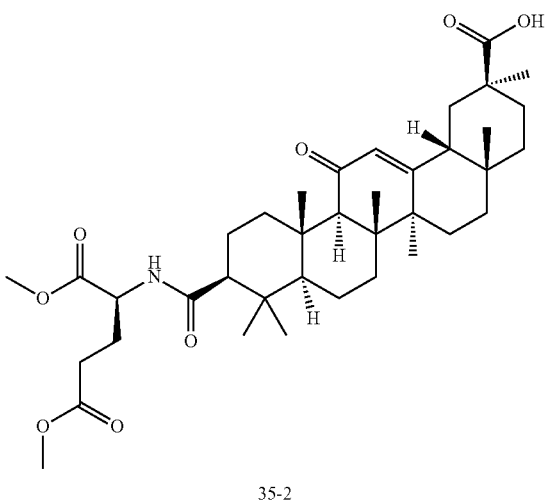

Synthesis of Dimethyl ((3S,4aS,6aR,6bS,8aS,11S,12aR,14aR,14bS)-11-((benzyloxy)carbonyl)-4,4,6a,6b,8a,11,14b-heptamethyl-14-oxo-1,2,3,4,4a,5,6,6a,6b,7,8,8a,9,10,11,12,12a,14,14a,14b-icosahydropicene-3-carbonyl)-L-glutamate (35-1). Into a 250-mL round-bottom flask, was placed 1,5-dimethyl (2S)-2-aminopentanedioate hydrochloride (261 mg, 1.23 mmol, 3.00 equiv.), DCM (15 mL), TEA (0.171 mL, 3.00 equiv.), a solution of 1-7 (250 mg, 0.41 mmol, 1.00 equiv.) in DCM (5 mL). The resulting solution was stirred for 1 h at room temperature. The resulting mixture was concentrated under vacuum. This resulted in 250 mg (81%) of 35-1 as an off-white solid.

Synthesis of (2S,4aS,6aS,6bR,8aS,10S,12aS,12bR,14bR)-10-(((S)-1,5-Dimethoxy-1,5-dioxo pentan-2-yl)carbamoyl)-2,4a,6a,6b,9,9,12a-heptamethyl-13-oxo-1,2,3,4,4a,5,6,6a,6b,7,8,8a,9,10, 11,12,12a,12b,13,14b-icosahydropicene-2-carboxylic acid (35-2). Into a 100-mL round-bottom flask, was placed 35-1 (250 mg, 0.34 mmol, 1.00 equiv.), EtOAc (20 g, 226.99 mmol, 677.32 equiv.), Pd/C (30 mg). To the above hydrogen (1 atm) was introduced in. The resulting solution was stirred for 1 h at room temperature. The solids were filtered out. The crude product was purified by Prep-HPLC with the following conditions: Column, XBridge Shield RP18 OBD Column, 5 um, 19*150 mm; mobile phase, water (0.05% TFA) and ACN (53.0% ACN up to 71.0% in 8 min); Detector, UV 254 nm. This resulted in 33.3 mg (15%) of 35-2 as a white solid. MS (ES, m/z): $[M+H]^+$=656.35; $^1H$ NMR (300 MHz, Chloroform-d, ppm): δ 0.75 (d, J=11.1 Hz, 1H), 0.84 (s, 3H), 0.91 (s, 3H), 0.97 (s, 1H), 1.02 (s, 1H), 1.05 (s, 3H), 1.14 (s, 3H), 1.19 (s, 3H), 1.23 (s, 3H), 1.24-1.30 (m, 1H), 1.33-1.49 (m, 9H), 1.59-1.68 (m, 3H), 1.83-2.07 (m, 7H), 2.17-2.22 (m, 2H), 2.24-2.49 (m, 3H), 2.86 (d, J=13.5, 1H), 3.68 (s, 3H), 3.75 (s, 3H), 4.60-4.64 (m, 1H), 5.71 (s, 1H), 6.28 (d, J=7.5 Hz, 1H).

Example 21 (2S,4aS,6aS,6bR,8aS,10S,12aS,12bR, 14bR)-10-(((R)-1,4-Dimethoxy-1,4-dioxobutan-2-yl) carbamoyl)-2,4a,6a,6b,9,9,12a-heptamethyl-13-oxo-1,2,3,4,4a,5,6,6a,6b, 7,8,8a,9,10,11,12,12a,12b,13, 14b-icosahydropicene-2-carboxylic acid (37-2)

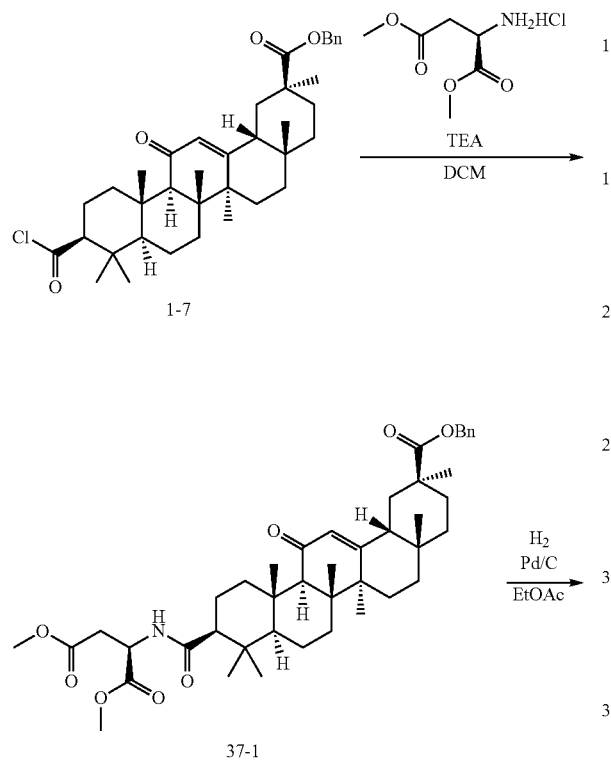

Synthesis of Dimethyl((3S,4aS,6aR,6bS,8aS,11S,12aR, 14aR,14bS)-11-((benzyloxy)carbonyl)-4,4,6a,6b,8a,11,14b-heptamethyl-14-oxo-1,2,3,4,4a,5,6,6a,6b,7,8,8a,9,10,11,12, 12a,14,14a,14b-icosahydropicene-3-carbonyl)-D-aspartate (37-1). Into a 100-mL round-bottom flask, was placed 1,4-dimethyl (2R)-2-aminobutanedioate hydrochloride (201 mg, 1.02 mmol, 1.00 equiv.), DCM (20 mL), TEA (0.353 mL, 5.00 equiv.). The resulting solution was stirred 0.5 h at room temperature. Then this was followed by the addition of a solution of 1-7 (309 mg, 0.51 mmol, 1.00 equiv.) in DCM (10 mL) dropwise with stirring at room temperature. The resulting solution was stirred overnight at room temperature. The resulting mixture was concentrated under vacuum. This resulted in 372 mg (100%) of 37-1 as a light yellow crude solid.

Synthesis of (2S,4aS,6aS,6bR,8aS,10S,12aS,12bR, 14bR)-10-(((R)-1,4-Dimethoxy-1,4-dioxo butan-2-yl)carbamoyl)-2,4a,6a,6b,9,9,12a-heptamethyl-13-oxo-1,2,3,4,4a, 5,6,6a,6b,7,8,8a,9,10, 11,12,12a,12b,13,14b-icosahydropicene-2-carboxylic acid (37-2). Into a 100-mL round-bottom flask purged and maintained with an inert atmosphere of $H_2$, was placed 37-1 (372 mg, 0.51 mmol, 1.00 equiv.), MeOH (10 mL), THF (10 mL), Pd/C (37 mg). The resulting solution was stirred overnight at room temperature. The solids were filtered out. The resulting mixture was concentrated under vacuum. The crude product was purified by Prep-HPLC with the following conditions: Column, XBridge Shield RP18 OBD Column, 5 um, 19*150 mm; mobile phase, water (0.05% TFA) and ACN (5.0% ACN up to 56.0% in 1 min, up to 72.0% in 7 min); Detector, UV 254 nm. This resulted in 206 mg (63%) of 37-2 as a white solid. MS (ES, m/z): $[M+H]^+=642$; $^1H$ NMR (400 MHz, MeOH-$d_4$ ppm): δ 0.84 (s, 4H), 0.91 (s, 3H), 0.95-1.00 (m, 5H), 1.13-1.21 (m, 9H), 1.25 (d, J=13.2 Hz, 1H), 1.38-1.52 (m, 9H), 1.62-1.81 (m, 3H), 1.82-2.04 (m, 4H), 2.05-2.26 (m, 3H), 2.49 (s, 1H), 2.72-2.86 (m, 2H), 2.95 (dd, J=16.4, 5.2 Hz, 1H), 3.65 (s, 3H), 3.72 (s, 3H), 4.76 (dd, J=8.0, 5.6 Hz, 1H), 5.58 (s, 1H).

Example 22 (2S,4aS,6aS,6bR,8aS,10S,12aS,12bR, 14bR)-10-(((S)-1-Methoxy-1-oxopropan-2-yl)carbamoyl)-2,4a,6a,6b,9,9,12a-heptamethyl-13-oxo-1,2, 3,4,4a,5,6,6a,6b,7,8,8a,9,10,11,12, 12a,12b,13,14b-icosahydropicene-2-carboxylic acid (39-2)

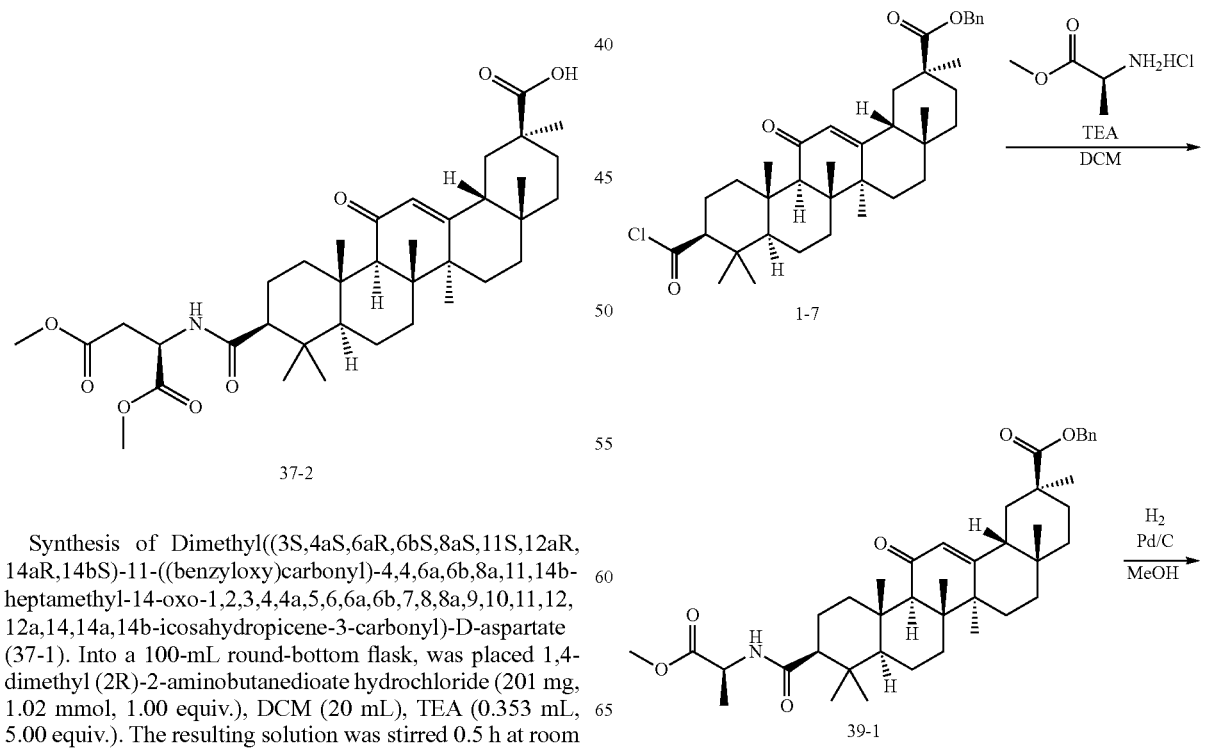

Example 23 (2S,4aS,6aS,6bR,8aS,10S,12aS,12bR, 14bR)-10-(((S)-3-Hydroxy-1-methoxy-1-oxopropan-2-yl)carbamoyl)-2,4a,6a,6b,9,9,12a-heptamethyl-13-oxo-1,2,3,4,4a,5,6,6a,6b,7,8,8a, 9,10,11,12,12a,12b, 13,14b-icosahydropicene-2-carboxylic acid (41-2)

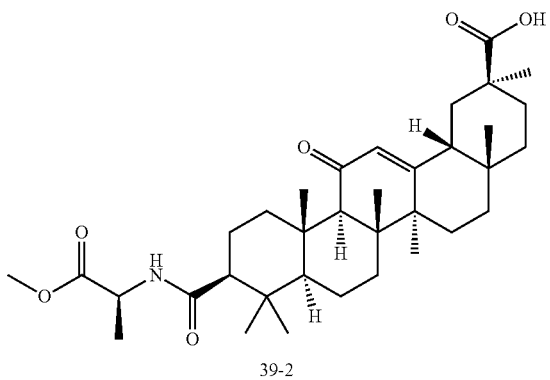

39-2

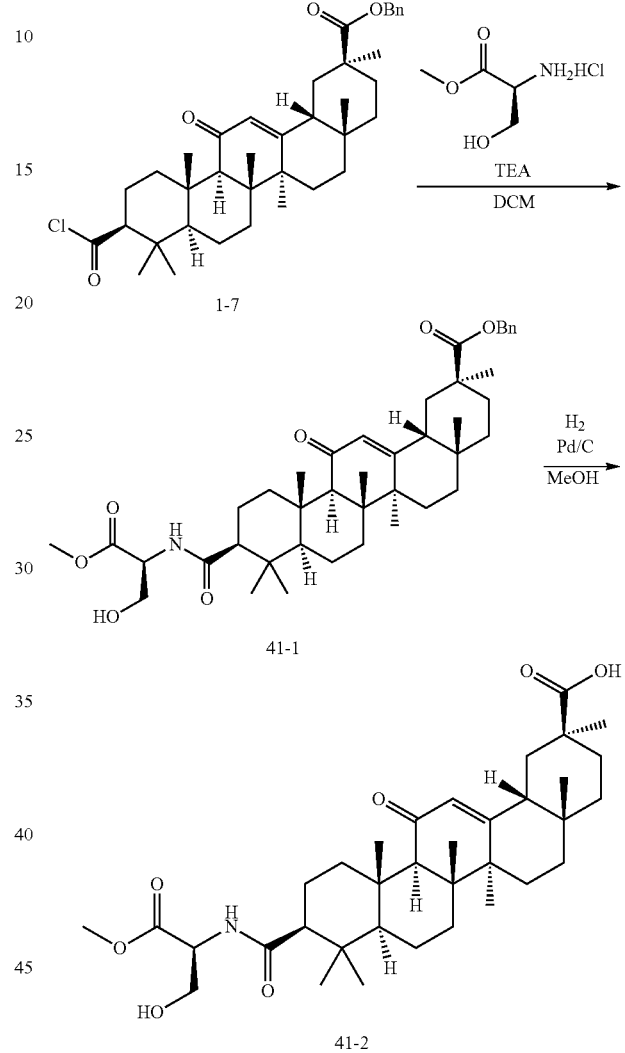

Synthesis of Benzyl (2S,4aS,6aS,6bR,8aS,10S,12aS, 12bR,14bR)-10-(((S)-1-methoxy-1-oxo propan-2-yl)carbamoyl)-2,4a,6a,6b,9,9,12a-heptamethyl-13-oxo-1,2,3,4,4a, 5,6,6a,6b,7,8,8a,9, 10,11,12,12a,12b,13,14b-icosahydropicene-2-carboxylate (39-1). Into a 100-mL round-bottom flask, was placed methyl (2S)-2-aminopropanoate hydrochloride (172 mg, 1.23 mmol, 2.993 equiv.), DCM (15 mL), TEA (0.171 mL, 1.23 mmol, 2.988 equiv.), a solution of 1-7 (250 mg, 0.41 mmol, 1 equiv.) in DCM (5 mL). The resulting solution was stirred for 1 hr at room temperature. The resulting mixture was concentrated. This resulted in 250 mg (90.11%) of PH-RDX-013-455-1 as a light yellow solid.

Synthesis of (2S,4aS,6aS,6bR,8aS,10S,12aS,12bR, 14bR)-10-(((S)-1-Methoxy-1-oxopropan-2-yl)carbamoyl)-2,4a,6a,6b,9,9,12a-heptamethyl-13-oxo-1,2,3,4,4a,5,6,6a, 6b,7,8,8a,9,10,11,12, 12a,12b,13,14b-icosahydropicene-2-carboxylic acid (39-2). Into a 100-mL round-bottom flask, was placed 39-1 (250 mg, 0.37 mmol, 1.00 equiv.), MeOH (25 mL), Pd/C (25 mg). To the above hydrogen (1 atm) was introduced in. The resulting solution was stirred for 1 h at room temperature. The solids were filtered out. The crude product was purified by Prep-HPLC with the following conditions: Column, XBridge Shield RP18 OBD Column, 5 um, 19*150 mm; mobile phase, water (0.05% TFA) and ACN (53.0% ACN up to 71.0% in 8 min); Detector, UV 254 nm. This resulted in 31.7 mg (15%) of 39-2 as a white solid. (ES, m/z): $[M+H]^+=584.35$; $^1H$ NMR (300 MHz, Chloroform-d, ppm): δ 0.77 (d, J=11.7 Hz, 1H), 0.87 (s, 3H), 0.95 (s, 3H), 1.09 (s, 3H), 1.17 (s, 3H), 1.22 (s, 3H), 1.26 (s, 3H), 1.29-1.32 (m, 1H), 1.32-1.51 (m, 11H), 1.59-1.79 (m, 3H), 1.83-2.07 (m, 9H), 2.19 (d, J=10.5, 1H), 2.37 (s, 1H), 2.86 (d, J=13.5 Hz, 1H), 3.75 (s, 3H), 4.56-4.66 (m, 1H), 5.71 (s, 1H), 5.95 (d, J=7.2 Hz, 1H).

Synthesis of benzyl (2S,4aS,6aS,6bR,8aS,10S,12aS, 12bR,14bR)-10-(((S)-3-Hydroxy-1-methoxy-1-oxopropan-2-yl)carbamoyl)-2,4a,6a,6b,9,9,12a-heptamethyl-13-oxo-1, 2,3,4,4a,5,6, 6a,6b,7,8,8a,9,10,11,12,12a,12b,13,14b-icosahydropicene-2-carboxylate (41-1). Into a 100-mL round-bottom flask, was placed methyl (2S)-2-amino-3-hydroxypropanoate hydrochloride (211 mg, 1.36 mmol, 2.00 equiv.), DCM (20 mL), TEA (0.283 mL, 3.00 equiv.). The resulting solution was stirred for 0.5 h at room temperature. Then this was followed by the addition of a solution of 1-7 (412 mg, 0.68 mmol, 1.00 equiv.) in DCM (10 mL) dropwise with stirring at room temperature. The resulting solution was stirred for 1 h at room temperature. The resulting mixture was concentrated under vacuum. This resulted in 468 mg (100%) of 41-1 as a light yellow crude solid.

Synthesis of (2S,4aS,6aS,6bR,8aS,10S,12aS,12bR, 14bR)-10-(((S)-3-hydroxy-1-methoxy-1-oxopropan-2-yl)

carbamoyl)-2,4a,6a,6b,9,9,12a-heptamethyl-13-oxo-1,2,3,4, 4a,5,6,6a,6b,7,8,8a, 9,10,11,12,12a,12b,13,14b-icosahydropicene-2-carboxylic acid (41-2). Into a 100-mL round-bottom flask purged and maintained with an inert atmosphere of $H_2$, was placed 41-1 (468 mg, 0.68 mmol, 1.00 equiv.), MeOH (20 mL), THF (10 mL), Pd/C (50 mg). The resulting solution was stirred overnight at room temperature. The solids were filtered out. The resulting mixture was concentrated under vacuum. The crude product was purified by Prep-HPLC with the following conditions: Column, XBridge Shield RP18 OBD Column, 5 um, 19*150 mm; mobile phase, water (0.05% TFA) and ACN (45.0% ACN up to 63.0% in 8 min); Detector, UV 254 nm. This resulted in 283 mg (70%) of 41-2 as a white solid. MS (ES, m/z): [M+H]$^+$=600.40; $^1$H NMR (400 MHz, MeOH-d$_4$, ppm): δ 0.81-0.89 (m, 4H), 0.91 (s, 3H), 0.95-1.07 (m, 2H), 1.10 (s, 3H), 1.13-1.20 (m, 9H), 1.20-1.30 (m, 1H), 1.40 (s, 3H), 1.43-1.52 (m, 5H), 1.61-1.79 (m, 3H), 1.80-2.08 (m, 4H), 2.09-2.29 (m, 3H), 2.50 (s, 1H), 2.78 (dt, J=13.2, 3.2 Hz, 1H), 3.34 (s, 1H), 3.72 (s, 3H), 3.78 (dd, J=11.2, 4.8 Hz, 1H), 3.88 (dd, J=11.2, 4.8 Hz, 1H), 4.40-4.57 (m, 1H), 5.58 (s, 1H), 7.87 (d, J=7.7 Hz, 1H).

Example 24 (2S,4aS,6aS,6bR,8aS,10S,12aS,12bR,14bR)-10-((2-(2-(1H-imidazol-1-yl)ethoxy)-2-oxo-ethyl)carbamoyl)-2,4a,6a,6b,9,9,12a-heptamethyl-13-oxo-1,2,3,4,4a,5,6,6a,6b, 7,8,8a,9,10,11,12,12a, 12b,13,14b-icosahydropicene-2-carboxylic acid (44-2)

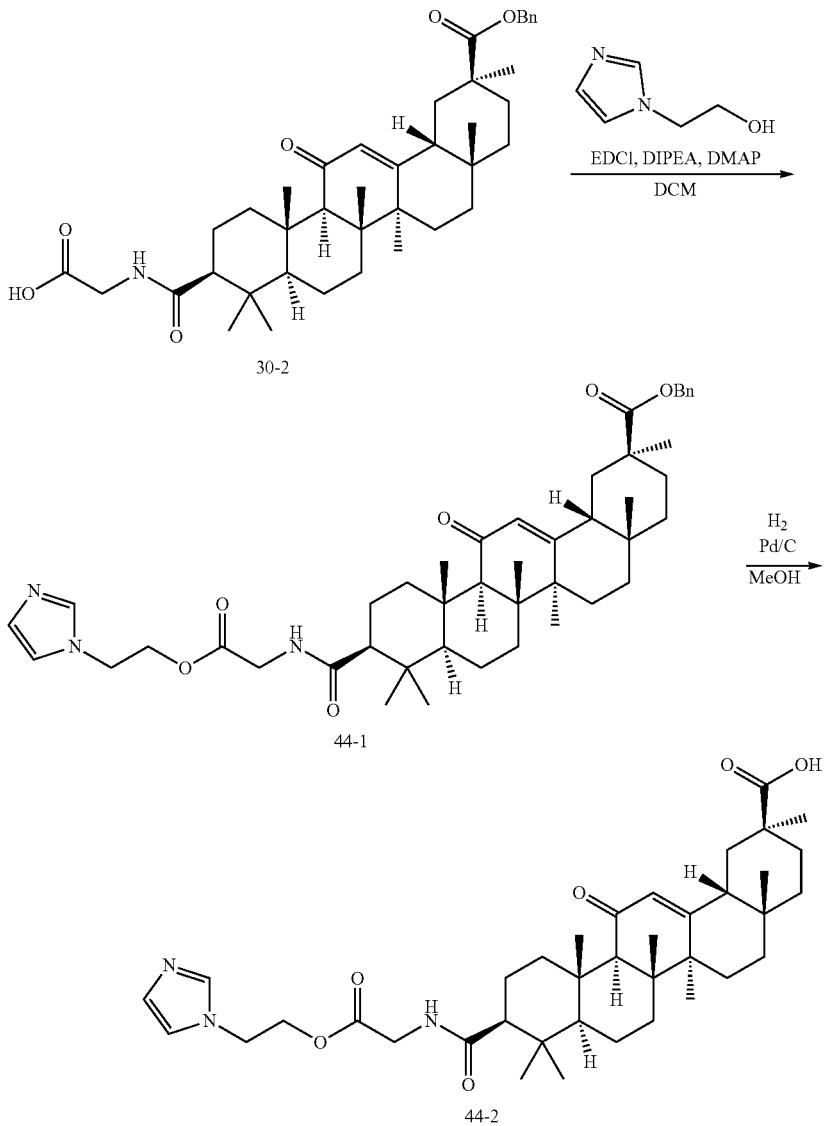

Synthesis of benzyl (2S,4aS,6aS,6bR,8aS,10S,12aS, 12bR,14bR)-10-((2-(2-(1H-Imidazol-1-yl)ethoxy)-2-oxo-ethyl)carbamoyl)-2,4a,6a,6b,9,9,12a-heptamethyl-13-oxo-1,2,3,4,4a,5,6,6a,6b, 7,8,8a,9,10,11,12,12a,12b,13,14b-icosahydropicene-2-carboxylate (44-1). Into a 100-mL round-bottom flask, was placed EDCI (53.4 mg, 0.28 mmol, 1.50 equiv.), DCM (15 mL), DMAP (113 mg, 0.92 mmol, 5.00 equiv.). The resulting solution was stirred for 1 h at room temperature. 30-2 (120 mg, 0.19 mmol, 1.00 equiv.) was added. The resulting solution was allowed to react, with stirring, for an additional 1 h at 55° C. 2-(1H-imidazol-1-yl)ethan-1-ol (83 mg, 0.74 mmol, 4.00 equiv.) was added. The resulting solution was allowed to react, with stirring, for an additional overnight at 55° C. The resulting mixture was concentrated under vacuum. The residue was applied onto a silica gel column with DCM/MeOH (9:1). This resulted in 85 mg (62%) of 44-1 as an off-white solid.

Synthesis of (2S,4aS,6aS,6bR,8aS,10S,12aS,12bR,14bR)-10-((2-(2-(1H-Imidazol-1-yl)ethoxy)-2-oxoethyl)carbamoyl)-2,4a,6a,6b,9,9,12a-heptamethyl-13-oxo-1,2,3,4,4a,5,6,6a,6b,7,8,8a,9,10,11,12,12a,12b,13,14b-icosahydropicene-2-carboxylic acid (44-2). Into a 100-mL round-bottom flask, was placed 44-1 (125 mg, 0.17 mmol, 1.00 equiv.), MeOH (20 mL), Pd/C (30 mg). To the above hydrogen (1 atm) was introduced in. The resulting solution was stirred overnight at room temperature. The resulting mixture was concentrated under vacuum. The solids were filtered out. The crude product was purified by Prep-HPLC with the following conditions: Column, XBridge Shield RP18 OBD Column, 5 um, 19*150 mm; mobile phase, water (0.05% TFA) and ACN (32.0% ACN up to 50.0% in 8 min); Detector, UV 254 nm. This resulted in 108.9 mg (99%) of 44-2 as a white solid. MS (ES, m/z): [M+H]$^+$=650.45; $^1$H NMR (400 MHz, MeOH-d$_4$, ppm): δ 0.84 (s, 3H), 0.85 (s, 1H), 0.91 (s, 3H), 0.94-0.99 (m, 1H), 1.04 (s, 3H), 1.05-1.07 (m, 1H), 1.15 (s, 3H), 1.17 (s, 3H), 1.19 (s, 3H), 1.26 (d, J=13.8 Hz, 1H), 1.37-1.48 (m, 9H), 1.66-1.75 (m, 3H), 1.83-2.19 (m, 7H), 2.49 (s, 1H), 2.78 (dt, J=13.4 Hz, 3.3 Hz, 1H), 3.87-3.91 (m, 2H), 4.51-4.55 (m, 4H), 5.58 (s, 1H), 7.56 (s, 1H), 7.69 (s, 1H), 8.20 (t, J=5.8 Hz, 1H), 8.98 (s, 1H).

Example 25 (2S,4aS,6aS,6bR,8aS,10S,12aS,12bR,14bR)-10-((2-(2-Hydroxyethoxy)-2-oxoethyl)carbamoyl)-2,4a,6a,6b,9,9,12a-heptamethyl-13-oxo-1,2,3,4,4a,5,6,6a,6b,7,8,8a 9,10,11,12,12a,12b,13,14b-icosahydropicene-2-carboxylic acid (45-2)

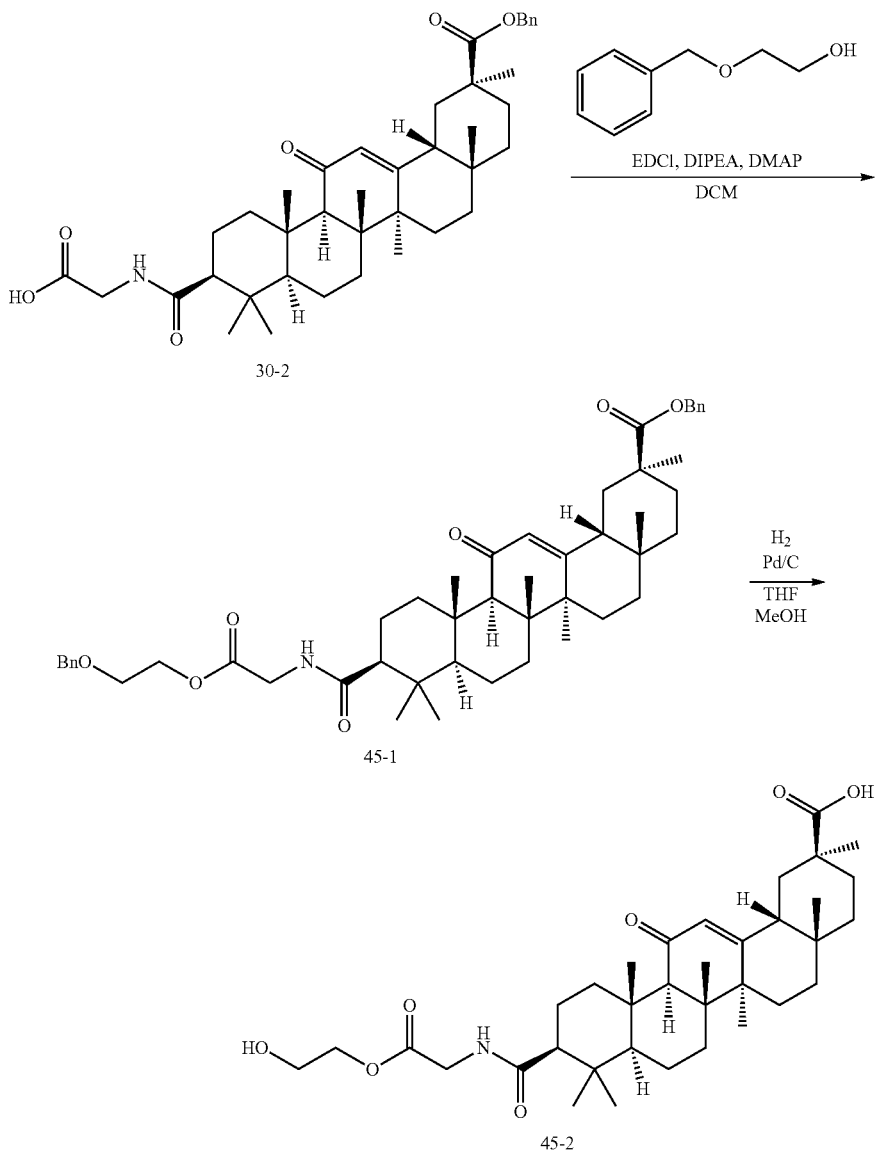

Synthesis of Benzyl (2S,4aS,6aS,6bR,8aS,10S,12aS,12bR,14bR)-10-((2-(2-(benzyloxy)ethoxy)-2-oxoethyl)carbamoyl)-2,4a,6a,6b,9,9,12a-heptamethyl-13-oxo-1,2,3,4,4a,5,6,6a,6b,7,8,8a, 9,10,11,12,12a,12b,13,14b-icosahydropicene-2-carboxylate (45-1). Into a 100-mL round-bottom flask, was placed EDCI (44 mg, 0.23 mmol, 1.50 equiv.), DCM (15 mL), DMAP (95 mg, 0.78 mmol, 5.00 equiv.). The resulting solution was stirred for 1 h at room temperature. 30-2 (100 mg, 0.15 mmol, 1.00 equiv.) was added. The resulting solution was allowed to react, with stirring, for an additional 1 h at 55° C. 2-(benzyloxy)ethan-1-ol (0.088 mL, 4.00 equiv.) was added. The resulting solution was allowed to react, with stirring, for an additional overnight at 55° C. The resulting mixture was concentrated under vacuum. The residue was applied onto a silica gel column with DCM/MeOH (9:1). This resulted in 95 mg (79%) of 45-1 as an off-white solid.

Synthesis of (2S,4aS,6aS,6bR,8aS,10S,12aS,12bR,14bR)-10-((2-(2-Hydroxyethoxy)-2-oxoethyl)carbamoyl)-2,4a,6a,6b,9,9,12a-heptamethyl-13-oxo-1,2,3,4,4a,5,6,6a,6b,7,8,8a,9,10, 11,12,12a,12b,13,14b-icosahydropicene-2-carboxylic acid (45-2). Into a 100-mL round-bottom flask, was placed 45-1 (120 mg, 0.15 mmol, 1.00 equiv.), THF (10 mL), MeOH (10 mL), Pd/C (30 mg). To the above hydrogen (1 atm) was introduced in. The resulting solution was stirred for 2 days at room temperature. The solids were filtered out. The resulting mixture was concentrated under vacuum. The crude product was purified by Prep-HPLC with the following conditions: Column, XBridge Shield RP18 OBD Column, 5 um, 19*150 mm; mobile phase, water (0.05% TFA) and ACN (42.0% ACN up to 61.0% in 8 min); Detector, UV 254 nm. This resulted in 58.8 mg (64%) of 45-2 as a white solid. MS (ES, m/z): $[M+H]^+ = 600.35$; $^1H$ NMR (300 MHz, MeOH-$d_4$ ppm): δ 0.83 (s, 3H), 0.86 (s, 1H), 0.92 (s, 3H), 0.96-1.01 (m, 2H), 1.07 (s, 3H), 1.15 (s, 3H), 1.17 (s, 3H), 1.19 (s, 3H), 1.25 (d, J=13.9 Hz, 1H), 1.40-1.52 (m, 9H), 1.71 (t, J=13.4 Hz, 3H), 1.81-2.03 (m, 4H), 2.07-2.24 (m, 3H), 2.50 (s, 1H), 2.79 (dt, J=13.2 Hz, 3.3 Hz, 1H), 3.71-3.74 (m, 2H), 3.88 (d, J=17.4 Hz, 1H), 3.99 (d, J=17.4 Hz, 1H), 4.17-4.20 (m, 2H), 5.58 (s, 1H).

Example 26 (2S,4aS,6aS,6bR,8aS,10S,12aS,12bR,14bR)-2,4a,6a,6b,9,9,12a-heptamethyl-10-((2-(2-morpholinoethoxy)-2-oxoethyl)carbamoyl)-13-oxo-1,2,3,4,4a,5,6,6a,6b,7,8,8a,9,10,11,12,12a,12b,13,14b-icosahydropicene-2-carboxylic acid (46-2)

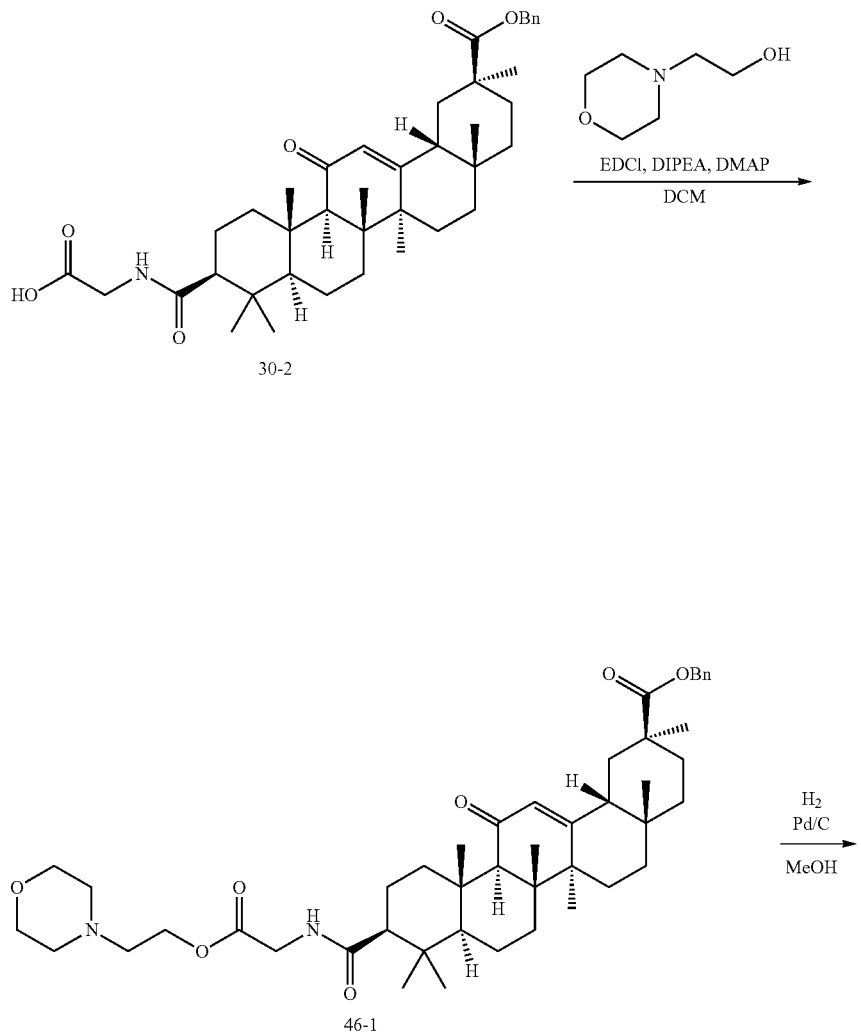

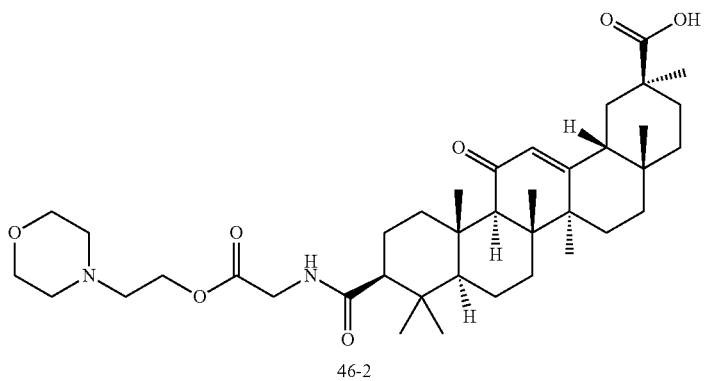

46-2

Synthesis of benzyl (2S,4aS,6aS,6bR,8aS,10S,12aS, 12bR,14bR)-2,4a,6a,6b,9,9,12a-heptamethyl-10-((2-(2-morpholinoethoxy)-2-oxoethyl)carbamoyl)-13-oxo-1,2,3,4, 4a,5,6,6a, 6b,7,8,8a,9,10,11,12,12a,12b,13,14b-icosahydropicene-2-carboxylate (46-1). Into a 100-mL round-bottom flask, was placed EDCI (53.4 mg, 0.28 mmol, 1.50 equiv.), DCM (15 mL), DMAP (226 mg, 1.85 mmol, 10.00 equiv.). The resulting solution was stirred for 1 h at room temperature. 30-2 (120 mg, 0.19 mmol, 1.00 equiv.) was added. The resulting solution was allowed to react, with stirring, for an additional 1 h at 55° C. 2-(morpholin-4-yl) ethan-1-ol (0.09 mL, 4.00 equiv.) was added. The resulting solution was allowed to react, with stirring, for an additional 2 days at 55° C. The resulting mixture was concentrated under vacuum. The residue was applied onto a silica gel column with DCM/MeOH (9:1). This resulted in 125 mg (89%) of 46-1 as an off-white solid.

Synthesis of (2S,4aS,6aS,6bR,8aS,10S,12aS,12bR, 14bR)-2,4a,6a,6b,9,9,12a-heptamethyl-10-((2-(2-morpholinoethoxy)-2-oxoethyl)carbamoyl)-13-oxo-1,2,3,4,4a,5,6,6a, 6b,7,8,8a,9,10,11,12, 12a,12b,13,14b-icosahydropicene-2-carboxylic acid (46-2). Into a 100-mL round-bottom flask, was placed 46-1 (160 mg, 0.21 mmol, 1.00 equiv.), MeOH (15 mL), Pd/C (30 mg). To the above hydrogen was introduced (1 atm) in. The resulting solution was stirred for 1 h at room temperature. The solids were filtered out. The crude product was purified by Prep-HPLC with the following conditions: Column, XBridge Shield RP18 OBD Column, 5 um, 19*150 mm; mobile phase, water (0.05% TFA) and ACN (32.0% ACN up to 50.0% in 8 min); Detector, UV 254 nm. This resulted in 77.2 mg (55%) of 46-2 as a white solid. MS (ES, m/z): [M+H]$^+$=669.45; $^1$H NMR (300 MHz, MeOH-d$_4$, ppm) δ 0.87 (s, 3H), 0.92 (s, 1H), 0.96 (s, 3H), 1.02-1.07 (m, 2H), 1.09 (s, 3H), 1.16 (s, 3H), 1.17 (s, 3H), 1.19 (s, 3H), 1.29 (d, J=14.3 Hz, 1H), 1.40-1.56 (m, 10H), 1.73 (t, J=13.5 Hz, 3H), 1.82-2.10 (m, 4H), 2.14-2.29 (m, 3H), 2.50 (s, 1H), 2.80 (dt, J=13.3 Hz, 3.3 Hz, 1H), 3.53 (t, J=5.0 Hz, 4H), 3.72-4.20 (m, 6H), 4.53 (q, J=4.6 Hz, 2H), 5.58 (s, 1H).

Example 27 (2S,4aS,6aS,6bR,8aS,10S,12aS,12bR, 14bR)-2,4a,6a,6b,9,9,12a-Heptamethyl-13-oxo-10-(((pivaloyloxy)methoxy)carbonyl)-1,2,3,4,4a,5,6,6a, 6b,7,8,8a,9,10,11,12,12a,12b, 13,14b-icosahydropicene-2-carboxylic acid (47-2)

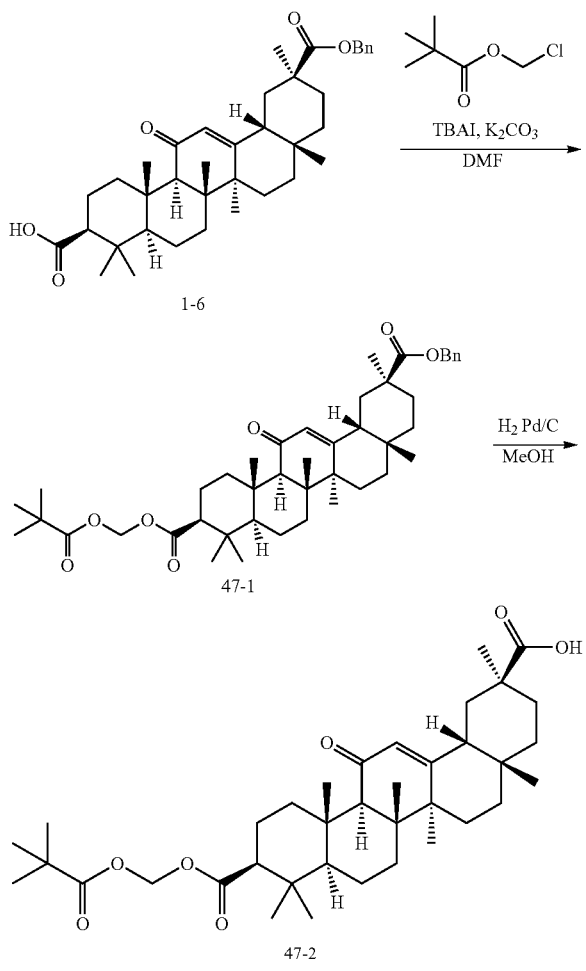

Synthesis of 2-Benzyl 10-((pivaloyloxy)methyl) (2S,4aS, 6aS,6bR,8aS,10S,12aS,12bR,14bR)-2,4a,6a,6b,9,9,12a-heptamethyl-13-oxo-1,2,3,4,4a,5,6,6a,6b,7,8,8a,9,10,11,12, 12a,12b,13,14b-icosahydropicene-2,10-dicarboxylate (47-1). Into a 100-mL round-bottom flask, was placed 1-6 (100 mg, 0.17 mmol, 1 equiv.), DMF (5 mL, 0.07 mmol), chloromethyl 2,2-dimethylpropanoate (30 mg, 0.20 mmol, 1.173 equiv.), TBAI (30 mg, 0.08 mmol, 0.478 equiv.), $K_2CO_3$ (28 mg, 0.20 mmol, 1.193 equiv.). The resulting solution was stirred for 2 hr at 65° C. The resulting solution was diluted with 30 mL of DCM. The resulting mixture was washed with 2×15 mL of brine. The mixture was dried over anhydrous sodium sulfate. The solids were filtered out. The resulting mixture was concentrated. The residue was applied onto a silica gel column with EtOAc/petroleum ether (1:3). This resulted in 65 mg (54.45%) of 47-1 as yellow oil.

Synthesis of (2S,4aS,6aS,6bR,8aS,10S,12aS,12bR, 14bR)-2,4a,6a,6b,9,9,12a-Heptamethyl-13-oxo-10-(((pivaloyloxy)methoxy)carbonyl)-1,2,3,4,4a,5,6,6a,6b,7,8,8a,9, 10,11,12,12a,12b,13, 14b-icosahydropicene-2-carboxylic acid (47-2). Into a 100-mL round-bottom flask purged and maintained with an inert atmosphere of $H_2$ (1 atm), was placed 47-1 (300 mg, 0.43 mmol, 1 equiv.), MeOH (10 mL, 0.31 mmol, 0.733 equiv.), Pd/C (30 mg, 0.662 equiv.). The resulting solution was stirred for 1 hr at room temperature. The solids were filtered out. The crude product was purified by Prep-HPLC with the following conditions: Column, XBridge Shield RP18 OBD Column, 5 um, 19*150 mm; mobile phase, water (0.05% TFA) and ACN (5% Phase B up to 80% in 1 min, up to 95% in 7 min); Detector, UV 254 nm. This resulted in 47.6 mg (18.25%) of 47-2 as a white solid. MS (ES, m/z): $[M+H]^+$=613.46; $^1H$ NMR (400 MHz, MeOH-$d_4$, ppm): δ 0.83-0.89 (m, 7H), 1.00-1.06 (m, 5H), 1.15-1.19 (m, 18H), 1.22-1.29 (m, 3H), 1.40-1.51 (m, 8H), 1.65-1.68 (m, 3H), 1.82-1.98 (m, 3H), 2.14-2.29 (m, 3H), 2.50 (s, 1H), 2.77 (d, J=13.6 Hz, 1H), 5.58 (s, 1H), 5.69 (d, J=5.6 Hz, 1H), 5.78 (d, J=5.6 Hz, 1H).

Example 28 (2S,4aS,6aS,6bR,8aS,10S,12aS,12bR, 14bR)-10-((((isopropoxycarbonyl) oxy)methoxy) carbonyl)-2,4a,6a,6b,9,9,12a-heptamethyl-13-oxo-1, 2,3,4,4a,5,6,6a,6b,7,8,8a, 9,10,11,12,12a,12b,13, 14b-icosahydropicene-2-carboxylic acid (48-2)

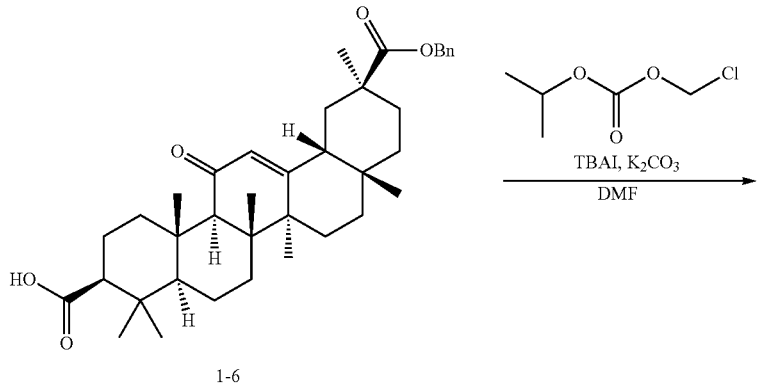

1-6

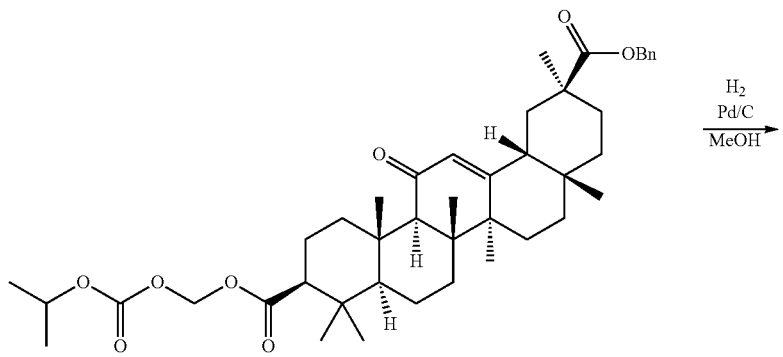

48-1

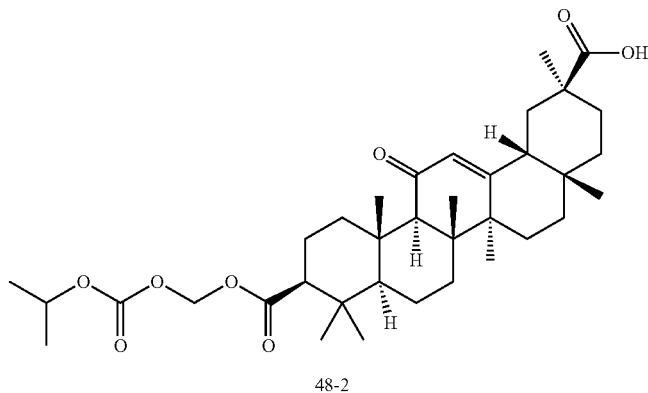

48-2

Synthesis of 2-benzyl 10-(((isopropoxycarbonyl)oxy) methyl) (2S,4aS,6aS,6bR,8aS,10S, 12aS,12bR,14bR)-2,4a, 6a,6b,9,9,12a-heptamethyl-13-oxo-1,2,3,4,4a,5,6,6a,6b,7,8, 8a,9,10,11, 12,12a,12b,13,14b-icosahydropicene-2,10-dicarboxylate (48-1). Into a 100-mL round-bottom flask, was placed 1-6 (300 mg, 0.51 mmol, 1 equiv.), DMF (5 mg, 0.07 mmol, 0.134 equiv.), chloromethyl propan-2-yl carbonate (93 mg, 0.61 mmol, 1.196 equiv.), K₂CO₃ (84 mg, 0.61 mmol, 1.193 equiv.), TBAI (90 mg, 0.24 mmol, 0.478 equiv.). The resulting solution was stirred for 2 hr at 65° C. The resulting solution was diluted with 50 mL of DCM. The resulting mixture was washed with 2×25 mL of brine. The mixture was dried over anhydrous sodium sulfate. The solids were filtered out. The resulting mixture was concentrated. The residue was applied onto a silica gel column with EtOAc/petroleum ether (1:3). This resulted in 200 mg (55.69%) of 48-1 as a white solid.

Synthesis of (2S,4aS,6aS,6bR,8aS,10S,12aS,12bR, 14bR)-10-((((isopropoxycarbonyl)oxy) methoxy)carbonyl)-2,4a,6a,6b,9,9,12a-heptamethyl-13-oxo-1,2,3,4,4a,5,6,6a, 6b,7,8,8a,9,10,11, 12,12a,12b,13,14b-icosahydropicene-2-carboxylic acid (48-2). Into a 100-mL round-bottom flask purged and maintained with an inert atmosphere of H₂ (1 atm), was placed 48-1 (300 mg, 0.43 mmol, 1 equiv.), MeOH (10 mL, 0.31 mmol, 0.733 equiv.), Pd/C (30 mg, 0.662 equiv.).

The resulting solution was stirred for 1 hr at room temperature. The solids were filtered out. The crude product was purified by Prep-HPLC with the following conditions: Column, XBridge Shield RP18 OBD Column, 5 um, 19*150 mm; mobile phase, water (0.05% TFA) and ACN (5% Phase B up to 74% in 1 min, up to 88% in 7 min); Detector, UV 254 nm. This resulted in 148.2 mg (56.64%) of 48-2 as a white solid. MS (ES, m/z): [M+H]⁺=615.40; ¹H NMR (400 MHz, MeOH-d₄, ppm): δ 0.83-0.89 (m, 7H), 0.97-1.06 (m, 5H), 1.13-1.23 (m, 16H), 1.40-1.53 (m, 9H), 1.66-2.03 (m, 7H), 2.11-2.30 (m, 3H), 2.50 (s, 1H), 2.77 (d, J=13.2 Hz, 1H), 4.84-4.90 (m, 1H), 5.58 (s, 1H), 5.68 (d, J=5.6 Hz, 1H), 5.75 (d, J=5.6 Hz, 1H).

Example 29 (2S,4aS,6aS,6bR,8aS,10S,12aS,12bR, 14bR)-10-(((S)-1-((isopropoxycarbonyl) oxy) ethoxy)carbonyl)-2,4a,6a,6b,9,9,12a-heptamethyl-13-oxo-1,2,3,4,4a,5,6,6a,6b,7,8,8a,9,10, 11,12,12a, 12b,13,14b-icosahydropicene-2-carboxylic acid (49-2)

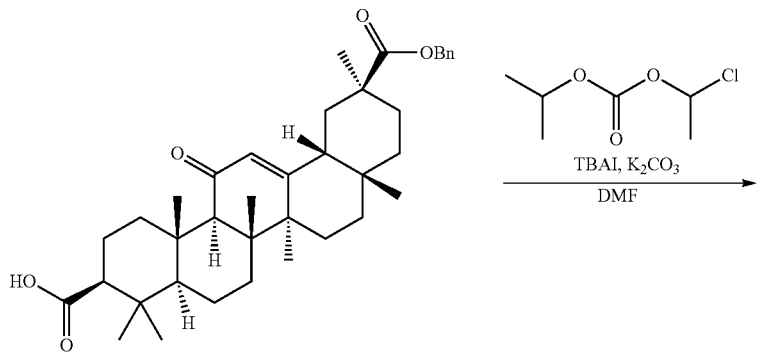

1-6

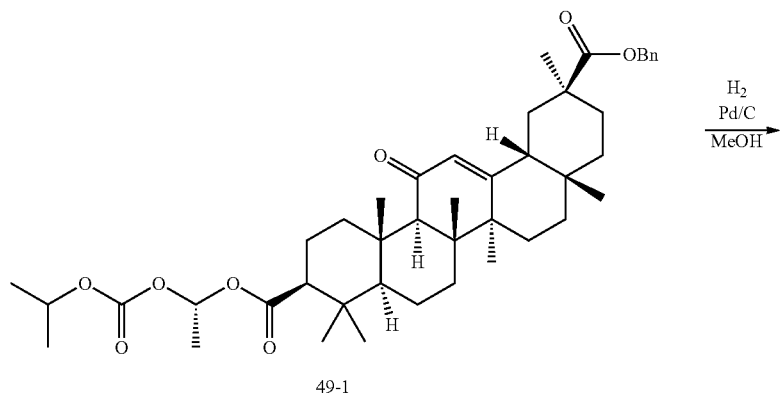

49-1

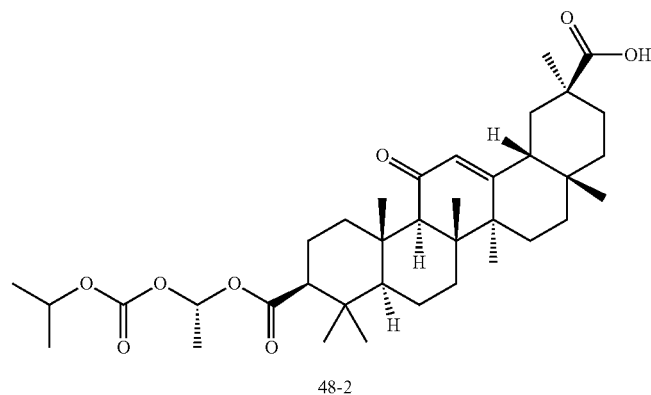

48-2

Synthesis of 2-Benzyl 10-(1-((isopropoxycarbonyl)oxy) ethyl) (2S,4aS,6aS,6bR,8aS,10S,12aS, 12bR,14bR)-2,4a,6a, 6b,9,9,12a-heptamethyl-13-oxo-1,2,3,4,4a,5,6,6a,6b,7,8,8a, 9,10,11,12,12a, 12b,13,14b-icosahydropicene-2,10-dicarboxylate (49-1). Into a 100-mL round-bottom flask, was placed 1-6 (400 mg, 0.68 mmol, 1.00 equiv.), 1-chloroethyl propan-2-yl carbonate (135.8 mg, 0.82 mmol, 1.20 equiv.), TBAI (125 mg, 0.89 mmol, 0.50 equiv.), potassium methaneperoxoate (112 mg, 0.80 mmol, 1.20 equiv.), DMF (15 mL). The resulting solution was stirred for 2 h at room temperature. The resulting solution was extracted with 3×150 mL of DCM and the organic layers combined. The resulting mixture was washed with 2×250 mL of brine. The mixture was dried over anhydrous sodium sulfate and concentrated under vacuum. The residue was applied onto a silica gel column with EtOAc/petroleum ether (1:3). This resulted in 450 mg of mixed stereoisomers. Further purification by prep-SFC, and collection of the faster eluting peak provided 180 mg of 49-1.

Synthesis of (2S,4aS,6aS,6bR,8aS,10S,12aS,12bR, 14bR)-10-(((S)-1-((isopropoxycarbonyl)oxy) ethoxy)carbonyl)-2,4a,6a,6b,9,9,12a-Heptamethyl-13-oxo-1,2,3,4,4a,5,6, 6a,6b,7,8,8a,9,10,11, 12,12a,12b,13,14b-icosahydropicene-2-carboxylic acid (49-2). Into a 100-mL round-bottom flask, was placed 49-1, Pd/C (40 mg), MeOH (20 mL), hydrogen (1 atm) was introduced in. The resulting solution was stirred overnight at room temperature. The solids were filtered out. The resulting mixture was concentrated under vacuum. The crude product was purified by Prep-HPLC with the following conditions: mobile phase, water (0.05% TFA) and ACN (5.0% ACN up to 80.0% in 1 min, up to 90.0% in 7 min); Detector, UV 254 nm. This resulted in 87.6 mg (56%) of 49-2. MS (ES, m/z): [M+H]$^+$=629.4; $^1$H NMR (400 MHz, MeOH-$d_4$, ppm): δ 0.82 (s, 4H), 0.91 (s, 3H), 0.96-1.11 (m, 5H), 1.15-1.28 (m, 9H), 1.28-1.36 (m, 7H), 1.33-1.58 (m, 12H), 1.71-1.82 (m, 3H), 1.82-2.02 (m, 2H), 2.10-2.25 (m, 3H), 2.53 (s, 1H), 2.80 (dt, J=13.6, 3.6 Hz, 1H), 4.89 (d, J=6.4 Hz, 1H), 5.60 (s, 1H), 6.73 (q, J=5.4 Hz, 1H).

Example 30 (2S,4aS,6aS,6bR,8aS,10S,12aS,12bR,14bR)-10-(((R)-1-((Isopropoxycarbonyl) oxy) ethoxy)carbonyl)-2,4a,6a,6b,9,9,12a-heptamethyl-13-oxo-1,2,3,4,4a,5,6,6a,6b,7,8,8a,9, 10,11,12,12a,12b,13,14b-icosahydropicene-2-carboxylicacid (50-2)

6,6a,6b,7,8,8a,9,10,11,12, 12a,12b,13,14b-icosahydropicene-2-carboxylic acid (50-2). Into a 100-mL round-bottom flask, was placed 50-1 (150 mg, 0.21 mmol, 1.00 equiv.), Pd/C (40 mg), MeOH (20 mL), H$_2$ (1 atm) was introduced in. The resulting solution was stirred overnight at room temperature. The solids were filtered out. The crude product was purified by Prep-HPLC with the following

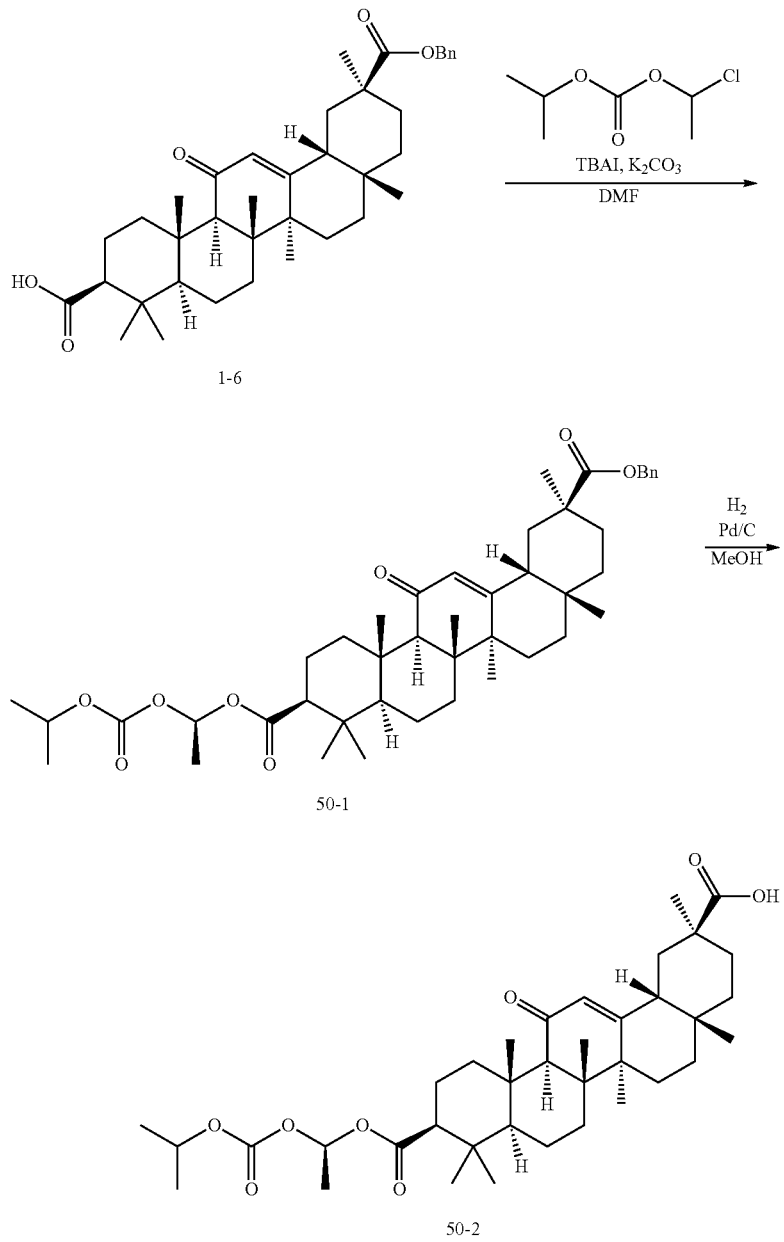

Synthesis of 2-Benzyl 10-((R)-1-((isopropoxycarbonyl) oxy)ethyl) (2S,4aS,6aS,6bR,8aS,10S, 12aS,12bR,14bR)-2,4a,6a,6b,9,9,12a-heptamethyl-13-oxo-1,2,3,4,4a,5,6,6a,6b,7,8,8a,9,10,11, 12,12a,12b,13,14b-icosahydropicene-2,10-dicarboxylate (50-1). Collection of the slower eluting peak in the purification of 49-1 provided 150 mg of 50-1.

Synthesis of (2S,4aS,6aS,6bR,8aS,10S,12aS,12bR,14bR)-10-(((R)-1-((Isopropoxycarbonyl)oxy) ethoxy)carbonyl)-2,4a,6a,6b,9,9,12a-heptamethyl-13-oxo-1,2,3,4,4a,5, conditions; mobile phase, water (0.05% TFA) and ACN (5.0% ACN up to 80.0% in 1 min, up to 90.0% in 7 min); Detector, UV 254 nm. This resulted in 79 mg (60%) of 50-2 as a white solid. MS (ES, m/z): [M+H]$^+$=629.93; $^1$H NMR (400 MHz, MeOH-d$_4$, ppm): δ 0.78-0.93 (m, 7H), 0.95-1.15 (m, 5H), 1.15-1.21 (m, 9H), 1.21-1.33 (m, 7H), 1.33-1.56 (m, 12H), 1.60-1.80 (m, 3H), 1.83-2.02 (m, 4H), 2.06-2.25 (m, 3H), 2.52 (s, 1H), 2.79 (dt, J=13.4, 3.6 Hz, 1H), 4.86 (d, J=1.8 Hz, 1H), 5.60 (s, 1H), 6.75 (q, J=5.4 Hz, 1H).

Example 31 (2S,4aS,6aS,6bR,8aS,10S,12aS,12bR, 14bR)-10-((2-(Diethylamino)-2-oxoethoxy)carbonyl)-2,4a,6a,6b,9,9,12a-heptamethyl-13-oxo-1,2,3,4, 4a,5,6,6a,6b,7,8,8a,9,10, 11,12,12a,12b,13,14b-icosahydropicene-2-carboxylic acid (51-2)

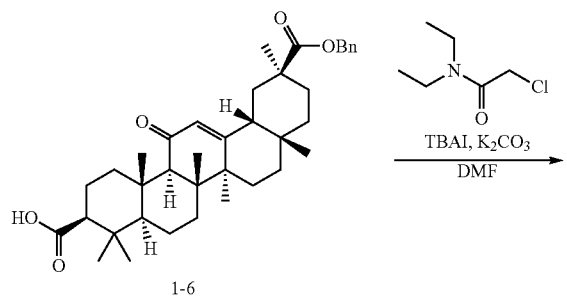

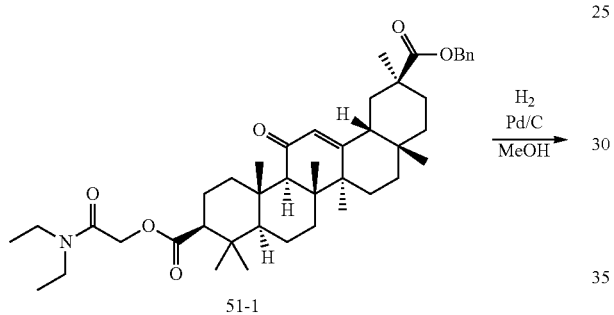

Synthesis of 2-Benzyl 10-(2-(diethylamino)-2-oxoethyl) (2S,4aS,6aS,6bR,8aS, 10S,12aS,12bR,14bR)-2,4a,6a,6b,9, 9,12a-heptamethyl-13-oxo-1,2,3,4,4a,5,6,6a,6b,7,8,8a,9, 10,11,12,12a,12b,13,14b-icosahydropicene-2,10-dicarboxylate (51-1). Into a 100-mL round-bottom flask, was placed 1-6 (589 mg, 1.00 mmol, 1 equiv.), DMF (10 mg, 0.14 mmol), TBAI (185 mg, 0.501 equiv.), K₂CO₃ (165 mg, 1.19 mmol, 1.194 equiv.), 2-chloro-N, N-diethylacetamide (180 mg, 1.20 mmol, 1.203 equiv.). The resulting solution was stirred for 2 hr at 65° C. The resulting mixture was concentrated. The residue was applied onto a silica gel column with EtOAc/petroleum ether (1:3). This resulted in 600 mg (85.45%) of 51-1 as a white solid.

Synthesis of (2S,4aS,6aS,6bR,8aS,10S,12aS,12bR, 14bR)-10-((2-(Diethylamino)-2-oxoethoxy) carbonyl)-2,4a, 6a,6b,9,9,12a-heptamethyl-13-oxo-1,2,3,4,4a,5,6,6a,6b,7,8, 8a,9,10,11,12,12a, 12b,13,14b-icosahydropicene-2-carboxylic acid (51-2). Into a 100-mL round-bottom flask purged and maintained with an inert atmosphere of H₂ (1 atm), was placed 51-1 (200 mg, 0.28 mmol, 1 equiv.), MeOH (10 mL, 0.31 mmol), Pd/C (30 mg, 0.1 equiv.). The resulting solution was stirred for 1 overnight at room temperature. The solids were filtered out. The crude product was purified by Prep-HPLC with the following conditions: Column, XBridge Shield RP18 OBD Column, 5 um, 19*150 mm; mobile phase, water (0.05% TFA) and ACN (5% Phase B up to 66% in 1 min, up to 80% in 7 min); Detector, UV 254 nm. This resulted in 91.4 mg (52.43%) of 51-2 as a white solid. MS (ES, m/z): [M+H]⁺=612.55; ¹H NMR (400 MHz, MeOH-d₄, ppm): δ 0.84-0.98 (m, 4H), 0.93-1.01 (m, 3H), 1.04-1.10 (m, 2H), 1.10-1.18 (m, 15H), 1.21-1.27 (m, 4H), 1.38-1.48 (m, 8H), 1.57-1.60 (m, 1H), 1.61-1.75 (m, 3H), 1.76-2.03 (m, 4H), 2.15-2.19 (m, 2H), 2.34 (d, J=13.2 Hz, 1H), 2.51 (s, 1H), 2.77 (d, J=13.2 Hz, 1H), 3.30-3.40 (m, 4H), 4.76 (s, 2H), 5.58 (s, 1H).

Example 32 (2S,4aS,6aS,6bR,8aS,10S,12aS,12bR, 14bR)-2,4a,6a,6b,9,9,12a-Heptamethyl-10-((2-morpholino-2-oxoethoxy)carbonyl)-13-oxo-1,2,3,4,4a,5, 6,6a,6b,7,8,8a,9,10,11,12,12a,12b, 13,14b-icosahydropicene-2-carboxylicacid (52-2)

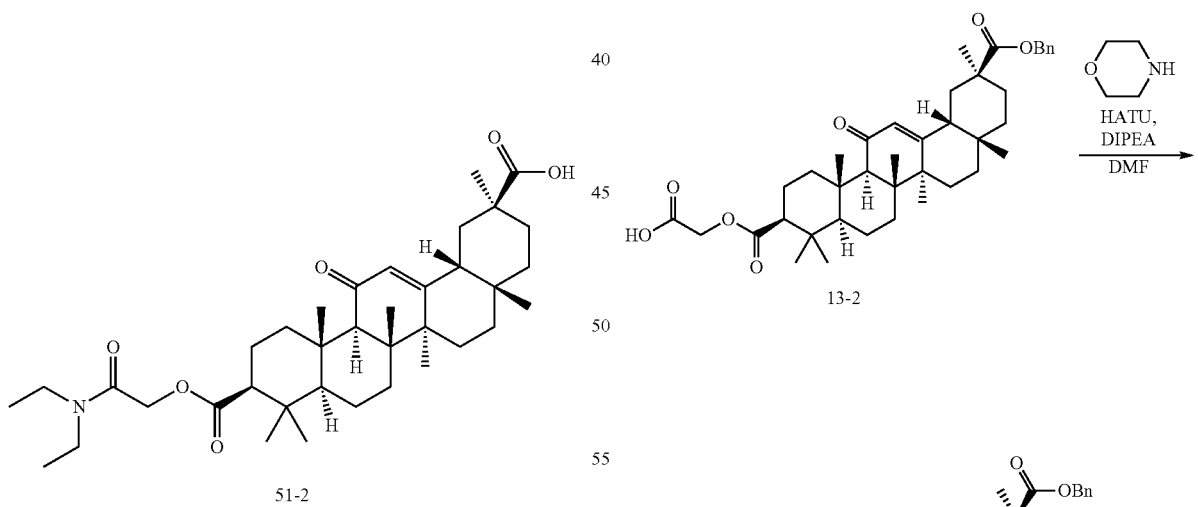

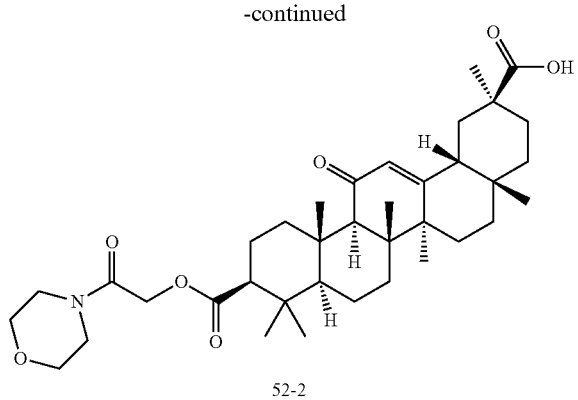

52-2

Synthesis of 2-Benzyl 10-(2-morpholino-2-oxoethyl) (2S, 4aS,6aS,6bR,8aS,10S,12aS,12bR, 14bR)-2,4a,6a,6b,9,9, 12a-heptamethyl-13-oxo-1,2,3,4,4a,5,6,6a,6b,7,8,8a,9,10, 11,12,12a,12b, 13,14b-icosahydropicene-2,10-dicarboxylate (52-1). Into a 100-mL round-bottom flask, was placed 13-2 (150 mg, 0.23 mmol, 1 equiv.), DMF (15 mL), HATU (0.2 g, 0.47 mmol, 2.041 equiv.), morpholine (0.06 mL, 3 equiv.), DIPEA (0.08 mL, 0.48 mmol, 2.087 equiv.). The resulting solution was stirred for 2 hr at room temperature. The resulting solution was extracted with 500 mL of DCM. The resulting mixture was washed with 1×500 mL of water. The resulting mixture was washed with 1×500 mL of brine. The mixture was dried over anhydrous sodium sulfate. The solids were filtered out. This resulted in 200 mg (120.46%, crude) of 52-1 as a white solid.

Synthesis of (2S,4aS,6aS,6bR,8aS,10S,12aS,12bR, 14bR)-2,4a,6a,6b,9,9,12a-Heptamethyl-10-((2-morpholino-2-oxoethoxy)carbonyl)-13-oxo-1,2,3,4,4a,5,6,6a,6b,7,8,8a, 9,10,11,12,12a,12b, 13,14b-icosahydropicene-2-carboxylic acid (52-2). Into a 100-mL round-bottom flask, was placed 52-1 (200 mg, 0.28 mmol, 1 equiv.), EA (16 mL), Pd/C (5.9 mg, 0.06 mmol, 0.198 equiv.). To the above $H_2$ (g) was introduced in. The resulting solution was stirred overnight at room temperature. The solids were filtered out. The resulting mixture was concentrated. The crude product was purified by Prep-HPLC with the following conditions: Column, XBridge Prep OBD C18 Column, 19*250 mm, 5 um; mobile phase, water (0.05% TFA) and ACN (5% Phase B up to 60% in 2 min, up to 75% in 8 min); Detector, UV. This resulted in 56.7 mg (32.43%) of 52-2 as a white solid. MS (ES, m/z): $[M+H]^+$=626.45; $^1$H NMR (300 MHz, MeOH-$d_4$, ppm): 0.85 (s, 3H), 0.89-1.00 (m, 4H), 1.02-1.31 (m, 15H), 1.33-1.52 (m, 8H), 1.52-1.64 (m, 1H), 1.63-1.80 (m, 3H), 1.81-2.08 (m, 4H), 2.09-2.27 (m, 2H), 2.28-2.42 (m, 1H), 2.52 (s, 1H), 2.72-2.88 (m, 1H), 3.42-3.61 (m, 4H), 3.62-3.78 (m, 4H), 4.80-4.86 (m, 2H), 5.58 (s, 1H).

Example 33 (2S,4aS,6aS,6bR,8aS,10S,12aS,12bR, 14bR)-2,4a,6a,6b,9,9,12a-heptamethyl-10-((2-(4-methylpiperazin-1-yl)-2-oxoethoxy)carbonyl)-13-oxo-1,2,3,4,4a,5,6,6a,6b,7,8,8a,9,10, 11,12,12a,12b, 13,14b-icosahydropicene-2-carboxylic acid (53-2)

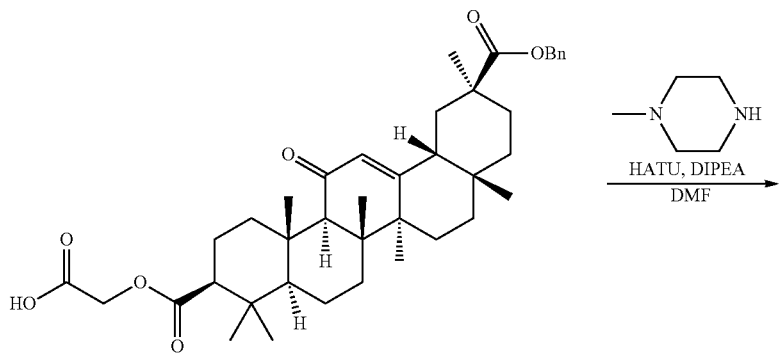

13-2

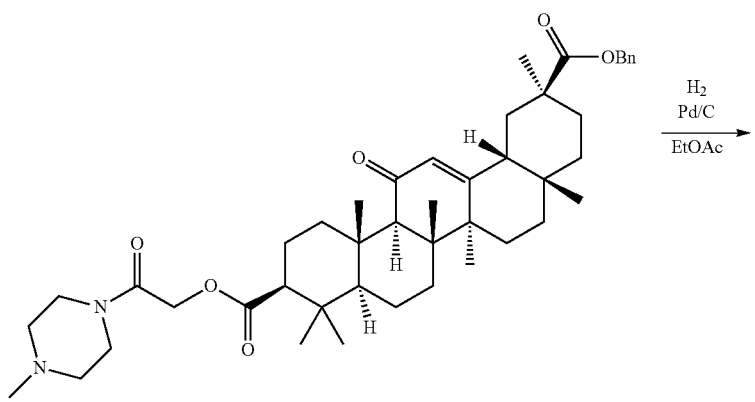

53-1

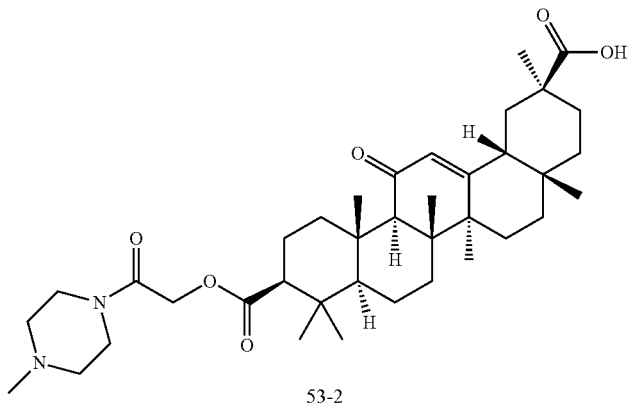

53-2

Synthesis of 2-Benzyl 10-(2-(4-methylpiperazin-1-yl)-2-oxoethyl) (2S,4aS,6aS,6bR,8aS,10S, 12aS,12bR,14bR)-2, 4a,6a,6b,9,9,12a-heptamethyl-13-oxo-1,2,3,4,4a,5,6,6a,6b, 7,8,8a,9,10, 11,12,12a,12b,13,14b-icosahydropicene-2,10-dicarboxylate (53-1). Into a 100-mL round-bottom flask, was placed 13-2 (150 mg, 0.23 mmol, 1 equiv.), DMF (15 mL), HATU (180 mg, 0.47 mmol, 2.041 equiv.), 1-methylpiperazine (0.077 mL, 3 equiv.), DIPEA (0.08 mL, 0.48 mmol, 2.087 equiv.). The resulting solution was stirred for 2 hr at room temperature. The resulting solution was extracted with 200 mL of DCM. The resulting mixture was washed with 1×200 mL of water. The resulting mixture was washed with 1×200 mL of brine. The mixture was dried over anhydrous sodium sulfate. The solids were filtered out. This resulted in 150 mg (88.73%) of 53-1 as a white semi-solid.

Synthesis of (2S,4aS,6aS,6bR,8aS,10S,12aS,12bR, 14bR)-2,4a,6a,6b,9,9,12a-Heptamethyl-10-((2-(4-methylpiperazin-1-yl)-2-oxoethoxy)carbonyl)-13-oxo-1,2,3,4, 4a,5,6,6a,6b,7,8,8a,9,10,11, 12,12a,12b,13,14b-icosahydropicene-2-carboxylic acid (53-2). Into a 100-mL round-bottom flask, was placed 53-1 (150 mg, 0.21 mmol, 1 equiv.), EA (16 mL), Pd/C (4.4 mg, 0.201 equiv.).

To the above H$_2$ (g) was introduced in. The resulting solution was stirred overnight at room temperature. The solids were filtered out. The resulting mixture was concentrated. The crude product was purified by Prep-HPLC with the following conditions: Column, XBridge Prep OBD C18 Column, 19*250 mm, 5 um; mobile phase, water (0.05% TFA) and ACN (41% Phase B up to 59% in 8 min); Detector, UV 254 nm. This resulted in 85.8 mg (65.27%) of 53-2 as a white solid. MS (ES, m/z): [M+H]$^+$=639.45; $^1$H NMR (300 MHz, MeOH-d$_4$, ppm): 0.79-1.00 (m, 8H), 1.02-1.15 (m, 5H), 1.15-1.22 (m, 9H), 1.23-1.35 (m, 2H), 1.36-1.51 (m, 8H), 1.52-1.64 (m, 2H), 1.73 (t, J=13.5 Hz, 3H), 1.80-2.27 (m, 7H), 2.32-2.46 (m, 1H), 2.52 (s, 1H), 2.70-2.88 (m, 1H), 2.95 (s, 3H), 3.20-3.28 (m, 1H), 3.34-3.47 (m, 2H), 3.52-4.09 (m, 3H), 5.58 (s, 1H).

Example 34 (2S,4aS,6aS,6bR,8aR,10S,12aS,12bR, 14bR)-10-((2-Methoxy-2-oxoethyl) amino)-2,4a,6a, 6b,9,9,12a-heptamethyl-13-oxo-1,2,3,4,4a,5,6,6a,6b, 7,8,8a,9,10,11,12,12a,12b, 13,14b-icosahydropicene-2-carboxylicacid (54-2)

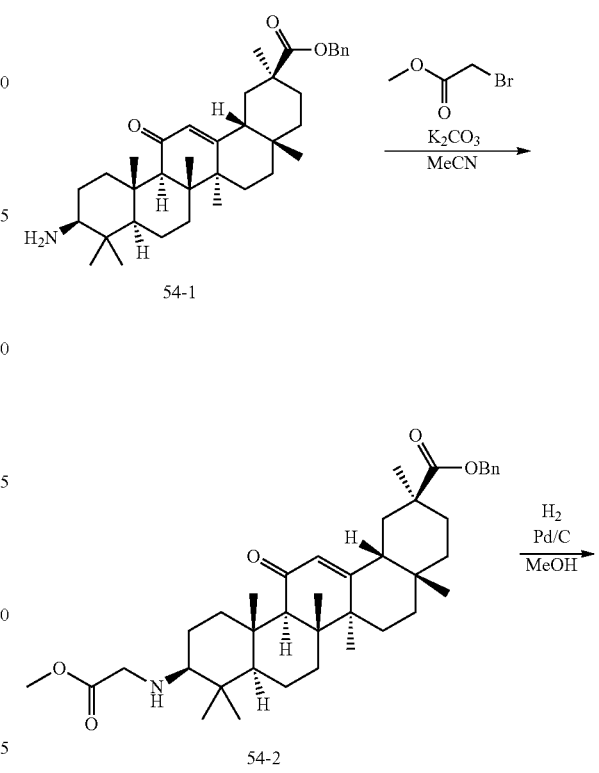

Example 35 (2S,4aS,6aS,6bR,8aR,10S,12aS,12bR, 14bR)-10-(bis(2-Methoxy-2-oxoethyl) amino)-2,4a, 6a,6b,9,9,12a-heptamethyl-13-oxo-1,2,3,4,4a,5,6,6a, 6b,7,8,8a,9,10,11,12,12a,12b, 13,14b-icosahydropicene-2-carboxylicacid (56-2)

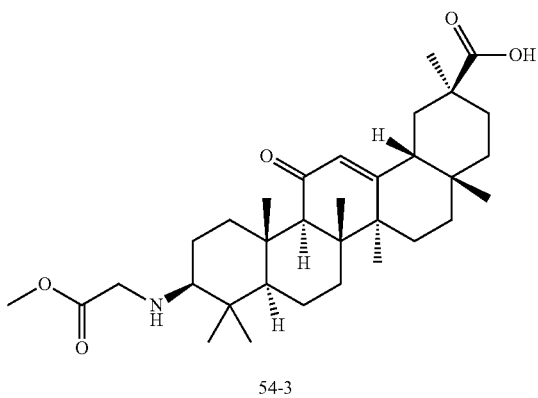

54-3

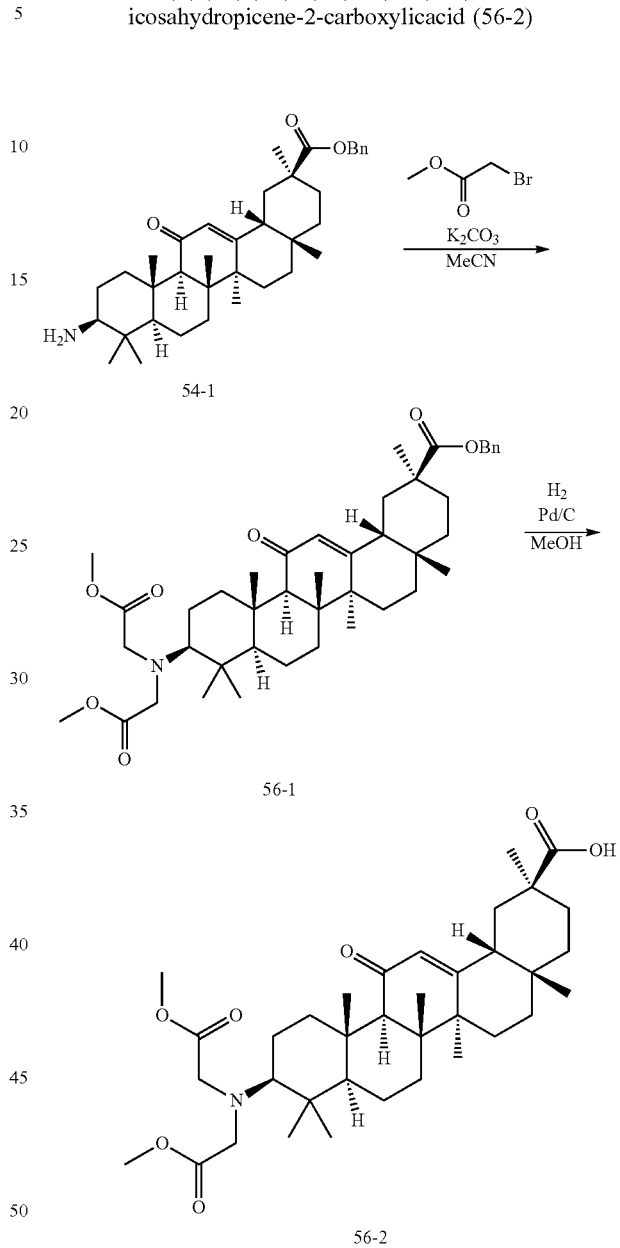

Synthesis of Benzyl (2S,4aS,6aS,6bR,8aR,10S,12aS, 12bR,14bR)-10-((2-methoxy-2-oxoethyl) amino)-2,4a,6a, 6b,9,9,12a-heptamethyl-13-oxo-1,2,3,4,4a,5,6,6a,6b,7,8,8a, 9,10,11,12,12a,12b, 13,14b-icosahydropicene-2-carboxylate (54-2). Into a 50-mL round-bottom flask, was placed 54-1 (prepared following the method described in *Bioorg. Med. Chem.* 2010, 18, 433-454)(100 mg, 0.18 mmol, 1.00 equiv.), $CH_3CN$ (5 mL), methyl 2-bromoacetate (55 mg, 0.36 mmol, 2.00 equiv.), potassium carbonate (74 mg, 0.54 mmol, 3.00 equiv.). The resulting solution was stirred overnight at 60° C. The resulting solution was extracted with 3×20 mL of EtOAc and the organic layers combined and dried over anhydrous sodium sulfate and concentrated under vacuum. The residue was applied onto a silica gel column with EtOAc/petroleum ether (1/2). The collected fractions were combined and concentrated under vacuum. This resulted in 100 mg (89%) 54-2 as a white solid.

Synthesis of (2S,4aS,6aS,6bR,8aR,10S,12aS,12bR, 14bR)-10-((2-Methoxy-2-oxoethyl)amino)-2,4a,6a,6b,9,9, 12a-heptamethyl-13-oxo-1,2,3,4,4a,5,6,6a,6b,7,8,8a,9,10, 11,12,12a,12b,13,14b-icosahydropicene-2-carboxylic acid (54-3). Into a 50-mL round-bottom flask, was placed 54-2 (160 mg, 0.25 mmol, 1.00 equiv.), Pd/C (80 mg), MeOH (5 mL) under hydrogen atmosphere. The resulting solution was stirred for 2 h at room temperature. The solids were filtered out. The resulting mixture was concentrated under vacuum. The crude product was purified by Prep-HPLC with the following conditions: Column, XBridge Shield RP18 OBD Column, 5 um, 19*150 mm; mobile phase, water (0.05% TFA) and ACN (30.0% ACN up to 48.0% in 8 min); Detector, UV 254 nm. This resulted in 30.7 mg (22%) of 54-3 as an off-white solid. MS (ES, m/z): $[M+H]^+$=542.45; $^1$H NMR (300 MHz, DMSO-d6) δ 9.05 (s, 1H), 8.15 (s, 1H), 5.42 (s, 1H), 4.22-3.94 (m, 3H), 3.77 (s, 3H), 2.85 (s, 1H), 2.67 (d, J=13.3 Hz, 1H), 2.36 (s, 1H), 2.07 (dd, J=11.7, 5.5 Hz, 2H), 1.93-1.49 (m, 7H), 1.35 (s, 8H), 1.11 (d, J=9.4 Hz, 7H), 1.04 (d, J=2.6 Hz, 6H), 0.97 (d, J=13.7 Hz, 2H), 0.85 (s, 4H), 0.76 (s, 3H).

Synthesis of Dimethyl 2,2'-(((3S,4aR,6aR,6bS,8aS,11S, 12aR,14aR,14bS)-11-((benzyloxy) carbonyl)-4,4,6a,6b,8a, 11,14b-heptamethyl-14-oxo-1,2,3,4,4a,5,6,6a,6b,7,8,8a,9, 10,11,12,12a, 14,14a,14b-icosahydropicen-3-yl)azanediyl) diacetate (56-1). Into a 50-mL round-bottom flask, was placed 54-1 (100 mg, 0.18 mmol, 1.00 equiv.), methyl 2-bromoacetate (273 mg, 1.78 mmol, 10.00 equiv.), ACN (10 mL), potassium carbonate (370 mg, 2.68 mmol, 15.00 equiv.). The resulting solution was stirred overnight at 60° C. The resulting solution was extracted with 3×20 mL of EtOAc and the organic layers combined and dried over anhydrous sodium sulfate and concentrated under vacuum. The residue was applied onto a silica gel column with EtOAc/petroleum ether (1/2). The collected fractions were combined and concentrated under vacuum. This resulted in 105 mg (84%) of 56-1 as a white solid.

Synthesis of (2S,4aS,6aS,6bR,8aR,10S,12aS,12bR,14bR)-10-(bis(2-Methoxy-2-oxoethyl) amino)-2,4a,6a,6b,9,9,12a-heptamethyl-13-oxo-1,2,3,4,4a,5,6,6a,6b,7,8,8a,9,10,11,12,12a,12b, 13,14b-icosahydropicene-2-carboxylic acid (56-2). Into a 25-mL round-bottom flask purged and maintained with an inert atmosphere of $H_2$, was placed 56-1 (80 mg, 0.11 mmol, 1.00 equiv.), MeOH (5 mL), Pd/C (80 mg). The resulting solution was stirred for 2 h at room temperature.

The solids were filtered out. The crude product was purified by Prep-HPLC with the following conditions: Column, XBridge Shield RP18 OBD Column, 5 um, 19*150 mm; mobile phase, water (0.05% TFA) and ACN (67.0% ACN up to 80.0% in 8 min); Detector, UV 254 nm. This resulted in 36.8 mg (53%) of 56-2 as a white solid. MS (ES, m/z): $[M+H]^+$=614; $^1$H NMR (300 MHz, MeOH-$d_4$) δ 5.55 (s, 1H), 3.71 (d, J=12.1 Hz, 1OH), 2.78 (d, J=13.3 Hz, 1H), 2.43 (s, 2H), 2.22-2.05 (m, 2H), 1.91 (s, 1H), 1.82 (d, J=13.7 Hz, 4H), 1.70 (d, J=13.3 Hz, 1H), 1.58 (s, 1H), 1.38 (d, J=4.9 Hz, 7H), 1.25 (d, J=6.8 Hz, 1H), 1.23-1.07 (m, 1OH), 1.02 (d, J=14.5 Hz, 6H), 0.80 (d, J=2.6 Hz, 7H).

Example 36 2,2'-(((3S,4aR,6aR,6bS,8aS,11S,12aR,14aR,14bS)-11-Carboxy-4,4,6a,6b,8a, 11,14b-heptamethyl-14-oxo-1,2,3,4,4a,5,6,6a,6b,7,8,8a,9,10,11,12,12a,14,14a,14b-icosahydro picen-3-yl)azanediyl) diacetic acid (57-2)

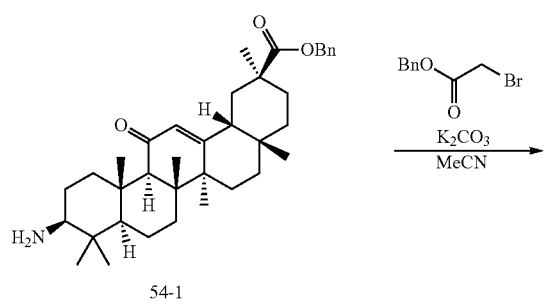

54-1

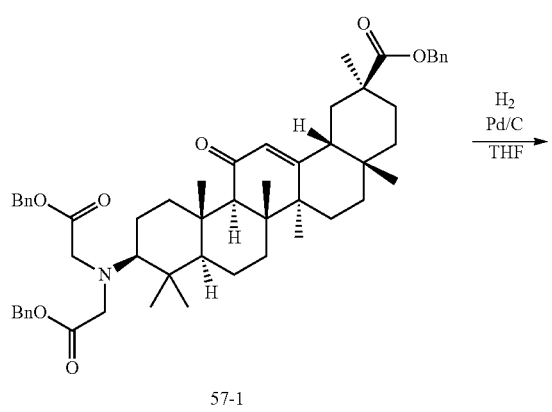

57-1

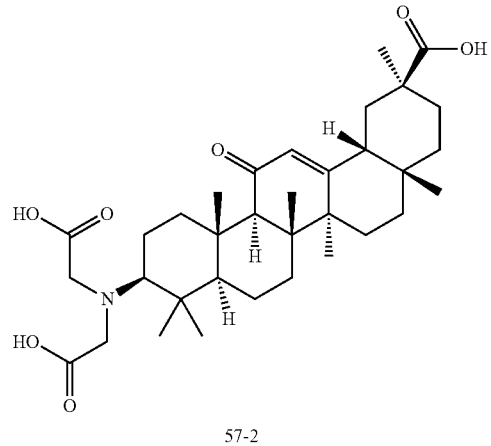

57-2

Synthesis of Dibenzyl 2,2'-(((3S,4aR,6aR,6bS,8aS,11S,12aR,14aR,14bS)-11-((benzyloxy) carbonyl)-4,4,6a,6b,8a,11,14b-heptamethyl-14-oxo-1,2,3,4,4a,5,6,6a,6b,7,8,8a,9,10,11,12,12a, 14,14a,14b-icosahydropicen-3-yl)azanediyl) diacetate (57-1). Into a 250-mL round-bottom flask, was placed 54-1 (500 mg, 0.89 mmol, 1.00 equiv.), $CH_3CN$ (50 mL), potassium carbonate (1.85 g, 13.39 mmol, 15.00 equiv.), benzyl 2-bromoacetate (1.42 g, 6.20 mmol, 10.00 equiv.). The resulting solution was stirred for overnight at 60° C. Add potassium carbonate (0.92 g, 7.50 equiv.), benzyl 2-bromoacetate (0.71 mg, 5.00 equiv.). The resulting solution was allowed to react, with stirring, for an additional 6 h at 60° C. The resulting mixture was concentrated under vacuum. The residue was dissolved in 100 mL of DCM. The resulting mixture was washed with 1×100 mL of water. The solid was dried in an oven under reduced pressure. The residue was applied onto a silica gel column with EtOAc/petroleum ether (1:5). This resulted in 380 mg (50%) of 57-1 as light yellow oil.

Synthesis of 2,2'-(((3S,4aR,6aR,6bS,8aS,11S,12aR,14aR,14bS)-11-Carboxy-4,4,6a,6b,8a,11, 14b-heptamethyl-14-oxo-1,2,3,4,4a,5,6,6a,6b,7,8,8a,9,10,11,12,12a,14,14a,14b-icosahydro picen-3-yl)azanediyl)diacetic acid (57-2). Into a 100-mL round-bottom flask, was placed 57-1 (466 mg, 0.54 mmol, 1.00 equiv.), THF (30 mL), Pd/C (50 mg). To the above hydrogen was introduced in. The resulting solution was stirred for overnight at room temperature. The solids were filtered out. The resulting mixture was concentrated under vacuum. The residue was dissolved in 10 mL of MeOH. The crude product was purified by Prep-HPLC with the following conditions: Column, XBridge Prep OBD C18 Column, 19*250 mm, 5 um; mobile phase, water (0.05% TFA) and ACN (32.0% ACN up to 55.0% in 8 min); Detector, UV 254 nm. This resulted in 263.9 mg (83%) of PH-RDX-013-431-0 as a white solid. MS (ES, m/z): $[M+H]^+$=586.35; $^1$H NMR (300 MHz, MeOH-$d_4$, ppm): δ 0.87 (s, 3H), 0.95 (s, 1H), 1.00 (s, 3H), 1.08 (d, J=13.6 Hz, 1H), 1.15 (s, 3H), 1.17 (s, 3H), 1.20 (s, 3H), 1.26 (s, 3H), 1.31-1.39 (m, 2H), 1.38-1.59 (m, 8H), 1.65-2.26 (m, 10H), 2.51 (s, 1H), 2.89-2.97 (m, 2H), 3.97 (d, J=3.3 Hz, 4H), 5.59 (s, 1H).

Example 37 (2S,4aS,6aS,6bR,8aR,10S,12aS,12bR, 14bR)-10-(3-Methoxy-2,2-dimethyl-3-oxopropanamido)-2,4a,6a,6b,9,9,12a-heptamethyl-13-oxo-1,2,3, 4,4a,5,6,6a,6b,7,8,8a,9,10,11, 12,12a,12b,13,14b-icosahydropicene-2-carboxylic acid (58-2)

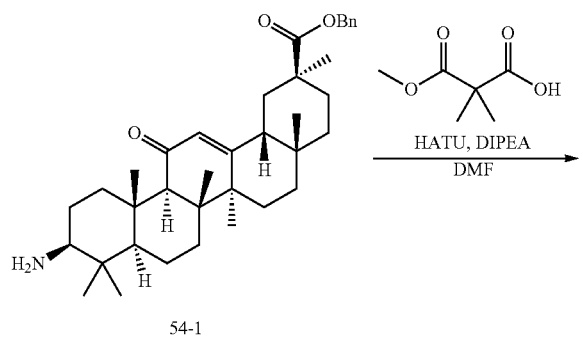

mido)-2,4a,6a,6b,9,9,12a-heptamethyl-13-oxo-1,2,3,4,4a,5, 6,6a,6b,7,8,8a,9,10,11, 12,12a,12b,13,14b-icosahydropicene-2-carboxylate (58-1). Into a 25-mL round-bottom flask purged and maintained with an inert atmosphere of nitrogen, was placed 3-methoxy-2,2-dimethyl-3-oxopropanoic acid (26 mg, 0.18 mmol, 1.00 equiv.), DMF (5 mL), 54-1 (100 mg, 0.18 mmol, 1.00 equiv.), DIEA (65 mg, 0.50 mmol, 3.00 equiv.), HATU (102 mg, 0.27 mmol, 1.50 equiv.). The resulting solution was stirred for 1 h at room temperature. The resulting solution was extracted with 3×10 mL of EtOAc and the organic layers combined and dried over anhydrous sodium sulfate and concentrated under vacuum. The residue was applied onto a silica gel column with EtOAc/petroleum ether (1/2). The collected fractions were combined and concentrated under vacuum. This resulted in 110 mg (90%) of 58-1 as a white solid.

Synthesis of (2S,4aS,6aS,6bR,8aR,10S,12aS,12bR, 14bR)-10-(3-methoxy-2,2-dimethyl-3-oxo propanamido)-2, 4a,6a,6b,9,9,12a-heptamethyl-13-oxo-1,2,3,4,4a,5,6,6a,6b, 7,8,8a,9,10,11,12, 12a,12b,13,14b-icosahydropicene-2-carboxylic acid (58-2). Into a 50-mL round-bottom flask purged and maintained with an inert atmosphere of $H_2$, was placed 58-1 (50 mg, 0.07 mmol, 1.00 equiv.), MeOH (10 mL), Pd/C (25 mg). The resulting solution was stirred for 1 h at room temperature. The solids were filtered out. The crude product was purified by Prep-HPLC with the following conditions: Column, XBridge Shield RP18 OBD Column, 5 um, 19*150 mm; mobile phase, water (0.05% TFA) and ACN (60.0% ACN up to 78.0% in 8 min); Detector, UV 254 nm. This resulted in 12.3 mg (28%) of 58-2 as a white solid. MS (ES, m/z): [M+H]$^+$=598; $^1$H NMR (300 MHz, MeOH-d$_4$) δ 0.81-0.98 (m, 12H), 1.06 (d, J=14.2 Hz, 2H), 1.13-1.33 (m, 12H), 1.43 (q, J=4.6, 4.1 Hz, 14H), 1.71 (dd, J=27.4, 13.7 Hz, 4H), 1.81-1.98 (m, 3H), 2.20 (s, 2H), 2.52 (s, 1H), 2.77 (d, J=13.7 Hz, 1H), 3.72 (s, 6H), 5.59 (s, 1H), 7.11 (d, J=9.6 Hz, 1H).

Example 38 (2S,4aS,6aS,6bR,8aR,10S,12aS,12bR, 14bR)-10-(2-methoxy-2-oxoacetamido)-2,4a,6a,6b, 9,9,12a-heptamethyl-13-oxo-1,2,3,4,4a,5,6,6a,6b,7, 8,8a,9,10,11,12,12a,12b,13,14b-icosahydropicene-2-carboxylicacid (60-2)

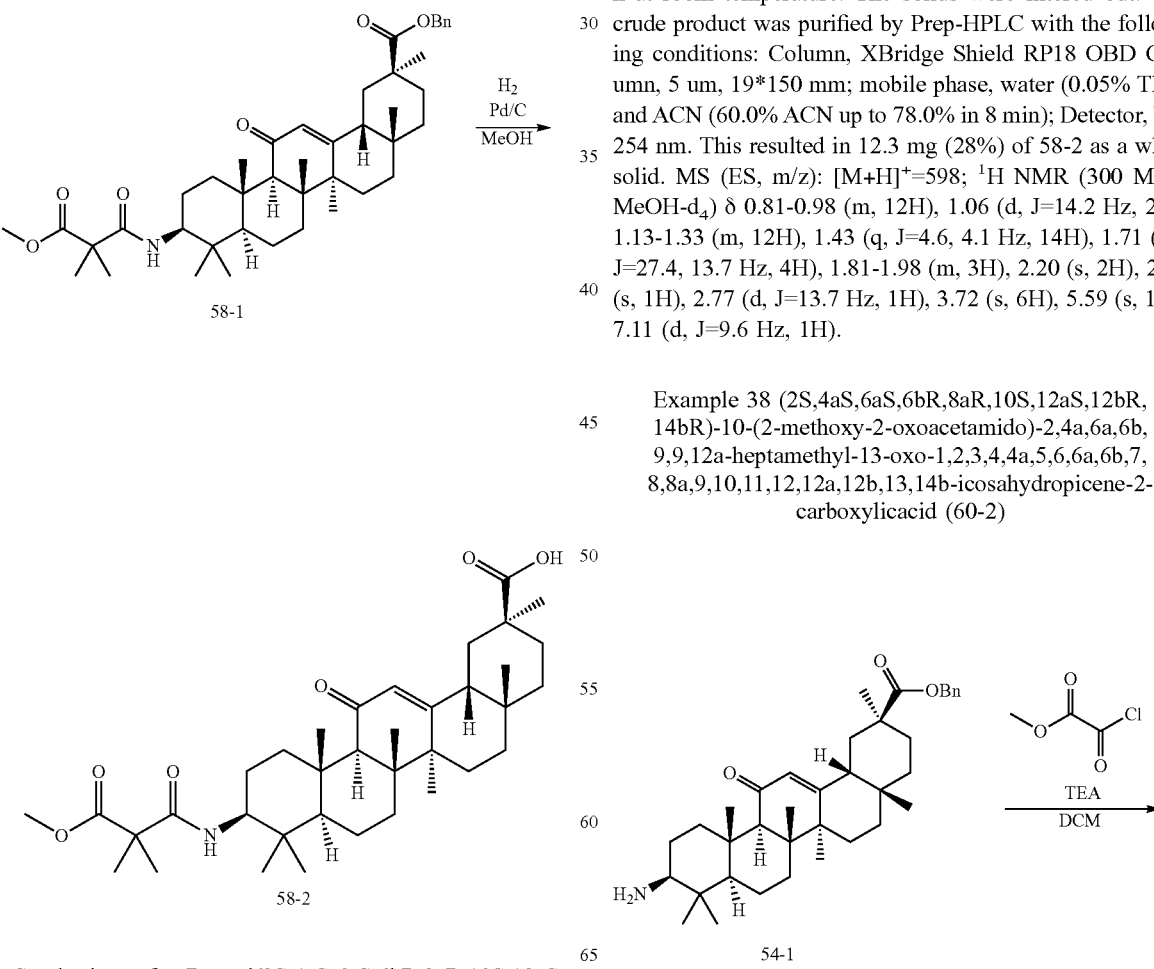

Synthesis of Benzyl(2S,4aS,6aS,6bR,8aR,10S,12aS, 12bR,14bR)-10-(3-methoxy-2,2-dimethyl-3-oxopropana- -continued

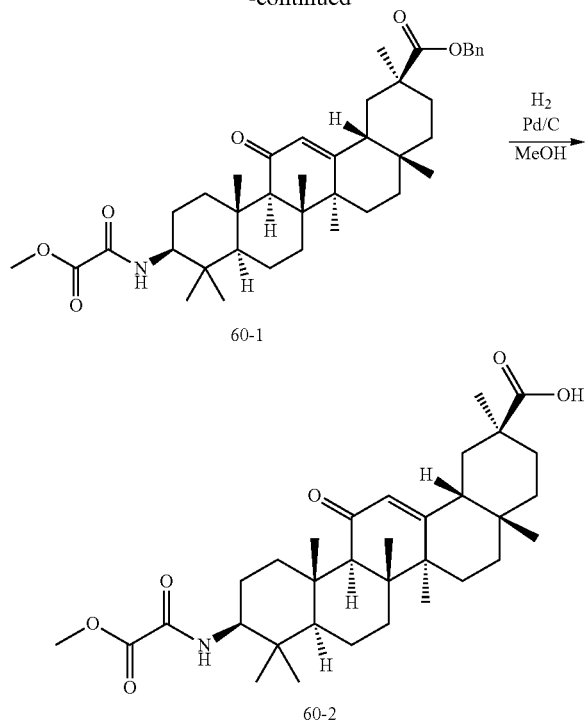

Synthesis of Benzyl (2S,4aS,6aS,6bR,8aR,10S,12aS,12bR,14bR)-10-(2-methoxy-2-oxo acetamido)-2,4a,6a,6b,9,9,12a-heptamethyl-13-oxo-1,2,3,4,4a,5,6,6a,6b,7,8,8a,9,10,11,12,12a, 12b,13,14b-icosahydropicene-2-carboxylate (60-1). Into a 50-mL round-bottom flask, was placed 54-1 (90 mg, 0.16 mmol, 1 equiv.), DCM (4 mL, 0.05 mmol, 0.293 equiv.), DIEA (45.7 mg, 0.35 mmol, 2.2 equiv.). This was followed by the addition of methyl 2-chloro-2-oxoacetate (21.7 mg, 0.18 mmol, 1.1 equiv.) dropwise with stirring. The resulting solution was stirred for 2 hr at room temperature. The resulting mixture was concentrated under vacuum. This resulted in 110 mg (105.94%) of 60-1 as a yellow crude solid.

Synthesis of (2S,4aS,6aS,6bR,8aR,10S,12aS,12bR,14bR)-10-(2-Methoxy-2-oxoacetamido)-2,4a,6a,6b,9,9,12a-heptamethyl-13-oxo-1,2,3,4,4a,5,6,6a,6b,7,8,8a,9,10,11,12,12a,12b,13,14b-icosahydropicene-2-carboxylic acid (60-2). Into a 25-mL round-bottom flask purged and maintained with an inert atmosphere of $H_2$, was placed 60-1 (104 mg, 0.16 mmol, 1 equiv.), MeOH (5 mg, 0.16 mmol, 0.969 equiv.), Pd/C (50 mg, 0.47 mmol, 2.918 equiv.). The resulting solution was stirred for 2.5 hr at room temperature. The solids were filtered out. The resulting mixture was concentrated. The crude product was purified by Prep-HPLC with the following conditions: Column, XBridge Shield RP18 OBD Column, 5 um, 19*150 mm; mobile phase, water (0.05% TFA) and ACN (58% Phase B up to 72% in 8 min); Detector, UV. This resulted in 45.5 mg (50.84%) of 60-2 as a white solid. MS (ES, m/z): [M+H]$^+$=555.76; $^1$H NMR (300 MHz, DMSO-d6) δ 12.18 (s, 1H), 8.30 (d, J=9.7 Hz, 1H), 5.41 (s, 1H), 3.77 (s, 3H), 3.57 (ddd, J=13.2, 9.6, 4.1 Hz, 1H), 2.63 (d, J=13.4 Hz, 1H), 2.41 (s, 1H), 2.08 (q, J=9.8, 6.6 Hz, 2H), 1.79 (d, J=13.5 Hz, 3H), 1.69 (d, J=7.0 Hz, 3H), 1.53 (d, J=13.2 Hz, 1H), 1.46-1.16 (m, 9H), 1.17-0.95 (m, 13H), 0.81-0.73 (m, 9H).

Example 39 (2S,4aS,6aS,6bR,8aR,10S,12aS,12bR,14bR)-10-(3-Methoxy-3-oxopropan amido)-2,4a,6a,6b,9,9,12a-heptamethyl-13-oxo-1,2,3,4,4a,5,6,6a,6b,7,8,8a,9,10,11,12,12a,12b, 13,14b-icosahydropicene-2-carboxylicacid (62-2)

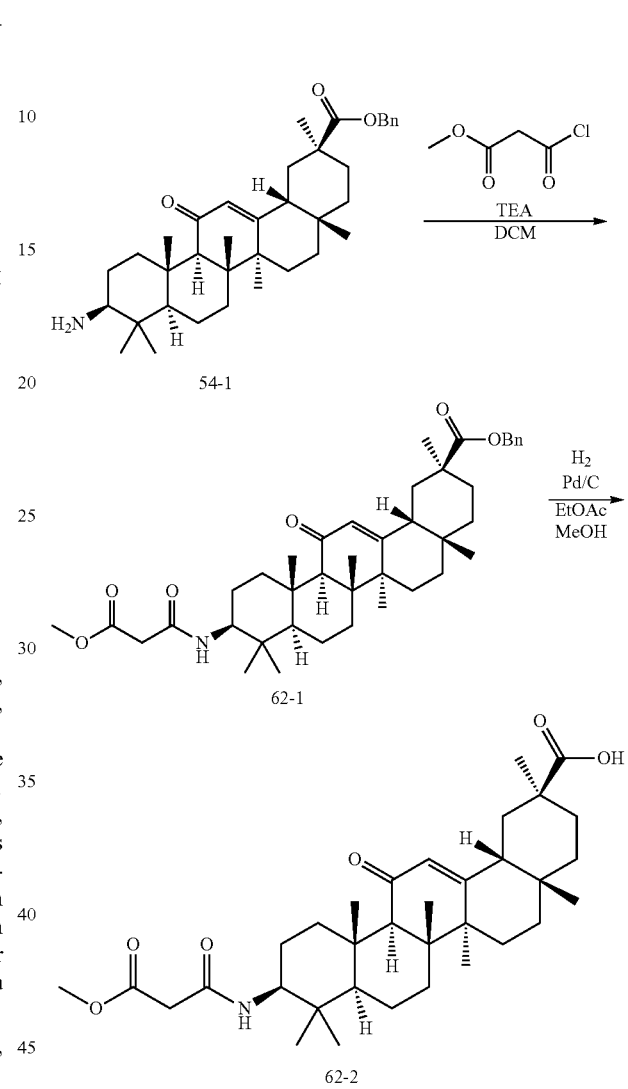

Synthesis of Benzyl (2S,4aS,6aS,6bR,8aR,1S,12aS,12bR,14bR)-10-(3-methoxy-3-oxopropan amido)-2,4a,6a,6b,9,9,12a-heptamethyl-13-oxo-1,2,3,4,4a,5,6,6a,6b,7,8,8a,9,10,11,12,12a,12b, 13,14b-icosahydropicene-2-carboxylate (62-1). Into a 100-mL round-bottom flask, was placed 54-1 (500 mg, 0.89 mmol, 1 equiv.), methyl 3-chloro-3-oxopropanoate (243.9 mg, 1.79 mmol, 2 equiv.), TEA (271.1 mg, 2.68 mmol, 3 equiv.), $CH_2Cl_2$ (10 mL, 0.12 mmol, 0.132 equiv.). The resulting solution was stirred for 1 hr at room temperature. The residue was applied onto a silica gel column with EtOAc/petroleum ether (1:1). This resulted in 439 mg (74.49%) of 62-1 as a white solid.

Synthesis of (2S,4aS,6aS,6bR,8aR,1S,12aS,12bR,14bR)-10-(3-Methoxy-3-oxopropanamido)-2,4a,6a,6b,9,9,12a-heptamethyl-13-oxo-1,2,3,4,4a,5,6,6a,6b,7,8,8a,9,10,11,12, 12a,12b,13,14b-icosahydropicene-2-carboxylic acid (62-2). Into a 100-mL round-bottom flask purged and maintained with an inert atmosphere of $H_2$, was placed 62-1 (439 mg, 0.67 mmol, 1 equiv.), THF (200 mg, 2.77 mmol, 4.169 equiv.), MeOH (10 mL, 0.31 mmol, 0.469 equiv.), Pd/C (10 mL). The resulting solution was stirred for 1 hr at room temperature. The solids were filtered out. The crude product was purified by Prep-HPLC with the following conditions: Column, XBridge Shield RP18 OBD Column, 5 um, 19*150 mm; mobile phase, water (0.05% TFA) and ACN (5% Phase B up to 56% in 1 min, up to 70% in 7 min); Detector, UV. This resulted in 61.4 mg (16.20%) of 62-2 as a white solid. MS (ES, m/z): [M+H]$^+$=570; $^1$H NMR (300 MHz, MeOH-d$_4$) δ 5.59 (s, 1H), 3.72 (s, 4H), 3.35 (s, 2H), 2.77 (dt, J=13.4, 3.7 Hz, 1H), 2.53 (s, 1H), 2.18 (ddd, J=19.3, 13.0, 4.5 Hz, 2H), 2.01-1.61 (m, 7H), 1.59-1.34 (m, 9H), 1.33-1.13 (m, 11H), 1.07 (d, J=14.9 Hz, 2H), 0.98-0.81 (m, 10H).

Example 40 (2S,4aS,6aS,6bR,8aR,10S,12aS,12bR, 14bR)-10-(4-Methoxy-4-oxobutanamido)-2,4a,6a, 6b,9,9,12a-heptamethyl-13-oxo-1,2,3,4,4a,5,6,6a,6b, 7,8,8a,9,10,11,12,12a,12b,13,14b-icosahydropicene-2-carboxylic acid (64-2)

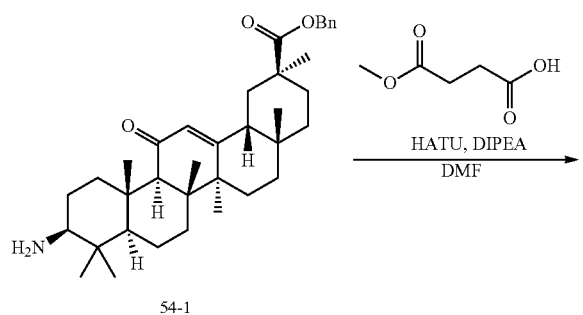

54-1

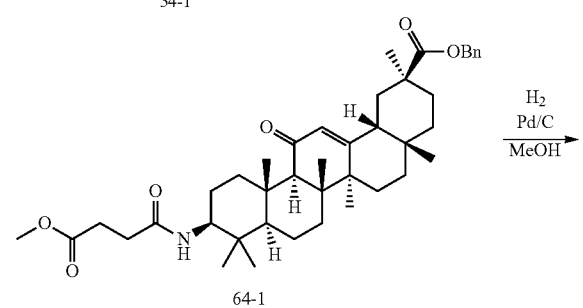

64-1

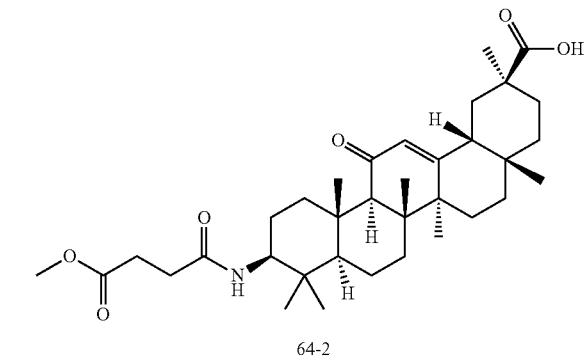

64-2

Synthesis of Benzyl (2S,4aS,6aS,6bR,8aR,10S,12aS, 12bR,14bR)-10-(4-methoxy-4-oxobutan amido)-2,4a,6a,6b, 9,9,12a-heptamethyl-13-oxo-1,2,3,4,4a,5,6,6a,6b,7,8,8a,9, 10,11,12,12a,12b, 13,14b-icosahydropicene-2-carboxylate (64-1). Into a 25-mL round-bottom flask, was placed 4-methoxy-4-oxobutanoic acid (28 mg, 0.21 mmol, 1.00 equiv.), 54-1 (120 mg, 0.21 mmol, 1.00 equiv.), DMF (5 mL), DIEA (78 mg, 0.60 mmol, 3.00 equiv.), HATU (122 mg, 0.32 mmol, 1.50 equiv.). The resulting solution was stirred for 1 h at room temperature. The resulting solution was extracted with 3×20 mL of EtOAc and the organic layers combined and dried over anhydrous sodium sulfate and concentrated under vacuum. The residue was applied onto a silica gel column with EtOAc/petroleum ether (1/2). The collected fractions were combined and concentrated under vacuum. This resulted in 140 mg (98%) of 64-1 as a white solid.

Synthesis of (2S,4aS,6aS,6bR,8aR,10S,12aS,12bR, 14bR)-10-(4-Methoxy-4-oxobutanamido)-2,4a,6a,6b,9,9, 12a-heptamethyl-13-oxo-1,2,3,4,4a,5,6,6a,6b,7,8,8a,9,10, 11,12,12a,12b,13,14b-icosahydropicene-2-carboxylic acid (64-2). Into a 50-mL round-bottom flask purged and maintained with an inert atmosphere of H$_2$, was placed 64-1 (50 mg, 0.07 mmol, 1.00 equiv.), MeOH (5 mL), Pd/C (25 mg). The resulting solution was stirred for 1 h at room temperature. The solids were filtered out. The crude product was purified by re-crystallization from ACN. This resulted in 39.9 mg (92%) of 64-2 as a white solid. MS (ES, m/z): [M+H]$^+$=584; $^1$H NMR (300 MHz, MeOH-d$_4$) δ 0.81-0.96 (m, 10H), 0.99-1.20 (m, 11H), 1.20-1.58 (m, 11H), 1.59-1.82 (m, 4H), 1.82-2.08 (m, 3H), 2.08-2.33 (m, 2H), 2.42-2.72 (m, 5H), 2.75 (dq, J=12.1, 5.0, 4.2 Hz, 1H), 3.67 (s, 4H), 5.65 (s, 1H).

Example 41 (2S,4aS,6aS,6bR,8aR,10S,12aS,12bR, 14bR)-10-((E)-4-Methoxy-4-oxobut-2-enamido)-2, 4a,6a,6b,9,9,12a-heptamethyl-13-oxo-1,2,3,4,4a,5,6, 6a,6b,7,8,8a,9,10,11,12,12a, 12b,13,14b-icosahydropicene-2-carboxylic acid (66-2)

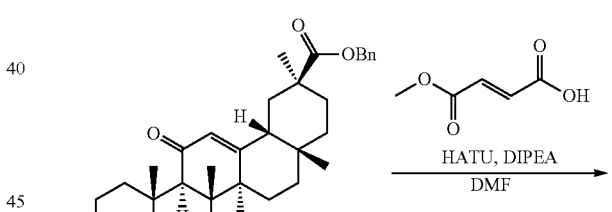

54-1

66-1

-continued

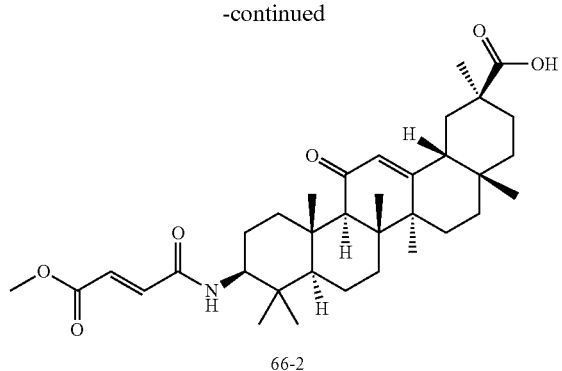

66-2

Synthesis of benzyl (2S,4aS,6aS,6bR,8aR,0S,12aS,12bR, 14bR)-10-((E)-4-methoxy-4-oxobut-2-enamido)-2,4a,6a, 6b,9,9,12a-heptamethyl-13-oxo-1,2,3,4,4a,5,6,6a,6b,7,8,8a, 9,10,11,12,12a, 12b,13,14b-icosahydropicene-2-carboxylate (66-1). Into a 8-mL round-bottom flask, was placed (2E)-4-methoxy-4-oxobut-2-enoic acid (66.48 mg, 0.51 mmol, 1.20 equiv.), 54-1 (200 mg, 0.36 mmol, 1.00 equiv.), DIEA (220.13 mg, 1.70 mmol, 4.00 equiv.), DMF (2 mL), HATU (343 mg, 0.90 mmol, 1.50 equiv.). The resulting solution was stirred for 1 h at room temperature. The resulting mixture was concentrated under vacuum. The residue was applied onto a silica gel column with EtOAc/ petroleum ether (100:1). This resulted in 200 mg (83%) of 66-1 as a yellow solid.

Synthesis of (2S,4aS,6aS,6bR,8aR,10S,12aS,12bR, 14bR)-10-((E)-4-methoxy-4-oxobut-2-enamido)-2,4a,6a, 6b,9,9,12a-heptamethyl-13-oxo-1,2,3,4,4a,5,6,6a,6b,7,8,8a, 9,10,11,12,12a, 12b,13,14b-icosahydropicene-2-carboxylic acid (66-2). Into a 100-mL round-bottom flask, was placed 66-1 (250 mg, 0.37 mmol, 1.00 equiv.), THF (10 mL), water (5 mL), sodium hydroxide (90 mg, 2.25 mmol, 6.00 equiv.), MeOH (10 mL). The resulting solution was stirred for 4 days at 60° C. The residue was applied onto a silica gel column with EtOAc/petroleum ether (0-35%). This resulted in 31.8 mg (15%) of 66-2 as a white solid. MS (ES, m/z): [M+H]$^+$=582; $^1$H NMR (300 MHz, MeOH-d$_4$) δ 8.26 (d, J=9.7 Hz, 1H), 7.08 (d, J=15.4 Hz, 1H), 6.69 (d, J=15.4 Hz, 1H), 5.59 (s, 1H), 3.71 (s, 4H), 3.35 (s, 2H), 2.79 (d, J=13.5 Hz, 1H), 2.57-2.50 (m, 1H), 2.16 (t, J=12.3 Hz, 2H), 2.04-1.61 (m, 6H), 1.56-1.38 (m, 8H), 1.38-1.21 (m, 2H), 1.21-0.80 (m, 20H).

Example 42 (2S,4aS,6aS,6bR,8aR,10S,12aS,12bR, 14bR)-10-(3-Carboxy-3-methylbutan amido)-2,4a, 6a,6b,9,9,12a-heptamethyl-13-oxo-1,2,3,4,4a,5,6,6a, 6b,7,8,8a,9,10,11,12,12a, 12b,13,14b-icosahydropicene-2-carboxylic acid (68-3)

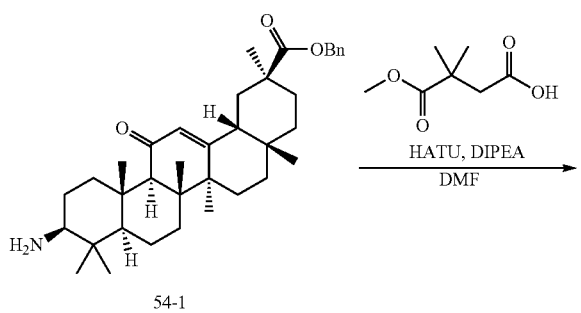

-continued

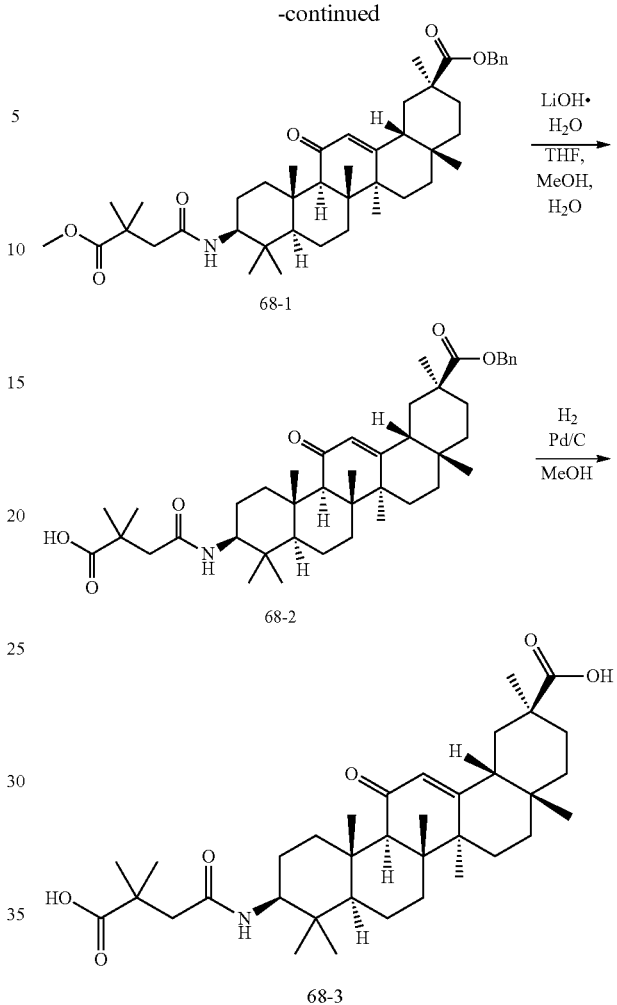

Synthesis of Benzyl (2S,4aS,6aS,6bR,8aR,10S,12aS, 12bR,14bR)-10-(4-methoxy-3,3-dimethyl-4-oxobutanamido)-2,4a,6a,6b,9,9,12a-heptamethyl-13-oxo-1,2,3,4,4a,5, 6,6a,6b,7,8,8a,9,10, 11,12,12a,12b,13,14b-icosahydropicene-2-carboxylate (68-1). Into a 25-mL round-bottom flask, was placed 54-1 (150 mg, 0.27 mmol, 1 equiv.), DMF (2 mL, 0.03 mmol, 0.102 equiv.), 4-methoxy-3,3-dimethyl-4-oxobutanoic acid (51.5 mg, 0.32 mmol, 1.2 equiv.), DIEA (138.5 mg, 1.07 mmol, 4.0 equiv.), HATU (152.8 mg, 0.40 mmol, 1.5 equiv.). The resulting solution was stirred for 1 overnight at room temperature. The resulting solution was diluted with of EA. The resulting mixture was washed with x of brine. The residue was applied onto a silica gel column with EtOAc/petroleum ether. This resulted in 170 mg (90.38%) of 68-1 as an off-white solid.

Synthesis of 4-(((3S,4aR,6aR,6bS,8aS,11S,12aR,14aR, 14bS)-11-((Benzyloxy)carbonyl)-4,4,6a, 6b,8a,11,14b-heptamethyl-14-oxo-1,2,3,4,4a,5,6,6a,6b,7,8,8a,9,10,11,12,12a, 14,14a,14b-icosahydropicen-3-yl)amino)-2,2-dimethyl-4-oxobutanoic acid (68-2). Into a 25-mL round-bottom flask, was placed 68-1 (100 mg, 0.14 mmol, 1 equiv.), MeOH (5 mL, 49.40 mmol, 346.760 equiv.), THF (5 mL, 24.69 mmol, 173.289 equiv.), H$_2$O (2 mL, 111.02 mmol, 779.31 equiv.), LiOH.H$_2$O (54 mg, 1.29 mmol, 9.033 equiv.). The resulting solution was stirred for 1 overnight at room temperature. The resulting mixture was concentrated. The pH value of the solution was adjusted to 5-6 with HCl. The resulting solution was extracted with 3×100 mL of EtOAc The residue was applied onto a silica gel column with DCM/MeOH. This resulted in 80 mg (81.63%) of 68-2 as a white solid.

Synthesis of (2S,4aS,6aS,6bR,8aR,10S,12aS,12bR,14bR)-10-(3-Carboxy-3-methylbutanamido)-2,4a,6a,6b,9,9,12a-heptamethyl-13-oxo-1,2,3,4,4a,5,6,6a,6b,7,8,8a,9,10,11,12,12a,12b,13,14b-icosahydropicene-2-carboxylic acid (68-3). Into a 25-mL round-bottom flask purged and maintained with an inert atmosphere of $H_2$, was placed 68-2 (80 mg, 0.12 mmol, 1 equiv.), MeOH (5 mL, 0.16 mmol, 1.342 equiv.), Pd/C (40 mg, 0.38 mmol, 3.232 equiv.). The resulting solution was stirred for 2 hr at room temperature. The solids were filtered out. The crude product was purified by Prep-HPLC with the following conditions: Column, XBridge Shield RP18 OBD Column, 5 um, 19*150 mm; mobile phase, water (10 mmol/L $NH_4HCO_3$+0.1% $NH_3.H_2O$) and ACN (48% Phase B up to 73% in 8 min); Detector, UV. This resulted in 14.1 mg (20.28%) of 68-3 as a white solid. MS (ES, m/z): $[M+H]^+$=598; $^1$H NMR (300 MHz, MeOH-$d_4$) δ 5.61 (s, 1H), 3.64-3.53 (m, 1H), 2.74 (d, J=13.6 Hz, 1H), 2.51 (s, 3H), 2.28-2.09 (m, 2H), 1.91 (dd, J=24.4, 10.9 Hz, 3H), 1.81-1.60 (m, 2H), 1.43 (d, J=10.2 Hz, 8H), 1.24 (d, J=1.8 Hz, 8H), 1.16 (d, J=4.3 Hz, 11H), 1.05 (d, J=14.1 Hz, 2H), 0.96-0.81 (m, 11H).

Example 43 (2S,4aS,6aS,6bR,8aR,10S,12aS,12bR,14bR)-10-(4-Methoxy-3,3-dimethyl-4-oxobutanamido)-2,4a,6a,6b,9,9,12a-heptamethyl-13-oxo-1,2,3,4,4a,5,6,6a,6b,7,8,8a,9,10,11,12,12a,12b,13,14b-icosahydropicene-2-carboxylic acid (69-1)

Into a 25-mL round-bottom flask purged and maintained with an inert atmosphere of $H_2$, was placed 68-1 (116 mg, 1 equiv.), MeOH (10 mL), Pd/C (100 mg). The resulting solution was stirred for 2 hr at room temperature. The solids were filtered out. The resulting mixture was concentrated. The crude product was purified by Prep-HPLC with the following conditions: Column, XBridge Prep C18 OBD Column 19*150 nm 5 umC-0013; mobile phase, water (0.05% TFA) and ACN (61% Phase B up to 81% in 8 min); Detector, UV. This resulted in 16.5 mg of 69-1 as a white solid. MS (ES, m/z): $[M+H]^+$=612; $^1$H NMR (300 MHz, MeOH-$d_4$) δ 5.59 (s, 1H), 3.68 (s, 3H), 3.53 (s, 1H), 2.75 (d, J=12.8 Hz, 1H), 2.52 (d, J=5.4 Hz, 3H), 2.18 (s, 2H), 1.98-1.81 (m, 3H), 1.70 (dd, J=27.6, 13.7 Hz, 4H), 1.43 (d, J=10.0 Hz, 10H), 1.33-1.12 (m, 16H), 1.05 (d, J=13.5 Hz, 2H), 0.90-0.80 (m, 9H).

Example 44 (2S,4aS,6aS,6bR,8aR,10S,12aS,12bR,14bR)-10-((2-Methoxy-2-oxoethyl) sulfonamido)-2,4a,6a,6b,9,9,12a-heptamethyl-13-oxo-1,2,3,4,4a,5,6,6a,6b,7,8,8a,9,10,11,12,12a,12b,13,14b-icosahydropicene-2-carboxylicacid (70-2)

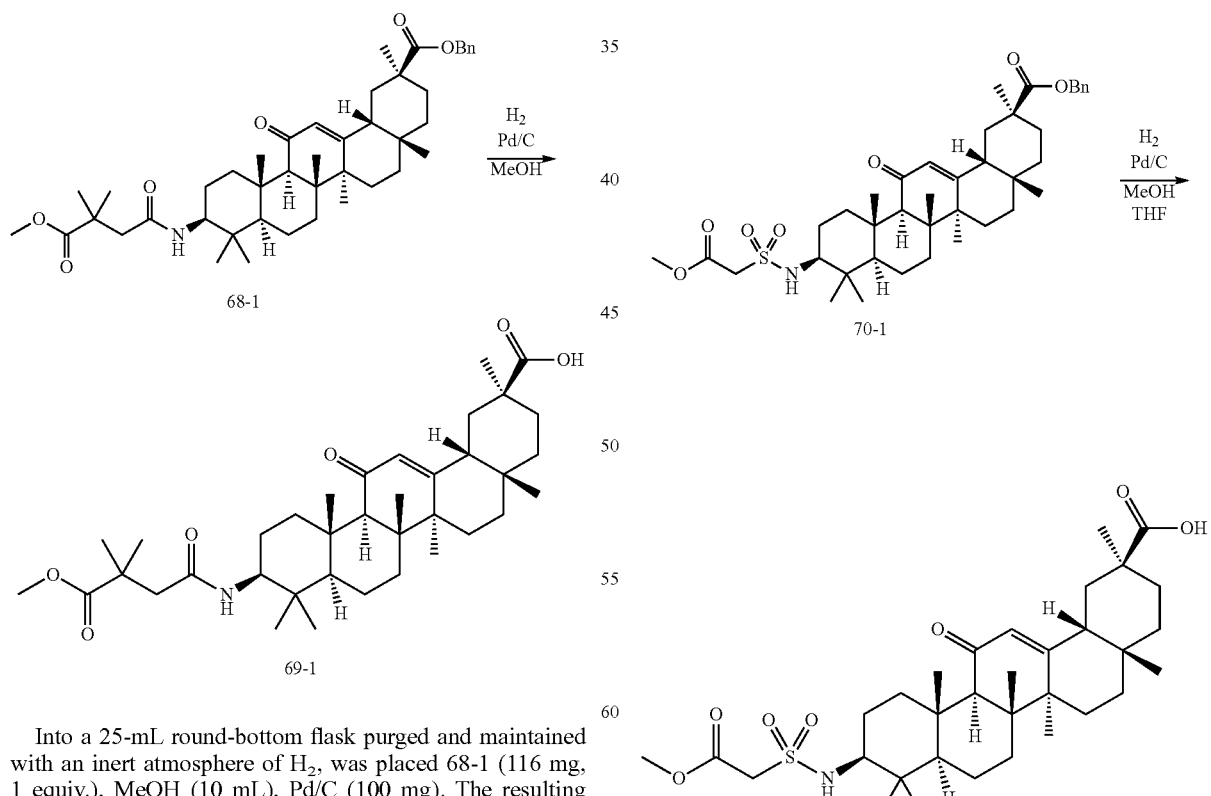

Synthesis of Benzyl (2S,4aS,6aS,6bR,8aR,10S,12aS, 12bR,14bR)-10-((2-methoxy-2-oxoethyl) sulfonamido)-2, 4a,6a,6b,9,9,12a-heptamethyl-13-oxo-1,2,3,4,4a,5,6,6a,6b, 7,8,8a,9,10,11,12,12a, 12b,13,14b-icosahydropicene-2-carboxylate (70-1). Into a 100-mL round-bottom flask, was placed 54-1 (500 mg, 0.89 mmol, 1 equiv.), methyl 2-(chlorosulfonyl)acetate (308.3 mg, 1.79 mmol, 2 equiv.), TEA (271.1 mg, 2.68 mmol, 3 equiv.), CH$_2$Cl$_2$ (15 mL, 235.95 mmol, 264.181 equiv.), DMAP (11 mg, 0.09 mmol, 0.101 equiv.). The resulting solution was stirred for 1 overnight at room temperature. The residue was applied onto a silica gel column with EtOAc/petroleum ether (1:1). This resulted in 250 mg (40.22%) of 70-1 as a yellow solid.

Synthesis of (2S,4aS,6aS,6bR,8aR,10S,12aS,12bR, 14bR)-10-((2-Methoxy-2-oxoethyl) sulfon amido)-2,4a,6a, 6b,9,9,12a-heptamethyl-13-oxo-1,2,3,4,4a,5,6,6a,6b,7,8,8a, 9,10,11,12,12a,12b, 13,14b-icosahydropicene-2-carboxylic acid (70-2). Into a 50-mL round-bottom flask purged and maintained with an inert atmosphere of H$_2$, was placed MeOH (5 mL), THF (5 mL), Pd/c (100 mg, 0.94 mmol, 1.308 equiv.), 70-1 (500 mg, 0.72 mmol, 1 equiv.). The resulting solution was stirred for 1 hr at room temperature. The solids were filtered out. The crude product was purified by Prep-HPLC with the following conditions: Column, XBridge Shield RP18 OBD Column, 5 um, 19*150 mm; mobile phase, water (0.05% TFA) and ACN (5% Phase B up to 59% in 1 min, up to 73% in 7 min); Detector, UV. This resulted in 44.5 mg (10.22%) of 70-2 as a white solid. MS (ES, m/z): [M+H]$^+$=606; $^1$H NMR (300 MHz, MeOH-d$_4$) δ 5.59 (s, 1H), 4.12 (s, 2H), 3.78 (s, 3H), 3.03 (dd, J=11.6, 5.1 Hz, 1H), 2.76 (dt, J=13.5, 3.5 Hz, 1H), 2.51 (s, 1H), 2.28-2.08 (m, 2H), 2.01-1.63 (m, 8H), 1.60-1.36 (m, 8H), 1.33-0.99 (m, 15H), 0.83 (d, J=8.6 Hz, 7H).

Example 45 (2S,4aS,6aS,6bR,8aR,10S,12aS,12bR, 14bR)-10-((3-Methoxy-3-oxopropyl) sulfonamido)- 2,4a,6a,6b,9,9,12a-heptamethyl-13-oxo-1,2,3,4,4a,5, 6,6a,6b,7,8,8a,9,10,11,12, 12a,12b,13,14b-icosahydropicene-2-carboxylicacid (72-2)

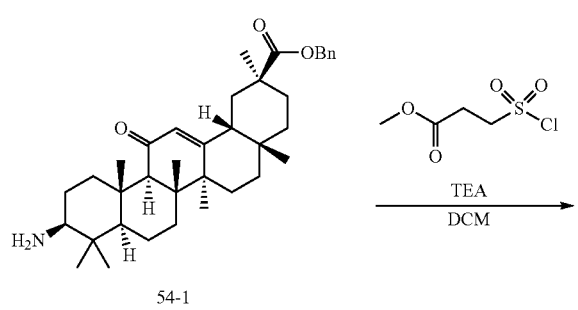

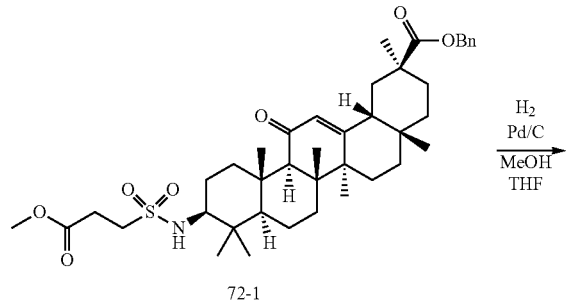

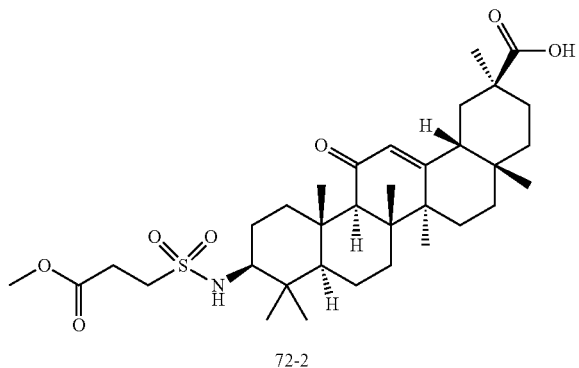

Synthesis of Benzyl(2S,4aS,6aS,6bR,8aR,10S,12aS, 12bR,14bR)-10-((3-methoxy-3-oxopropyl) sulfonamido)-2, 4a,6a,6b,9,9,12a-heptamethyl-13-oxo-1,2,3,4,4a,5,6,6a,6b, 7,8,8a,9,10,11,12,12a, 12b,13,14b-icosahydropicene-2-carboxylate (72-2). Into a 50-mL round-bottom flask, was placed 54-1 (300 mg, 1 equiv.), DCM (10 mL), methyl 3-(chlorosulfonyl)propanoate (200 mg, 2.0 equiv.), TEA (0.223 mL). The resulting solution was stirred overnight at room temperature. The resulting mixture was concentrated under vacuum. The residue was applied onto a silica gel column with EtOAc/petroleum ether (1:2). This resulted in 326 mg (86%) of 72-2 as a light yellow solid.

Synthesis of (2S,4aS,6aS,6bR,8aR,10S,12aS,12bR, 14bR)-10-((3-Methoxy-3-oxopropyl) sulfonamido)-2,4a,6a, 6b,9,9,12a-heptamethyl-13-oxo-1,2,3,4,4a,5,6,6a,6b,7,8,8a, 9,10,11,12,12a, 12b,13,14b-icosahydropicene-2-carboxylic acid (72-3). Into a 50-mL round-bottom flask purged and maintained with an inert atmosphere of H$_2$, was placed 72-2 (326 mg, 0.46 mmol, 1.00 equiv.), MeOH (10 mL), THF (10 mL), Pd/C (33 mg). The resulting solution was stirred overnight at room temperature. The solids were filtered out. The resulting mixture was concentrated under vacuum. The crude product was purified by Prep-HPLC with the following conditions: Column, XBridge Prep OBD C18 Column, 19*250 mm, 5 um; mobile phase, water (0.05% NH$_3$.H$_2$O) and ACN (34.0% ACN up to 50.0% in 9 min); Detector, UV 254 nm. This resulted in 200 mg (70%) of 72-3 as a white solid. MS (ES, m/z): [M+H]$^+$=620.70; $^1$H NMR (400 MHz, MeOH-d$_4$, ppm): δ 0.78-0.96 (m, 7H), 1.01-1.14 (m, 5H), 1.15-1.24 (m, 9H), 1.25-1.33 (m, 1H), 1.38-1.58 (m, 8H), 1.59-2.08 (m, 8H), 2.12-2.29 (m, 2H), 2.52 (s, 1H), 2.73-2.90 (m, 3H), 2.98 (dd, J=12.4, 4.0 Hz, 1H), 3.35-3.43 (m, 2H), 3.73 (s, 3H), 5.62 (s, 1H).

Example 46 (2S,4aS,6aS,6bR,8aR,10S,12aS,12bR, 14bR)-10-(2-(2-Methoxy-2-oxoethoxy) acetamido)-2,4a,6a,6b,9,9,12a-heptamethyl-13-oxo-1,2,3,4,4a,5, 6,6a,6b,7,8,8a,9,10,11,12,12a, 12b,13,14b-icosahydropicene-2-carboxylic acid (75-2)
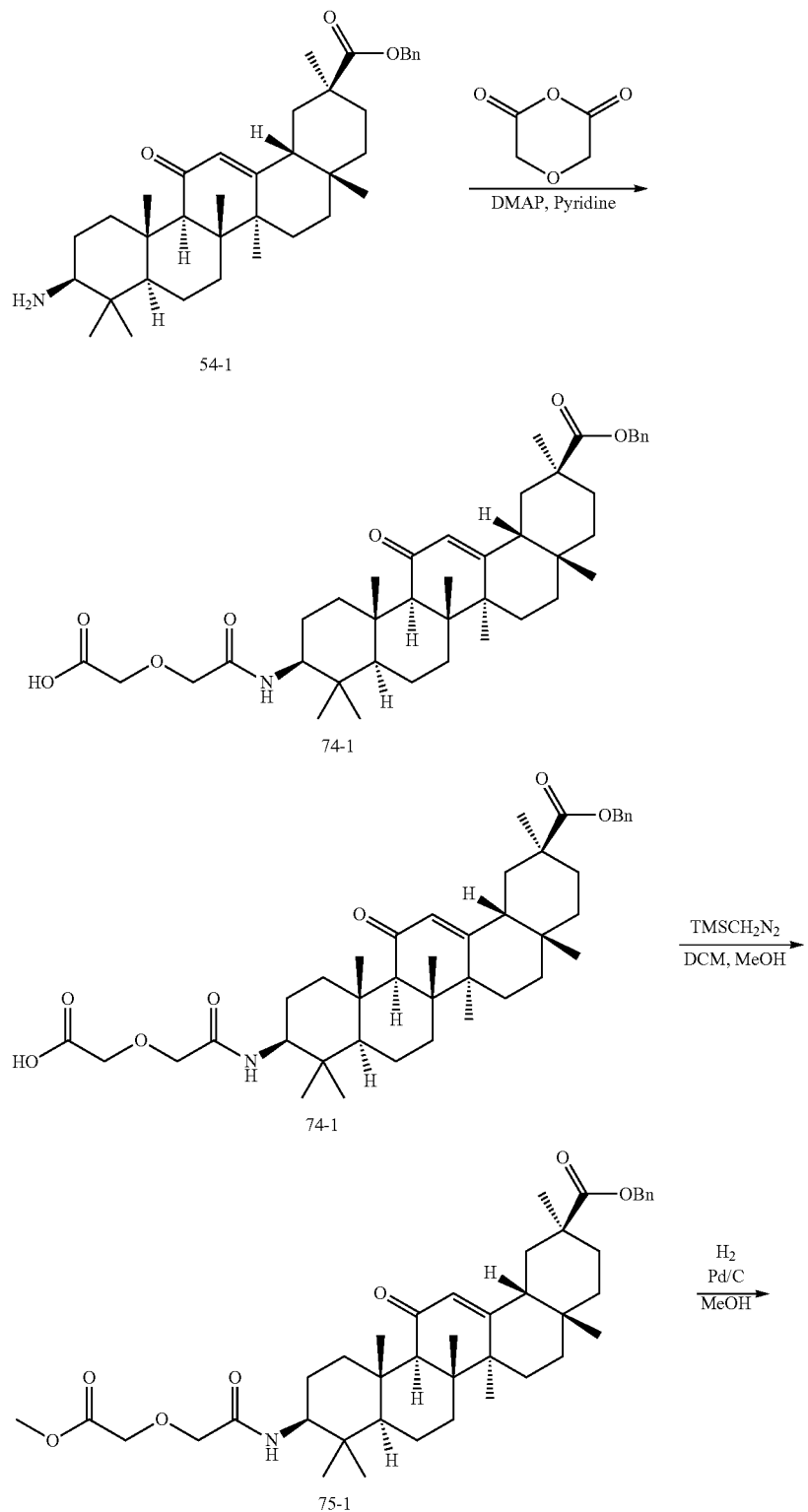

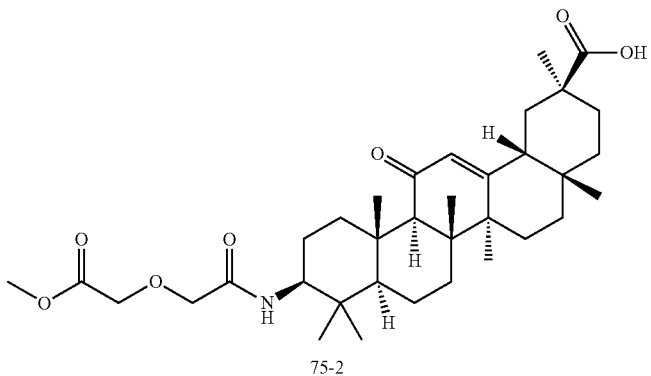

75-2

Synthesis of 2-(2-(((3S,4aR,6aR,6bS,8aS,11S,12aR, 14aR,14bS)-11-((Benzyloxy)carbonyl)-4,4,6a,6b,8a,11, 14b-heptamethyl-14-oxo-1,2,3,4,4a,5,6,6a,6b,7,8,8a,9,10, 11,12,12a,14,14a,14b-icosahydropicen-3-yl)amino)-2-oxoethoxy)acetic acid (74-1). Into a 100-mL round-bottom flask purged and maintained with an inert atmosphere of nitrogen, was placed 54-1 (1.0 g, 1.79 mmol, 1 eq.), DMAP (0.1 g, 0.893 mmol, 0.5 eq.), pyridine (10 mL, 0.13 mmol, 0.071 eq.). This was followed by the addition of 1,4-dioxane-2,6-dione (228 mg, 1.96 mmol, 1.100 eq.) dropwise with stirring at 0 degrees in ice bath. The resulting solution was stirred for 12 hr at 110 degrees C. in an oil bath. The resulting mixture was concentrated under vacuum. The resulting residue was diluted with 100 mL of Water. The pH value of the solution was adjusted to 7 with HCl (2 mol/L). The resulting solution was extracted with 3×30 ml of EtOAc dried over anhydrous sodium sulfate and concentrated under vacuum. The crude product was purified by TLC(PE:EA=1: 2). This resulted in 410 mg (33.96%) of 74-1 as a white solid.

Synthesis of Benzyl (2S,4aS,6aS,6bR,8aR,10S,12aS, 12bR,14bR)-10-(2-(2-methoxy-2-oxoethoxy)acetamido)-2, 4a,6a,6b,9,9,12a-heptamethyl-13-oxo-1,2,3,4,4a,5,6,6a,6b, 7,8,8a,9,10, 11,12,12a,12b,13,14b-icosahydropicene-2-carboxylate (75-1). Into a 25-mL round-bottom flask, was placed 74-1 (110 mg, 0.16 mmol, 1 equiv.), DCM (6 mL, 94.38 mmol, 579.919 equiv.), MeOH (2 mL, 49.40 mmol, 303.524 equiv.). This was followed by the addition of (trimethylsilyl)diazomethane (0.12 mL, 0.11 mmol, 1.5 equiv., 2M in THF) dropwise with stirring. The resulting solution was stirred for 12 hr at room temperature. The resulting mixture was concentrated under vacuum. The residue was applied onto a silica gel column with EtOAc/ petroleum ether (1:1). This resulted in 110 mg (97.97%) of 75-1 as a solid.

Synthesis of (2S,4aS,6aS,6bR,8aR,10S,12aS,12bR, 14bR)-10-(2-(2-Methoxy-2-oxoethoxy) acetamido)-2,4a,6a, 6b,9,9,12a-heptamethyl-13-oxo-1,2,3,4,4a,5,6,6a,6b,7,8,8a, 9,10,11,12,12a, 12b,13,14b-icosahydropicene-2-carboxylic acid (75-2). Into a 25-mL round-bottom flask purged and maintained with an inert atmosphere of $H_2$, was placed 75-1 (110 mg, 0.16 mmol, 1 equiv.), MeOH (2 mL, 0.06 mmol, 0.391 equiv.), Pd/C (50 mg, 0.47 mmol, 2.947 equiv.). The resulting solution was stirred for 2 hr at room temperature. The solids were filtered out. The resulting mixture was concentrated under vacuum. The crude product was purified by Prep-HPLC with the following conditions: Column, XBridge Shield RP18 OBD Column, 5 um, 19*150 mm; mobile phase, water (0.05% TFA) and ACN (5% Phase B up to 56% in 1 min, up to 70% in 7 min); Detector, UV. This resulted in 36.6 mg (38.27%) of 75-2 as a white solid. MS (ES, m/z): [M+H]$^+$=600.40; $^1$H NMR (300 MHz, DMSO-d6) δ 12.18 (s, 1H), 7.22 (d, J=9.7 Hz, 1H), 5.41 (s, 1H), 4.23 (s, 2H), 3.98 (s, 2H), 3.67 (s, 3H), 3.56 (t, J=11.2 Hz, 1H), 2.63 (d, J=13.4 Hz, 1H), 2.42 (s, 1H), 2.13-2.01 (m, 2H), 1.86-1.60 (m, 6H), 1.54 (d, J=14.9 Hz, 1H), 1.36 (d, J=14.0 Hz, 9H), 1.21-0.85 (m, 13H), 0.83-0.72 (m, 9H).

Example 47 (2S,4aS,6aS,6bR,8aR,10S,12aS,12bR, 14bR)-10-((1-(2-Methoxy-2-oxoethyl)-1H-1,2,3-triazol-4-yl)methoxy)-2,4a,6a,6b,9,9,12a-heptamethyl-13-oxo-1,2,3,4,4a,5,6,6a,6b,7,8,8a,9, 10,11,12, 12a,12b,13,14b-icosahydropicene-2-carboxylic acid (76-4)
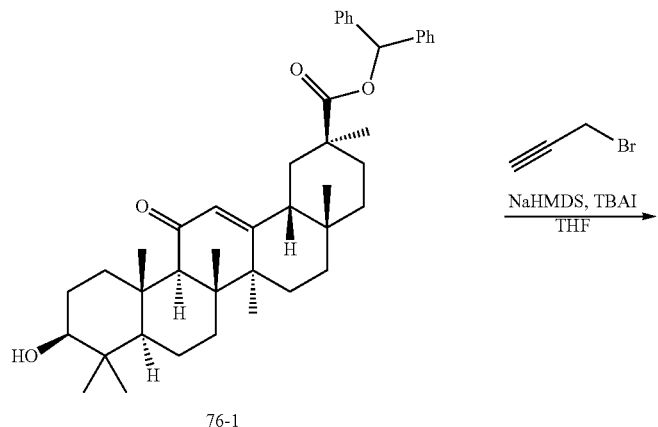
76-1
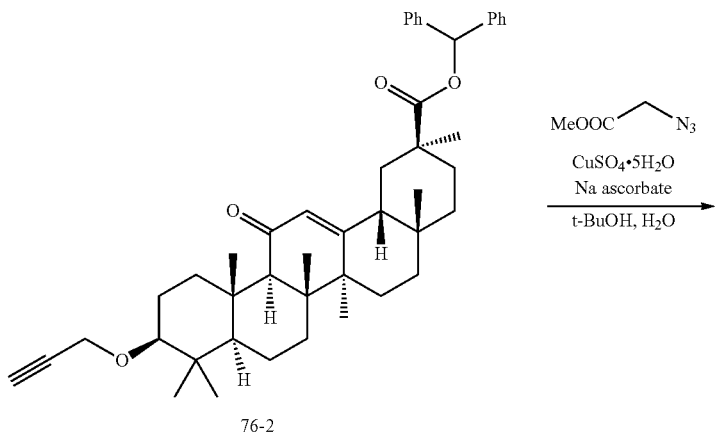
76-2
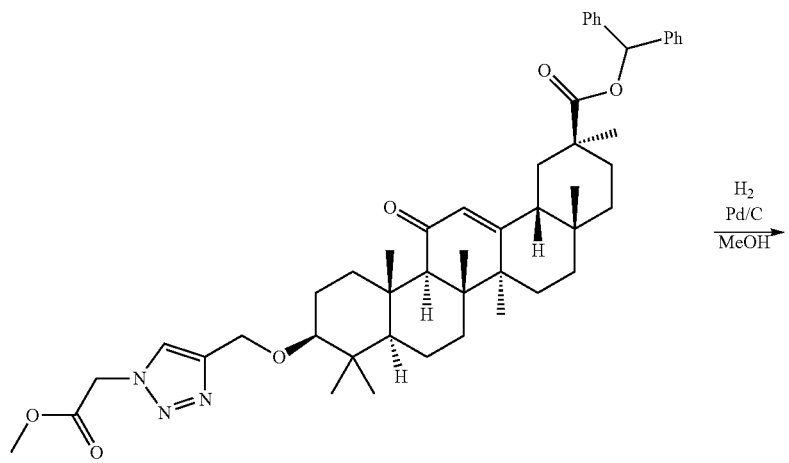
76-3

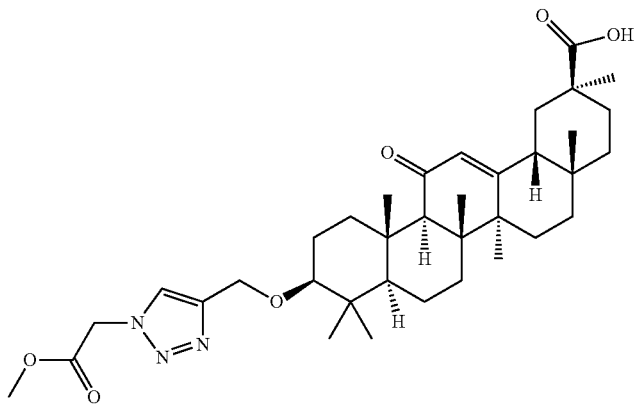

76-4

Synthesis of Benzhydryl (2S,4aS,6aS,6bR,8aR,10S,12aS, 12bR,14bR)-2,4a,6a,6b,9,9,12a-heptamethyl-13-oxo-10-(prop-2-yn-1-yloxy)-1,2,3,4,4a,5,6,6a,6b,7,8,8a,9,10,11,12, 12a,12b,13, 14b-icosahydropicene-2-carboxylate (76-2). Into a 25-mL round-bottom flask, was placed 76-1 (prepared as described in Bioorg. Med. Chem. 2010, 18, 433-454) (1.674 g, 2.63 mmol, 1.00 equiv), THE (2.15 mL), NaHMDS (2.63 mL, 2.00 equiv), 3-bromoprop-1-yne (0.45 mL, 2.00 equiv), TBAI (486 mg, 1.32 mmol, 0.50 equiv). The resulting solution was stirred for overnight at room temperature. The resulting solution was diluted with 30 mL of water. The resulting solution was extracted with 2×50 mL of DCM and the organic layers combined and dried over anhydrous sodium sulfate and concentrated under vacuum. The residue was applied onto a silica gel column with EtOAc/petroleum ether (1:10). This resulted in 1.395 g (79%) of 76-2 as a light yellow solid.

Synthesis of Benzhydryl (2S,4aS,6aS,6bR,8aR,10S,12aS, 12bR,14bR)-10-((1-(2-methoxy-2-oxoethyl)-1H-1,2,3-triazol-4-yl)methoxy)-2,4a,6a,6b,9,9,12a-heptamethyl-13-oxo-1,2,3,4,4a,5,6, 6a,6b,7,8,8a,9,10,11,12,12a,12b,13,14b-icosahydropicene-2-carboxylate (76-3). Into a 50-mL round-bottom flask, was placed 76-2 (100 mg, 0.15 mmol, 1.00 equiv), t-BuOH-H₂O(3:1) 8 mL, methyl 2-azidoacetate (0.043 mL, 3.00 equiv), Na ascorbate (17.6 mg, 0.09 mmol, 0.60 equiv), CuSO₄.5H₂O (11.1 mg, 0.04 mmol, 0.30 equiv). To the above N₂ (g) was introduced in. The resulting solution was stirred for 3 h at 40° C. The resulting mixture was concentrated under vacuum. The residue was applied onto a silica gel column with DCM/MeOH (10:1). This resulted in 110 mg (94%) of 76-3 as a white solid.

Synthesis of (2S,4aS,6aS,6bR,8aR,10S,12aS,12bR, 14bR)-10-((1-(2-Methoxy-2-oxoethyl)-1H-1,2,3-triazol-4-yl)methoxy)-2,4a,6a,6b,9,9,12a-heptamethyl-13-oxo-1,2,3, 4,4a,5,6,6a,6b,7,8,8a, 9,10,11,12,12a,12b,13,14b-icosahydropicene-2-carboxylic acid (76-4). Into a 50-mL round-bottom flask, was placed 76-3 (106 mg, 0.13 mmol, 1.00 equiv), EtOAc (15 mL), palladium on carbon (50 mg). To the above hydrogen was introduced in. The resulting solution was stirred for overnight at room temperature. The resulting mixture was concentrated under vacuum. The residue was dissolved in of. The crude product (8 mL) was purified by Prep-HPLC with the following conditions: Column, XBridge Prep OBD C18 Column, 19*250 mm, 5 um; mobile phase, water (0.05% TFA) and ACN (64.0% ACN up to 80.0% in 9 min); Detector, UV 254 nm.

This resulted in 35.4 mg (42%) of 76-4 as a white solid. MS (ES, m/z): [M+H]⁺=624.55; ¹H NMR (400 MHz, DMSO-d₆, ppm): δ 0.70-0.85 (d, 7H), 0.86 (s, 3H), 0.89-1.01 (m, 2H), 1.02-1.10 (m, 6H), 1.10-1.19 (m, 4H), 1.21-1.56 (m, 1OH), 1.62-1.81 (m, 6H), 2.05-2.09 (m, 2H), 2.33 (s, 1H), 2.66 (d, J=13.6 Hz, 1H), 2.96 (dd, J=11.6, 4.4 Hz, 1H), 3.71 (s, 3H), 4.45 (d, J=12.4 Hz, 1H), 4.67 (d, J=12.4 Hz, 1H), 5.40 (d, J=7.2 Hz, 3H), 8.07 (s, 1H), 12.21 (br s, 1H).

Example 48 (2S,4aS,6aS,6bR,8aR,10S,12aS,12bR, 14bR)-10-(2-Methoxy-2-oxoethoxy)-2,4a,6a,6b,9,9, 12a-heptamethyl-13-oxo-1,2,3,4,4a,5,6,6a,6b,7,8,8a, 9,10,11,12,12a,12b,13,14b-icosahydropicene-2-carboxylic acid (79-2)

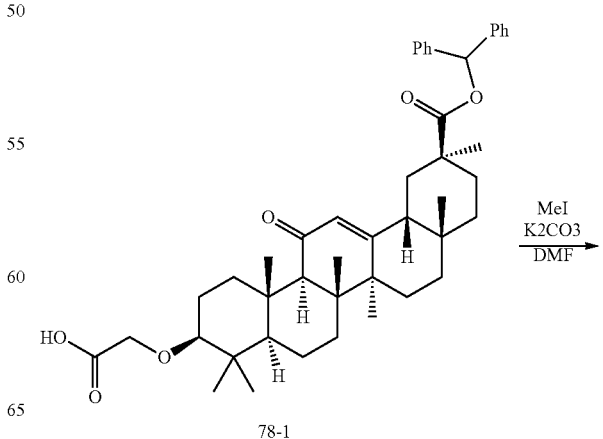

78-1

-continued

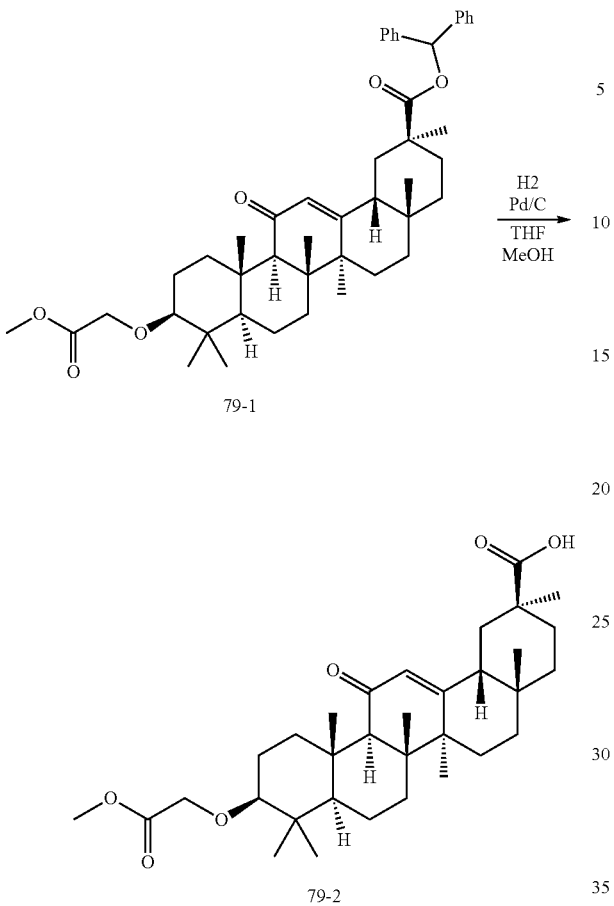

Synthesis of (2S,4aS,6aS,6bR,8aR,10S,12aS,12bR,14bR)-benzhydryl 10-(2-methoxy-2-oxoethoxy)-2,4a,6a,6b,9,9,12a-heptamethyl-13-oxo-1,2,3,4,4a,5,6,6a,6b,7,8,8a,9,10,11,12,12a,12b,13,14b-icosahydropicene-2-carboxylate (79-1). A mixture of 78-1 (50 mg 0.072 mmol), iodomethane (170 mg, 1.2 mmol) and K$_2$CO$_3$ (30 mg, 0.22 mmol) in DMF (0.30 mL) was stirred and heated at 60° C. After 3 hours, EtOAc (20 mL) was added and the mixture was washed with water (5 mL), 10% Na$_2$S$_2$O$_3$ (3 mL) and water (5 mL). The organic layer was dried (Na$_2$SO$_4$), concentrated and purified by flash chromatography (4 g SiO$_2$, 0-20% EtOAc/hexane) to give the title compound (32.7 mg).

Synthesis of (2S,4aS,6aS,6bR,8aR,10S,12aS,12bR,14bR)-10-(2-methoxy-2-oxoethoxy)-2,4a,6a,6b,9,9,12a-heptamethyl-13-oxo-1,2,3,4,4a,5,6,6a,6b,7,8,8a,9,10,11,12,12a,12b,13,14b-icosa hydropicene-2-carboxylic acid (79-2). A mixture of 79-1 (32.7 mg, 0.046 mmol) and 10% Pd/C (50% water, 18 mg wet weight) in MeOH (2.0 mL) and THF (1.0 mL) was stirred under 1 atm of H$_2$. After 2 hours, the mixture was filtered, concentrated and purified by flash chromatography (4 g SiO$_2$, 20-60% EtOAc/hexane) to give the title compound (24 mg). MS (ES, m/z): 543.3 [M+H]$^+$; $^1$H-NMR (CDCl$_3$) δ 5.71 (s, 1H), 4.17 (d, J=16.2 Hz, 1H), 4.08 (d, J=16.2 Hz, 1H), 3.74 (s, 3H), 2.94 (dd, J=11.8 Hz, J=4.5 Hz, 1H), 2.82 (dt, J=13.5 Hz, J=3.5 Hz, 1H), 2.34 (s, 1H), 2.18 (dd, J=13.3 Hz, J=3.5 Hz, 1H), 1.34 (s, 3H), 1.23 (s, 3h), 1.15 (s, 3H), 1.13 (s, 3H), 1.07 (s, 3H), 0.85 (s, 3H), 0.84 (s, 3H), 0.69 (d, J=10.2 Hz, 1H).

Example 49 (2S,4aS,6aS,6bR,8aR,10S,12aS,12bR,14bR)-10-((1,3-Dimethoxy-1,3-dioxopropan-2-yl)oxy)-2,4a,6a,6b,9,9,12a-heptamethyl-13-oxo-1,2,3,4,4a,5,6,6a,6b,7,8,8a,9,10,11,12,12a,12b,13,14b-icosahydropicene-2-carboxylic acid (80-3)

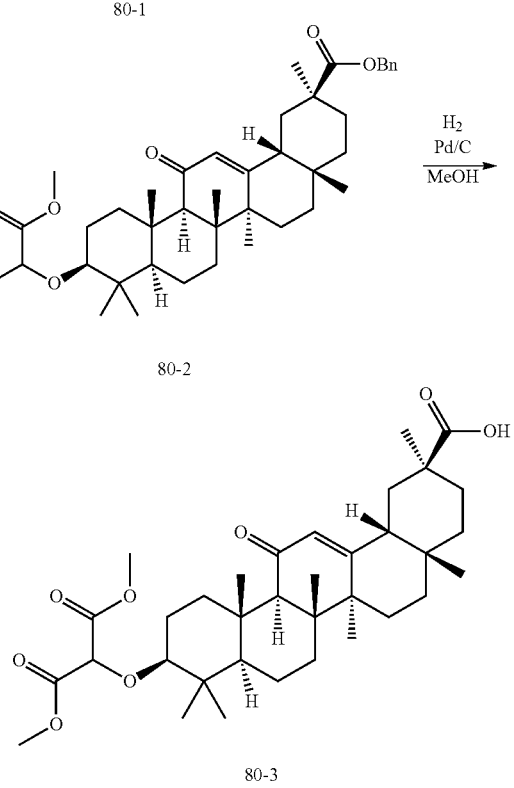

Synthesis of Dimethyl 2-(((3S,4aR,6aR,6bS,8aS,11S,12aR,14aR,14bS)-11-((benzyloxy) carbonyl)-4,4,6a,6b,8a,11,14b-heptamethyl-14-oxo-1,2,3,4,4a,5,6,6a,6b,7,8,8a,9,10,11,12,12a,14,14a,14b-icosahydropicen-3-yl)oxy) malonate (80-2). Into a 100-mL 3-necked round-bottom flask, was placed 80-1 ((prepared as described in *Bioorg. Med. Chem.* 2012, 22, 3473-3479) (680 mg, 1.21 mmol, 1.00 equiv), toluene (20 mL), Rh$_2$(OAc)$_4$ (8 mg). This was followed by the addition of a solution of 1,1-bis(methoxycarbonyl)diaziridin-1-ium (383 mg, 2.38 mmol, 1.96 equiv) in toluene (4 mL) dropwise with stirring at 90° C. in 1 hr. The resulting solution was stirred for 2 h at 90° C. The resulting mixture was concentrated under vacuum. The residue was applied onto a silica gel column with EtOAc/petroleum ether (1:3). This resulted in 700 mg (84%) of 80-2 as a white solid.

Synthesis of (2S,4aS,6aS,6bR,8aR,10S,12aS,12bR,14bR)-10-((1,3-Dimethoxy-1,3-dioxopropan-2-yl)oxy)-2,4a,6a,6b,9,9,12a-heptamethyl-13-oxo-1,2,3,4,4a,5,6,6a,6b,7,8,8a,9,10,11,12,12a,12b,13,14b-icosahydropicene-2-carboxylic acid (80-3). Into a 100-mL round-bottom flask purged and maintained with an inert atmosphere of $H_2$ (1 atm), was placed 80-2 (700 mg, 1.01 mmol, 1.00 equiv), MeOH (10 mL), palladium on carbon (70 mg). The resulting solution was stirred for 3 h at room temperature. The solids were filtered out. The crude product was purified by Prep-HPLC with the following conditions (2 # -AnalyseHPLC-SHIMADZU (HPLC-10)): Column, XBridge Prep C18 OBD Column, 19*150 mm, 5 um; mobile phase, water (0.05% TFA) and ACN (76.0% ACN up to 81.0% in 10 min); Detector, UV 254 nm. This resulted in 59.7 mg (10%) of 80-3 as a white solid. MS (ES, m/z): $[M+H]^+=601.40$; $^1$H-NMR (400 MHz, MeOH-$d_4$, ppm): δ 0.78-0.86 (m, 1H), 0.88-0.98 (m, 6H), 0.99-1.07 (m, 4H), 1.16-1.19 (m, 9H), 1.19-1.26 (m, 1H), 1.40-1.52 (m, 9H), 1.63-1.87 (m, 7H), 1.91-1.96 (m, 1H), 2.16-2.24 (m, 2H), 2.46 (s, 1H), 2.77 (d, J=13.2 Hz, 1H), 3.08-3.12 (m, 1H), 3.78 (s, 6H), 4.86 (s, 1H), 5.61 (s, 1H).

Example 50 (2S,4aS,6aS,6bR,8aR,10S,12aS,12bR,14bR)-10-(3-(4-(Ethoxycarbonyl)piperidin-1-yl)-2-hydroxypropoxy)-2,4a,6a,6b,9,9,12a-heptamethyl-13-oxo-1,2,3,4,4a,5,6,6a,6b,7,8,8a,9, 10,11,12,12a,12b,13,14b-icosahydropicene-2-carboxylicacid (88-2)

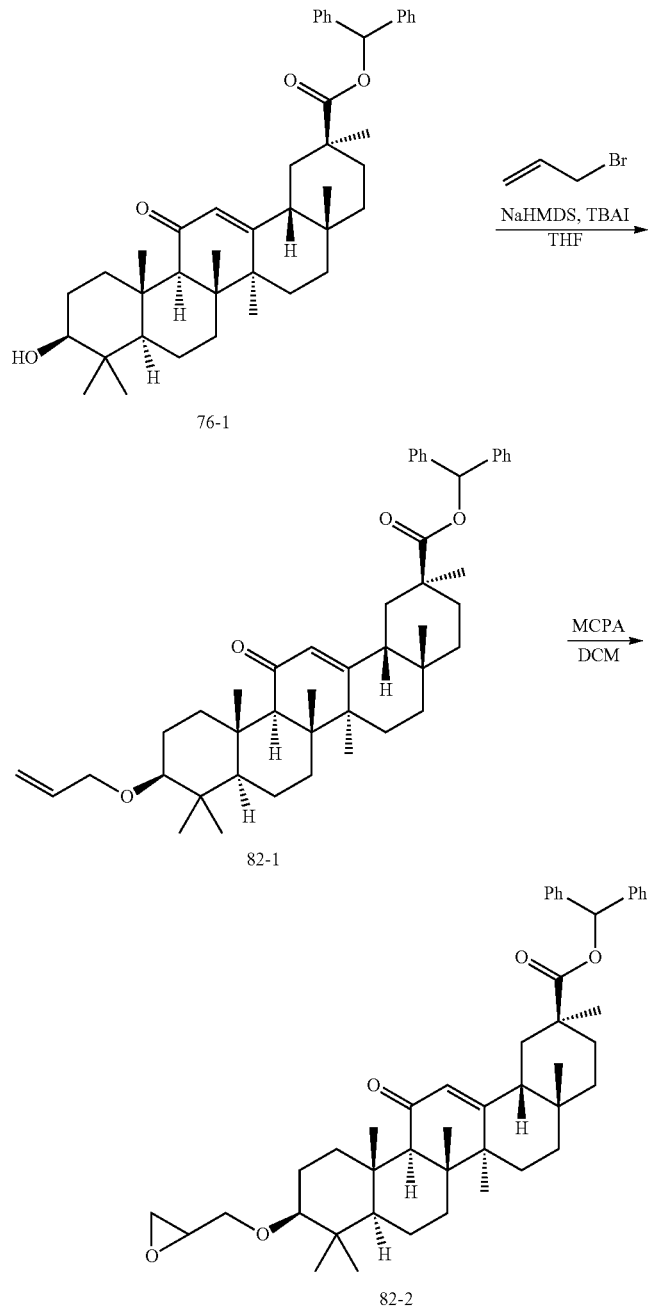

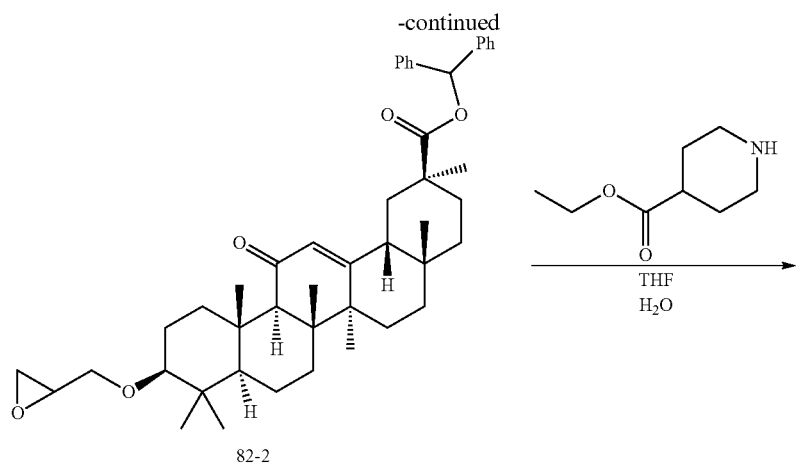

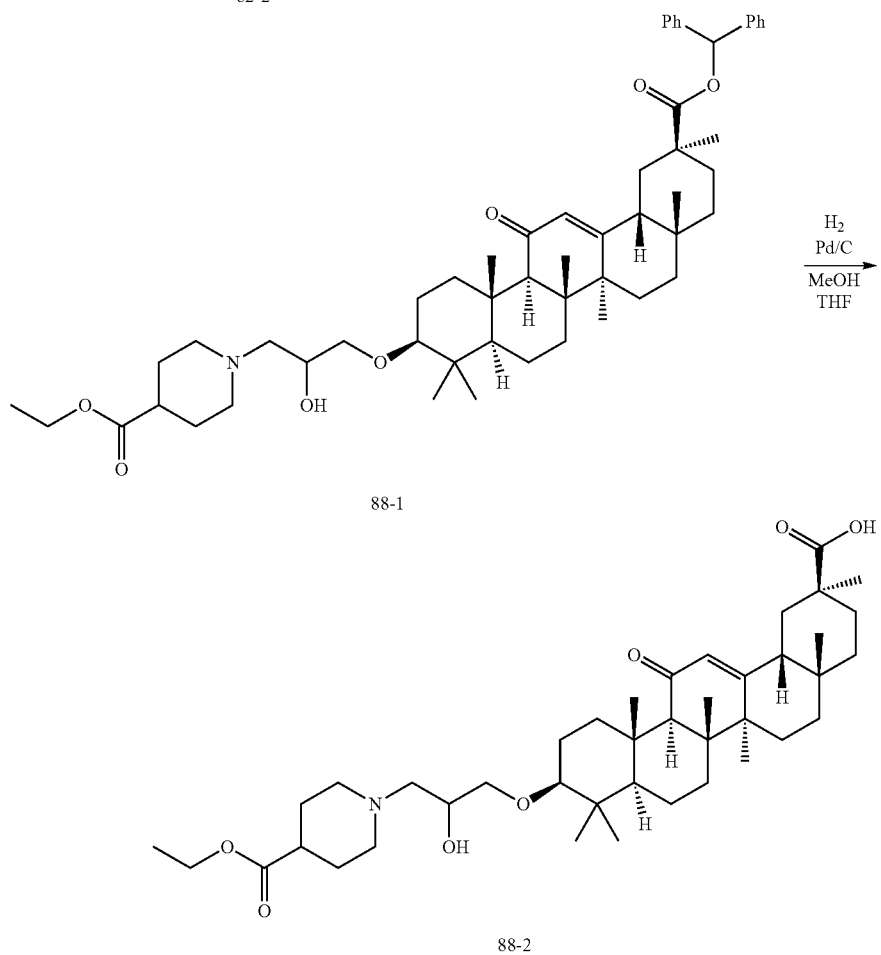

Synthesis of Benzhydryl (2S,4aS,6aS,6bR,8aR,10S,12aS, 12bR,14bR)-10-(allyloxy)-2,4a,6a,6b, 9,9,12a-heptamethyl-13-oxo-1,2,3,4,4a,5,6,6a,6b,7,8,8a,9,10,11,12,12a,12b,13, 14b-icosahydro picene-2-carboxylate (82-1). Into a 250-mL round-bottom flask, was placed 76-1 (2.3 g, 3.61 mmol, 1.00 equiv), THE (5 mL), NaHMDS (2M in THF) (3.61 mL, 2.00 equiv), 3-bromoprop-1-ene (870 mg, 7.19 mmol, 2.00 equiv), TBAI (667 mg, 0.50 equiv). The resulting solution was stirred for 5 h at 50° C. The resulting solution was diluted with 100 mL of EA. The resulting mixture was washed with 2×50 mL of $H_2O$. The mixture was dried over anhydrous sodium sulfate and concentrated under vacuum. The residue was applied onto a silica gel column with EtOAc/petroleum ether (1:50). This resulted in 1.37 g (56%) of 82-1 as a white solid.

Synthesis of benzhydryl (2S,4aS,6aS,6bR,8aR,10S,12aS, 12bR,14bR)-2,4a,6a,6b,9,9,12a-heptamethyl-10-(oxiran-2-ylmethoxy)-13-oxo-1,2,3,4,4a,5,6,6a,6b,7,8,8a,9,10,11,12, 12a,12b,13, 14b-icosahydropicene-2-carboxylate (82-2). Into a 250-mL round-bottom flask, was placed a solution of 82-1 (1.37 g, 2.02 mmol, 1.00 equiv) in DCM (10 mL). This was followed by the addition of a solution of m-CPBA (1.75 g, 10.14 mmol, 5.00 equiv) in DCM (10 mL) dropwise with stirring. The resulting solution was stirred overnight at 30° C. The reaction was then quenched by the addition of 15 mL of 3M sodium hydroxide. The resulting mixture was concentrated under vacuum. The resulting solution was extracted with 3×150 mL of EtOAc and the organic layers combined. The resulting mixture was washed with 1×100 mL of water and 1×100 mL of brine. The mixture was dried over anhydrous sodium sulfate and concentrated under vacuum. The residue was applied onto a silica gel column with DCM/EtOAc (50:1). The collected fractions were combined and concentrated under vacuum. This resulted in 1.1 g (78%) of 82-2 as a white solid.

Synthesis of ethyl 1-(3-(((3S,4aR,6aR,6bS,8aS,11S,12aR, 14aR,14bS)-11-((benzhydryloxy) carbonyl)-4,4,6a,6b,8a, 11,14b-heptamethyl-14-oxo-1,2,3,4,4a,5,6,6a,6b,7,8,8a,9, 10,11,12,12a, 14,14a,14b-icosahydropicen-3-yl)oxy)-2-hydroxypropyl)piperidine-4-carboxylate (88-1). A solution of 82-2 (430 mg, 0.62 mmol) and isonipecotate (340 mg) in THF (6.0 mL) and water (1.0 mL) was heated at 70° C. After 2.5 hours the reaction mixture was concentrated under vacuum and used directly in the next step. A mixture of 88-1 (0.62 mmol) and wet 10% Pd/C (50% water, 100 mg wet weight) in THF (4.0 mL) and MeOH (4.0 mL) was stirred under one atm of $H_2$. After 2 hours, the final product was purified by flash chromatography (4 g $SiO_2$, 0-15% MeOH/DCM) to give the title compound. MS (ES, m/z): 684.2 [M+H]$^+$; $^1$H-NMR (CDCl$_3$) δ 5.68 (s, 1H), 4.14 (quar, J=7.0 Hz, 2H), 3.95 (m, 1H), 3.67-3.55 (m, 1H), 3.36-3.25 (m, 1H), 3.08-2.92 (m, 2H), 2.33 (s, 1H), 1.36 (s, 3H), 1.25 (t, J=7.0 Hz, 3H), 1.20 (s, 3H), 1.13 (s, 3H), 1.12 (s, 3H), 0.98 (s, 3H), 0.82 (s, 3H), 0.79 (s, 3H).

Example 51 (2S,4aS,6aS,6bR,8aR,10S,12aS,12bR, 14bR)-10-(3-((Carboxymethyl)amino)-2-hydroxypropoxy)-2,4a,6a,6b,9,9,12a-heptamethyl-13-oxo-1, 2,3,4,4a,5,6,6a,6b,7,8,8a,9,10,11,12, 12a,12b,13, 14b-icosahydropicene-2-carboxylic acid (94-2)

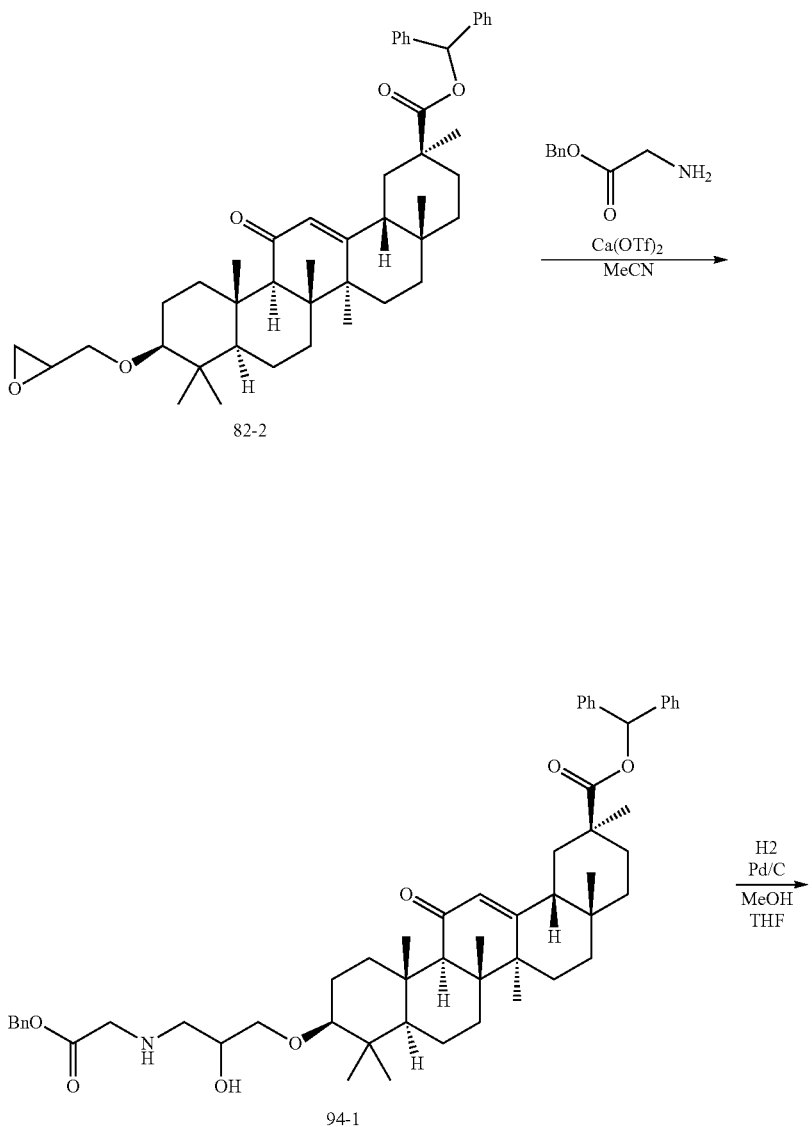

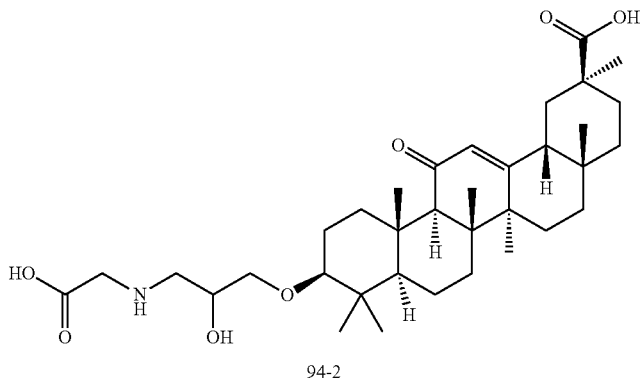

94-2

Synthesis of (2S,4aS,6aS,6bR,8aR,10S,12aS,12bR,14bR)-Benzhydryl 10-(3-(2-(benzyloxy)-2-oxoethylamino)-2-hydroxypropoxy)-2,4a,6a,6b,9,9,12a-heptamethyl-13-oxo-1,2,3,4,4a,5,6, 6a,6b,7,8,8a,9,10,11,12,12a, 12b,13,14b-icosahydropicene-2-carboxylate (94-1). A mixture of 82-2 (30 mg 0.043 mmol), benzyl glycinate (14 mg, 0.086 mmol) and calcium trifluoromethylsulfonate (5 mg, 0.014 mmol) in acetonitrile (0.5 mL) was heated at 80° C. for 2 hours and then cooled to RT overnight. The reaction mixture was then heated at 80° C. for 2 hours, added to 5% Na$_2$CO$_3$ (5 mL) and extracted with DCM (4×10 mL). The combined extracts were dried (Na$_2$SO$_4$) and concentrated to give the crude intermediate (57 mg).

Synthesis of (2S,4aS,6aS,6bR,8aR,10S,12aS,12bR,14bR)-10-(3-((Carboxymethyl)amino)-2-hydroxypropoxy)-2,4a,6a,6b,9,9,12a-heptamethyl-13-oxo-1,2,3,4,4a,5,6,6a, 6b,7,8,8a,9,10,11, 12,12a,12b,13,14b-icosahydropicene-2-carboxylic acid (94-2). A mixture of crude 94-1 from step 1 (57 mg) and wet 10% Pd/C (50% water, 10 mg wet weight) in MeOH (1 mL) and THF (1 mL) was stirred under 1 atm of H$_2$ for 2 days. The mixture was filtered, concentrated and purified by preparative HPLC to give a TFA salt of the title compound (2.5 mg) as a white powder. MS (ES, m/z): 602.2 [M+H]$^+$.

Example 52 (2S,4aS,6aS,6bR,8aR,10S,12aS,12bR, 14bR)-10-(3-(((Carboxymethyl)(methyl) amino)-2-hydroxypropoxy)-2,4a,6a,6b,9,9,12a-heptamethyl-13-oxo-1,2,3,4,4a,5,6,6a,6b,7,8,8a, 9,10,11,12,12a, 12b,13,14b-icosahydropicene-2-carboxylicacid (95-2)

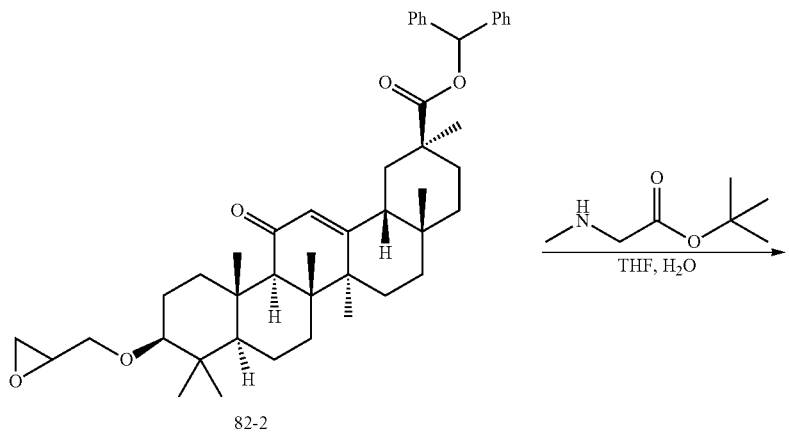

82-2

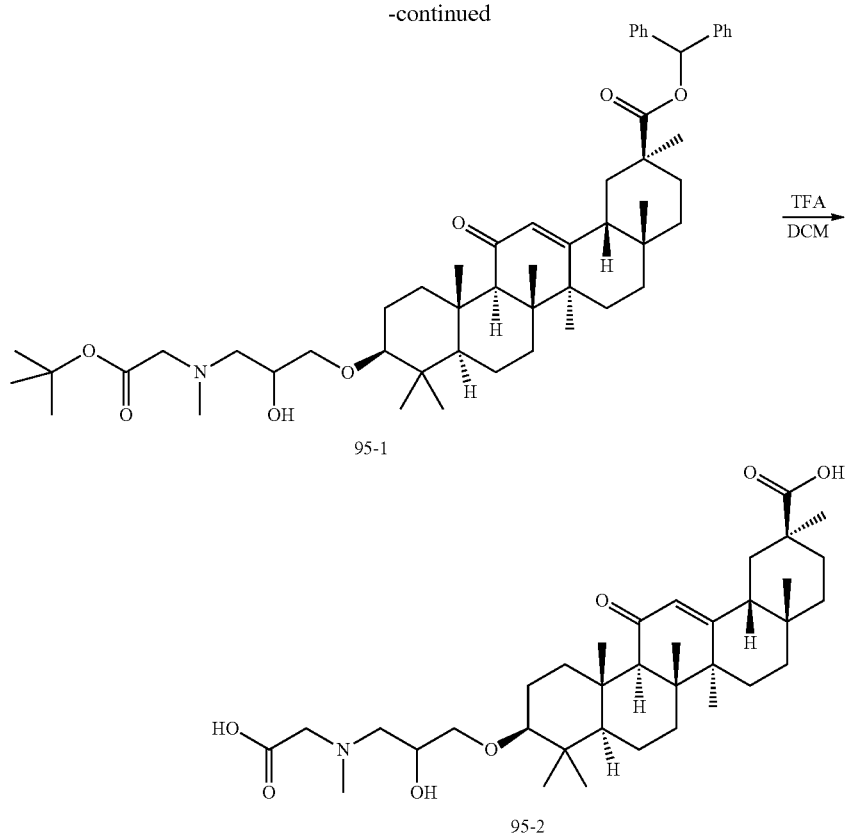

95-1

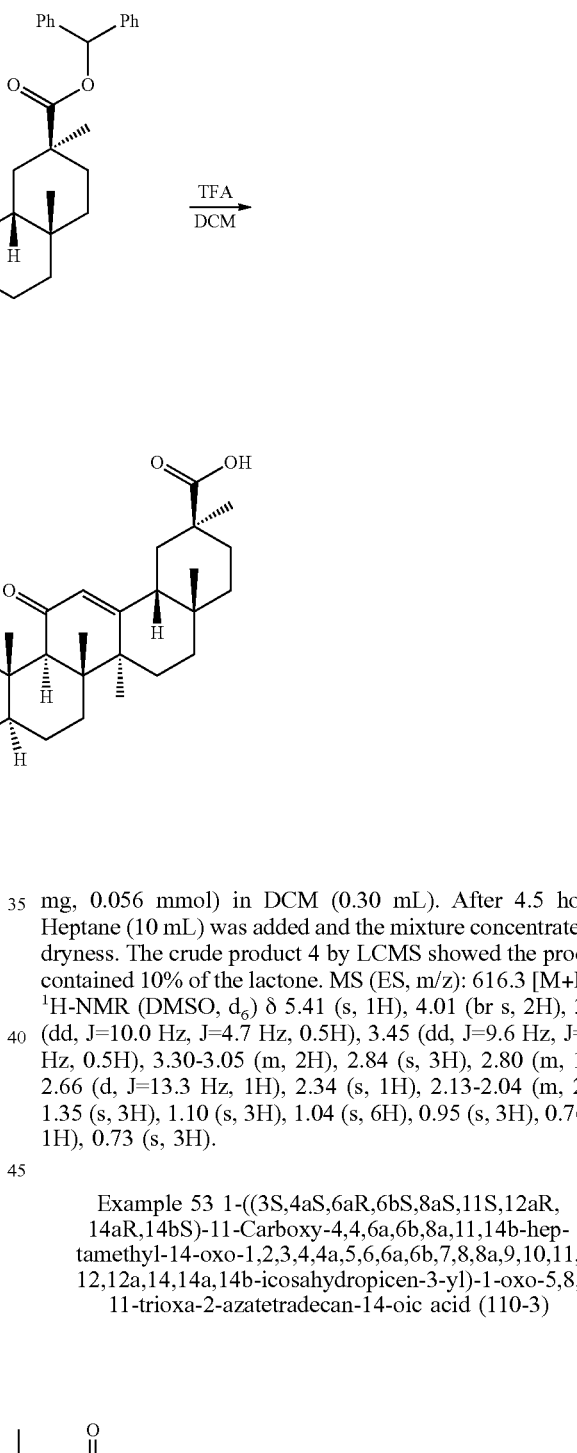

95-2

Synthesis of (2S,4aS,6aS,6bR,8aR,10S,12aS,12bR, 14bR)-Benzhydryl 10-(3-((2-tert-butoxy-2-oxoethyl) (methyl)amino)-2-hydroxypropoxy)-2,4a,6a,6b,9,9,12a-heptamethyl-13-oxo-1,2,3,4,4a, 5,6,6a,6b,7,8,8a,9,10,11,12, 12a,12b,13,14b-icosahydropicene-2-carboxylate (95-1). A solution of 82-2 (40 mg, 0.058 mmol) and tert-butyl sarcosine (46 mg, 0.32 mmol) in THF (0.50 mL) and water (0.10 mL) was heated at 65° C. for 5 hours. The reaction was concentrated to dryness and purified by flash chromatography (4 g SiO$_2$, 0-5% MeOH/DCM) to give the title compound (47 mg).

Synthesis of (2S,4aS,6aS,6bR,8aR,10S,12aS,12bR, 14bR)-10-(3-((Carboxymethyl)(methyl) amino)-2-hydroxypropoxy)-2,4a,6a,6b,9,9,12a-heptamethyl-13-oxo-1,2,3,4, 4a,5,6,6a,6b,7,8,8a,9, 10,11,12,12a,12b,13,14b-icosahydropicene-2-carboxylic acid (95-2). Trifluoroacetic acid (0.30 mL) was added slowly to a solution of 95-1 (47 mg, 0.056 mmol) in DCM (0.30 mL). After 4.5 hours, Heptane (10 mL) was added and the mixture concentrated to dryness. The crude product 4 by LCMS showed the product contained 10% of the lactone. MS (ES, m/z): 616.3 [M+H]$^+$; $^1$H-NMR (DMSO, d$_6$) δ 5.41 (s, 1H), 4.01 (br s, 2H), 3.57 (dd, J=10.0 Hz, J=4.7 Hz, 0.5H), 3.45 (dd, J=9.6 Hz, J=6.1 Hz, 0.5H), 3.30-3.05 (m, 2H), 2.84 (s, 3H), 2.80 (m, 1H), 2.66 (d, J=13.3 Hz, 1H), 2.34 (s, 1H), 2.13-2.04 (m, 2H), 1.35 (s, 3H), 1.10 (s, 3H), 1.04 (s, 6H), 0.95 (s, 3H), 0.76 (s, 1H), 0.73 (s, 3H).

Example 53 1-((3S,4aS,6aR,6bS,8aS,11S,12aR, 14aR,14bS)-11-Carboxy-4,4,6a,6b,8a,11,14b-heptamethyl-14-oxo-1,2,3,4,4a,5,6,6a,6b,7,8,8a,9,10,11, 12,12a,14,14a,14b-icosahydropicen-3-yl)-1-oxo-5,8, 11-trioxa-2-azatetradecan-14-oic acid (110-3)

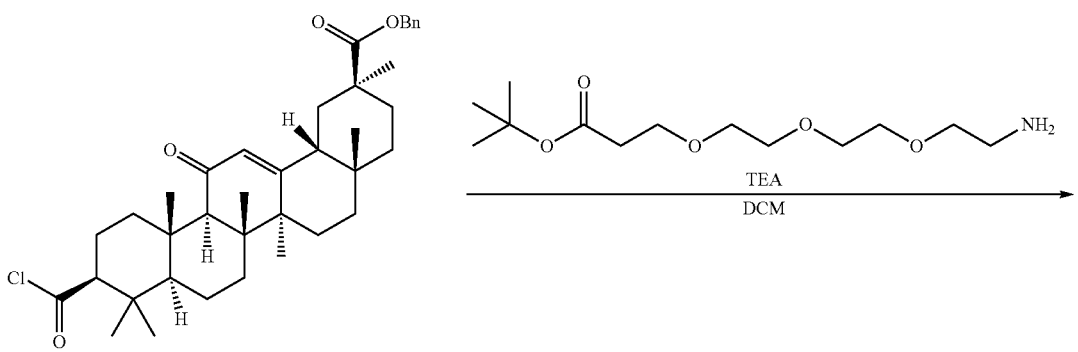

1-7

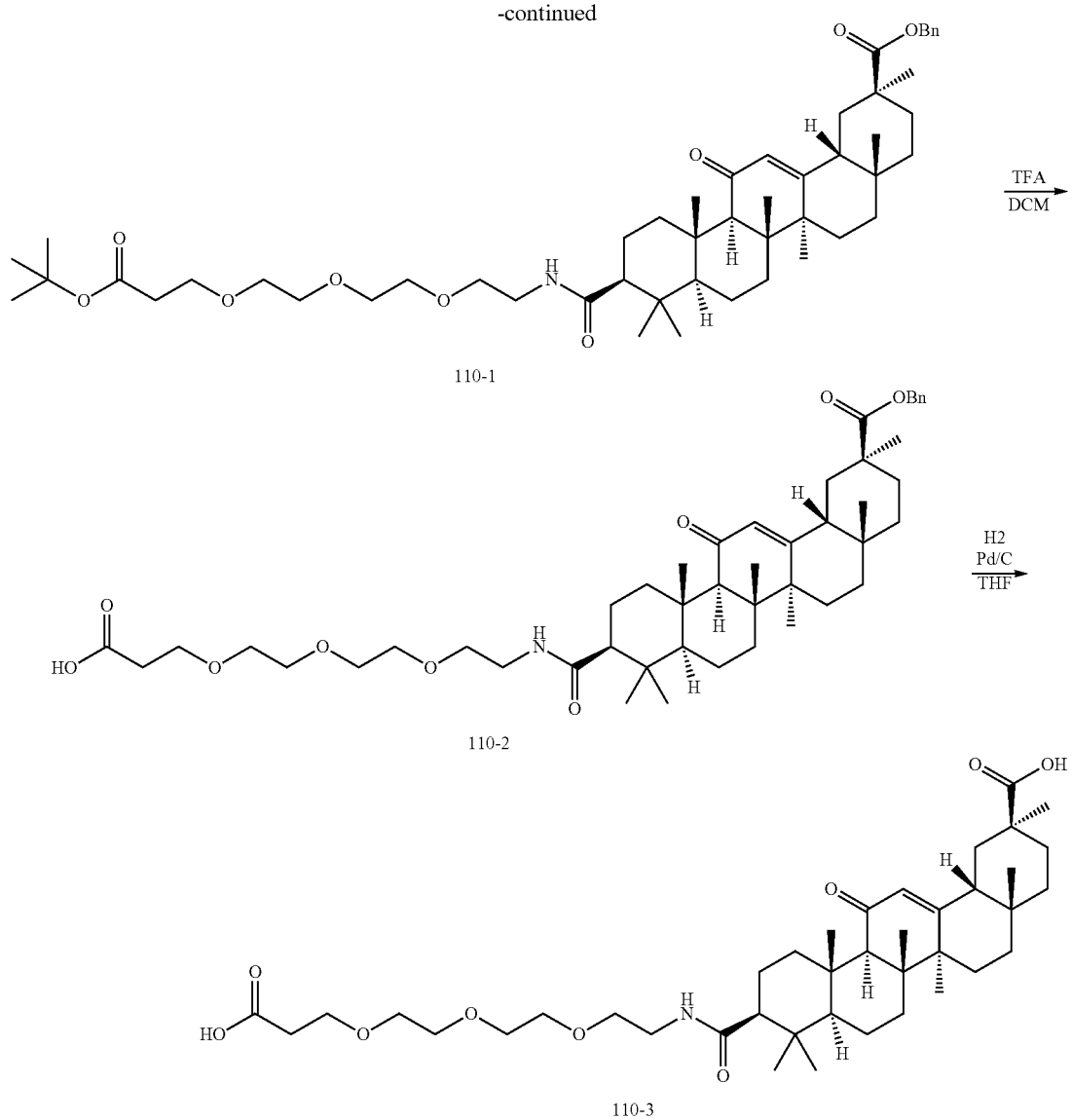

Synthesis of tert-Butyl 1-((3S,4aS,6aR,6bS,8aS,11S, 12aR,14aR,14bS)-11-((benzyloxy) carbonyl)-4,4,6a,6b,8a, 11,14b-heptamethyl-14-oxo-1,2,3,4,4a,5,6,6a,6b,7,8,8a,9, 10,11,12,12a, 14,14a,14b-icosahydropicen-3-yl)-1-oxo-5,8, 11-trioxa-2-azatetradecan-14-oate (110-1). Into a 250-mL round-bottom flask, was placed 1-7 (515 mg, 0.85 mmol, 1.00 equiv), DCM (50 mL), tert-butyl 3-2-[2-(2-aminoethoxy)ethoxy]ethoxypropanoate (589 mg, 2.12 mmol, 2.50 equiv), TEA (0.885 mL, 7.50 equiv). The resulting solution was stirred overnight at room temperature. The resulting mixture was concentrated under vacuum. The residue was applied onto a silica gel column with EtOAc/petroleum ether (1:1). This resulted in 533 mg (74%) of 110-1 as a light yellow solid.

Synthesis of 1-((3S,4aS,6aR,6bS,8aS,11S,12aR,14aR, 14bS)-11-((Benzyloxy)carbonyl)-4,4,6a, 6b,8a,11,14b-heptamethyl-14-oxo-1,2,3,4,4a,5,6,6a,6b,7,8,8a,9,10,11,12,12a, 14,14a,14b-icosahydropicen-3-yl)-1-oxo-5,8,11-trioxa-2-azatetradecan-14-oic acid (110-2). Into a 250-mL round-bottom flask, was placed 110-1 (533 mg, 0.63 mmol, 1.00 equiv), DCM (15 mL), trifluoroacetic acid (15 mL). The resulting solution was stirred for 1 h at room temperature. The resulting mixture was concentrated under vacuum. The resulting mixture was washed with 2×10 mL of diethyl ether. This resulted in 497 mg (100%) of 110-2 as light yellow crude oil.

Synthesis of 1-((3S,4aS,6aR,6bS,8aS,11S,12aR,14aR, 14bS)-11-Carboxy-4,4,6a,6b,8a,11,14b-heptamethyl-14-oxo-1,2,3,4,4a,5,6,6a,6b,7,8,8a,9,10,11,12,12a,14,14a,14b-icosahydropicen-3-yl)-1-oxo-5,8,11-trioxa-2-azatetradecan-14-oic acid (110-3). Into a 50-mL round-bottom flask purged and maintained with an inert atmosphere of $H_2$ (1 atm), was placed 110-2 (150 mg, 1 equiv), THF (10 mL), Pd/C (15 mg). The resulting solution was stirred overnight at room temperature. The solids were filtered out. The resulting mixture was concentrated under vacuum. The crude product was purified by Prep-HPLC with the following conditions: Column, XBridge Shield RP18 OBD Column, 5 um, 19*150 mm; mobile phase, water (0.05% TFA) and ACN (42% ACN up to 60% in 8 min); Detector, UV 254 nm. This resulted in 65.8 mg (49.5%) of 110-3 as a white solid. MS (ES, m/z): $[M+H]^+$=702.40; $^1$H NMR (400 MHz, MeOH-$d_4$, ppm): δ

0.86 (s, 3H), 0.88 (s, 1H), 0.94 (s, 3H), 0.99-1.11 (m, 5H), 1.17 (s, 3H), 1.19 (s, 3H), 1.21 (s, 3H), 1.21 (d, J=7.3 Hz, 1H), 1.35-1.55 (m, 9H), 1.61-2.08 (m, 8H), 2.10-2.29 (m, 2H), 2.52 (s, 1H), 2.57 (t, J=6.4 Hz, 2H), 2.80 (d, J=13.6 Hz, 1H), 3.34-3.47 (m, 2H), 3.55 (t, J=5.4 Hz, 2H), 3.60-3.69 (m, 8H), 3.76 (t, J=6.4 Hz, 2H), 5.60 (s, 1H).

Example 54 (2S,4aS,6aS,6bR,8aS,10S,12aS,12bR, 14bR)-2,4a,6a,6b,9,9,12a-Heptamethyl-13-oxo-10-((3-oxo-2,6,9,12-tetraoxatetradecan-14-yl)carbamoyl)-1,2,3,4,4a,5,6,6a,6b,7,8,8a,9,10, 11,12,12a,12b, 13,14b-icosahydropicene-2-carboxylic acid (113-2)

by the addition of TMSCHN$_2$ in n-hexane (2M) (0.96 mL, 3.00 equiv) dropwise with stirring at 0° C. The resulting solution was stirred for 1 h at room temperature. The resulting mixture was concentrated under vacuum. This resulted in 517 mg (100%) of 113-1 as a yellow crude solid.

Synthesis of (2S,4aS,6aS,6bR,8aS,10S,12aS,12bR, 14bR)-2,4a,6a,6b,9,9,12a-Heptamethyl-13-oxo-10-((3-oxo-2,6,9,12-tetraoxatetradecan-14-yl)carbamoyl)-1,2,3,4,4a,5, 6,6a,6b,7,8,8a,9, 10,11,12,12a,12b,13,14b-icosahydropicene-2-carboxylic acid (113-2). Into a 250-mL round-bottom flask purged and maintained with an inert atmosphere of H$_2$ (1 atm), was placed 113-1 (517 mg, 1 equiv), MeOH (10 mg), THF (10 mg), Pd/C (52 mg). The

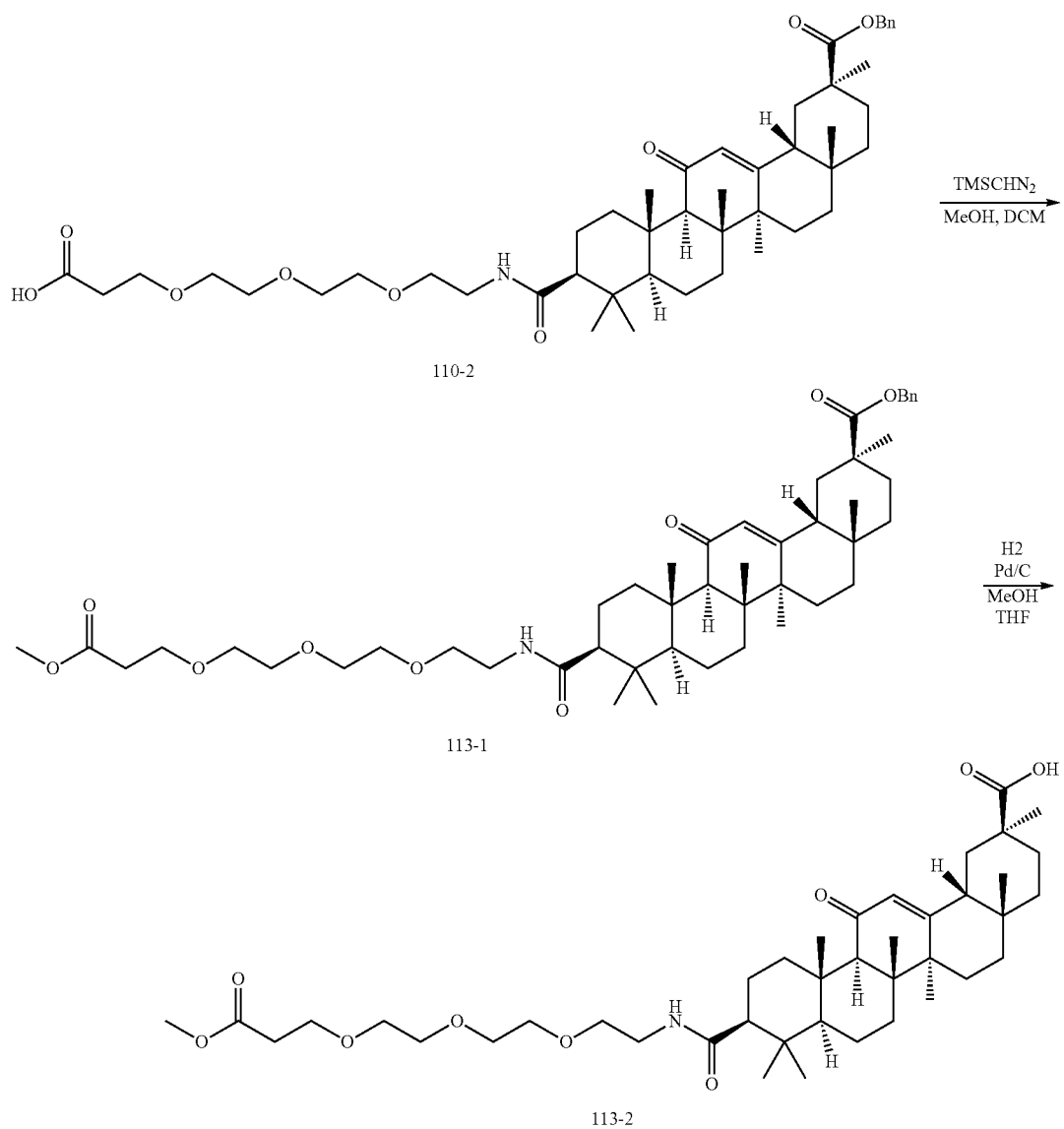

Synthesis of Methyl 1-((3S,4aS,6aR,6bS,8aS,11S,12aR, 14aR,14bS)-11-((benzyloxy)carbonyl)-4,4,6a,6b,8a,11,14b-heptamethyl-14-oxo-1,2,3,4,4a,5,6,6a,6b,7,8,8a,9,10,11,12, 12a,14,14a,14b-icosahydropicen-3-yl)-1-oxo-5,8,11-trioxa-2-azatetradecan-14-oate (113-1) Into a 250-mL round-bottom flask, was placed 110-2 (508 mg, 0.64 mmol, 1.00 equiv), DCM (15 mL), MeOH (15 mL). This was followed resulting solution was stirred overnight at room temperature. The solids were filtered out. The resulting mixture was concentrated under vacuum. The crude product was purified by Prep-HPLC with the following conditions: Column, XBridge Shield RP18 OBD Column, 5 um, 19*150 mm; mobile phase, water (0.05% TFA) and ACN (48% Phase B up to 68% in 8 min); Detector, UV 254 nm. This resulted in 29.6 mg (6.45%) of 113-2 as a white solid. MS (ES, m/z): [M+H]$^+$=716.45; $^1$H NMR (400 MHz, MeOH-d$_4$, ppm): δ 0.86 (s, 3H), 0.88 (s, 1H), 0.94 (s, 3H), 0.97-1.11 (m, 5H), 1.17 (s, 3H), 1.19 (s, 3H), 1.21 (s, 3H), 1.28 (d, J=13.8 Hz, 1H), 1.34-1.55 (m, 9H), 1.63-1.81 (m, 3H), 1.82-2.09 (m, 5H), 2.10-2.25 (m, 2H), 2.49 (s, 1H), 2.58 (t, J=6.2 Hz, 2H), 2.78 (d, J=13.6 Hz, 1H), 3.32-3.35 (m, 1H), 3.36-3.44 (m, 1H), 3.53 (t, J=5.2 Hz, 2H), 3.60 (s, 8H), 3.67 (s, 3H), 3.74 (t, J=6.2 Hz, 2H), 5.58 (s, 1H).
Example 55 (2S,4aS,6aS,6bR,8aR,10S,12aS,12bR,14bR)-2,4a,6a,6b,9,9,12a-Heptamethyl-13-oxo-10-((12-oxo-2,5,8,11-tetraoxatetradecane)sulfonamido)-1,2,3,4,4a,5,6,6a,6b,7,8,8a,9,10,11,12,12a,12b,13,14b-icosahydropicene-2-carboxylic acid (114-2)
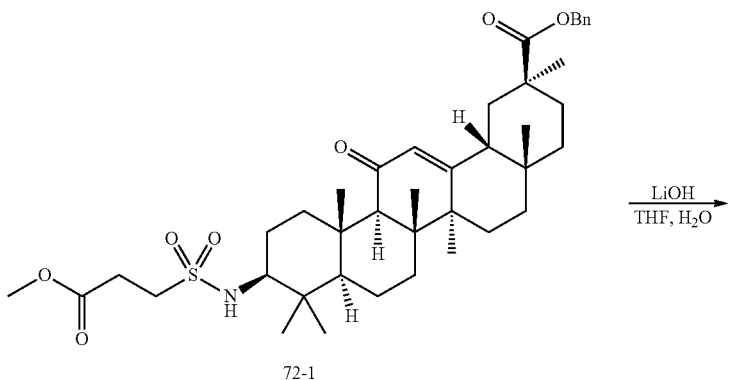
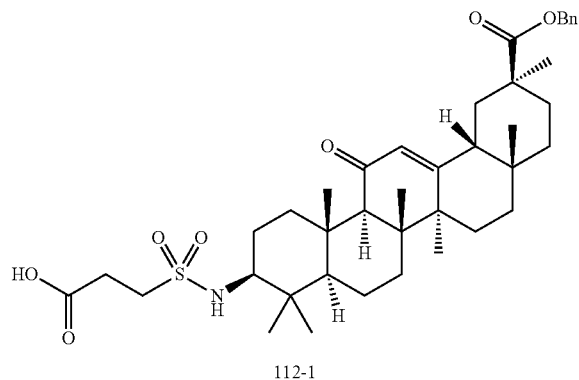
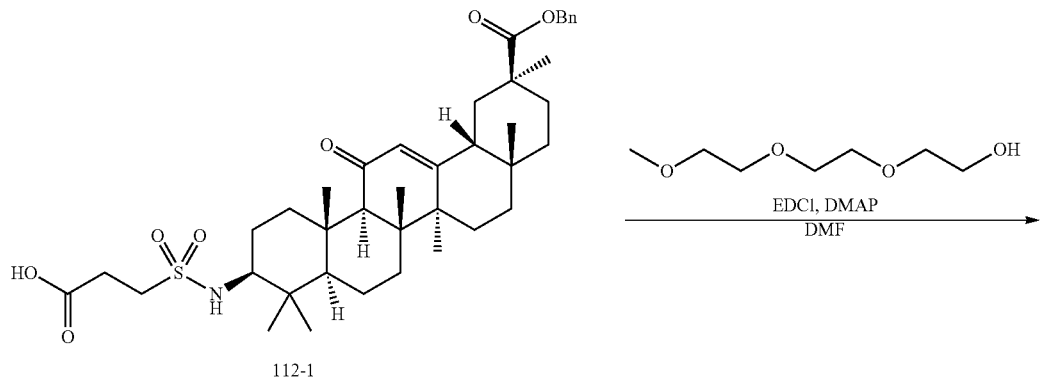

-continued

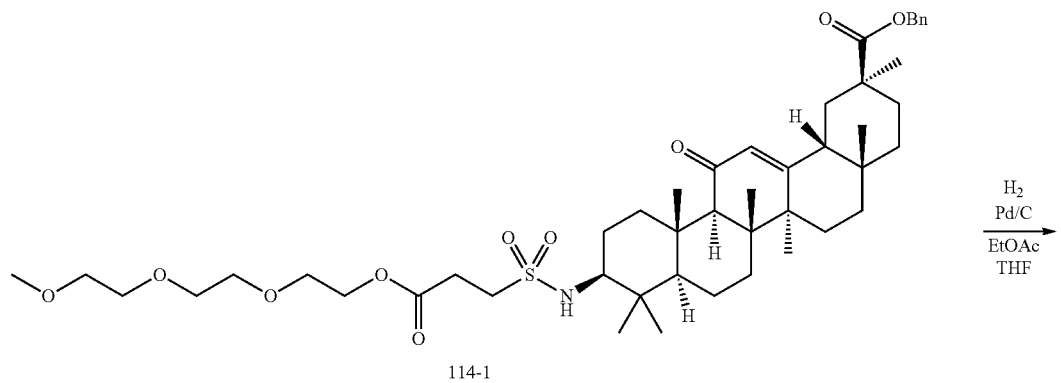

114-1

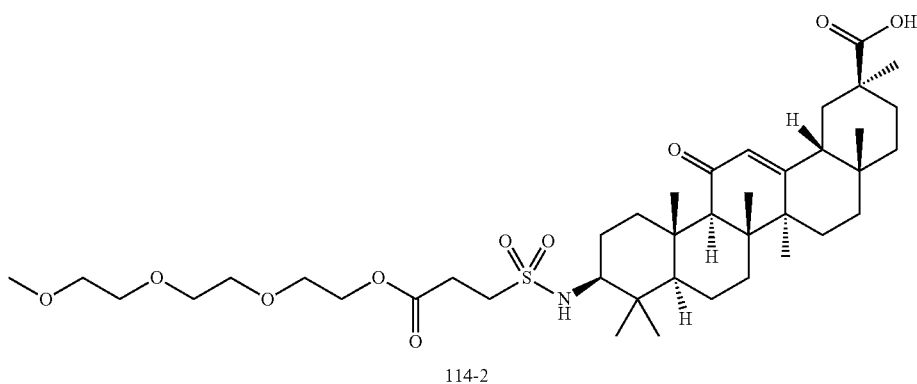

114-2

Synthesis of 3-(N-((3S,4aR,6aR,6bS,8aS,11S,12aR, 14aR,14bS)-11-((Benzyloxy)carbonyl)-4,4,6a,6b,8a,11, 14b-heptamethyl-14-oxo-1,2,3,4,4a,5,6,6a,6b,7,8,8a,9,10, 11,12,12a,14,14a,14b-icosahydropicen-3-yl)sulfamoyl) propanoic acid (112-1). 72-1 (200 mg, 0.282 mmol) and lithium hydroxide monohydrate (13.0 mg, 0.309 mmol) in THF and water were stirred for 4 hr at room temperature. The reaction was acidified with 6N HCl, partially evaporated under vacuum, diluted with water and extracted with DCM. The extract was dried ($Na_2SO_4$) and evaporated to give 0.195 g (99%) 112-1 as a white solid.

Synthesis of Benzyl (2S,4aS,6aS,6bR,8aR,10S,12aS, 12bR,14bR)-2,4a,6a,6b,9,9,12a-heptamethyl-13-oxo-10-((12-oxo-2,5,8,11-tetraoxatetradecane)sulfonamido)-1,2,3, 4,4a,5,6,6a, 6b,7,8,8a,9,10,11,12,12a,12b,13,14b-icosahydropicene-2-carboxylate (114-1). Into a 100-mL round-bottom flask, was placed 112-1 (200 mg, 0.29 mmol, 1 equiv), DMF (20 mL), 2-[2-(2-methoxyethoxy)ethoxy] ethan-1-ol (190 mg, 1.16 mmol, 4.03 equiv), EDCI (140 mg, 0.73 mmol, 2.54 equiv), DMAP (210 mg, 1.72 mmol, 5.98 equiv). The resulting solution was stirred overnight at 65° C. The resulting solution was extracted with 200 mL of EtOAc. The resulting mixture was washed with 1×200 mL of brine. The mixture was dried over anhydrous sodium sulfate. The solids were filtered out. This resulted in 100 mg (41.3%) of 114-1 as a white solid.

Synthesis of (2S,4aS,6aS,6bR,8aR,10S,12aS,12bR, 14bR)-2,4a,6a,6b,9,9,12a-Heptamethyl-13-oxo-10-((12-oxo-2,5,8,11-tetraoxatetradecane)sulfonamido)-1,2,3,4,4a, 5,6,6a,6b,7,8,8a,9,10,11, 12,12a,12b,13,14b-icosahydropicene-2-carboxylic acid (114-2). Into a 100-mL round-bottom flask, was placed 114-1 (100 mg, 0.12 mmol, 1 equiv), THF (5 mL), EA (10 mL), Pd/C (20 mg, 0.19 mmol, 1.583 equiv). To the above $H_2$ (g, 1 atm) was introduced in. The resulting solution was stirred overnight at room temperature. The solids were filtered out. The resulting mixture was concentrated. The crude product was purified by Prep-HPLC with the following conditions: Column, XBridge Shield RP18 OBD Column, 5 um, 19*150 mm; mobile phase, water (0.05% TFA) and ACN (54% Phase B up to 67% in 8 min); Detector, UV 254 nm. This resulted in 7.9 mg (8.9%) of 114-2 as a white solid. MS (ES, m/z): $[M+H]^+$=752.35; $^1$H NMR (400 MHz, MeOH-$d_4$, ppm): δ 0.78-0.94 (m, 7H), 0.95-1.24 (m, 15H), 1.53-2.07 (m, 9H), 2.08-2.28 (m, 2H), 2.52 (s, 1H), 2.70-2.90 (m, 3H), 2.97-3.11 (m, 2H), 3.35-3.45 (m, 5H), 3.52-3.62 (m, 3H), 3.63-3.72 (m, 9H), 3.73-3.86 (m, 2H), 4.20-4.32 (m, 2H), 5.60 (s, 1H), 7.25 (d, J=12.8 Hz, 1H).

Example 56 (2S,4aS,6aS,6bR,8aS,10S,12aS,12bR, 14bR)-2,4a,6a,6b,9,9,12a-Heptamethyl-13-oxo-10-(4-oxo-2,8,11,14-tetraoxa-5-azapentadecanoyl)-1,2, 3,4,4a,5,6,6a,6b,7,8,8a,9,10,11,2,12a, 12b,13,14b-icosahydropicene-2-carboxylic acid (115-2)

Synthesis of (2S,4aS,6aS,6bR,8aS,10S,12aS,12bR, 14bR)-2,4a,6a,6b,9,9,12a-Heptamethyl-13-oxo-10-(4-oxo-2,8,11,14-tetraoxa-5-azapentadecanoyl)-1,2,3,4,4a,5,6,6a, 6b,7,8,8a,9,10,11,12, 12a,12b,13,14b-icosahydropicene-2-carboxylic acid (115-2). Into a 100-mL round-bottom flask purged and maintained with an inert atmosphere of $H_2$ (1

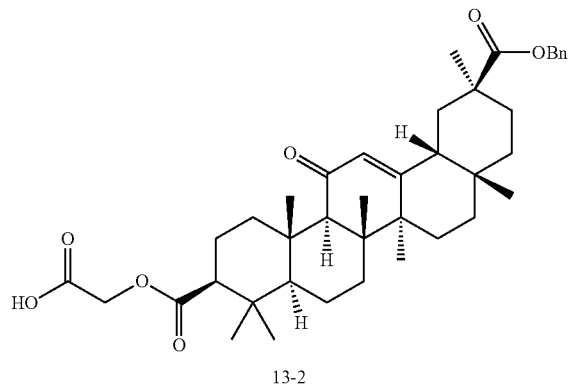

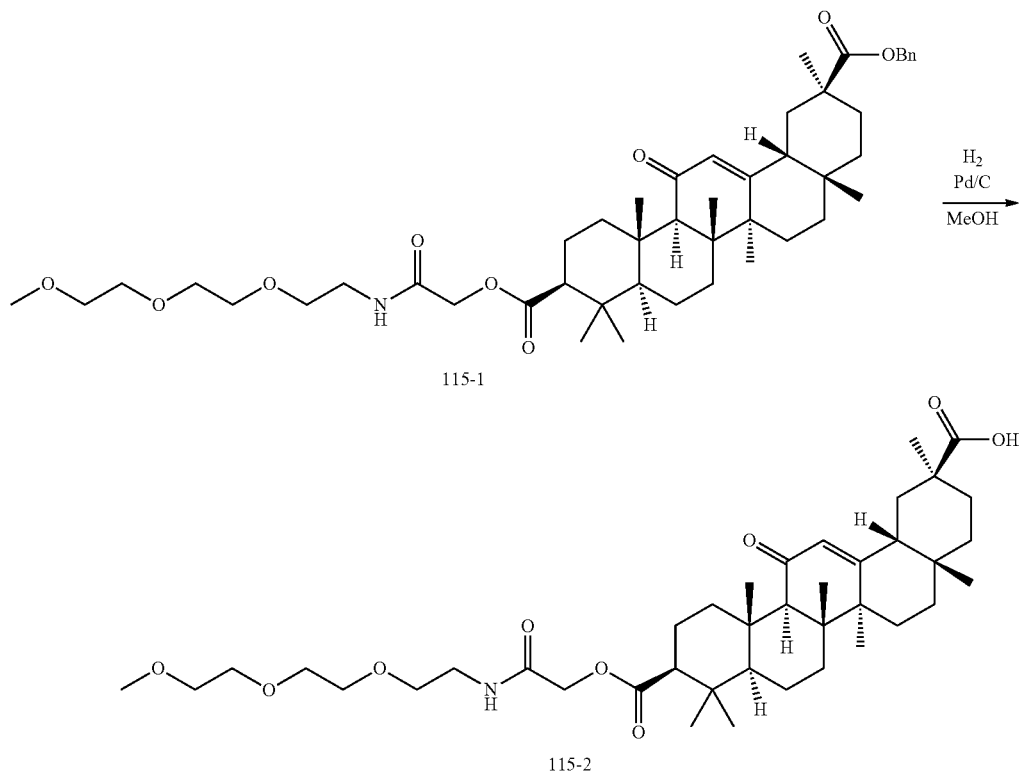

Synthesis of 2-Benzyl 10-(12-oxo-2,5,8-trioxa-11-azatri-decan-13-yl)(2S,4aS,6aS,6bR,8aS,10S, 12aS,12bR,14bR)-2,4a,6a,6b,9,9,12a-heptamethyl-13-oxo-1,2,3,4,4a,5,6,6a, 6b,7,8,8a,9,10,11,12, 12a,12b,13,14b-icosahydropicene-2, 10-dicarboxylate (115-1). Into a 200-mL round-bottom flask, was placed 13-2 (200 mg, 0.31 mmol, 1 equiv), DCM (10 mL, 0.12 mmol), DMAP (18 mg, 0.15 mmol, 0.477 equiv), EDCI (116 mg, 0.61 mmol, 1.957 equiv), 1-[2-(2-aminoethoxy)ethoxy]-2-methoxyethane (59 mg, 0.36 mmol, 1.169 equiv). The resulting solution was stirred overnight at room temperature. The resulting mixture was concentrated. The residue was applied onto a silica gel column with EtOAc/petroleum ether (1:1). This resulted in 200 mg (81.67%) 115-1 as a white solid.

atm), was placed 115-1 (200 mg, 0.25 mmol, 1 equiv), MeOH (10 mL, 0.31 mmol, 1.236 equiv), Pd/C (20 mg, 0.19 mmol, 0.744 equiv). The resulting solution was stirred overnight at room temperature. The resulting mixture was concentrated. The crude product was purified by Prep-HPLC with the following conditions (2 # -AnalyseHPLC-SHI-MADZU(HPLC-10)): Column, XBridge Shield RP18 OBD Column, 5 um, 19*150 mm; mobile phase, water (0.05% TFA) and ACN (53% Phase B up to 68% in 8 min); Detector, UV 254 nm. This resulted in 39.3 mg (22.17%) of 115-2 as a white solid. MS (ES, m/z): [M+H]$^+$=702.50; $^1$NMR-PH-RDX-013-585-0: (400 MHz, MeOH-d$_4$, ppm): δ 0.81-0.94 (m, 7H), 1.09-1.18 (m, 5H), 1.19-1.21 (m, 9H), 1.22-1.26

(m, 1H), 1.43-1.74 (m, 12H), 1.76-2.01 (m, 4H), 2.15-2.24 (m, 2H), 2.38 (d, J=12.8 Hz, 1H), 2.53 (s, 1H), 2.81 (d, J=13.2 Hz, 1H), 3.33-3.34 (m, 3H), 3.35-3.43 (m, 2H), 3.56-3.67 (m, 10H), 4.70 (AB q, J=11.6 Hz, 2H), 5.60 (s, 1H).
Example 57 (2S,4aS,6aS,6bR,8aR,9S,10S,12aS, 12bR,14bR)-10-Hydroxy-9-(methoxy carbonyl)-2, 4a,6a,6b,9,12a-hexamethyl-13-oxo-1,2,3,4,4a,5,6,6a, 6b,7,8,8a,9,10,11,12,12a,12b, 13,14b-icosahydropicene-2-carboxylic acid (123-2)
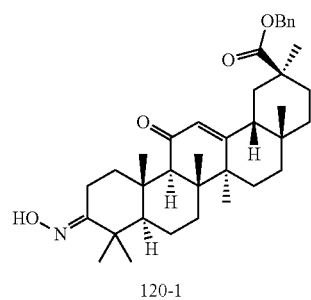
120-1
1. Na₂PdCl₄, NaOAc, HOAc
2. Ac₂O, TEA, DMAP·DCM
3. Pb(OAc)₄, Py, HOAc, THF
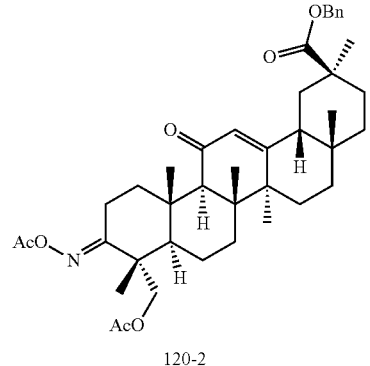
120-2
Na₂CO₃ / MeOH
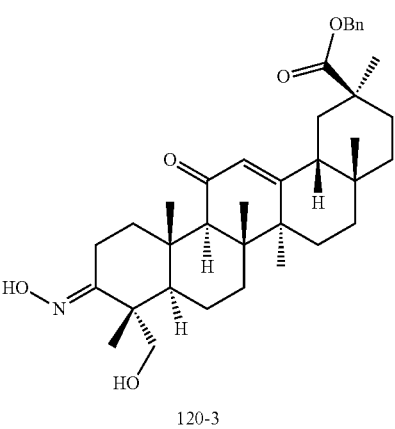
120-3
TiCl₃, NH₄OAc / THF
-continued
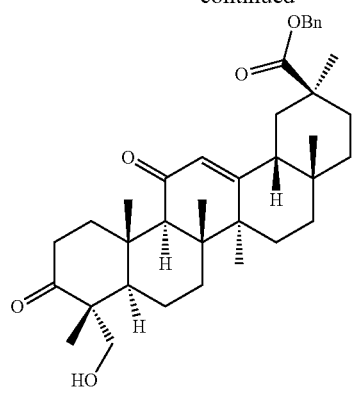
120-4
NaBH₄ / MeOH
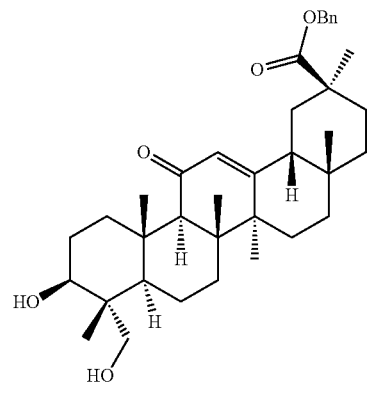
121-1
TEMPO, NCS, TBACl / DCM, pH = 7 buffer
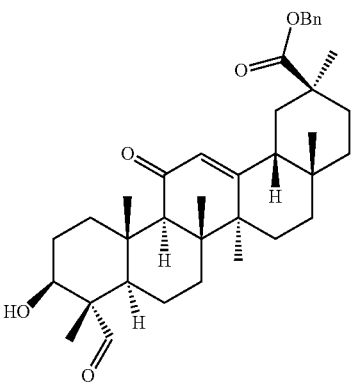
122-1
NaClO₂, NaH₂PO₄ / t-BuOH, H₂O,
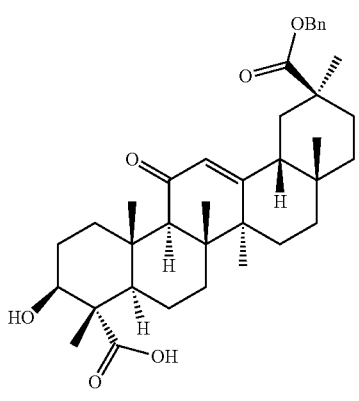
122-2
TMSCH₂N₂ / MeOH, DCM

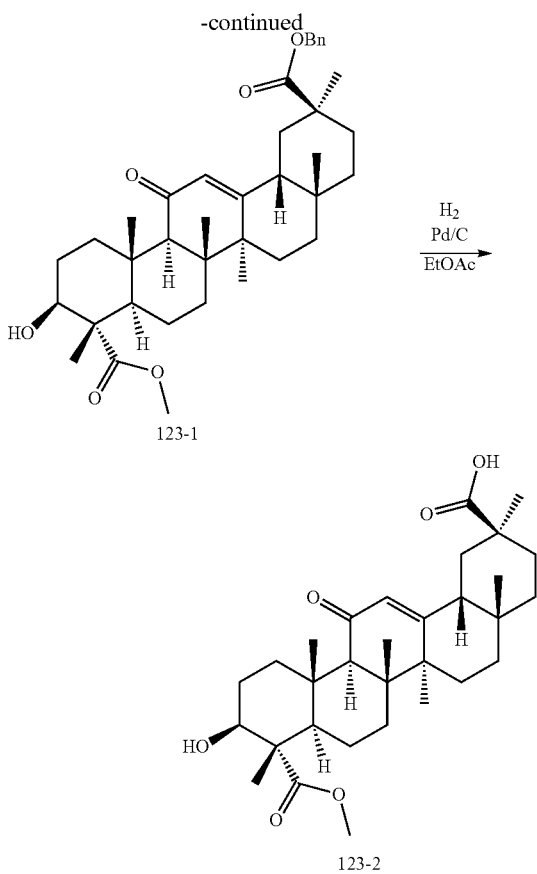

Synthesis of Benzyl (2S,4aS,6aS,6bR,8aR,9S,12aS,12bR, 14bR,E)-10-(acetoxyimino)-9-(acetoxymethyl)-2,4a,6a,6b, 9,12a-hexamethyl-13-oxo-1,2,3,4,4a,5,6,6a,6b,7,8,8a,9,10, 11,12,12a,12b,13,14b-icosahydropicene-2-carboxylate (120-2). Into a 250-mL round-bottom flask, was placed 120-1 (prepared from 109-1 as described in *Bioorg. Med. Chem.* 2010, 18, 433-454) (1.0 g, 1.7 mmol, 1.00 equiv), AcOH (100 mL), Na$_2$PdCl$_4$ (0.76 g, 2.04 mmol, 1.20 equiv), NaOAc (0.21 g, 1.36 mmol, 0.80 equiv). The mixture was stirred at room temperature (~15-20° C.) for 72 h. It was then poured onto ice. After a few hours, the precipitate was collected by filtration, the mixture was dried over anhydrous sodium sulfate. The solids were filtered out. The resulting mixture was concentrated under vacuum. Then DCM (120 mL), acetic anhydride (0.435 g, 3.24 mmol, 1.80 equiv), TEA (0.364 g, 2.72 mmol, 1.60 equiv) and DMAP (6 mg, 0.02 equiv) were added. The resulting solution was stirred for 1 h at room temperature. The resulting mixture was washed with 1×300 mL of water. The mixture was dried over anhydrous sodium sulfate. The solids were filtered out. The resulting mixture was concentrated under vacuum. Pyridine (0.6 mL), THF (100 mL) was added, and the solution was stirred at room temperature for 15 min. After cooled to –78° C., Pb(OAc)$_4$ (4.9 g, 8.5 mmol, 5 equiv) dissolved in AcOH (100 mL) was added slowly. After complete addition, the mixture was allowed to warm to room temperature and was then stirred at room temperature for 16 h. A solution of NaBH$_4$ (60 mg) in 1 N aqueous NaOH solution (50 mL) was added, and stirring was continued for 10 min. The mixture was filtered through celite. The resulting solution was extracted with 300 mL of DCM and the organic layers combined. The resulting mixture was washed with 3×300 mL of sat. NaHCO$_3$ and 2×300 mL of brine. The mixture was dried over anhydrous sodium sulfate. The solids were filtered out. The resulting mixture was concentrated under vacuum. This resulted in 1.03 g (88%, crude) of 120-2 as a light yellow solid.

Synthesis of Benzyl (2S,4aS,6aS,6bR,8aR,9S,12aS,12bR, 14bR,E)-10-(hydroxyimino)-9-(hydroxymethyl)-2,4a,6a, 6b,9,12a-hexamethyl-13-oxo-1,2,3,4,4a,5,6,6a,6b,7,8,8a,9, 10,11,12,12a,12b,13,14b-icosahydropicene-2-carboxylate (120-3). Into a 250-mL round-bottom flask, was placed 120-2 (1.03 g, 1.53 mmol, 1.00 equiv), MeOH (120 mL), sodium carbonate (820 mg, 7.74 mmol, 5.00 equiv). The resulting solution was stirred for 16 h at room temperature. The resulting mixture was concentrated under vacuum. The resulting solution was extracted with 200 mL of DCM and the organic layers combined. The resulting mixture was washed with 2×200 mL of sodium bicarbonate and 1×200 mL of brine. The solid was dried in an oven under reduced pressure. The solids were filtered out. The resulting mixture was concentrated under vacuum. This resulted in 1.1 g (crude) of 120-3 as a yellow solid.

Synthesis of Benzyl (2S,4aS,6aS,6bR,8aR,9R,12aS, 12bR,14bR)-9-(hydroxymethyl)-2,4a,6a,6b,9,12a-hexamethyl-10,13-dioxo-1,2,3,4,4a,5,6,6a,6b,7,8,8a,9,10,11,12, 12a,12b,13,14b-icosahydropicene-2-carboxylate (120-4). Into a 250-mL round-bottom flask, was placed NH$_4$OAc (3.88 g, 27.00 equiv), water (80 mL), TiCl$_3$ (4 mL). This was followed by the addition of a solution of 120-3 (1.1 g, 1.87 mmol, 1.00 equiv) in THE (70 mL) dropwise with stirring in 15 min. To this was added THE (70 mL). The resulting solution was stirred overnight at room temperature. The resulting mixture was concentrated under vacuum. The resulting solution was extracted with 200 mL of DCM and the organic layers combined. The resulting mixture was washed with 1×200 mL of sodium bicarbonate and 1×200 mL of brine. The mixture was dried over anhydrous sodium sulfate. The solids were filtered out. The resulting mixture was concentrated under vacuum. The residue was applied onto a silica gel column with EtOAc/petroleum ether (1:1). This resulted in 190 mg (18%) of 120-4 as a white solid.

Synthesis of Benzyl (2S,4aS,6aS,6bR,8aR,9R,10S,12aS, 12bR,14bR)-10-hydroxy-9-(hydroxymethyl)-2,4a,6a,6b,9, 12a-hexamethyl-13-oxo-1,2,3,4,4a,5,6,6a,6b,7,8,8a,9,10,11, 12,12a,12b,13,14b-icosahydropicene-2-carboxylate (121-1). Into a 100-mL round-bottom flask, was placed 120-4 (150 mg, 0.26 mmol, 1.00 equiv), MeOH (20 mL), NaBH$_4$ (40 mg, 1.06 mmol, 4.00 equiv). The resulting solution was stirred for 1 h at room temperature. The reaction was then quenched by the addition of 5 mL of water. The resulting mixture was concentrated under vacuum. The resulting solution was extracted with 100 mL of DCM and the organic layers combined. The resulting mixture was washed with x mL of and 1×100 mL of brine. The mixture was dried over anhydrous sodium sulfate. This resulted in 140 mg (93%) of 121-1 as a white solid.

Synthesis of Benzyl (2S,4aS,6aS,6bR,8aR,9S,10S,12aS, 12bR,14bR)-9-formyl-10-hydroxy-2,4a,6a,6b,9,12a-hexamethyl-13-oxo-1,2,3,4,4a,5,6,6a,6b,7,8,8a,9,10,11,12,12a, 12b,13,14b-icosahydropicene-2-carboxylate (122-1). Into a 100-mL round-bottom flask, was placed 121-1 (300 mg, 0.52 mmol, 1.00 equiv), DCM (25 mL), PH 8.6 buffer (5 mL), TEMPO (240 mg, 1.54 mmol, 3.00 equiv), TBACl (0.36 g, 2.50 equiv), NCS (280 mg, 2.10 mmol, 4.00 equiv). The resulting solution was stirred overnight at 40° C. The resulting solution was extracted with 200 mL of DCM and the organic layers combined. The resulting mixture was washed with 1×200 mL of water and 1×200 mL of brine. The mixture was dried over anhydrous sodium sulfate. This resulted in 0.4 g (134%, crude) of 122-1 as a yellow semi-solid.

Synthesis of (3S,4S,4aR,6aR,6bS,8aS,11S,12aR,14aR, 14bS)-11-((Benzyloxy)carbonyl)-3-hydroxy-4,6a,6b,8a,11, 14b-hexamethyl-14-oxo-1,2,3,4,4a,5,6,6a,6b,7,8,8a,9,10, 11,12,12a,14,14a,14b-icosahydropicene-4-carboxylic acid (122-2). Into a 250-mL round-bottom flask, was placed 122-1 (400 mg, 0.70 mmol, 1.00 equiv), tert-butanol (12 mL), water (6 mL), 2-methylbut-2-ene (2 mL), NaH$_2$PO$_4$ (0.5 g, 6.00 equiv), NaClO$_2$ (0.38 g, 6.00 equiv). The resulting solution was stirred for 30 min at −2° C. The resulting mixture was concentrated under vacuum. The resulting solution was extracted with 200 mL of DCM and the organic layers combined. The resulting mixture was washed with 1×200 mL of brine. The mixture was dried over anhydrous sodium sulfate. The solids were filtered out. The resulting mixture was concentrated under vacuum. This resulted in 0.758 g (184%, crude) of 122-2 as a yellow semi-solid.

Synthesis of 2-Benzyl 9-methyl (2S,4aS,6aS,6bR,8aR,9S, 10S,12aS,12bR,14bR)-10-hydroxy-2,4a,6a,6b,9,12a-hexamethyl-13-oxo-1,2,3,4,4a,5,6,6a,6b,7,8,8a,9,10,11,12,12a, 12b,13,14b-icosahydropicene-2,9-dicarboxylate (123-1). Into a 100-mL round-bottom flask, was placed 122-2 (500 mg, 0.85 mmol, 1.00 equiv.), DCM (10 mL), MeOH (10 mL), TMSCH$_2$N2 (5 mL, 10.00 equiv). The resulting solution was stirred for 1 h at room temperature. The resulting mixture was concentrated under vacuum. The resulting solution was extracted with 200 mL of DCM and the organic layers combined. The resulting mixture was washed with 1×200 mL of water and 1×200 mL of brine. The mixture was dried over anhydrous sodium sulfate. The solids were filtered out. The resulting mixture was concentrated under vacuum. This resulted in 0.6 g (117%, crude) of 123-1 as a yellow semi-solid.

Synthesis of (2S,4aS,6aS,6bR,8aR,9S,10S,12aS,12bR, 14bR)-10-Hydroxy-9-(methoxycarbonyl)-2,4a,6a,6b,9,12a-hexamethyl-13-oxo-1,2,3,4,4a,5,6,6a,6b,7,8,8a,9,10,11,12, 12a,12b,13,14b-icosahydropicene-2-carboxylic acid (123-2). Into a 100-mL round-bottom flask, was placed 123-1 (600 mg, 0.99 mmol, 1.00 equiv), EtOAc (20 mL), palladium on carbon (0.12 g, 0.20 equiv).

To the above hydrogen (1 atm) was introduced in. The resulting solution was stirred overnight at room temperature. The solids were filtered out. The resulting mixture was concentrated under vacuum. The crude product was purified by Prep-HPLC with the following conditions: Column, XBridge Shield RP18 OBD Column, 5 um, 19*150 mm; mobile phase, water (0.05% TFA) and ACN (48.0% ACN up to 62.0% in 8 min); Detector, UV 254 nm. This resulted in 29.7 mg (6%) of 123-2 as a white solid. MS (ES, m/z): [M+H]$^+$=515.30; $^1$H NMR (400 MHz, MeOH-d$_4$, ppm): δ 0.75 (s, 3H), 0.88-1.01 (m, 2H), 1.02-1.18 (m, 14H), 1.28-1.39 (m, 7H), 1.43 (d, J=11.6 Hz, 1H), 1.48-1.59 (m, 2H), 1.60-1.70 (m, 3H), 1.71-1.92 (m, 3H), 2.01-2.22 (m, 2H), 2.53 (s, 1H), 2.79 (dt, J=13.6, 3.5 Hz, 1H), 3.64 (s, 3H), 3.87 (dd, J=11.8, 4.7 Hz, 1H), 5.54 (s, 1H).

Example 58 (2S,4aS,6aS,6bR,8aR,10S,12aS,12bR, 14bR)-2,4a,6a,6b,9,9,12a-Heptamethyl-13-oxo-10-((2-oxo-2-(((R)-quinuclidin-3-yl)oxy)ethyl)carbamoyl)-1,2,3,4,4a,5,6,6a,6b,7,8,8a,9,10, 11,12,12a,12b, 13,14b-icosahydropicene-2-carboxylic acid (124-2)

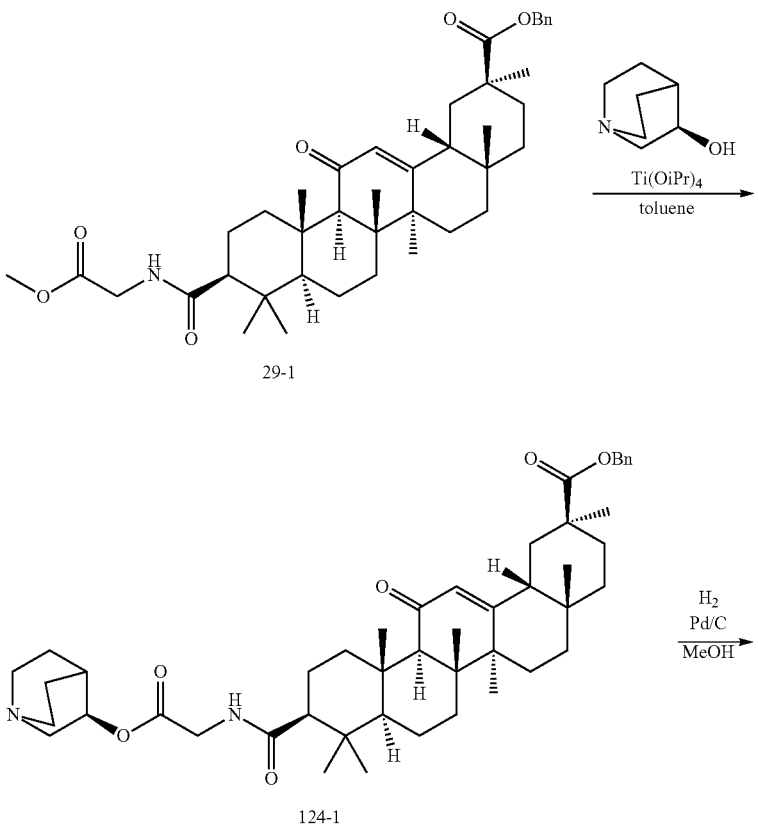

29-1

124-1

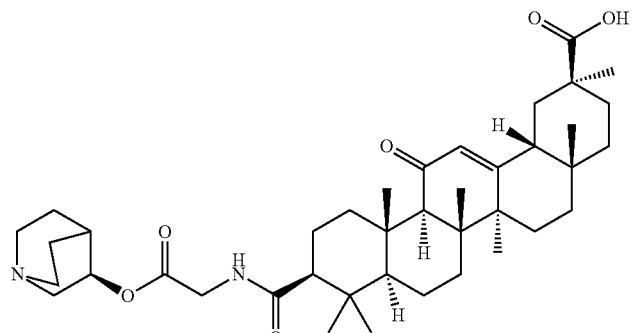

124-2

Synthesis of Benzyl (2S,4aS,6aS,6bR,8aS,10S,12aS,12bR,14bR)-2,4a,6a,6b,9,9,12a-hepta methyl-13-oxo-10-((2-oxo-2-(((R)-quinuclidin-3-yl)oxy)ethyl)carbamoyl)-1,2,3,4,4a,5,6,6a,6b, 7,8,8a,9,10,11,12,12a,12b,13,14b-icosahydropicene-2-carboxylate (124-1). Into a 50-mL round-bottom flask, was placed 29-1 (100 mg, 0.15 mmol, 1.00 equiv), toluene (10 mL), (3R)-1-azabicyclo[2.2.2]octan-3-ol (60 mg, 0.47 mmol, 3.00 equiv), titanium(IV) isopropoxide (0.14 mL, 3.00 equiv). The resulting solution was stirred overnight at 110° C. The resulting mixture was concentrated under vacuum. The residue was applied onto a silica gel column with DCM/MeOH (5:1). This resulted in 20 mg (17%) of 124-1 as an off-white solid.

Synthesis of (2S,4aS,6aS,6bR,8aS,10S,12aS,12bR,14bR)-2,4a,6a,6b,9,9,12a-Heptamethyl-13-oxo-10-((2-oxo-2-(((R)-quinuclidin-3-yl)oxy)ethyl)carbamoyl)-1,2,3,4,4a,5,6,6a,6b,7,8,8a,9,10, 11,12,12a,12b,13,14b-icosahydropicene-2-carboxylic acid (124-2). Into a 100-mL round-bottom flask, was placed 124-1 (45 mg, 0.06 mmol, 1.00 equiv), MeOH (20 mL), palladium on carbon (10 mg). To the above hydrogen (1 atm) was introduced in. The resulting solution was stirred for 1 h at room temperature. The solids were filtered out. The crude product was purified by Prep-HPLC with the following conditions: Column, XBridge Shield RP18 OBD Column, 5 um, 19*150 mm; mobile phase, water (0.05% TFA) and ACN (30.0% ACN up to 56.0% in 8 min); Detector, UV 254/220 nm. This resulted in 11.6 mg (29%) of 124-2 as a white solid. MS (ES, m/z): [M+H]$^+$=665.45; $^1$H NMR (300 MHz, MeOH-$d_4$, ppm): δ 0.84 (s, 3H), 0.87 (s, 1H), 0.92 (s, 3H), 0.96-1.01 (m, 2H), 1.07 (s, 3H), 1.16 (s, 3H), 1.17 (s, 3H), 1.19 (s, 3H) 1.23-1.29 (m, 1H), 1.40-1.53 (m, 8H), 1.63-1.76 (m, 3H), 1.79-2.32 (m, 11H), 2.38 (s, 1H), 2.50 (s, 1H), 2.80 (dt, J=13.5 Hz, 3.3 Hz, 1H), 3.33-3.40 (m, 6H), 3.70-3.79 (m, 1H), 3.88 (d, J=17.3 Hz, 1H), 3.99 (d, J=17.3 Hz, 1H), 5.10-5.17 (m, 1H), 5.58 (s, 1H).

Example 59 HSD2 Activity

Human descending colon epithelial stem cells were cultured as 3D organoids in accordance with Sato et al. Gastroenterology. 2011 November; 141(5):1762-72. Organoids were dissociated using TrypLE Express (life technologies) and plated on 96-well transwells (corning) in supplemented basal media (SBM—advanced DMEM/F12 containing 10 mM HEPES, 1:100 Glutamax, 1:100 penicillin/streptomycin, 1:100 N2, 1:50 B27, 1 mM N-acetylcysteine, 10 nM [Leu15]-gastrin I) containing 100 ng/mL Wnt3A (W), 50 ng/mL EGF (E), 100 ng/mL Noggin (N), 500 ng/mL RSpondin1 (R), 500 nM A83-01 (A) and 2.5 uM thiazovivin (T). Cultures were differentiated using SBM containing ENRA and 30 nM aldosterone on day 3, and cultures were used for assay on day 6 or 7. Compounds were diluted in DMSO and serial dilutions prepared by titrating in DMSO. Compounds were then diluted into DMEM/F12. Transwell plates containing descending colon cultures were washed twice with DMEM/F12 and compound was added to the apical compartment. Cells were incubated with test compound for 30 minutes at 37° C., 5% $CO_2$ to equilibrate across the cell membrane. A second compound plate was prepared in which the serially diluted compounds in DMSO were diluted into DMEM/F12 containing 40 nM cortisol. Following the 30 minute pre-incubation step, the apical media was aspirated and compounds diluted in DMEM/F12 with 40 nM cortisol were added to the apical side of the transwell. The plate was then incubated for four hours at 37° C., 5% $CO_2$. Cortisol levels were measured using a cortisol HTRF assay kit as described by the manufacturer (Cisbio). Concentration-response curves were then plotted and $IC_{50}$ values were determined using least squares non-linear regression.

Example 60 Stability Assays

Sample were analyzed on an Agilent 6410 triple-quadrapole LC-MS system consisting of an Agilent 1260 LC with a Phenomenex Gemini 5 μm column (NX-C18, 110A, 30×2 mm) and the mass spectrometer with an electrospray interface running under a positive ionization mode. Mobile phases were 0.1% formic acid in water and 0.1% formic acid in acetonitrile. Plasma Stability—Plasma from pooled male rat or human (purchased from BioreclamationIVT, LLC) were pre-warmed to 37° C. Compounds were then added to the plasma samples to make a final concentration of 1 μM and vortexed. Duplicate samples of 100 μL each were taken out at Time 0, 10, 20, 30 and 60 min for extraction and analysis. Extraction and analysis of parent drug were by addition of 300 μL of acetonitrile containing 500 ng/mL of internal standard (labetalol), vortexing, and centrifugation.

150 μL of the supernatant was added to 100 μL of deionized water and 10 μL injected onto LC/MS.

Liver S9 Homogenate Stability—Liver S9 homogenate from pooled male rat or human (purchased from Xenotech, LLC, 20 mg protein/mL) was diluted with 0.05M $KH_2PO_4$, pH 7.4 buffer to make 0.8 mg protein/mL and pre-warmed to 37° C. Compounds were then added to the homogenate samples to make a final concentration of 1 μM and vortexed. Duplicate samples of 100 μL each were taken out at Time 0, 5, 15, 30 and 120 min for extraction and analysis. Extraction and analysis of parent drug were by addition of 300 μL of acetonitrile containing 100 ng/mL of internal standard (labetalol), vortexing, and centrifugation. 150 μL of the supernatant was added to 100 μL of deionized water and 10 μL injected onto LC/MS.

Liver Microsomal Stability—Liver microsome from pooled male rat or human (purchased from Xenotech, LLC, 20 mg protein/mL) was diluted with 0.05M $KH_2PO_4$, pH 7.4 buffer containing 5 mM MgCl2 to make 0.5 mg protein/mL and pre-warmed to 37° C. Compounds were then added to the homogenate samples to make a final concentration of 1 μM and vortexed. NADPH in 0.05M $KH_2PO_4$, pH 7.4 buffer was then added to make the final concentration of 2 mM to start the reaction. Duplicate samples of 100 μL each were taken out at Time 0, 3, 6, 10, 15, 20 and 30 min for extraction and analysis. Extraction and analysis of parent drug were by addition of 100 μL of acetonitrile containing 100 ng/mL of internal standard (labetalol), vortexing, and centrifugation. 10 μL of the supernatant was injected onto LC/MS. An incubation without the NADPH addition was used as a control for the experiment.

Cecal-Colonic Extract Stability—Female rats (non-fasted) were euthanized and the cecum and colon taken out and weighed. The intestinal contents in the cecum and colon were flushed out with 20 mL deionized water and the tissues re-weighed. Deionized water was added to the cecal-colonic content mixture to make a 10× w/v dilution. The mixture was then homogenized by a Polytron homogenizer for 2 minutes and centrifuged at 5000 rpm in a Beckman Allegra 25r centrifuge for 10 minutes. The supernatant was taken out and warmed to 37° C. in a shaking water. 1.5 mL Aliquots were then added compounds to make a final concentration of 1 μM and vortexed. Duplicate samples of 100 μL each were taken out at Time 0, 10, 20, 40, 60 and 180 min for extraction and analysis. Extraction and analysis of parent drug were by addition of 300 μL of acetonitrile containing 500 ng/mL of internal standard (labetalol), vortexing, and centrifugation. 150 μL of the supernatant was added to 100 μL of deionized water and 10 μL injected onto LC/MS.

What is claimed is:

1. A compound of formula I or a salt thereof:

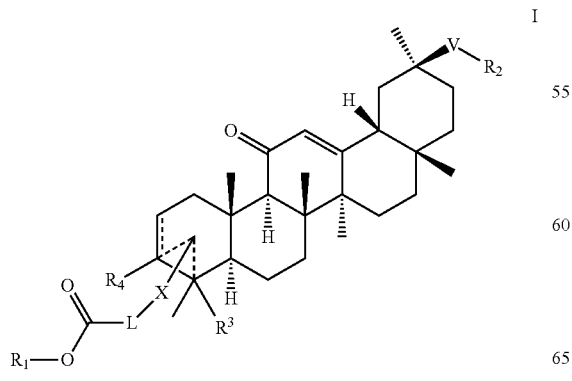

wherein,

X is a bond, —O—, —C(O)—, —N($R_x$)—, —C(O)N($R_x$)—, —N($R_x$)—C(O)—, —S(O)$_n$—N($R_x$)— or —N($R_x$)—S(O)$_n$—;

V is —C(O)O—, —C(O)N($R_5$)—, —C(O)N($R_5$)O—, —NH—C(O)—N($R_5$)— or NH—S(O)$_n$—;

L is a bond, alkylene wherein one or more non-adjacent methylene groups of said alkylene are replaced with —O—; divalent aryl or divalent heteroaryl; or L is alkylene-Y-alkylene wherein Y is O, N$R_x$, S, SO, $SO_2$ or a divalent heterocycle; wherein said alkylene groups are optionally substituted with OH, —C(O)O—$R_1$, alkyl or alkyl substituted with OH or —C(O)O—$R_1$; and wherein a carbon of said alkylene groups and $R_x$ optionally together form a heterocycle; provided that when X is other than a bond, then L is other than a bond;

$R_1$ is alkyl optionally substituted with halogen, OH, amino, oxo, carboxy, acyloxy, alkoxycarbonyl, alkoxyacyloxy, alkoxycarbonyloxy, aminocarbonyl, a carbocycle optionally substituted with alkyl, haloalkyl, oxo, amino and halogen and a heterocycle optionally substituted with alkyl, oxo, amino and halogen; and a carbocycle or heterocycle optionally substituted with alkyl, haloalkyl, oxo, amino and halogen; wherein one or more non-adjacent methylene groups in any of the foregoing alkyl groups is replaced with O;

$R_2$ is H or $R_1$;

$R_3$ is absent, Me; provided that when —X-L-C(O)O—$R_1$ depends from the carbon to which $R_3$ depends then $R_3$ is absent; or $R_3$ is —Z-L-C(O)O—$R_1$ wherein Z is a bond, —O—, —N($R_x$)—, —C(O)N($R_x$)—, —N($R_x$)—C(O)—, —S(O)$_n$—N($R_x$)— or —N($R_x$)—S(O)$_n$—; and $R_4$ is absent, H or OH; provided that when —X-L-C(O)O—$R_1$ depends from the carbon to which $R_4$ depends then $R_4$ is H or absent;

$R_5$ is H or alkyl;

$R_x$ is H, —C(O)O—$R_1$, or alkyl optionally substituted with —C(O)O—$R_1$; and n is 1 or 2.

2. The compound or salt of claim 1, having the structure of any one of Formula Ia-Ir:

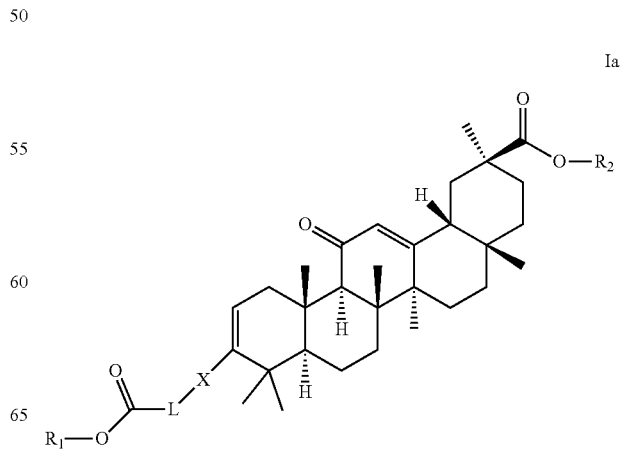

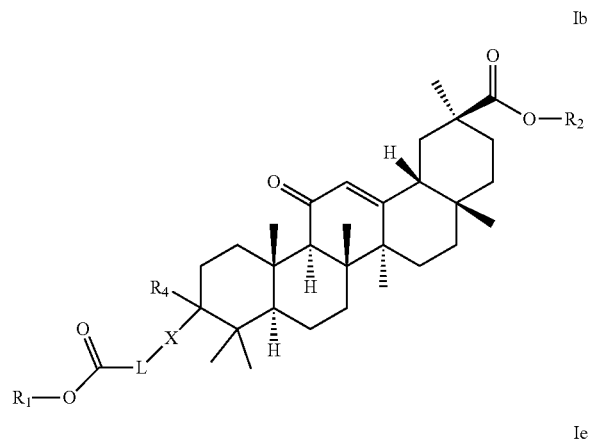
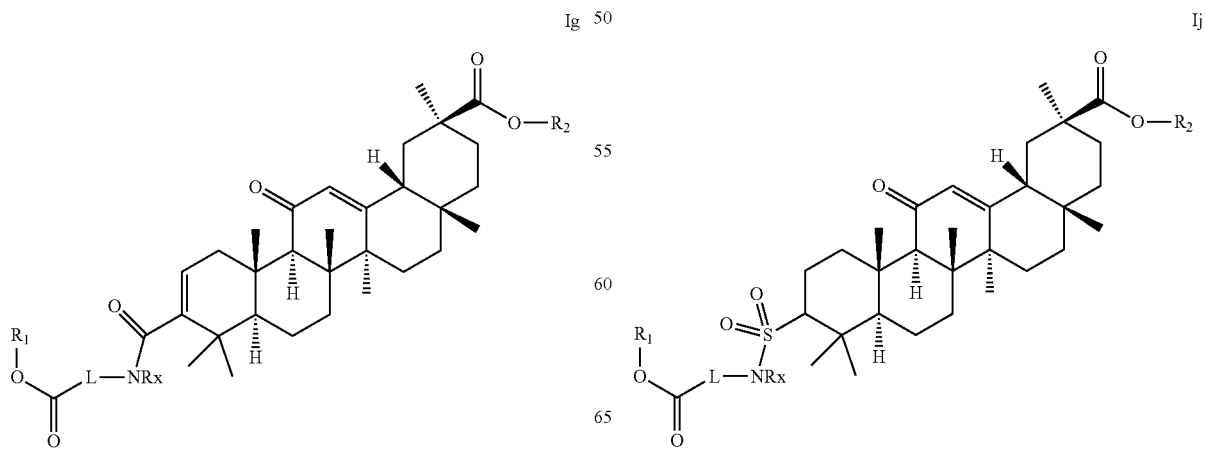
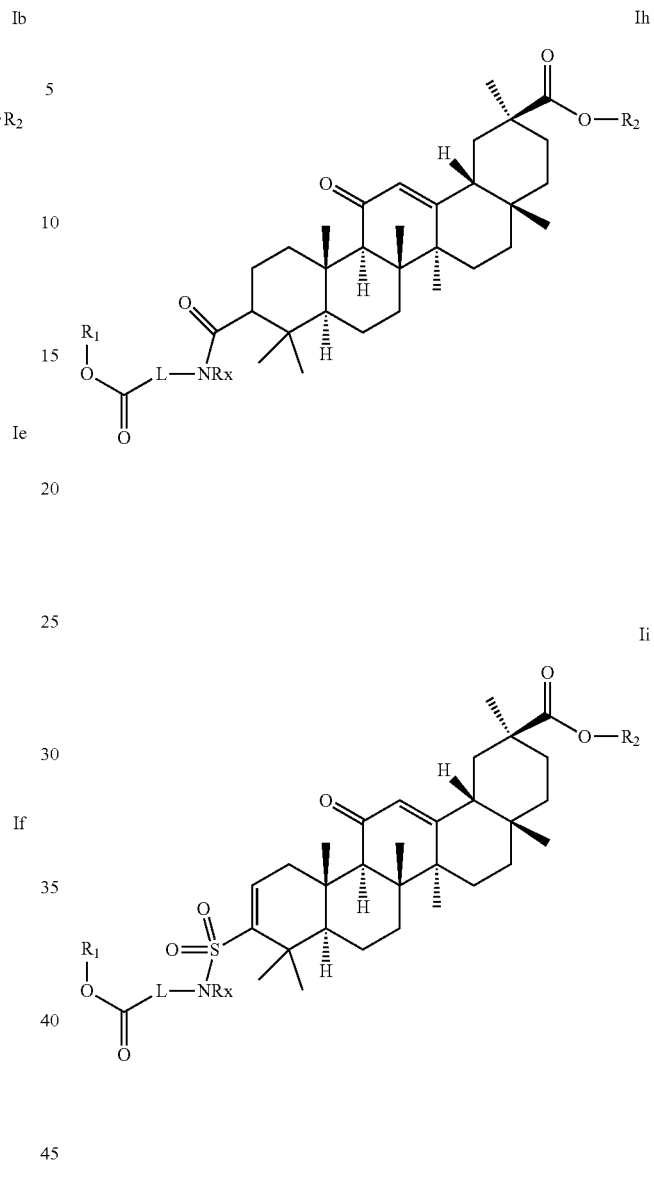

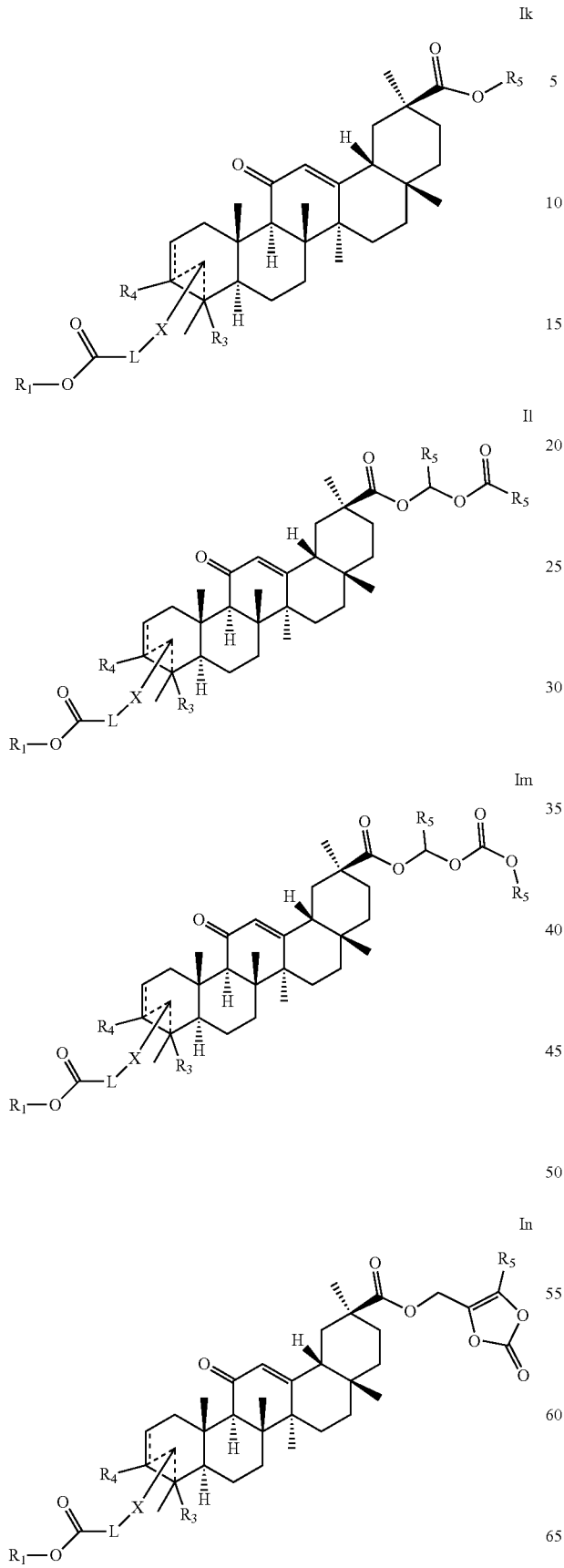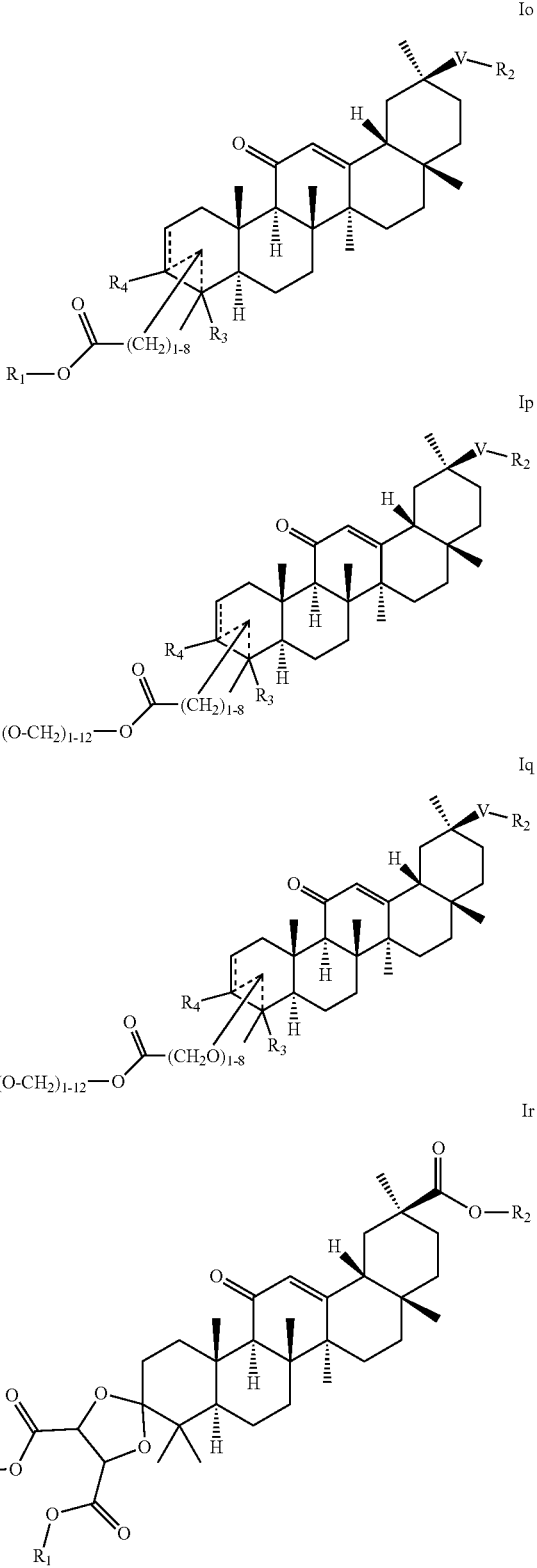
or a salt thereof.
3. The compound or salt of claim 1, wherein X is a bond.
4. The compound or salt of claim 1, wherein L is a bond.
5. The compound or salt of claim 1, wherein X and L are both bonds.

6. The compound or salt as claimed in claim 1, wherein $R_2$ is H.

7. The compound or salt as claimed in claim 1, wherein $R_3$ is H.

8. The compound or salt as claimed in claim 1, wherein $R_4$ is H.

9. The compound salt as claimed in claim 1, wherein X is absent and L is aryl or heteroaryl.

10. The compound or salt of claim 9, wherein L is phenyl, triazole or isoxazole.

11. The compound or salt of claim 10 wherein $R_3$ is hydrogen.

12. The compound or salt as claimed in claim 11 wherein $R_2$ and $R_4$ are each H.

13. The compound or salt as claimed in claim 1, wherein X is O.

14. The compound or salt as claimed in claim 1, wherein X is —C(O)—.

15. The compound or salt as claimed in claim 1, wherein $R_1$ is alkyl optionally substituted with halogen, OH, amino, oxo, carboxy, acyloxy, alkoxycarbonyl, alkoxyacyloxy, alkoxycarbonyloxy, aminocarbonyl, a carbocycle optionally substituted with alkyl, haloalkyl, oxo, amino and halogen and a heterocycle optionally substituted with alkyl, oxo, amino and halogen; and heterocycle optionally substituted with alkyl, haloalkyl, oxo, amino and halogen; wherein one or more non-adjacent methylene groups in said alkyl is replaced with O.

16. The compound or salt of claim 15, wherein $R_1$ is methyl, propyl, hydroxyethyl, 2,2,2-trifluoroethyl, 1,1-trifluoromethylethyl, 2-morpholinoethyl, 2-(1H-imidazol-1-yl)ethyl, 2-(pyridin-2-yl)ethyl, —CH$_2$—C(O)OH, —CH$_2$—C(O)O-Me, —CH$_2$—C(O)NH$_2$, —CH$_2$—C(O)NMe$_2$, —CH$_2$—C(O)O-t-butyl, (5-methyl-2-oxo-1,3-dioxol-4-yl)methyl, (pivaloyloxy)methyl, ((isopropoxycarbonyl)oxy)methyl, (S)-1-((isopropoxycarbonyl)oxy)ethyl, (R)-1-((isopropoxycarbonyl)oxy)ethyl, 2-morpholino-2-oxoethyl, 2-(4-methylpiperazin-1-yl)-2-oxoethyl or (R)-quinuclidin-3-yl.

17. The compound or salt of claim 15, wherein $R_1$ is methyl.

18. A method of inhibiting conversion of cortisol to cortisone by HSD2 comprising contacting HSD2 with a compound of claim 1 or a pharmaceutically acceptable salt thereof.

* * * * *

UNITED STATES PATENT AND TRADEMARK OFFICE
CERTIFICATE OF CORRECTION

PATENT NO. : 11,768,319 B2
APPLICATION NO. : 16/636596
DATED : September 26, 2023
INVENTOR(S) : Gary Luehr et al.

It is certified that error appears in the above-identified patent and that said Letters Patent is hereby corrected as shown below:

In the Claims

Column 196, Lines 19-22, Claim 18, please delete "A method of inhibiting conversion of cortisol to 20 cortisone by HSD2 comprising contacting HSD2 with a compound of claim 1 or a pharmaceutically acceptable salt thereof." and insert --A pharmaceutical composition comprising a compound as claimed in claim 1 or a pharmaceutically acceptable salt thereof and a pharmaceutically acceptable carrier, diluentor excipient.-- therefor.

Signed and Sealed this
Seventh Day of May, 2024

Katherine Kelly Vidal
*Director of the United States Patent and Trademark Office*